(12) United States Patent
Fukunaga et al.

(10) Patent No.: US 11,426,473 B2
(45) Date of Patent: Aug. 30, 2022

(54) NITROGEN-CONTAINING COMPOUND OR SALT THEREOF, OR METAL COMPLEX THEREOF

(71) Applicants: FUJIFILM Corporation, Tokyo (JP); PDRadiopharma Inc., Tokyo (JP)

(72) Inventors: Hirofumi Fukunaga, Ashigarakami-gun (JP); Hiroyuki Dozono, Togane (JP); Akihiro Hino, Chiba (JP); Shinobu Oshikiri, Chiba (JP); Akio Nagano, Oamishirasato (JP)

(73) Assignees: FUJIFILM Corporation, Tokyo (JP); PDRADIOPHARMA INC., Tokyo (JP)

( * ) Notice: Subject to any disclaimer, the term of this patent is extended or adjusted under 35 U.S.C. 154(b) by 711 days.

(21) Appl. No.: 15/078,738

(22) Filed: Mar. 23, 2016

(65) Prior Publication Data

US 2016/0199520 A1   Jul. 14, 2016

Related U.S. Application Data

(63) Continuation of application No. PCT/JP2014/075332, filed on Sep. 24, 2014.

(30) Foreign Application Priority Data

Sep. 24, 2013   (JP) .............................. JP2013-196712

(51) Int. Cl.
| | | |
|---|---|---|
| *A61K 51/08* | (2006.01) | |
| *C07K 5/08* | (2006.01) | |
| *C07K 5/10* | (2006.01) | |
| *C07D 401/12* | (2006.01) | |
| *A61K 51/04* | (2006.01) | |
| *C07D 471/04* | (2006.01) | |

(Continued)

(52) U.S. Cl.
CPC ........ *A61K 51/088* (2013.01); *A61K 51/0455* (2013.01); *A61K 51/0478* (2013.01); *A61K 51/0482* (2013.01); *C07D 213/73* (2013.01); *C07D 213/75* (2013.01); *C07D 401/12* (2013.01); *C07D 401/14* (2013.01); *C07D 471/04* (2013.01); *C07D 519/00* (2013.01); *C07K 5/08* (2013.01); *C07K 5/10* (2013.01); *C07K 5/0606* (2013.01); *Y02P 20/55* (2015.11)

(58) Field of Classification Search
CPC .. A61K 31/785; A61K 31/555; A61K 31/223; A61K 31/145; A61K 31/27; A61K 31/395; C07D 257/02; C07D 471/04; C07D 487/00; C07D 255/02; A61P 35/00; A61P 9/00; A61P 43/00; C07F 5/00; C07F 1/08; C07B 59/00; Y02P 20/55
See application file for complete search history.

(56) References Cited

U.S. PATENT DOCUMENTS 5,919,792 A   7/1999   Duggan et al.
5,952,306 A   9/1999   Hartman et al.
(Continued)

FOREIGN PATENT DOCUMENTS

DE   102009000854 A1   8/2010
EA     002822 B1   10/2002
(Continued)

OTHER PUBLICATIONS

Extended European Search Report, dated Mar. 15, 2017, for corresponding European Application No. 14849898.3.
Japanese Office Action, dated Apr. 25, 2017, for corresponding Japanese Application No. 2015-539283, with an English machine translation.
Beer et al. "[18F] Galacto-RGD Positron Emission Tomography for Imaging of Alpha-v beta-3 Expression on the Neovasculature in Patients with Squamous Cell Carcinoma of the Head and Neck", Clin. Cancer Res., vol. 13, p. 6610-6616, Nov. 15, 2007.
Beer et al. "Positron EmissionTomography Using [18F] Galacto-RGD Identifies the Level of Integrin Alpha-v beta-3 Expression in Man", Clin. Cancer Res., vol. 12, p. 3942-3949, Jul. 1, 2006.
(Continued)

*Primary Examiner* — Michael G. Hartley
*Assistant Examiner* — Leah H Schlientz
(74) *Attorney, Agent, or Firm* — Birch, Stewart, Kolasch & Birch, LLP

(57) ABSTRACT

The present invention provides a compound represented by the formula (1) or a salt thereof, or a complex of the compound or the salt with a metal, in the formula (1), $A^1$ represents a chelate group; $R^1$ represents a hydrogen atom or the like; $R^2$ represents a hydrogen atom or the like; and $Z^1$, $Z^2$, $Z^3$, $Z^4$, and $Z^5$ are the same or different and each represent a nitrogen atom or $CR^3$ or the like wherein $R^3$ represents a hydrogen atom or an optionally substituted $C_{1-6}$ alkyl group or the like; $L^1$ represents a group represented by the formula (3) wherein $R^{13}$, $R^{14}$, $R^{15}$, and $R^{16}$ are the same or different and each represent a hydrogen atom or the like; $L^2$ represents an optionally substituted $C_{1-6}$ alkylene group; and $L^3$ represents an optionally substituted $C_{1-6}$ alkylene group.

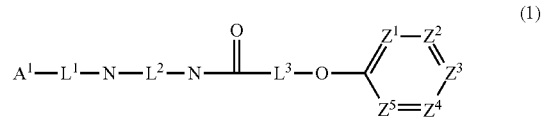

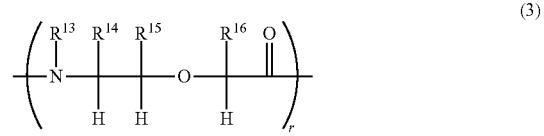

36 Claims, 9 Drawing Sheets

(51) Int. Cl.
  *C07D 519/00* (2006.01)
  *C07D 401/14* (2006.01)
  *C07D 213/75* (2006.01)
  *C07D 213/73* (2006.01)
  *C07K 5/062* (2006.01)

(56) References Cited

U.S. PATENT DOCUMENTS

| | | |
|---|---|---|
| 5,952,341 A | 9/1999 | Duggan et al. |
| 5,981,548 A | 11/1999 | Duggan et al. |
| 6,001,961 A | 12/1999 | Jonczyk et al. |
| 6,017,925 A | 1/2000 | Duggan |
| 6,017,926 A | 1/2000 | Askew et al. |
| 6,040,311 A | 3/2000 | Duggan et al. |
| 6,048,861 A | 4/2000 | Askew et al. |
| 6,066,648 A | 5/2000 | Duggan et al. |
| 6,090,944 A | 7/2000 | Hutchinson |
| 6,130,231 A | 10/2000 | Wityak et al. |
| 6,211,184 B1 | 4/2001 | Duggan et al. |
| 6,211,191 B1 | 4/2001 | Duggan et al. |
| 6,232,308 B1 | 5/2001 | Askew |
| 6,294,549 B1 | 9/2001 | Hartman et al. |
| 6,358,970 B1 | 3/2002 | Duggan et al. |
| 6,358,976 B1 | 3/2002 | Wityak et al. |
| 6,407,241 B1 | 6/2002 | Jensen et al. |
| 6,410,526 B1 | 6/2002 | Duggan et al. |
| 6,413,955 B1 | 7/2002 | Askew et al. |
| 6,423,845 B1 | 7/2002 | Rivera et al. |
| 6,495,560 B1 | 12/2002 | Miller et al. |
| 6,511,648 B2 | 1/2003 | Harris et al. |
| 6,514,964 B1 | 2/2003 | Chen et al. |
| 6,683,163 B2 | 1/2004 | Harris et al. |
| 6,689,337 B2 | 2/2004 | Harris et al. |
| 6,689,787 B1 | 2/2004 | McKearn et al. |
| 6,693,101 B2 | 2/2004 | Askew et al. |
| 6,743,412 B2 | 6/2004 | Harris et al. |
| 6,794,518 B1 | 9/2004 | Rajopadhye et al. |
| 7,052,673 B2 | 5/2006 | Rajopadhye et al. |
| 7,153,862 B2 | 12/2006 | Askew et al. |
| 7,241,789 B2 | 7/2007 | Lu et al. |
| 7,321,045 B2 | 1/2008 | Rajopadhye et al. |
| 7,332,149 B1 | 2/2008 | Rajopadhye et al. |
| 7,650,848 B2 | 1/2010 | Brennan et al. |
| 8,361,438 B2 | 1/2013 | Cesati et al. |
| 9,439,986 B2 | 9/2016 | Lee et al. |
| 9,770,520 B2 | 9/2017 | Port et al. |
| 2001/0053853 A1 | 12/2001 | Askew et al. |
| 2002/0010176 A1 | 1/2002 | Askew et al. |
| 2002/0015680 A1 | 2/2002 | Harris |
| 2002/0019402 A1 | 2/2002 | Dominguez et al. |
| 2002/0037889 A1 | 3/2002 | Duggan et al. |
| 2002/0040030 A1 | 4/2002 | Coleman et al. |
| 2002/0040039 A1 | 4/2002 | Hartman et al. |
| 2002/0041878 A1 | 4/2002 | Harris et al. |
| 2002/0049224 A1 | 4/2002 | Arison et al. |
| 2002/0061909 A1 | 5/2002 | Harris et al. |
| 2002/0065291 A1 | 5/2002 | Humphrey et al. |
| 2002/0072518 A1 | 6/2002 | Khanna et al. |
| 2002/0077321 A1 | 6/2002 | Khanna et al. |
| 2002/0147334 A1 | 10/2002 | Miller et al. |
| 2002/0169200 A1 | 11/2002 | Lu et al. |
| 2002/0182147 A1 | 12/2002 | Harris et al. |
| 2002/0187988 A1 | 12/2002 | Sturr et al. |
| 2002/0188001 A1 | 12/2002 | Xu et al. |
| 2003/0004171 A1 | 1/2003 | Humphrey et al. |
| 2003/0018064 A1 | 1/2003 | Anaclerio et al. |
| 2003/0171368 A1 | 9/2003 | Seitz et al. |
| 2003/0232053 A1 | 12/2003 | Harris et al. |
| 2004/0019035 A1 | 1/2004 | Patane |
| 2004/0019037 A1 | 1/2004 | Askew et al. |
| 2004/0024044 A1 | 2/2004 | Di Salle et al. |
| 2004/0030134 A1 | 2/2004 | McWilliams et al. |
| 2004/0038963 A1 | 2/2004 | Wang |
| 2004/0043988 A1 | 3/2004 | Khanna et al. |
| 2004/0043994 A1 | 3/2004 | Khanna et al. |
| 2004/0053968 A1 | 3/2004 | Hartman et al. |
| 2004/0077638 A1 | 4/2004 | Geneste et al. |
| 2004/0077684 A1 | 4/2004 | De Corte et al. |
| 2004/0082557 A1 | 4/2004 | Wajszczuk et al. |
| 2004/0092538 A1 | 5/2004 | Nagarajan et al. |
| 2004/0132733 A1 | 7/2004 | Su et al. |
| 2004/0142919 A1 | 7/2004 | Meissner et al. |
| 2004/0192670 A1 | 9/2004 | Hutchinson et al. |
| 2004/0198718 A1 | 10/2004 | Peyman et al. |
| 2004/0208823 A1 | 10/2004 | Carpenter, Jr. |
| 2004/0224986 A1 | 11/2004 | De Corte et al. |
| 2004/0234624 A1 | 11/2004 | McKearn et al. |
| 2004/0248907 A1 | 12/2004 | Peymann et al. |
| 2004/0249158 A1 | 12/2004 | Wells et al. |
| 2004/0259826 A1 | 12/2004 | Fraley et al. |
| 2005/0004189 A1 | 1/2005 | Wendt et al. |
| 2005/0004200 A1 | 1/2005 | Penning et al. |
| 2005/0020591 A1 | 1/2005 | Su et al. |
| 2005/0026917 A1 | 2/2005 | Kinney et al. |
| 2005/0043344 A1 | 2/2005 | Boys et al. |
| 2005/0154185 A1 | 7/2005 | Rajopadhye et al. |
| 2005/0178286 A1 | 8/2005 | Bohn, Jr. et al. |
| 2005/0209225 A1 | 9/2005 | Lu et al. |
| 2005/0250771 A1 | 11/2005 | Lu et al. |
| 2006/0030581 A1 | 2/2006 | DeBusi et al. |
| 2006/0052312 A1 | 3/2006 | Erhardt et al. |
| 2006/0099592 A1 | 5/2006 | Freskgard et al. |
| 2006/0121470 A1 | 6/2006 | Pedersen et al. |
| 2006/0149069 A1 | 7/2006 | Bishop et al. |
| 2006/0258661 A1 | 11/2006 | William P et al. |
| 2007/0219233 A1 | 9/2007 | Lu et al. |
| 2008/0045521 A1 | 2/2008 | Arnould et al. |
| 2008/0058348 A1 | 3/2008 | Lefrancois et al. |
| 2008/0064716 A1 | 3/2008 | Nagarajan |
| 2008/0090794 A1 | 4/2008 | Dinsmore et al. |
| 2008/0182842 A1 | 7/2008 | Arnould et al. |
| 2008/0221082 A1 | 9/2008 | Geneste et al. |
| 2008/0255183 A1 | 10/2008 | Arnould et al. |
| 2009/0062267 A1 | 3/2009 | Arnould et al. |
| 2009/0104116 A1 | 4/2009 | Zischinsky et al. |
| 2009/0118200 A1 | 5/2009 | Bergmann et al. |
| 2010/0226943 A1 | 9/2010 | Brennan et al. |
| 2012/0196856 A1 | 8/2012 | Breslin et al. |
| 2012/0252780 A1 | 10/2012 | Ng et al. |
| 2012/0289481 A1 | 11/2012 | O'Neil et al. |
| 2013/0064766 A1 | 3/2013 | Lee et al. |
| 2013/0309176 A1 | 11/2013 | Port et al. |
| 2014/0142085 A1 | 5/2014 | Bondy et al. |
| 2014/0221410 A1 | 8/2014 | Askew et al. |
| 2014/0234223 A1 | 8/2014 | Port et al. |
| 2014/0323468 A1 | 10/2014 | Balestra et al. |
| 2015/0274750 A1 | 10/2015 | Lan et al. |
| 2015/0320889 A1* | 11/2015 | Robic ............... A61K 49/1806 424/9.3 |
| 2016/0075698 A1 | 3/2016 | Askew et al. |
| 2016/0199520 A1 | 7/2016 | Fukunaga et al. |
| 2016/0280705 A1 | 9/2016 | Anderson et al. |
| 2018/0008583 A1 | 1/2018 | Fukunaga et al. |

FOREIGN PATENT DOCUMENTS

| | | |
|---|---|---|
| EP | 0416740 A2 | 3/1991 |
| EP | 0770622 A2 | 5/1997 |
| EP | 1230240 B1 | 7/2003 |
| EP | 1522313 A1 | 4/2005 |
| EP | 2583966 A2 | 4/2013 |
| EP | 3050878 A1 | 8/2016 |
| EP | 3202424 A1 | 8/2017 |
| JP | 2002-508355 A | 3/2002 |
| JP | 2002-532440 A | 10/2002 |
| JP | 2003-520271 A | 7/2003 |
| JP | 2004-533993 A | 11/2004 |
| JP | 2016-183151 A | 10/2016 |
| WO | WO 97/26250 A1 | 7/1997 |
| WO | WO 98/08840 A1 | 3/1998 |
| WO | WO 98/18461 A1 | 5/1998 |
| WO | WO 98/23608 A1 | 6/1998 |
| WO | WO 98/31359 A1 | 7/1998 |
| WO | WO 98/44797 A1 | 10/1998 |

(56) References Cited

FOREIGN PATENT DOCUMENTS

| | | |
|---|---|---|
| WO | WO 98/46220 A1 | 10/1998 |
| WO | WO 99/30709 A1 | 6/1999 |
| WO | WO 99/30713 A1 | 6/1999 |
| WO | WO 99/31061 A1 | 6/1999 |
| WO | WO 99/31099 A1 | 6/1999 |
| WO | WO 99/45927 A1 | 9/1999 |
| WO | WO 00/35488 A2 | 6/2000 |
| WO | WO 00/35492 A2 | 6/2000 |
| WO | WO 0035495 A2 | 6/2000 |
| WO | WO 00/61545 A1 | 10/2000 |
| WO | WO 01/53262 A1 | 7/2001 |
| WO | WO 01/98294 A2 | 12/2001 |
| WO | WO 02/14320 A2 | 2/2002 |
| WO | WO 02/18340 A1 | 3/2002 |
| WO | WO 02/28840 A1 | 4/2002 |
| WO | WO 02/053099 A2 | 7/2002 |
| WO | WO 02/060438 A1 | 8/2002 |
| WO | WO 02/072106 A2 | 9/2002 |
| WO | WO 03/032961 A2 | 4/2003 |
| WO | WO 03/072042 A2 | 9/2003 |
| WO | WO 2006/108040 A1 | 10/2006 |
| WO | WO 2010/114308 A1 | 10/2010 |
| WO | WO 2011/149250 A2 | 12/2011 |
| WO | WO 2012/084981 A1 | 6/2012 |
| WO | WO 2013/045333 A1 | 4/2013 |
| WO | WO 2013/048996 A1 | 4/2013 |
| WO | WO 2014/114724 A1 | 7/2014 |
| WO | WO 2015/046278 A1 | 4/2015 |
| WO | WO 2015/073575 A2 | 5/2015 |
| WO | WO 2016/125182 A1 | 8/2016 |
| WO | WO 2017/070793 A1 | 5/2017 |
| WO | WO 2018/047081 A1 | 3/2018 |
| WO | WO 2019/246445 A1 | 12/2019 |

OTHER PUBLICATIONS

Desgrosellier et al. "Integrins in cancer: biological implications and therapeutic opportunities", Nature Reviews Cancer, vol. 10, p. 9-23, Jan. 2010.

Haubner et al. "Noninvasive Imaging of Alpha-v beta-3 Integrin Expression Using 18F-labeled RGD-containing Glycopeptide and Positron Emission Tomography1", Cancer Res., vol. 61, p. 1781-1785, Mar. 1, 2001.

Higuchi et al. "Assessment of Alpha-v beta-3 integrin expression after myocardial infarction by positron emission tomography", Cardiovascular Research, vol. 78, p. 395-403, 2008.

International Search Report, issued in PCT/JP2014/075332, PCT/ISA/210, dated Dec. 9, 2014.

Janssen et al. "Tumor Targeting with Radiolabeled Alpha-v beta-3 Integrin Binding Peptides in a Nude Mouse Model", Cancer Res., vol. 62, p. 6146-6151, Nov. 1, 2002.

Kenny et al. "Phase I Trial of the Positron-Emitting Arg-Gly-Asp (RGD) Peptide Radioligand 18F-AH111585 in Breast Cancer Patients", J. Nucl. Med., vol. 49, p. 879-886, 2008.

Sun et al. "Temporal Response and Localization of Integrins β1 and β3 in the Heart After Myocardial Infarction", Circulation, vol. 107, p. 1046-1052, 2003.

Yoshimoto et al. "Alpha-v beta-3 Integrin-targeting radionuclide therapy and imaging with monomeric RGD peptide", Int. J. Cancer, vol. 123, p. 709-715, 2008.

Canadian Office Action, dated Mar. 9, 2018, for Canadian Application No. 2,961,935.

European Office Action for European Application No. 14849898.3, dated Apr. 18, 2019.

Adams et al., "Structure Activity Relationships of $\alpha_v$ Integrin Antagonists for Pulmonary Fibrosis by Variation in Aryl Substituents," ACS Medicinal Chemistry Letters, vol. 5, No. 11, 2014 (Published Sep. 19, 2014), pp. 1207-1212.

Aita el al., "NIR Fluorescent Ytterbium Compound for in vivo Fluorescence Molecular Imaging," Luminescence, vol. 25, No. 1, Jan.-Feb. 2010 (Published online May 29, 2009), pp. 19-24 (total 10 pages).

Atsumi et al., "Luminescence-based Colorimetric Discrimination of Single-Nucleotide Transversions by the Combined Use of the Derivatives of DOTA-conjugated Naphthyridine . . . ," Tetrahedron Letters, vol. 50, No. 19, May 13, 2009 (Available online Feb. 25, 2009), pp. 2177-2180 (total 16 pages).

Boys et al., "Convergent, Parallel Synthesis of a Series of β-substituted 1,2,4-oxadiazole Butanoic Acids as Potent and Selective $\alpha_v\beta_2$ Receptor Antagonists," Bioorganic & Medicinal Chemistry Letters, vol. 16, No. 4, 2006 (Available online Nov. 17, 2005), pp. 839-844.

Brashear et al., "Non-peptide $\alpha_v\beta_3$ Antagonists. Part 5: Identification of Potent RGD Mimetics Incorporating 2-Aryl β-Amino Acids as Aspartic Acid Replacements," Bioorganic & Medicinal Chemistry Letters, vol. 12, No. 23, 2002 (Dec. 2, 2002), pp. 3483-3486 (total 11 pages).

Breslin et al., "Nonpeptide $\alpha_v\beta_3$ Antagonists. Part 10: In vitro and in vivo Evaluation of a Potent 7-methyl substituted tetrahydro-[1,8]naphthyridine Derivative," Bioorganic & Medicinal Chemistry Letters vol. 14, No. 17, Sep. 6, 2004 (Available online Jul. 17, 2004), pp. 4515-4518 (total 19 pages).

Breslin et al., "Non-Peptide $\alpha_v\beta_3$ Antagonists. Part 6: Design and Synthesis of $\alpha_v\beta_3$ Antagonists Containing a Pyridone or Pyrazinone Central Scaffold," Bioorganic & Medicinal Chemistry Letters, vol. 13, No. 10, May 19, 2003, pp 1809-1812 (total 10 pages).

Coleman et al. "Non-Peptide $\alpha_v\beta_3$ Antagonists. Part 3: Identification of Potent RGD Mimetics Incorporating Novel β-Amino Acids as Aspartic Acid Replacements," Bioorganic & Medicinal Chemistry Letters, vol. 12, No. 1, 2002, pp. 31-34.

Coleman et al., "Nonpeptide $\alpha_v\beta_3$ Antagonists. Part 11: Discovery and Preclinical Evaluation of Potent $\alpha_v\beta_3$ Antagonists for the Prevention and Treatment of Osteoporosis," Journal of Medicinal Chemistry, vol. 47, No. 20, 2004, (Sep. 23, 2004), pp. 4829-4837 (total 18 pages).

Coleman et al., "Non-Peptide $\alpha_v\beta_3$ Antagonists. Part 4: Potent and Orally Bioavailable Chain-Shortened RGD Mimetics," Bioorganic & Medicinal Chemistry Letters, vol. 12, No. 17, 2002 (Sep. 2, 2002), pp. 2463-2465 (total 11 pages).

Cui et al., "In vitro and in vivo Metabolism of a Potent and Selective Integrin $\alpha_v\beta_3$ Antagonist in Rats, Dogs, and Monkeys," Drug Metabolism and Disposition, vol. 32, No. 8, 2004 (Aug. 2004), pp. 848-861 (total 18 pages).

De Corte et al., "Piperidine-containing β-arylpropionic Acids as Potent Antagonists of $\alpha_v\beta_3$/ $\alpha_v\beta_5$ Integrins," Bioorganic & Medicinal Chemistry Letters, vol. 14, No. 20, 2004 (Oct. 18, 2004), pp. 5227-5232 (total 20 pages).

Delouvrié et al., "Structure-activity Relationship of a Series of Non Peptidic RGD Integrin Antagonists Targeting $\alpha_5\beta_1$: Part 1," Bioorganic & Medicinal Chemistry Letters, vol. 22, No. 12, Jun. 15, 2012 (Apr. 21, 2012), pp. 4111-4116 (total 28 pages).

Duggan et al., "Nonpeptide $\alpha_v\beta_3$ Antagonists. 1. Transformation of a Potent, Integrin-Selective $\alpha$IIb$\beta_3$ Antagonist into a Potent $\alpha_v\beta_3$ Antagonist," Journal of Medicinal Chemistry, vol. 43, No. 20, 2000 (Oct. 5, 2000), pp. 3736-3745 (total 20 pages).

Eckert et al., "Design and Evaluation of a Novel Class-Directed 2D Fingerprint to Search for Structurally Diverse Active Compounds," Journal of Chemical Information and Modeling, vol. 46, No. 6, 2006, pp. 2515-2526 (19 pages).

Feuston et al., "Binding Model for Nonpeptide Antagonists of $\alpha_v\beta_3$ Integrin," Journal of Medicinal Chemistry, vol. 45, No. 26, 2002 (Dec. 19, 2002), pp. 5640-5648 (total 18 pages).

Feuston et al., Molecular Model of the $\alpha$IIb$\beta_3$ Integrin, Journal of Medicinal Chemistry, vol. 46, No. 25, 2003, (Dec. 4, 2003), pp. 5316-5325 (total 20 pages).

Ghosh et al., "1,2,3,4-Tetrahydroquinoline-containing $\alpha_v\beta_3$ Integrin Antagonists with Enhanced Oral Bioavailability," Bioorganic & Medicinal Chemistry Letters, vol. 14, No. 23, Dec. 6, 2004 (Available online Oct. 7, 2004), pp. 5937-5941 (total 20 pages).

Harris et al., "Design, Synthesis, and Evaluation of Radiolabeled Integrin $\alpha_v\beta_3$ Receptor Antagonists for Tumor Imaging and Radiotherapy," Cancer Biotherapy & Radiopharmaceuticals, vol. 18, No. 4, 2003, pp. 627-641.

Harris et al., "Radiolabeled Divalent Peptidomimetic Vitronectin Receptor Antagonists as Potential Tumor Radiotherapeutic and

(56) References Cited

OTHER PUBLICATIONS

Imaging Agents," Bioconjugate Chem, vol. 18, No. 4, Jul./Aug. 2007 (Published on Web Jun. 19, 2007), pp. 1266-1279 (total 21 pages).
Harris et al., "Structure-Activity Relationships of [111]In- and [99m]Tc-Labeled Quinolin-4-one Peptidomimetics as Ligands for the Vitronectin Receptor Potential Tumor . . . ," Bioconjugate Chem, vol. 17, No. 5, Sep./Oct. 2006 (Published on Web Aug. 8, 2006), pp. 1294-1313 (24 pages).
Hartner et al., "Methods for the Synthesis of 5,6,7,8-Tetrahydro-1,8-naphthyridine Fragments for $\alpha_v\beta_3$ Integrin Antagonists," Journal of Organic Chemistry, vol. 69, No. 25, Dec. 10, 2004, (Published on Web Nov. 13, 2004), pp. 8723-8730 (total 22 pages).
Hutchinson et al., Nonpeptide $\alpha_v\beta_3$ Antagonists. 8. In Vitro and in Vivo Evaluation of a Potent $\alpha_v\beta_3$ Antagonist for the Prevention and Treatment of Osteoporosis, Journal of Medicinal Chemistry, vol. 46, No. 22, Oct. 23, 2003 (Published on Web Sep. 27, 2003), pp. 4790-4798.
Kinney et al., "Suzuki-Miyaura Approach to JNJ-26076713, an Orally Active Tetrahydroquinoline-Containing $\alpha_v\beta_3/\alpha_v\beta_5$ Integrin Antagonist. Enantioselective Synthesis . . . ," Journal of Organic Chemistry, vol. 73, No. 6, 2008 (Mar. 21, 208), pp. 2302-2310 (total 25 pages).
Kling et al., "Design and Synthesis of 1,5- and 2,5-Substituted Tetrahydrobenzazepinones as Novel Potent and Selective Integrin $\alpha_v\beta_3$ Antagonists," Bioorganic & Medicinal Chemistry, vol. 11, No. 7, 2003 (Apr. 3, 2003), pp. 1319-1341 (total 29 pages).
Lawson et al., "Structure-Function Study of Quinazolinone-Based Vitronectin Receptor $\alpha_v\beta_3$ Antagonists: Computer-Assisted Analysis of Ligand-Receptor Interactions," Letters in Drug Design & Discovery, vol. 1, No. 1, 2004, pp. 14-18.
Leonard et al., "Non-peptidic $\alpha_v\beta_3$ Antagonists Containing Indol-1-yl Propionic Acids," Bioorganic & Medicinal Chemistry Letters, vol. 15, No. 10, May 16, 2005 (Available online Apr. 12, 2005), pp. 2679-2684 (total 23 pages).
Liu et al., Anaerobic [90]Y- and [177]Lu-Labeling of a DOTA-Conjugated Nonpeptide Vitronectin Receptor Antagonist, Bioconjugate Chem, vol. 14, No. 5, Sep./Oct. 2003 (Published on Web Jul. 11, 2003), pp. 1030-1037 (total 13 pages).
Luci et al., "A Concise Synthesis of an Indenopyrrolidine-based Dual $\alpha_v\beta_3/\alpha_v\beta_5$ Integrin Antagonist," Heterocycles, vol. 62, 2004 (Jan. 1, 2004), pp. 543-557 (total 36 pages).
Marchand-Brynaert et al., "From Medicinal Chemistry to Functionalized Biomaterials: Development of Graftable RGD-Peptitomimetics for Cell Adhesion and Cell Addressing," Materials Science Forum, vols. 638-642, Pt. 1, THERMEC 2009, 2009, pp. 612-617 (total 17 pages).
Meissner et al., "Nonpeptide $\alpha_v\beta_3$ Antagonists. Part 2: Constrained Glycyl Amides Derived from the RGD Tripeptide," Bioorganic & Medicinal Chemistry Letters, vol. 12, No. 1, Jan. 7, 2002, pp. 25-29 (total 10 pages).
Miller et al., "Phenylbutyrates as Potent, Orally Bioavailable Vitronectin Receptor (Integrin $\alpha_v\beta_3$) Antagonists," Bioorganic & Medicinal Chemistry Letters, vol. 13, No. 8, 2003 (Apr. 17, 2003), pp. 1483-1486 (total 9 pages).
Mousa et al., "Antiangiogenesis and Anticancer Efficacy of TA138, a Novel $\alpha_v\beta_3$ Antagonist," Anticancer Research, vol. 24, 2005 (Jan. 2005), pp. 197-206 (total 11 pages).
Nagarajan et al., "Discovery of +(2-{4-[2-(5,6,7,8-tetrahydro-1,8-naphthyridin-2-yl)ethoxy]phenyl)-cyclopropyl)acetic Acid as Potent and Selective $\alpha_v\beta_3$ Inhibitor: Design . . . ," Bioorganic & Medicinal Chemistry, vol. 15, No. 10, 2007 (Available online Mar. 13, 2007), pp. 3390-3412 (total 34 pages).
Nagarajan et al., "Discovery of Diphenylmethanepropionic and Dihydrostilbeneacetic Acids as Antagonists of the Integrin $\alpha_v\beta_3$," Chemical Biology & Drug Design, vol. 67, No. 2, 2006 (Feb. 2006), 177-181 (total 9 pages).
Onthank et al., "[90]Y and [111]In Complexes of a DOTA-Conjugated Integrin $\alpha_v\beta_3$ Receptor Antagonist: Different but Biologically Equivalent," Bioconjugate Chem. vol. 15, No. 2, Mar./Apr. 2004 (Published on Web Feb. 17, 2004), pp. 235-241 (total 12 pages).
Penning et al., "Synthesis of Pyrazoles and Isoxazoles as Potent $\alpha_v\beta_3$ Receptor Antagonists," Bioorganic & Medicinal Chemistry Letters, vol. 16, No. 12, Jun. 15, 2006 (Available online Apr. 18, 2006). 3156-3161 (total 24 pages).
Perkins et al., "Non-peptide $\alpha_v\beta_3$ Antagonists: Identification of Potent, Chain-shortened RGD Mimetics that Incorporate a Central Pyrrolidinone Constraint," Bioorganic & Medicinal Chemistry Letters, vol. 13, No. 24, 2003 (Dec. 15, 2003), pp. 4285-4288 (total 11 pages).
Perron-Sierra et al. "Substituted Benzocyloheptenes as Potent and Selective $\alpha_v$ Integrin Antagonists," Bioorganic & Medicinal Chemistry Letters, vol. 12, No. 22, 2002 (Nov. 18, 2002), pp. 3291-3296 (total 12 pages).
Pitts et al., "Isoxazolines as Potent Antagonists of the integrin $\alpha_v\beta_3$," Journal of Medicinal Chemistry, vol. 43, No. 1, Jan. 13, 2000 (Published on Web Dec. 10, 1999), pp. 27-40 (total 21 pages).
Pollard et al., "Asymmetric Reduction of α, β-Unsaturated Ketone to (R) Allylic Alcohol by Candida Chilensis," Biotechnology and Bioengineering, vol. 93, No. 4, Mar. 5, 2006, (Available online Jan. 4, 2006), pp. 674-686 (total 16 pages).
Prueksaritanont et al., "Differences in the Absorption, Metabolism and Biliary Excretion of a Diastereomeric Pair of $\alpha_v\beta_3$-Antagonists in Rat: Limited Role of P-glycoprotein," Xenobiotica, vol. 32, No. 3, 2002 (Mar. 2002), pp. 207-220 (total 17 pages).
Prueksaritanont et al., "Disposition of a Novel and Potent $\alpha_v\beta_3$ Antagonist in Animals, and Extrapolation to Man," Xenobiotica, vol. 34, No. 1, Jan. 2004, pp. 103-115 (total 16 pages).
Prueksaritanont et al., "Renal Elimination of a Novel and Potent $\alpha_v\beta_3$ Integrin Antagonist in Animals," Xenobiolica, vol. 34, No. 11/12, Nov./Dec. 2004, pp. 1059-1074 (total 19 pages).
Raboisson et al., "Identification of Novel Short Chain 4-substituted Indoles as Potent $\alpha_v\beta_3$ Antagonist Using Structure-based Drug Design," European Journal of Medicinal Chemistry, vol. 42, No. 3, Mar. 2007 (Available online Dec. 20, 2006), pp. 334-343 (total 18 pages).
Raboisson et al., "Novel Potent and Selective $\alpha_v\beta_3/\alpha_v\beta_5$ Integrin Dual Antagonists with Reduced Binding Affinity for Human Serum Albumin," European Journal of Medicinal Chemistry, vol. 41, No. 7, Jul. 2006 (Available online May 11, 2006), pp. 847-861 (total 22 pages).
Rerat et al., "$\alpha_v\beta_3$ Integrin-Targeting Arg-Gly-Asp (RGD) Peptidomimetics Containing Oligoethylene Glycol (OEG) Spacers," Journal of Medicinal Chemistry, vol. 52, No. 22, 2009 (Nov. 26, 2009), pp. 7029-7043 (total 15 pages).
Santulli et al., "Studies with an Orally Bioavailable $\alpha_v$ Integrin Antagonist in Animal Models of Ocular Vasculopathy: Retinal Neovascularization in Mice and Retinal Vascular . . . ," Journal of Pharmacology and Experimental Therapeutics, vol. 324, No. 3, 2008 (Mar. 2008), pp. 894-901 (total 14 pages).
Wang et al., "Non-peptide $\alpha_v\beta_3$ Antagonists. Part 7: 3-Substituted tetrahydro-[1,8]naphthyridineDerivatives," Bioorganic & Medicinal Chemistry Letters, vol. 14, No. 4, 2004 (Feb. 23, 2004), pp. 1049-1052 (total 20 pages).
Wendt et al., "Synthesis of 2,5-thiazole Butanoic Acids as Potent and Selective $\alpha_v\beta_3$ Integrin Receptor Antagonists with Improved Oral Pharmacokinetic Properties," Bioorganic & Medicinal Chemistry Letters, vol. 16, No. 4, Feb. 15, 2006 (Available online Nov. 21, 2005), pp. 845-849 (total 26 pages).
Whitman et al., "Nonpeptide $\alpha_v\beta_3$ Antagonists. Part 9: Improved Pharmacokinetic Profile through the Use of an Aliphatic, des-amide Backbone," Bioorganic & Medicinal Chemistry Letters, vol. 14, No. 17, 2004, pp. 4411-4415.
Yasuda et al., "An Efficient Synthesis of an $\alpha_v\beta_3$ Antagonist," Journal of Organic Chemistry, vol. 69, No. 6, 2004 (Mar. 19, 2004), pp. 1959-1966 (23 pages).
Yoshimoto et al., "Fluorescence-based Affinity Labeling of Nucleobase by Hydrogen-bond Forming Metal Complex," Nucleic Acids Symposium Series, vol. 51, 2007, pp. 303-304.

(56) References Cited

OTHER PUBLICATIONS

Zartman et al., "Nonpeptide $\alpha_v\beta_3$ Antagonists: Identification of Potent, Chain-shortened 7-oxo RGD Mimetics," Bioorganic & Medicinal Chemistry Letters, vol. 15, No. 6, 2005 (Mar. 15, 2005), pp. 1647-1650.
Zhang et al. "High-throughput Sample Preparation Procedures for the Quantitation of a New Bone Integrin $\alpha_v\beta_3$ Antagonist in Human Plasma and Urine Using Liquid . . . ," Journal of Chromatography B, vol. 806, No. 2, Jul. 5, 2004 (Available online Apr. 27, 2004), pp. 167-175 (total 13 pages).
Zhang et al., "Investigation of High-Throughput Ultrafiltration for the Determination of an Unbound Compound in Human Plasma Using Liquid Chromatography and Tandem . . . ," Journal of Chromatography B, vol. 843, No. 1, Oct. 20, 2006 (Available online Jul. 3, 2006), pp. 47-56 (total 15 pages).
Extended European Search Report for corresponding European Application No. 21187649.5, dated Aug. 30, 2021.
2 Singaporean Supplementary Search Reports for corresponding Singaporean Application No. 11201707899S, dated Jan. 16, 2020.
Canadian Office Action for Application No. 2,980,268, dated Jul. 15, 2019.
Australian Examination Report No. 1 for Standard Patent Application, dated Oct. 22, 2021, for corresponding Australian Application No. 2020244578.
Australian Examination Report No. 1 for Standard Patent Application, dated Oct. 22, 2021, for corresponding Australian Application No. 2020244580.
Australian Examination Report No. 2, dated Sep. 26, 2019, for corresponding Australian Application No. 2016237099.
Australian Office Action, dated Oct. 29, 2018, for corresponding Australian Application No. 2016237099.
Brazilian Office Action and Search Report, dated Oct. 28, 2020, for corresponding Brazilian Application No. BR1120170204843, with an English translation.
Colombian Office Action and Search Report, dated Nov. 19, 2020, for corresponding Colombian Application No. NC2020/0009028, with an English translation.
Colombian Office Action for Colombian Application No. NC2017/0010806, dated Apr. 4, 2019, with English translation.
Colombian Office Action, dated Aug. 15, 2018, for Colombian Application No. NC2017/0010806, with an English translation.
Columbian Office Action dated Jul. 14, 2021, issued in corresponding Columbian Patent Application No. NC2020/0009028, wiih an English translation.
European Communication pursuant to Article 94(3) EPC for European Application No. 16768957.9, dated Nov. 8, 2019.
European Office Action dated Feb. 22, 2019, for corresponding European Application No. 16768957.9.
Extended European Search Report for corresponding European Application No. 16768957.9, dated Feb. 7, 2018.
Extended European Search Report for corresponding European Application No. 21168086.3, dated May 18, 2021.
Indian Office Action for corresponding Indian Application No. 201747033642, dated Feb. 26, 2019, with English translation.
Indian Office Action for corresponding Indian Application No. 201948033299, dated Mar. 31, 2021, with English translation.
International Preliminary Report on Patentability and Written Opinion of the International Searching Authority (Forms PCT/IB/373, PCT/IB/326 and PCT/ISA/237), dated Oct. 5, 2017, for International Application No. PCT/JP2016/059729, with an English translation of the Written Opinion.
International Search Report dated Jun. 28, 2016, for corresponding International Application No. PCT/JP2016/059729, with English translation.
Israeli Office Action dated Jun. 10, 2020 for corresponding Israeli Application No. 254532, with an English translation.
Israeli Office Action, dated Jan. 5, 2020, for corresponding Israeli Application No. 254532, with an English translation.
Japanese Office Action for corresponding Japanese Application No. 2017-508476, dated Jun. 5, 2018, with English translation.
Korean Office Action dated Nov. 1, 2018, for corresponding Korean Application No. 10-2017-7026236, with English translation.
Non-Final Office Action dated Dec. 26, 2019, for U.S. Appl. No. 15/712,815.
Non-Final Office Action dated Jan. 4, 2019, for U.S. Appl. No. 15/712,815.
Notice of Allowance dated Jul. 1, 2020, for U.S. Appl. No. 15/712,815.
Notice of Allowance dated Jul. 30, 2019, for U.S. Appl. No. 15/712,815.
Partial Supplementary European Search Report for corresponding European Application No. 16768957.9, dated Dec. 18, 2017.
Restriction Requirement dated Jun. 20, 2018, for U.S. Appl. No. 15/712,815.
Russian Office Action and Search Report for corresponding Russian Application No. 2017133107, dated Jul. 13, 2018, with English translation.
Singaporean Office Action and Search Report for corresponding Singaporean Application No. 11201707899S, dated Oct. 23, 2018.
Harris et al., "Radiolabeled Indazole-Based $\alpha v\beta 3$ Antagonists as Potential Tumor Imaging Agents", J. Labelled Cpd. Radiopharm. 44, Suppl. 1 (2001), Symposium Abstracts, S60-S62.

* cited by examiner

[Figure 1]
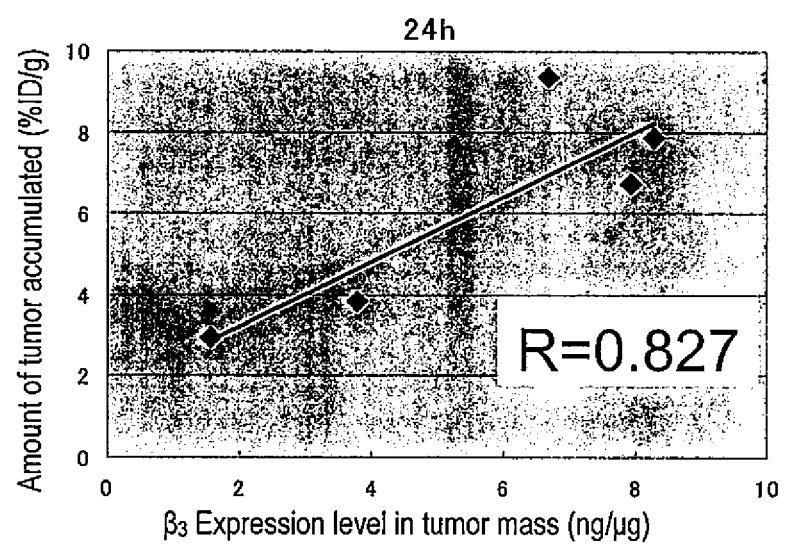

[Figure 2]
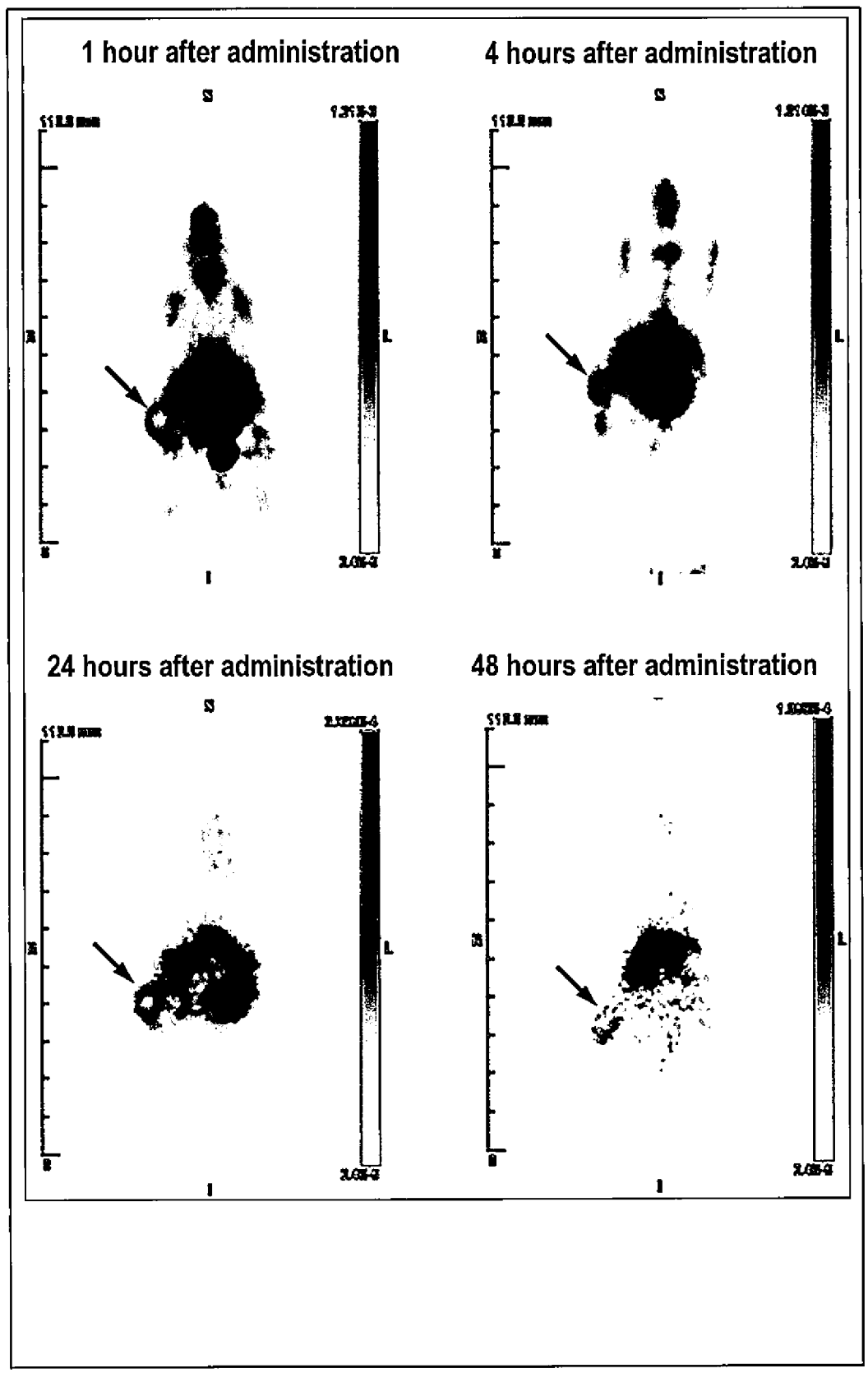

[Figure 3]
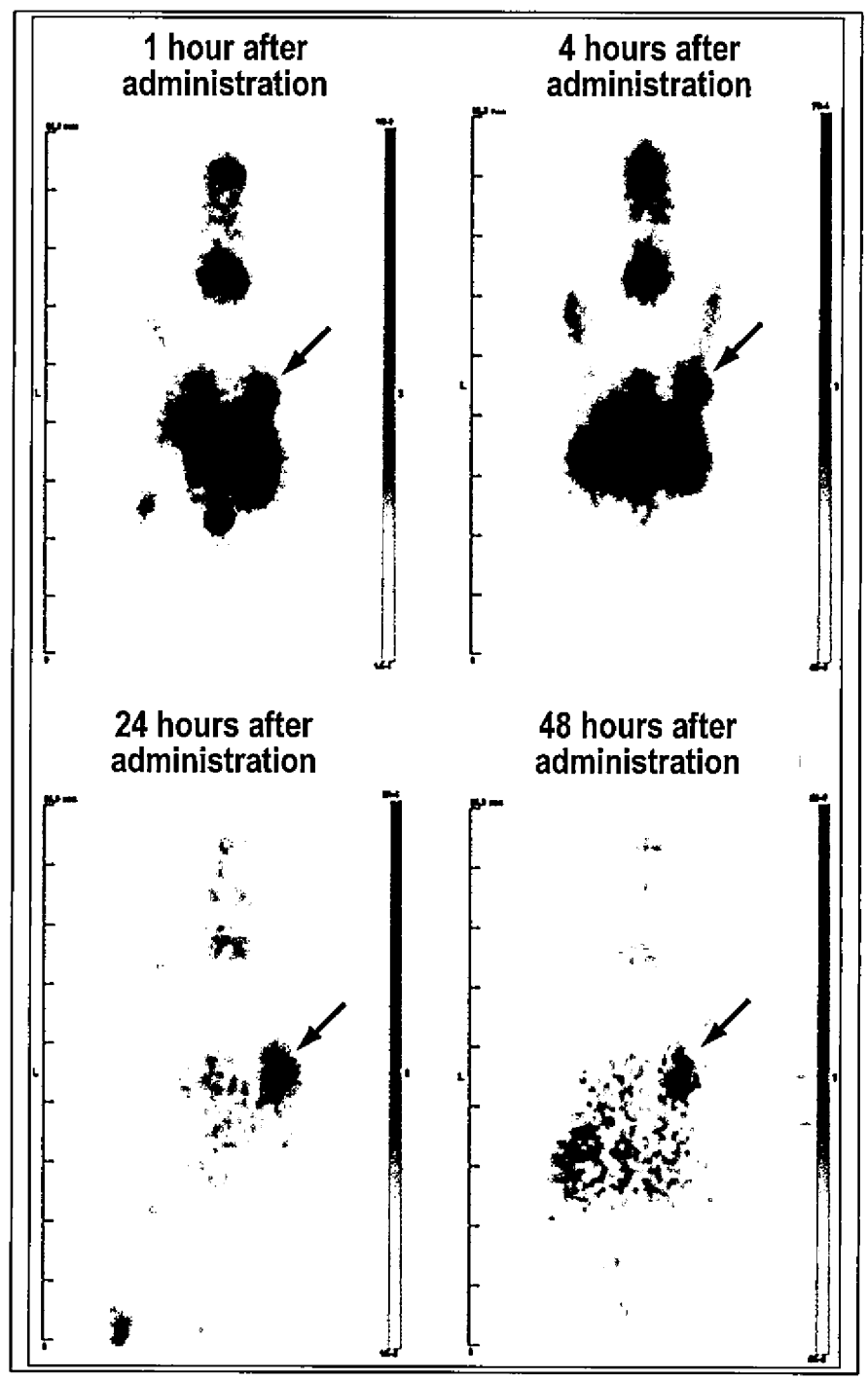

[Figure 4]
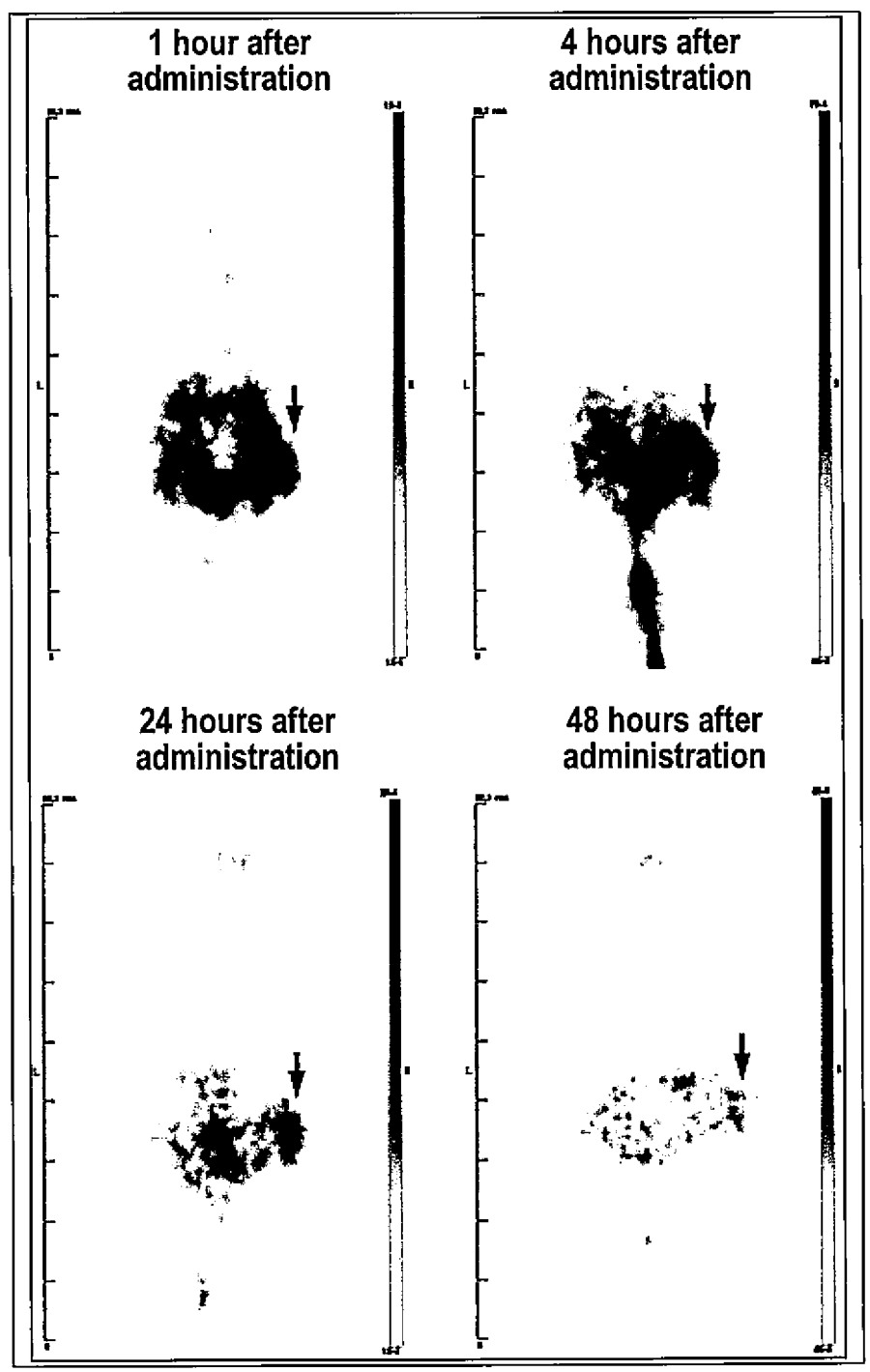

[Figure 5]
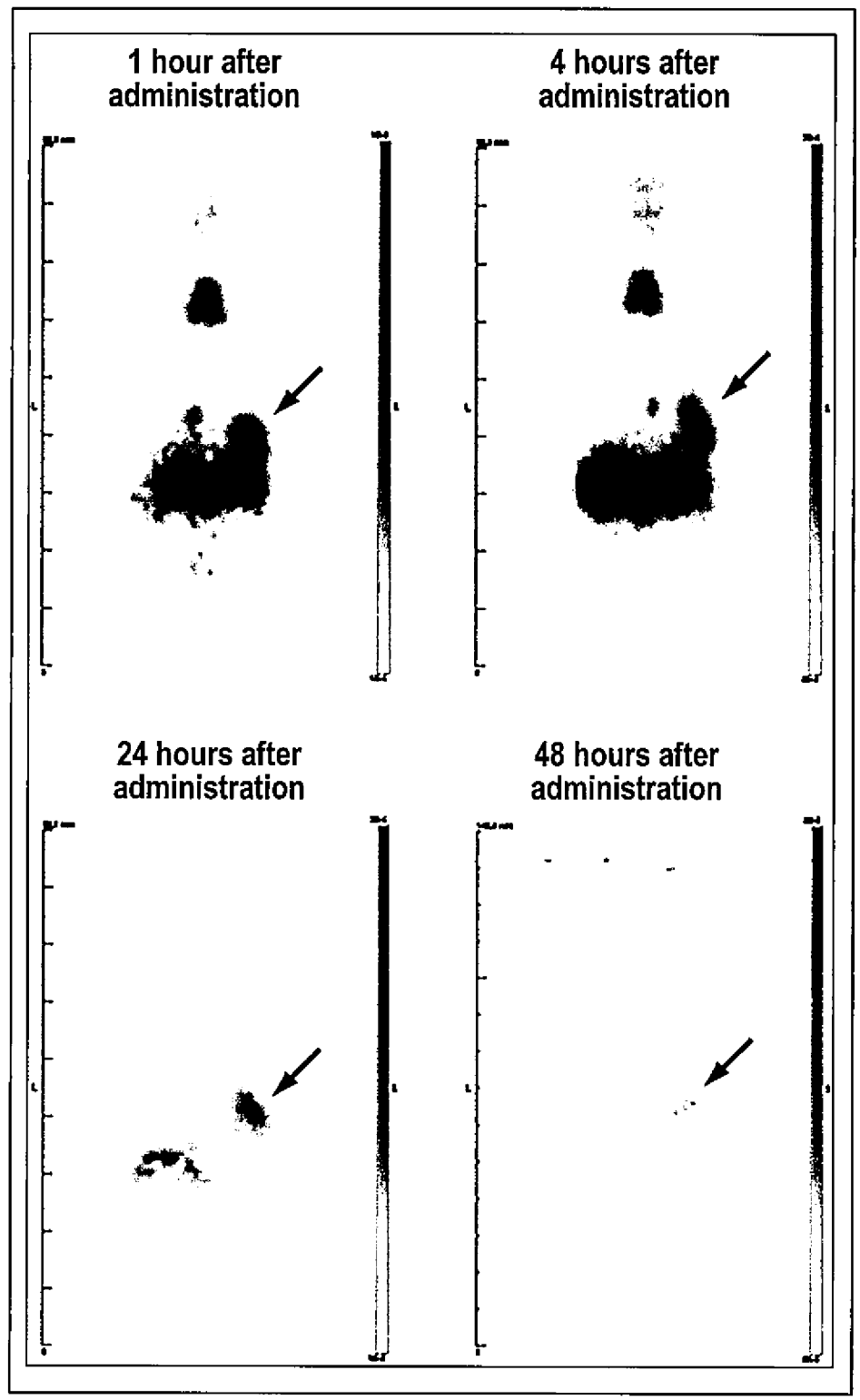

[Figure 6]
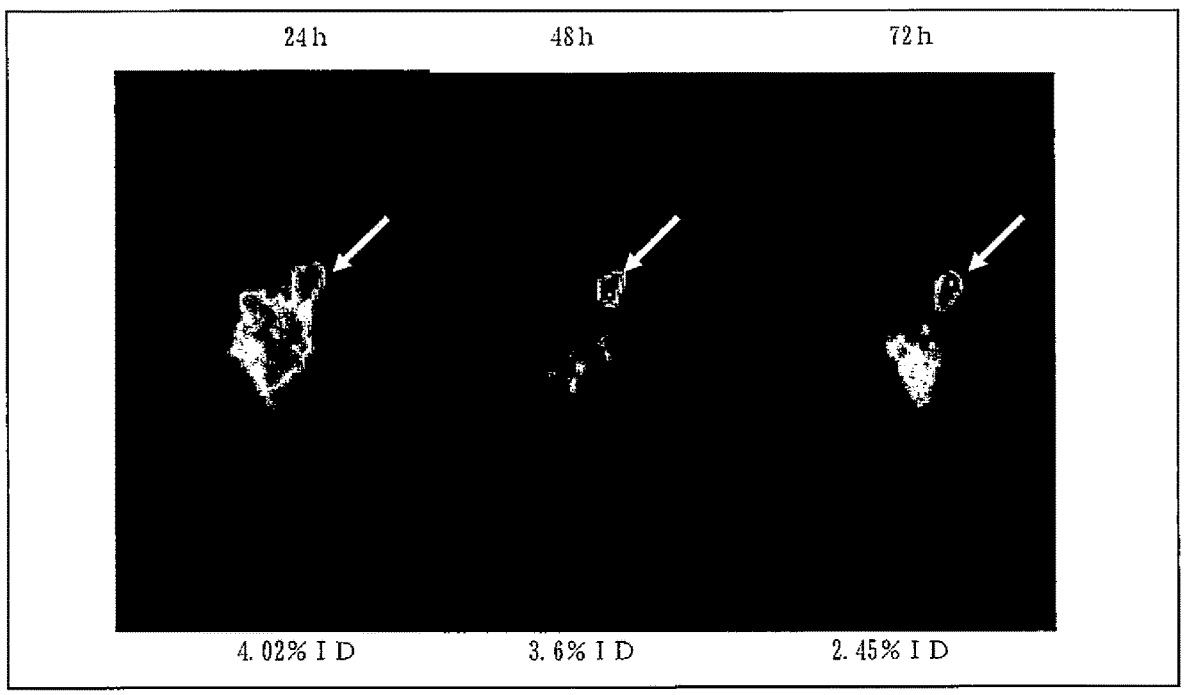

[Figure 7]
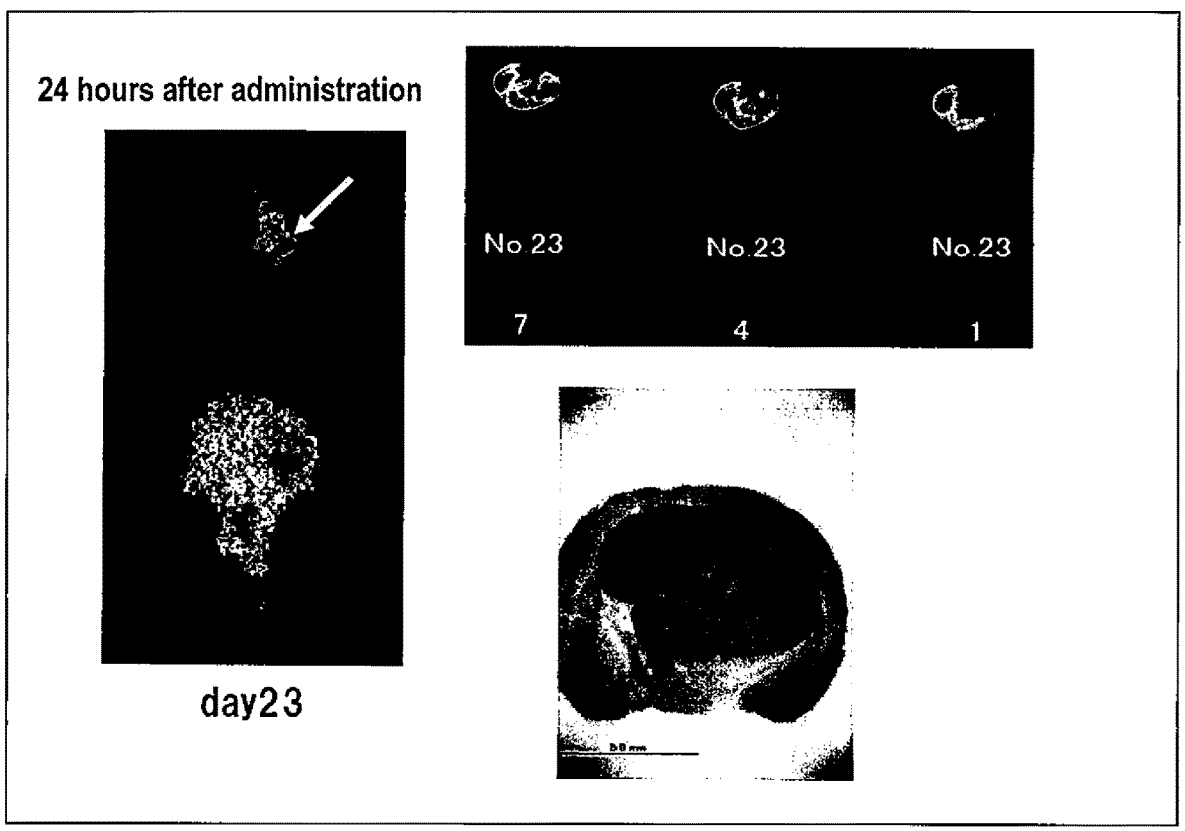

[Figure 8]
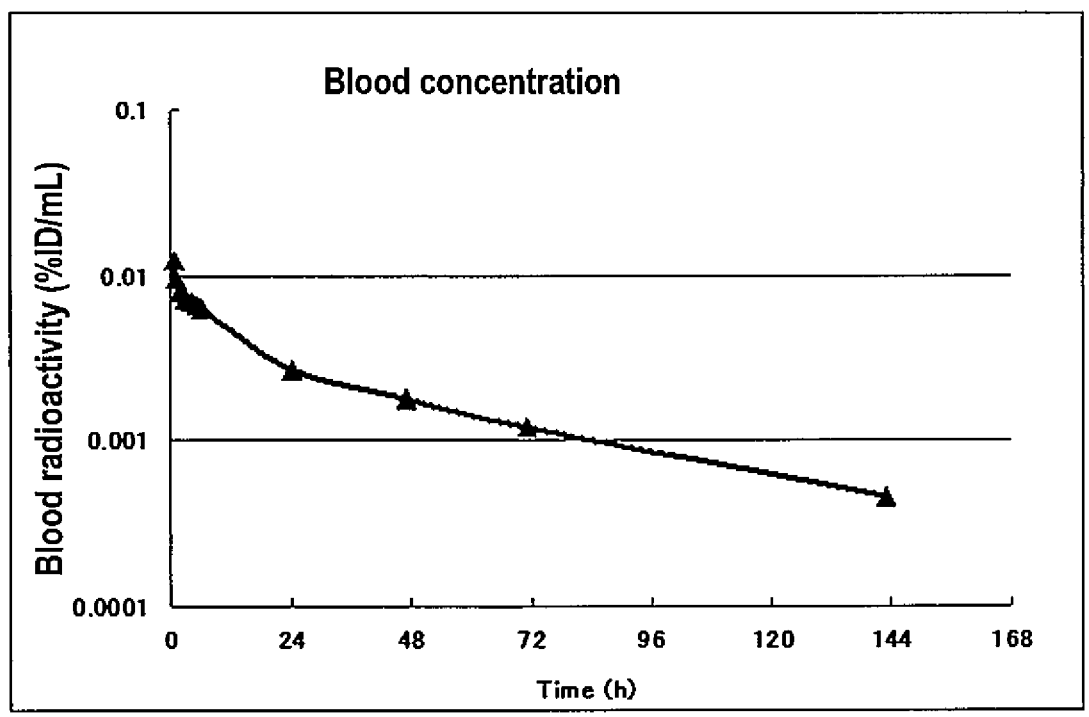

[Figure 9]
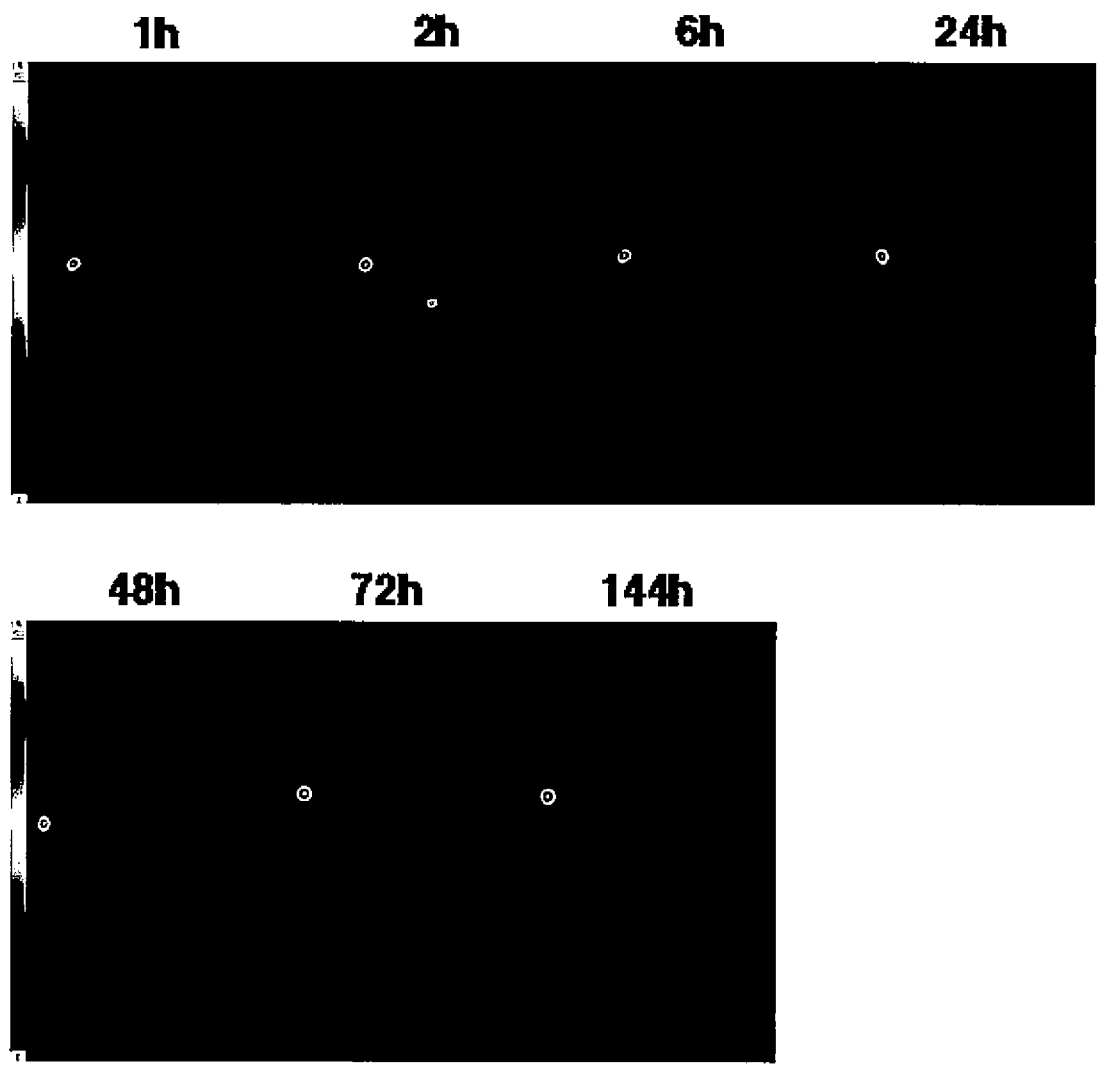

NITROGEN-CONTAINING COMPOUND OR SALT THEREOF, OR METAL COMPLEX THEREOF

CROSS REFERENCE TO RELATED APPLICATIONS

This application is a Continuation of PCT International Application No. PCT/JP2014/075332 filed on Sep. 24, 2014, which claims priority under 35 U.S.C. § 119(a) to Japanese Patent Application No. 2013-196712 filed on Sep. 24, 2013, all of which are hereby expressly incorporated by reference into the present application.

TECHNICAL FIELD

The present invention relates to a novel nitrogen-containing compound or a salt thereof, or a complex of the compound or the salt with a metal.

BACKGROUND ART

Integrins constitute a family of heterodimeric glycoprotein complexes composed of α and β subunits and are one kind of cell adhesion receptor involved mainly in cell adhesion to extracellular matrix and signal transduction from extracellular matrix. Among the integrins, integrins $\alpha_v\beta_3$ and $\alpha_v\beta_5$, which are vitronectin receptors, are known to be low expressed on epithelial cells or mature endothelial cells, but overexpressed on various tumor cells or neovessels. The overexpression of the integrins $\alpha_v\beta_3$ and $\alpha_v\beta_5$ is reportedly involved in the exacerbation of cancers, including infiltration, metastasis, accompanied by tumor angiogenesis, and highly related to the degree of malignancy (Non Patent Literature 1). For example, head and neck cancer, colorectal cancer, breast cancer, small-cell lung cancer, non-small cell lung cancer, glioblastoma, malignant melanoma, pancreatic cancer, and prostate cancer have been found as the cancers in which these integrins are overexpressed (Non Patent Literature 2). As for further integrin-related diseases, integrin overexpression on vascular endothelial cells during angiogenesis after ischemia has been revealed in ischemic diseases such as ischemic heart disease or peripheral vascular disease (Non Patent Literature 3).

The relationship between these diseases and integrin expression is interesting as a target for drugs. Treatment or imaging of disease site using low-molecular compounds (Patent Literatures 1 to 4) or compounds labeled with a radioisotope (Patent Literatures 5 to 7) has been reported.

For example, Non Patent Literatures 4 and 5 have been reported as attempts of imaging using a peptide ligand having an Arg-Gly-Asp (RGD) sequence, and Patent Literature 5 has been reported as an attempt using a non-peptide low molecule. Also, the visualization of human tumors using compounds carrying a positron nuclide [18]F (Non Patent Literatures 6 and 7) or the like has been attempted (Non Patent Literatures 8 and 9).

CITATION LIST

Patent Literature

Patent Literature 1: U.S. Pat. No. 6,001,961
Patent Literature 2: U.S. Pat. No. 6,130,231
Patent Literature 3: U.S. Patent Application Publication No. 2002/169200
Patent Literature 4: U.S. Patent Application Publication No. 2001/53853
Patent Literature 5: JP-A-2002-532440
Patent Literature 6: International Publication No. WO 2013/048996
Patent Literature 7: International Publication No. WO 2011/149250

Non Patent Literature

Non Patent Literature 1: Nature Reviews Cancer, Vol. 10, p. 9-23, 2010
Non Patent Literature 2: Clin. Cancer Res., Vol. 12, p. 3942-3949, 2006
Non Patent Literature 3: Circulation, Vol. 107, p. 1046-1052, 2003
Non Patent Literature 4: Cancer Res., Vol. 61, p. 1781-1785, 2001
Non Patent Literature 5: Cardiovascular Research, Vol. 78, p. 395-403, 2008
Non Patent Literature 6: Clin. Cancer Res., Vol. 13, p. 6610-6616, 2007
Non Patent Literature 7: J. Nucl. Med., Vol. 49, p. 879-886, 2008
Non Patent Literature 8: Cancer Res., Vol. 62, p. 6146-6151, 2002
Non Patent Literature 9: Int. J. Cancer, Vol. 123, p. 709-715, 2008

SUMMARY OF THE INVENTION

Technical Problem

The conventional peptide having an RGD sequence is not sufficiently effective when applied to imaging or treatment, because of its low tumor accumulation and persistence as imaging and therapeutic drugs.

In terms of imaging, slow blood clearance may require about several days to 1 week for taking images with decreased blood values as a background. This is a serious disadvantage in consideration of the short half-life of a radioactive metal suitable for imaging. In terms of treatment using a therapeutic nuclide, long-term blood circulation means the dominant irradiation of the bone marrow and tends to cause severe bone marrow toxicity.

Thus, an object of the present invention is to provide an integrin-binding compound which has high accumulation and persistence in neovessels and tumors involving an integrin and exhibits fast blood clearance, and an agent for diagnosis or treatment, etc., comprising the compound as an active ingredient.

Solution to Problem

Under such circumstances, the present inventors have conducted diligent studies and consequently found that a complex of a compound represented by the following formula (1) or a salt thereof with a metal is useful as an agent for of diagnosis or treatment, etc., of a disease involving an integrin. The present inventors have also found that the compound represented by the following formula (1) or the salt thereof is useful as an intermediate for producing such a complex.

The present inventors have further found that a compound represented by the formula (S1a) shown below or a salt thereof is useful as an intermediate for producing the compound represented by the formula (1) or the salt thereof, or the complex of the compound or the salt with a metal. On the basis of these findings, the present invention has been completed.

Specifically, the present invention provides the following [1] to [26]: [1] A compound represented by the formula (1) or a salt thereof, or a complex of the compound or the salt with a metal:

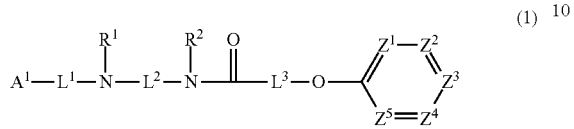

(1)

wherein $A^1$ represents a chelating agent; $R^1$ represents a hydrogen atom, an optionally substituted $C_{1-6}$ alkyl group, or an amino-protecting group; $R^2$ represents a hydrogen atom, an optionally substituted $C_{1-6}$ alkyl group, or an amino-protecting group; $Z^1$, $Z^2$, $Z^3$, $Z^4$, and $Z^5$ are the same or different and each represent a nitrogen atom or $CR^3$ wherein $R^3$ represents a hydrogen atom, a halogen atom, an optionally substituted $C_{1-6}$ alkyl group, an optionally substituted $C_{1-6}$ alkoxy group, or a group represented by the formula (2):

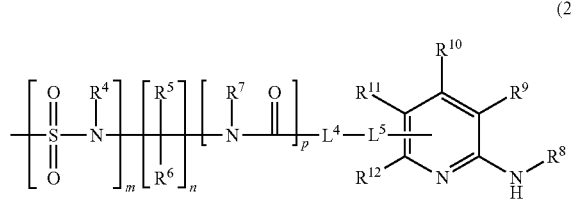

(2)

wherein $R^4$ represents a hydrogen atom, an optionally substituted $C_{1-6}$ alkyl group, or an amino-protecting group; n number of $R^5$ and n number of $R^6$ are the same or different and each represent a hydrogen atom, a halogen atom, an optionally substituted $C_{1-6}$ alkyl group, or an optionally protected carboxyl group; $R^7$ represents a hydrogen atom, an optionally substituted $C_{1-6}$ alkyl group, or an amino-protecting group; $R^8$ represents a hydrogen atom, an optionally substituted $C_{1-6}$ alkyl group, or a bond with $L^5$; $R^9$, $R^{10}$, $R^{11}$, and $R^{12}$ are the same or different and each represent a hydrogen atom, a halogen atom, an optionally protected amino group, an optionally substituted $C_{1-6}$ alkyl group, an optionally substituted $C_{1-6}$ alkylamino group, an optionally substituted di($C_{1-6}$ alkyl)amino group, or a bond with $L^5$; or $R^8$ and $R^9$ together represent an optionally substituted $C_{1-6}$ alkylene group, provided that any one of $R^8$, $R^9$, $R^{10}$, $R^{11}$, and $R^{12}$ represents a bond with $L^3$, and the other 4 moieties do not represent a bond with $L^5$; $L^4$ represents an optionally substituted divalent aromatic hydrocarbon group, an optionally substituted divalent heterocyclic group, or a bond; $L^5$ represents an optionally substituted $C_{1-6}$ alkylene group, an optionally substituted —O—$C_{1-6}$ alkylene group wherein the left bond binds to $L^4$, or an optionally substituted —NH—$C_{1-6}$ alkylene group wherein the left bond binds to $L^4$; m represents 0 or 1; n represents an integer of 1 to 3; and p represents 0 or 1, provided that when $R^8$ bonds to $L^5$, $L^4$ represents an optionally substituted divalent aromatic hydrocarbon group, provided that at least one of $Z^1$, $Z^2$, $Z^3$, $Z^4$, and $Z^5$ represents $CR^{3a}$ wherein $R^{3a}$ represents a group represented by the formula (2):

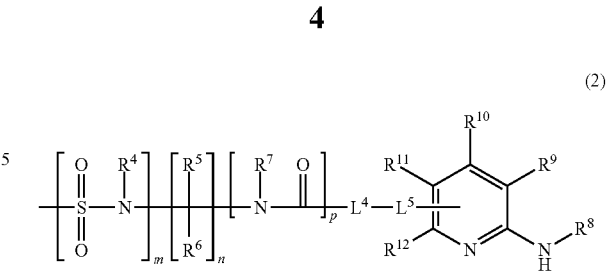

(2)

wherein $R^4$, $R^5$, $R^6$, $R^7$, $R^8$, $R^9$, $R^{10}$, $R^{11}$, $R^{12}$, $L^4$, $L^5$, m, n, and p are as defined above;
$L^2$ represents an optionally substituted $C_{1-6}$ alkylene group;
$L^3$ represents an optionally substituted $C_{1-6}$ alkylene group;
and $L^1$ represents a group represented by the formula (3):

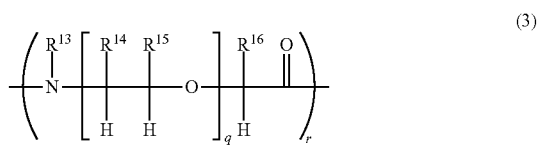

(3)

wherein r number of $R^{13}$ are the same or different and each represent a hydrogen atom, an optionally substituted $C_{1-6}$ alkyl group, or an amino-protecting group; q×r number of $R^{14}$ and q×r number of $R^{15}$ are the same or different and each represent a hydrogen atom or an optionally substituted $C_{1-6}$ alkyl group; r number of $R^{16}$ are the same or different and each represent a hydrogen atom, an optionally substituted $C_{1-6}$ alkyl group, or a group represented by the formula (4):

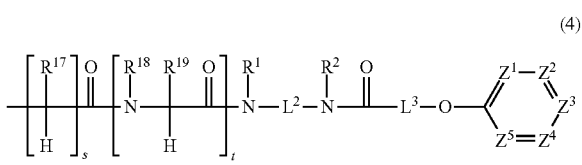

(4)

wherein s number of $R^{17}$ are the same or different and each represent a hydrogen atom or an optionally substituted $C_{1-6}$ alkyl group; t number of $R^{18}$ are the same or different and each represent a hydrogen atom, an optionally substituted $C_{1-6}$ alkyl group, or an amino-protecting group; t number of $R^{19}$ are the same or different and each represent a hydrogen atom or an optionally substituted $C_{1-6}$ alkyl group; s represents an integer of 1 to 3; t represents an integer of 0 to 3; and $R^1$, $R^2$, $Z^1$, $Z^2$, $Z^3$, $Z^4$, $Z^5$, $L^2$, and $L^3$ are as defined above; q represents an integer of 0 to 3; and r represents an integer of 0 to 3. [2] The compound or the salt thereof, or the complex of the compound or the salt with a metal according to [1], wherein $Z^1$, $Z^2$, $Z^4$, and $Z^5$ are the same or different and each represent $CR^{3b}$ wherein $R^{3b}$ represents a hydrogen atom, a halogen atom, an optionally substituted $C_{1-6}$ alkyl group, or an optionally substituted $C_{1-6}$ alkoxy group; and $Z^3$ represents $CR^{3c}$ wherein $R^{3c}$ represents a group represented by the formula (2a):

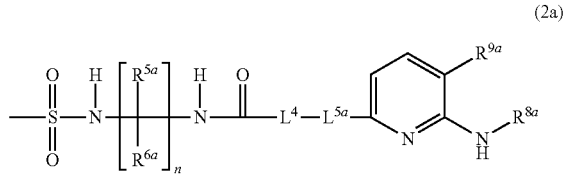

(2a)

wherein n number of $R^{5a}$ and n number of $R^{6a}$ are the same or different and each represent a hydrogen atom, an optionally substituted $C_{1-6}$ alkyl group, or an optionally protected carboxyl group; $R^{8a}$ represents a hydrogen atom or an optionally substituted $C_{1-6}$ alkyl group; $R^{9a}$ represents a hydrogen atom; or $R^{8a}$ and $R^{9a}$ together represent an optionally substituted $C_{1-6}$ alkylene group; $L^{5a}$ represents an optionally substituted $C_{1-6}$ alkylene group; and $L^4$ and n are as defined above.

[3] The compound or the salt thereof, or the complex of the compound or the salt with a metal according to [2], wherein $R^{3c}$ is a group represented by the formula (2b):

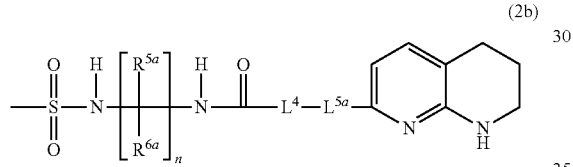

(2b)

wherein $R^{5a}$, $R^{6a}$, $L^4$, $L^{5a}$, and n are as defined above. [4] The compound or a salt thereof, or a complex of the compound or the salt with a metal according to any one of [1] to [3], wherein $A^1$ is a group having a polyazamacrocyclic structure, a group having a polyaminopolycarboxylic acid structure, or a group having a polyaminopolyphosphonic acid structure.

[5] The compound or the salt thereof, or the complex of the compound or the salt with a metal according to any one of [1] to [4], wherein $A^1$ is a group represented by the formula (5), (6), (7), (8), (9), (10), (11), or (12):

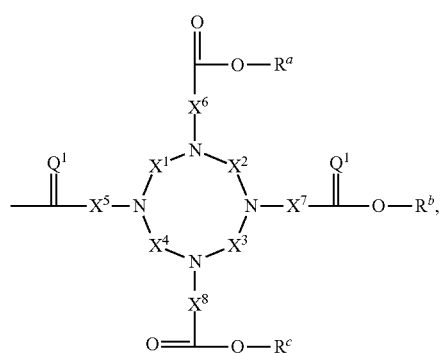

(5)

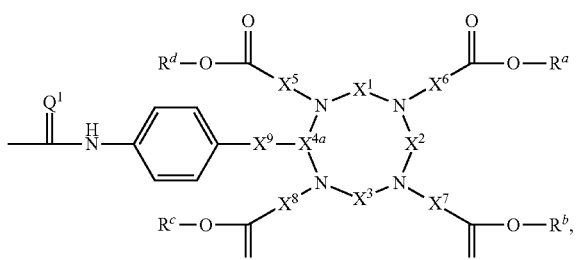

(6)

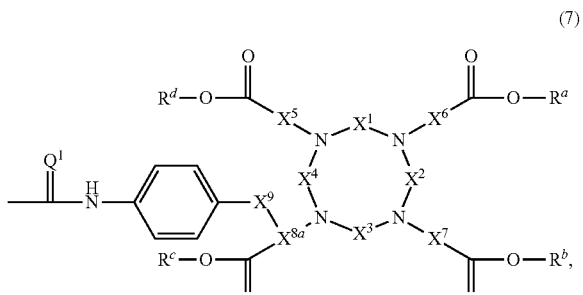

(7)

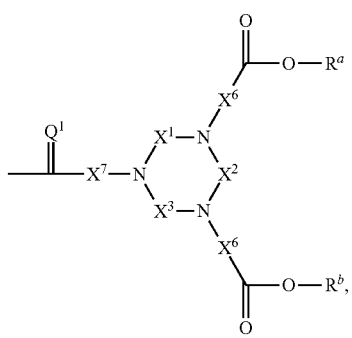

(8)

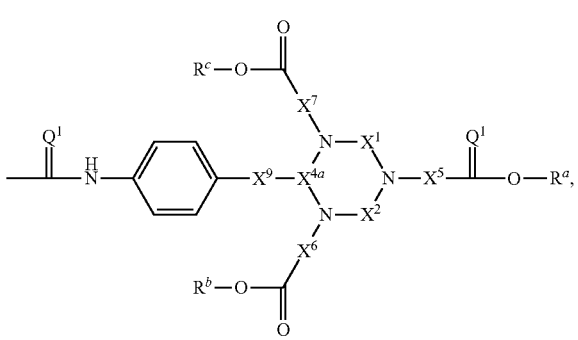

(9)

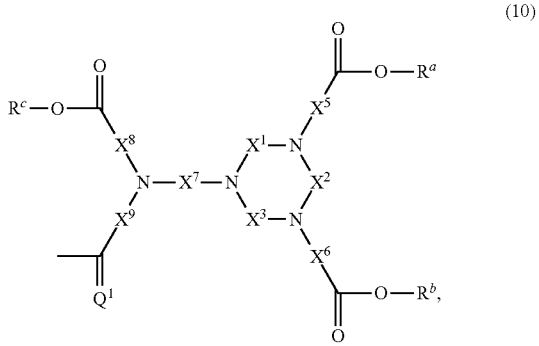

(10)

(11)

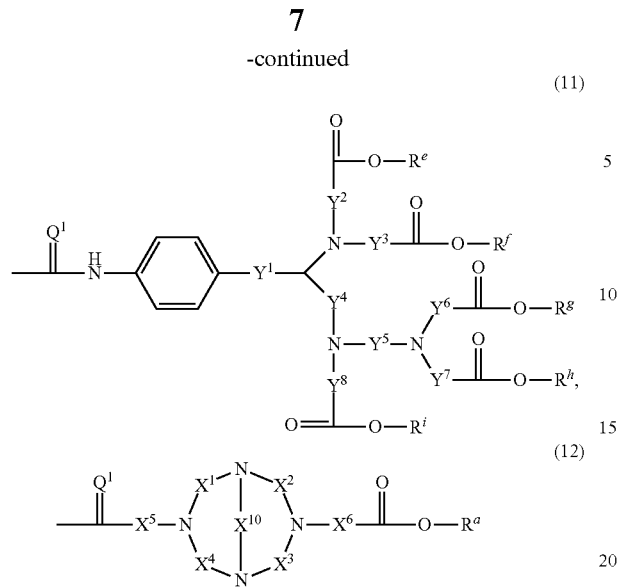

(12)

wherein $R^a$, $R^b$, $R^c$, $R^d$, $R^e$, $R^f$, $R^g$, $R^h$, and $R^i$ are the same or different and each represent a hydrogen atom or a carboxyl-protecting group; $X^1$, $X^2$, $X^3$, $X^4$, $X^5$, $X^6$, $X^7$, $X^8$, $X^9$, $Y^1$, $Y^2$, $Y^3$, $Y^4$, $Y^5$, $Y^6$, $Y^7$, and $Y^8$ are the same or different and each represent an optionally substituted $C_{1-6}$ alkylene group or an optionally substituted $C_{3-8}$ cycloalkylene group; $X^{10}$ represents an optionally substituted $C_{1-6}$ alkylene group; $X^{4a}$ and $X^{8a}$ are the same or different and each represent an optionally substituted $C_{1-6}$ alkanetriyl group: and $Q^1$ represents an oxygen atom or a sulfur atom.

[6] The compound or the salt thereof, or the complex of the compound or the salt with a metal according to any one of [1] to [5], wherein A is a group represented by the formula (5a), (6a), (7a), (8a), (8b), (8c), (9a), (10a), (10b), (11a), (11b), (11c), or (12a):

(5a)

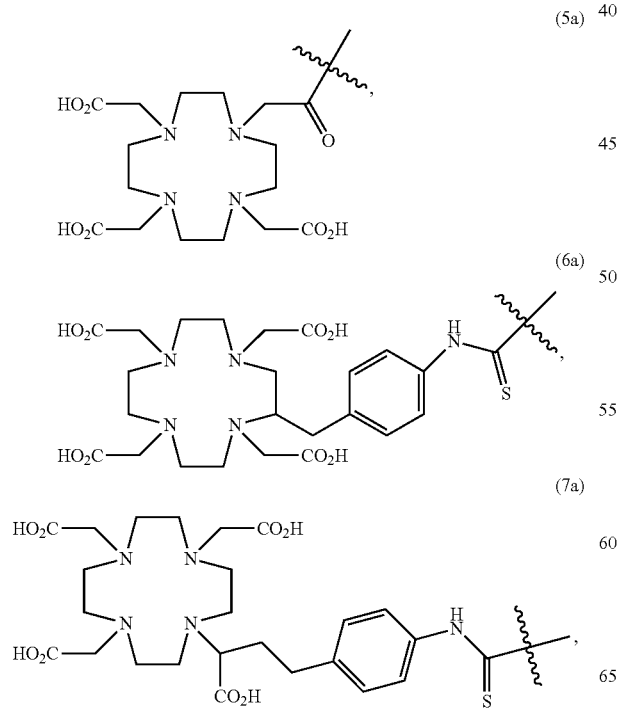

(6a)

(7a)

(8a)

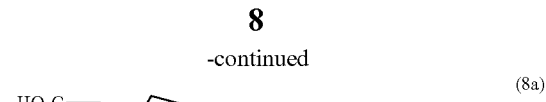

(8b)

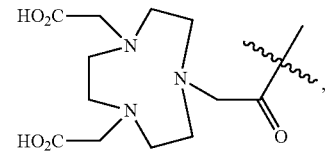

(8c)

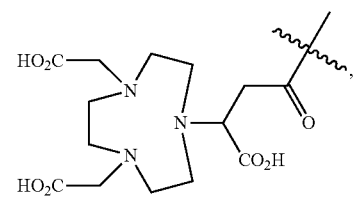

(9a)

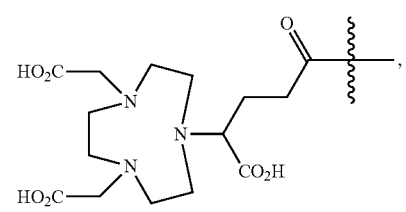

(10a)

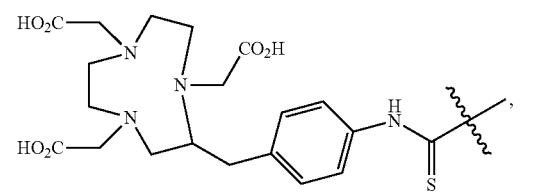

(10b)

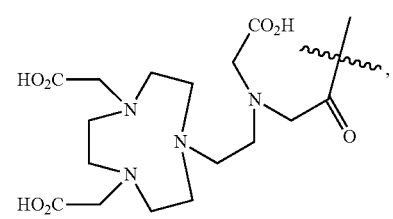

(11a)

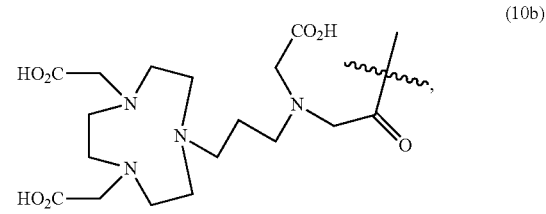

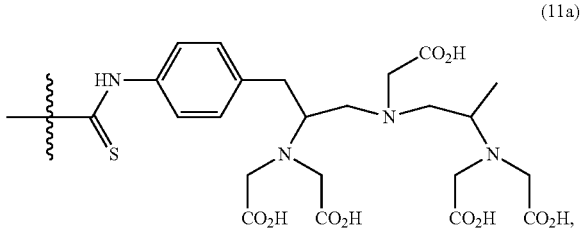

-continued (11b)

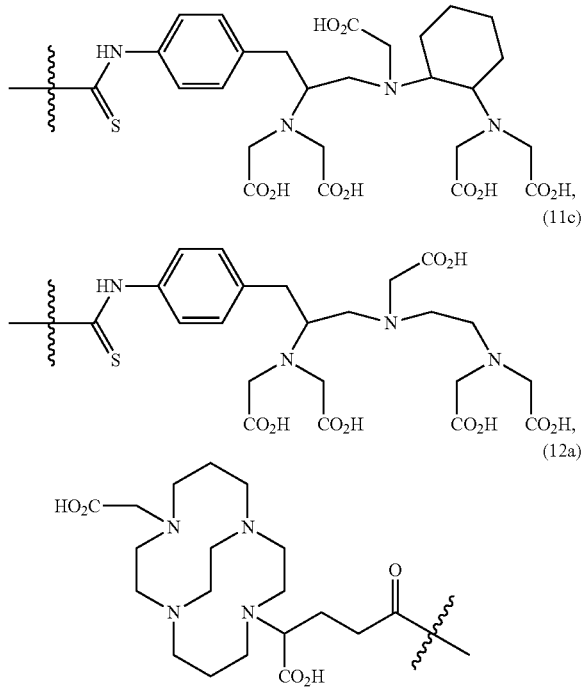

(11c)

(12a)

[7] The compound or the salt thereof, or the complex of the compound or the salt with a metal according to [1], wherein the compound represented by the formula (1) or the salt thereof is a compound or a salt thereof selected from the group consisting of 2,2',2"-(10-((4R,7R)-16-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid, 2,2',2"-(10-(2-(((R)-1-((2-(4-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl) triacetic acid, 2,2',2'-((10-((4R,7R,10R)-19-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-2,5,8,11,16-pentaoxo-4,7,10-tris(sulfomethyl)-3,6,9,12,15-pentaazanonadecyl)-1,4,7,10-tetraazacyclododecane-1,4,7-triyl)triacetic acid, (S)-2,2',2'-(10-(19-(4-(N-(1-carboxy-2-(4-(2-(5,6,7,8-tetrahydro-1,8-naphthyridin-2-yl)ethyl)benzamido)ethyl)sulfamoyl)-3,5-dimethylphenoxy)-2,11,16-trioxo-6,9-dioxa-3,12,15-triazanionadecyl)-1,4,7,10-tetraazacyclododecane-1,4,7-triyl)triacetic acid, 2,2',2"-(10-((S)-4-(4-aminobutyl)-22-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-2,5,14,19-tetraoxo-9,12-dioxa-3,6,15,18-tetraazadocosyl)-1,4,7,10-tetraazacyclododecane-1,4,7-triyl)triacetic acid, (S)-2,2',2'-(10-(28-(4-(N-(1-carboxy-2-(4-(2-(5,6,7,8-tetrahydro-1,8-naphthyridin-2-yl)ethyl)benzamido)ethyl)sulfamoyl)-3,5-dimethylphenoxy)-2,11,20,25-tetraoxo-6,9,15,18-tetraoxa-3,12,21,24-tetraazaoctacosyl)-1,4,7,10-tetraazacyclododecane-1,4,7-triyl)triacetic acid, 2,2',2'-(10-((R)-22-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-2,5,14,19-tetraoxo-4-(sulfomethyl)-9,12-dioxa-3,6,15,18-tetraazadocosyl)-1,4,7,10-tetraazacyclododecane-1,4,7-triyl)triacetic acid, 2,2',2'-(10-((9R)-18-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-4-(((R)-1-((2-(4-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)butanamido)ethyl)amino)-1-oxo-3-sulfopropan-2-yl) carbamoyl)-2,7,10,15-tetraoxo-9-(sulfomethyl)-3,8,11,14-tetraazaoctadecyl)-1,4,7,10-tetraazacyclododecane-1,4,7-triyl)triacetic acid, 2,2',2'-(10-((4R,7R)-16-((5-(2-carboxy-1-(5-(2-(5,6,7,8-tetrahydro-1,8-naphthyridin-2-yl) ethoxy)-1H-indol-1-yl)ethyl)pyridin-3-yl)oxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid, 2,2',2'-(10-((4R,7R)-16-((5-(2-carboxy-1-(4-(2-(5,6,7,8-tetrahydro-1,8-naphthyridin-2-yl)ethyl)-1H-indol-1-yl)ethyl)pyridin-3-yl)oxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid, 2,2',2"-(10-(2-(((R)-1-((2-(4-(4-(N—(R)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl) triacetic acid, 2,2',2"-(10-((4S,9R)-18 (4-(N-((s)-2-(4-(2-(6-aminopyridin-2-yl)ethyl)benzamido)-1-carboxyethyl)sulfamoyl)-3,5-dimethylphenoxy)-4-(((R)-1-((2-(4-(4-(N—((S)-2-(4-(2-(6-aminopyridin-2-yl)ethyl)benzamido)-1-carboxyethyl)sulfamoyl)-3,5-dimethylphenoxy)butanamido)ethyl)amino)-1-oxo-3-sulfopropan-2-yl) carbamoyl)-2,7,10,15-tetraoxo-9-(sulfomethyl)-3,8,11,14-tetraazaoctadecyl)-1,4,7,10-tetraazacyclododecane-1,4,7-triyl)triacetic acid, 2,2',2"-(10-(2-(((R)-1-((2-(4-(4-(N—((S)-2-(4-(2-(6-aminopyridin-2-yl)ethyl)benzamido)-1-carboxyethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid, 2,2',2"-(10-((4R,7R)-16-(4-(N—((S)-2-(4-(2-(6-aminopyridin-2-yl)ethyl)benzamido)-1-carboxyethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7triyl)triacetic acid, 2,2',2"-(10-((4R,7R)-16-(4-(N—((S)-1-carboxy-2-(5-(5,6,7,8-tetrahydro-1,8-naphthyridin-2-yl)pentanamido)ethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid, 2,2',2'-(10-(2-(((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl) triacetic acid, 2,2',2'-(10-((4R,7R)-16-(4-((S)-2-carboxy-1-(4-(2-(5,6,7,8-tetrahydro-1,8-naphthyridin-2-yl)ethyl)benzamido)ethyl)-2-fluorophenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid, 2,2'-((1-(((S)-2-(bis(carboxymethyl)amino)-3-(4-(3-((R)-1-(((R)-1-((2-(4-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)butanamido)ethyl)amino)-1-oxo-3-sulfopropan-2-yl)amino)-1-oxo-3-sulfopropan-2-yl)thioureido)phenyl)propyl)(carboxymethyl)amino)propan-2-yl)azanediyl)diacetic acid, (S)-2,2',2''-(10-(2-((2-(4-(4-(N-(1-carboxy-2-(4-(2-(5,6,7,8-tetrahydro-1,8-naphthyridin-2-yl)ethyl)benzamido)ethyl)sulfamoyl)-3,5-dimethylphenoxy)butanamido)ethyl)amino)-2-oxoethyl)-1,4,7,10-tetraazacyclododecane-1,4,7-triyl)triacetic acid, 2,2',2'',2'''-(2-(4-(3-((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)thioureido)benzyl)-1,4,7,10-tetraazacyclododecane-1,4,7,10-tetrayl)tetraacetic acid, 2,2'-((1-(((S)-2-(bis(carboxymethyl)amino)-3-(4-(3-((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)thioureido)phenyl)propyl)(carboxymethyl)amino)propan-2-yl) azanediyl)diacetic acid, 2,2',2'-(10-(2-(((R)-1-((2-(4-(4-(N—((S)-1-carboxy-2-(4-(5,6,7,8-tetrahydro-1,8-naphthyridin-2-yl)butanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid, 2,2',2'-(10-(2-(((R)-1-((2-(4-(4-(N—((S)-1-carboxy-2-(6-(5,6,7,8-tetrahydro-1,8-naphthyridin-2-yl)hexanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid, 2,2',2'-(10-((4R,7R)-16-(4-(N—((S)-1-carboxy-2-(5-(2-(5,6,7,8-tetrahydro-1,8-naphthyridin-2-yl)ethyl)thiophene-2-carboxamido)ethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid, 2,2',2'-(10-((4R,7R)-16-(4-(N—((S)-1-carboxy-2-(4-(2-(5,6,7,8-tetrahydro-1,8-naphthyridin-2-yl)ethyl)benzamido)ethyl)sulfamoyl)phenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid hexasodium salt, 2,2',2''-(10-((4R,7R)-16-(4-(N—((S)-1-carboxy-2-(4-(3-(pyridin-2-ylamino)propyl)benzamido)ethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid, 2,2'-(7-((R)-1-carboxy-4-(((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-4-oxobutyl)-1,4,7-triazonane-1,4-diyl)diacetic acid, and 5-(((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-(11-(carboxymethyl)-1,4,8,11-tetraazabicyclo[6.6.2]hexadecan-4-yl)-5-oxopentanoic acid.

[8] The complex according to any one of [1] to [7], wherein the metal is a cytotoxic radioactive metal.

[9] The complex according to [8], wherein the cytotoxic radioactive metal is a metal selected from the group consisting of $^{64}$Cu, $^{67}$Cu, $^{90}$Y, $^{166}$Ho, $^{153}$Sm, $^{177}$Lu, and $^{225}$Ac.

[10] A pharmaceutical composition comprising the complex according to [8] or [9].

[11] The pharmaceutical composition according to [10], wherein the pharmaceutical composition is an agent for treatment of a disease involving an integrin.

[12] The complex according to any one of [1] to [7], wherein the metal is a noncytotoxic radioactive metal.

[13] The complex according to [12], wherein the noncytotoxic radioactive metal is a metal selected from the group consisting of an $^{18}$F aluminum complex, $^{111}$In, $^{64}$Cu, $^{67}$Ga, $^{68}$Ga, and $^{89}$Zr.

[14] A pharmaceutical composition comprising the complex according to [12] or [13].

[15] The pharmaceutical composition according to [14], wherein the pharmaceutical composition is an agent for diagnosis of a disease involving an integrin.

[16] A kit for preparing an agent for diagnosis or treatment by adding a metal, the kit comprising a compound or a salt thereof according to any of [1] to [7].

[17] A method for producing a compound represented by the formula (1): comprising

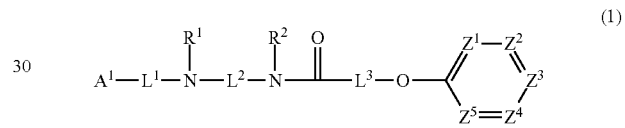

wherein $A^1$, $R^1$, $R^2$, $Z^1$, $Z^2$, $Z^3$, $Z^4$, $Z^5$, $L^1$, $L^2$, and $L^3$ are as defined above,
allowing a compound represented by the formula (S1a) or a salt thereof:

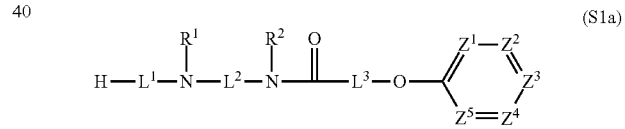

wherein $R^1$, $R^2$, $Z^1$, $Z^2$, $Z^3$, $Z^4$, $Z^5$, $L^1$, $L^2$, and $L^3$ are as defined above, to react with a compound represented by the formula (S2):

wherein $R^B$ represents a hydroxyl group or a leaving group; and $A^1$ is as defined above, or a compound represented by the formula (S3):

wherein $B^1$ represents a chelate residue: and $Q^1$ is as defined above.

[18] A compound represented by the formula (S1a) or a salt thereof:

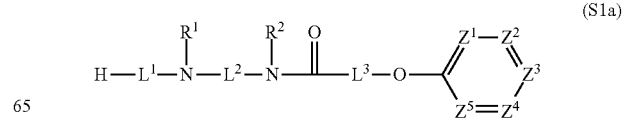

wherein $R^1$, $R^2$, $Z^1$, $Z^2$, $Z^3$, $Z^4$, $Z^5$, $L^1$, $L^2$, and $L^3$ are as defined above.

[19] The compound or the salt thereof according to [18], wherein $Z^1$, $Z^2$, $Z^4$, and $Z^5$ are the same or different and each represent $CR^{3b}$ wherein $R^{3b}$ is as defined above; and $Z^3$ represents $CR^{3c}$ wherein $R^{3c}$ is as defined above.

[20] The compound or the salt thereof according to [18] or [19], wherein $R^{3c}$ represents a group represented by the formula (2b):

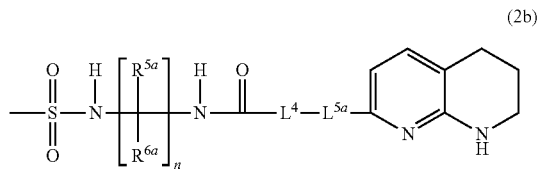

(2b)

wherein $R^{5a}$, $R^{6a}$a, $L^4$, $L^{5a}$, and n are as defined above.

[21] The complex according to [8] or [9] for use in the treatment of a disease involving an integrin.

[22] The complex according to [12] or [13] for use in the diagnosis of a disease involving an integrin.

[23] Use of the complex according to [8] or [9] for producing an agent for the treatment of a disease involving an integrin.

[24] Use of the complex according to [12] or [13] for producing an agent for the diagnosis of a disease involving an integrin.

[25] A method for treating a disease involving an integrin, comprising administering the complex according to [8] or [9].

[26] A method for diagnosing a disease involving an integrin, comprising administering the complex according to [12] or [13].

Advantageous Effects of Invention

The complex of the compound represented by the formula (1) or a salt thereof with a metal of the present invention has high accumulation and persistence in integrin-expressing cells such as cancer cells and exhibits fast blood clearance. Therefore, the complex is useful for a procedure of diagnosis or treatment, etc., of a disease involving an integrin. Moreover, the compound represented by the formula (1) or the salt thereof of the present invention is useful as an intermediate for producing the complex. Furthermore, the compound represented by the formula (S1a) of the present invention or a salt thereof is useful as an intermediate for producing the compound represented by the formula (1) or the salt thereof, or the complex of the compound or the salt with a metal of the present invention.

BRIEF DESCRIPTION OF DRAWINGS

FIG. 1 is a diagram showing the correlation between the amount of tumor accumulated and an integrin β3 expression level in a tumor mass.

FIG. 2 shows results of imaging an integrin-expressing tumor by PET using [$^{64}$Cu]-(P2).

FIG. 3 shows results of imaging an integrin-expressing tumor by PET using [$^{64}$Cu]-(Aa7).

FIG. 4 shows results of imaging an integrin-expressing tumor by PET using [$^{64}$Cu]-(Ab9-a).

FIG. 5 shows results of imaging an integrin-expressing tumor by PET using [$^{64}$Cu]-(Ab9-b).

FIG. 6 shows results of imaging an integrin-expressing tumor with a gamma camera.

FIG. 7 shows results of imaging an integrin-expressing tumor in an intracranial tumor model.

FIG. 8 shows blood concentration transition of radioactivity in a monkey using [$^{111}$In]-(P2).

FIG. 9 shows results of time-dependent planar imaging of a monkey using [$^{111}$In]-(P2).

DESCRIPTION OF EMBODIMENTS

Hereinafter, the present invention will be described in detail. The group represented by the following formula:

used in the present invention means a group in which x number of A are bonded.

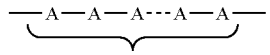

The number of A: x
x number of A may be the same or may be different.
In the present invention, each term has the following meaning, unless otherwise specified.

The halogen atom means a fluorine atom, a chlorine atom, a bromine atom, or an iodine atom.

The $C_{1-4}$alkyl group means a methyl, ethyl, propyl, isopropyl, butyl, sec-butyl, isobutyl, or tert-butyl group. The $C_{1-6}$alkyl group means a linear or branched $C_{1-6}$ alkyl group such as methyl, ethyl, propyl, isopropyl, butyl, sec-butyl, isobutyl, tert-butyl, pentyl, isopentyl, 2-methylbutyl, 2-pentyl, 3-pentyl, and hexyl groups. The aryl group means a $C_{6-10}$ aryl group such as phenyl and naphthyl groups. The ar-$C_{1-6}$ alkyl group means a $C_{6-10}$ ar-$C_{1-6}$ alkyl group such as benzyl, diphenylmethyl, trityl, phenethyl, 2-phenylpropyl, 3-phenylpropyl, and naphthylmethyl groups.

The $C_{1-4}$ alkylene group means a linear or branched $C_{1-4}$ alkylene group such as methylene, ethylene, propylene, and butylene groups. The $C_{1-6}$ alkylene group means a linear or branched $C_{1-6}$ alkylene group such as methylene, ethylene, propylene, butylene, pentylene, and hexylene groups. The —O—$C_{1-6}$ alkylene group means a group in which the $C_{1-6}$ alkylene group is bonded to an oxygen atom, such as oxyethylene, oxypropylene, and oxybutylene groups. The —NH—$C_{1-6}$ alkylene group means a group in which the $C_{1-6}$ alkylene group is bonded to an amino group, such as aminoethylene, aminopropylene, and aminobutylene groups. The $C_{3-8}$ cycloalkylene group means a cyclopropylene, cyclobutylene, cyclopentylene, cyclohexylene, cycloheptylene, or cyclooctylene group.

The $C_{1-4}$alkanetriyl group means a linear or branched $C_{1-4}$alkanetriyl group such as methanetriyl, ethanetriyl, propanetriyl, and butanetriyl groups. The $C_{1-6}$ alkanetriyl group means a linear or branched $C_{1-6}$ alkanetriyl group such as methanetriyl, ethanetriyl, propanetriyl, butanetriyl, pentanetriyl, and hexanetriyl groups.

The $C_{1-6}$ alkoxy group means a linear, cyclic, or branched $C_{1-6}$ alkyloxy group such as methoxy, ethoxy, propoxy, isopropoxy, cyclopropoxy, butoxy, isobutoxy, sec-butoxy, tert-butoxy, cyclobutoxy, pentyloxy, and hexyloxy groups.

The $C_{1-6}$alkoxy-$C_{1-6}$alkyl group means a $C_{1-6}$ alkyloxy-$C_{1-6}$ alkyl group such as methoxymethyl and 1-ethoxyethyl groups.

The $C_{1-6}$alkylamino group means a linear, branched, or cyclic $C_{1-6}$ alkylamino group such as methylamino, ethylamino, propylamino, isopropylamino, cyclopropylamino, butylamino, sec-butylamino, tert-butylamino, cyclobutylamino, pentylamino, cyclopentylamino, hexylamino, and cyclohexylamino groups. The di($C_{1-6}$ alkyl)amino group means a linear, branched, or cyclic di($C_{1-6}$ alkyl)amino group such as dimethylamino, diethylamino, dipropylamino, diisopropylamino, dibutylamino, di(tert-butyl)amino, dipentylamino, dihexylamino, (ethyl)(methyl)amino, (methyl)(propyl)amino, (cyclopropyl)(methyl)amino, (cyclobutyl)(methyl)amino, and (cyclohexyl)(methyl)amino groups.

The $C_{2-6}$ alkanoyl group means a linear or branched $C_{2-6}$ alkanoyl group such as acetyl, propionyl, valeryl, isovaleryl, and pivaloyl groups. The aroyl group means a $C_{6-10}$ aroyl group such as benzoyl and naphthoyl groups. The heterocyclic carbonyl group means a monocyclic or bicyclic heterocyclic carbonyl group such as furoyl, thenoyl, pyrrolidinylcarbonyl, piperidinylcarbonyl, piperazinylcarbonyl, morpholinylcarbonyl, and pyridinylcarbonyl groups. The acyl group means a formyl group, a succinyl group, a glutaryl group, a maleoyl group, a phthaloyl group, a $C_{2-6}$ alkanoyl group, an aroyl group, or a heterocyclic carbonyl group.

The $C_{1-6}$ alkoxycarbonyl group means a linear or branched $C_{1-6}$ alkyloxycarbonyl group such as methoxycarbonyl, ethoxycarbonyl, isopropoxycarbonyl, tert-butoxycarbonyl, and 1,1-dimethylpropoxycarbonyl groups. The ar-$C_{1-6}$ alkoxycarbonyl group means a $C_{6-10}$ ar-$C_{1-6}$alkyloxycarbonyl group such as benzyloxycarbonyl and phenethyloxycarbonyl groups.

The $C_{1-6}$alkylthio group means a $C_{1-6}$ alkylthio group such as methylthio, ethylthio, propylthio, and butylthio groups. The $C_{1-6}$ alkylsulfonyl group means a $C_{1-6}$ alkylsulfonyl group such as methylsulfonyl, ethylsulfonyl, and propylsulfonyl groups. The arylsulfonyl group means a $C_{6-10}$ arylsulfonyl group such as benzenesulfonyl, p-toluenesulfonyl, and naphthalenesulfonyl groups. The $C_{1-6}$ alkylsulfonyloxy group means a $C_{1-6}$ alkylsulfonyloxy group such as methylsulfonyloxy and ethylsulfonyloxy groups. The arylsulfonyloxy group means a $C_{6-10}$ arylsulfonyloxy group such as benzenesulfonyloxy and p-toluenesulfonyloxy groups.

The monocyclic nitrogen-containing heterocyclic group means a monocyclic heterocyclic group containing only a nitrogen atom as a heteroatom constituting the ring, such as aziridinyl, azetidinyl, pyrrolidinyl, pyrrolinyl, pyrrolyl, piperidyl, tetrahydropyridyl, dihydropyridyl, pyridyl, homopiperidinyl, octahydroazocinyl, imidazolidinyl, imidazolinyl, imidazolyl, pyrazolidinyl, pyrazolinyl, pyrazolyl, piperazinyl, pyrazinyl, pyridazinyl, pyrimidinyl, homopiperazinyl, triazolyl, and tetrazolyl groups. The monocyclic oxygen-containing heterocyclic group means a monocyclic heterocyclic group containing only an oxygen atom as a heteroatom constituting the ring, such as oxetanyl, tetrahydrofuranyl, furanyl, tetrahydropyranyl, pyranyl, 1,3-dioxanyl, and 1,4-dioxanyl groups. The monocyclic sulfur-containing heterocyclic group means a monocyclic heterocyclic group containing only a sulfur atom as a heteroatom constituting the ring, such as a thienyl group. The monocyclic nitrogen- and oxygen-containing heterocyclic group means a monocyclic heterocyclic group containing only a nitrogen atom and an oxygen atom as heteroatoms constituting the ring, such as oxazolyl, isoxazolyl, oxadiazolyl, morpholinyl, and oxazepanyl groups. The monocyclic nitrogen- and sulfur-containing heterocyclic group means a monocyclic heterocyclic group containing only a nitrogen atom and a sulfur atom as heteroatoms constituting the ring, such as thiazolyl, isothiazolyl, thiadiazolyl, thiomorpholinyl, 1-oxidothiomorpholinyl, and 1,1-dioxidothiomorpholinyl groups. The monocyclic heterocyclic group means a monocyclic nitrogen-containing heterocyclic group, a monocyclic oxygen-containing heterocyclic group, a monocyclic sulfur-containing heterocyclic group, a monocyclic nitrogen- and oxygen-containing heterocyclic group, or a monocyclic nitrogen- and sulfur-containing heterocyclic group.

The bicyclic nitrogen-containing heterocyclic group means a bicyclic heterocyclic group containing only a nitrogen atom as a heteroatom constituting the rings, such as indolinyl, indolyl, isoindolinyl, isoindolyl, benzimidazolyl, indazolyl, benzotriazolyl, pyrazolopyridinyl, quinolyl, tetrahydroquinolinyl, quinolyl, tetrahydroisoquinolinyl, isoquinolinyl, quinolizinyl, cinnolinyl, phthalazinyl, quinazolinyl, dihydroquinoxalinyl, quinoxalinyl, naphthyridinyl, purinyl, pteridinyl, and quinuclidinyl groups. The bicyclic oxygen-containing heterocyclic group means a bicyclic heterocyclic group containing only an oxygen atom as a heteroatom constituting the rings, such as 2,3-dihydrobenzofuranyl, benzofuranyl, isobenzofuranyl, chromanyl, chromenyl, isochromanyl, 1,3-benzodioxolyl, 1,3-benzodioxanyl, and 1,4-benzodioxanyl groups. The bicyclic sulfur-containing heterocyclic group means a bicyclic heterocyclic group containing only a sulfur atom as a heteroatom constituting the rings, such as 2,3-dihydrobenzothienyl and benzothienyl groups. The bicyclic nitrogen- and oxygen-containing heterocyclic group means a bicyclic heterocyclic group containing only a nitrogen atom and an oxygen atom as heteroatoms constituting the rings, such as benzoxazolyl, benzisoxazolyl, benzoxadiazolyl, benzomorpholinyl, dihydropyranopyridyl, dioxolopyridyl, furopyridinyl, dihydrodioxinopyridyl, and dihydropyridooxazinyl groups. The bicyclic nitrogen- and sulfur-containing heterocyclic group means a bicyclic heterocyclic group containing a nitrogen atom and a sulfur atom as heteroatoms constituting the rings, such as benzothiazolyl, benzisothiazolyl, and benzothiadiazolyl groups. The bicyclic heterocyclic group means a bicyclic nitrogen-containing heterocyclic group, a bicyclic oxygen-containing heterocyclic group, a bicyclic sulfur-containing heterocyclic group, a bicyclic nitrogen- and oxygen-containing heterocyclic group, or a bicyclic nitrogen- and sulfur-containing heterocyclic group.

The heterocyclic group means a monocyclic heterocyclic group or a bicyclic heterocyclic group.

The divalent aromatic hydrocarbon group means an optionally partially hydrogenated divalent aromatic hydrocarbon group such as phenylene, pentalenylene, indenylene, indenylene, and naphthylene groups. The divalent heterocyclic group means a group formed by the further removal of one hydrogen atom from a heterocyclic group, such as pyrrolediyl, imidazolediyl, triazolediyl, tetrazolediyl, pyrrolidinediyl, imidazolidinediol, furandiyl, thiophenediyl, oxazolediyl, thiazolediol, pyridinediyl, pyrimidinediyl, indolediol, quinolinediol, and isoquinolinediol groups.

The amino-protecting group includes all groups which may be used as usual protecting groups for the amino group. Examples thereof include groups described in W. Greene et al., Protective Groups in Organic Synthesis, Vol. 4, p. 696-926, 2007, John Wiley & Sons, INC. Specific examples thereof include ar-$C_{1-6}$ alkyl groups, $C_{1-6}$alkoxy-$C_{1-6}$ alkyl groups, acyl groups, $C_{1-6}$ alkoxycarbonyl groups, ar-$C_{1-6}$ alkoxycarbonyl groups, $C_{1-6}$ alkylsulfonyl groups, arylsulfonyl groups, and silyl groups.

The hydroxyl-protecting group includes all groups which may be used as usual protecting groups for the hydroxyl group. Examples thereof include groups described in W. Greene et al., Protective Groups in Organic Synthesis, Vol. 4, p. 16-366, 2007, John Wiley & Sons, INC. Specific examples thereof include $C_{1-6}$ alkyl groups, ar-$C_{1-6}$ alkyl groups, $C_{1-6}$alkoxy-$C_{1-6}$ alkyl groups, acyl groups, $C_{1-6}$ alkoxycarbonyl groups, ar-$C_{1-6}$ alkoxycarbonyl groups, $C_{1-6}$ alkylsulfonyl groups, arylsulfonyl groups, silyl groups, a tetrahydrofuranyl group, and a tetrahydropyranyl group.

The carboxyl-protecting group includes all groups which may be used as usual protecting groups for the carboxyl group. Examples thereof include groups described in W. Greene et al., Protective Groups in Organic Synthesis, Vol. 4, p. 533-646, 2007, John Wiley & Sons, INC. Specific examples thereof include $C_1$, alkyl groups, aryl groups, ar-$C_{1-6}$ alkyl groups, $C_{1-6}$ alkoxy-$C_{1-6}$ alkyl groups, and silyl groups.

The thiol-protecting group includes all groups which may be used as usual protecting groups for the thiol group. Examples thereof include groups described in W. Greene et al., Protective Groups in Organic Synthesis, Vol. 4, p. 647-695, 2007, John Wiley & Sons, INC. Specific examples thereof include $C_{1-6}$ alkyl groups, ar-$C_{1-6}$ alkyl groups, $C_{1-6}$ alkoxy-$C_{1-6}$ alkyl groups, acyl groups, and silyl groups.

The silyl group means, for example, a trimethylsilyl, triethylsilyl, tributylsilyl, or tert-butyldimethylsilyl group.

Examples of the leaving group include halogen atoms, $C_{1-6}$alkylsulfonyloxy groups, and arylsulfonyloxy groups. The $C_{1-6}$ alkylsulfonyloxy groups and the arylsulfonyloxy groups are each optionally substituted.

The chelate group means an organic group capable of forming a chelate bond with a metal. Specific examples thereof include groups having an alkylenediamine structure, a bipyridine structure, an alkylenediamine tetraacetic acid structure, a phenanthroline structure, a porphyrin structure, a crown ether structure, a polyazamacrocyclic structure, a polyaminopolycarboxylic acid structure, or a polyaminopolyphosphonic acid structure. The polyazamacrocyclic structure means a structure having a cyclic backbone in which 3 to 5 nitrogen atoms are interconnected by the same number of $C_{1-6}$ alkylene groups as the number of the nitrogen atoms. Examples thereof include cyclen, cyclam, bridged-cyclam, ET-cyclam, and diamsar. The polyaminopolycarboxylic acid structure means a structure having a backbone in which 3 to 5 nitrogen atoms are interconnected by the same number of $C_{1-6}$ alkylene groups as the number of the nitrogen atoms resulting in closure and a $C_{1-6}$ alkyl group substituted by at least one carboxyl group is bonded to each of at least two of the nitrogen atoms, or a structure having a backbone in which 2 to 4 nitrogen atoms are interconnected by $C_{1-6}$ alkylene groups and/or $C_{3-8}$ cycloalkylene groups fewer by one than the number of the nitrogen atoms resulting in open chain and a $C_{1-6}$ alkyl group substituted by at least one carboxyl group is bonded to each of at least two of the nitrogen atoms. Examples thereof include DOTA, DO3A, DO2A, CB-DO2A, TETA, TE3A, TE2A, CB-TE2A, NOTA, NODASA, NODAGA, BCNOTA, EDTA, DTPA, 1B4M-DTPA, and CHX-DTPA. The polyaminopolyphosphonic acid structure means a backbone in which at least one carboxyl group in the backbone of the polyaminopolycarboxylic acid structure is replaced with a phosphono group. Examples thereof include DOTP, NOTP, EDTP, HDTP, and NTP. The group having a polyazamacrocyclic structure, a polyaminopolycarboxylic acid structure, or a polyaminopolyphosphonic acid structure forms a coordinate bond with a metal as the chelate group through a plurality of nitrogen atoms, carboxyl groups, and/or phosphono groups to form a complex, while the N terminus of $L^1$ is linked to the metal via a carboxyl group which is not involved in the coordination, a phosphono group which is not involved in the coordination, or a side chain introduced onto the backbone. Such a side chain is preferably a side chain capable of binding to $L^1$ easily, and groups having an active group such as an anhydride group, a bromoacetamide group, an iodoacetamide group, an isothiocyanato group, a N-hydroxysuccinimide group, or a maleimide group are known (Liu et al., Advanced Drug Delivery Reviews 60: 1347-1370 (2008)).

The halogenated hydrocarbons mean methylene chloride, chloroform, and dichloroethane. The ethers mean diethyl ether, diisopropyl ether, dioxane, tetrahydrofuran, anisole, ethylene glycol dimethyl ether, diethylene glycol dimethyl ether, and diethylene glycol diethyl ether. The alcohols mean methanol, ethanol, propanol, 2-propanol, butanol, and 2-methyl-2-propanol. The ketones mean acetone, 2-butanone, 4-methyl-2-pentanone, and methyl isobutyl ketone. The esters mean methyl acetate, ethyl acetate, propyl acetate, and butyl acetate. The amides mean N,N-dimethylformamide, N,N-dimethylacetamide, and N-methylpyrrolidone. The nitriles mean acetonitrile and propionitrile. The sulfoxides mean dimethyl sulfoxide and sulfolane. The aromatic hydrocarbons mean benzene, toluene, and xylene.

The inorganic base means sodium hydroxide, potassium hydroxide, sodium tert-butoxide, potassium tert-butoxide, sodium bicarbonate, sodium carbonate, potassium carbonate, or cesium carbonate. The organic base means triethylamine, N,N-diisopropylethylamine, 1,8-diazabicyclo(5.4.0)undec-7-ene (DBU), 4-dimethylaminopyridine, or N-methylmorpholine.

Examples of the salts of the compound represented by the formula (1) and the compound represented by the formula (S1a) can include usually known salts of basic groups such as an amino group or acidic groups such as a hydroxyl group or a carboxyl group. Examples of the salts of basic groups include: salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid. Examples of the salts of acidic groups include: salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine. Among these salts, preferred examples of the salt include pharmaceutically acceptable salts.

The procedure means, for example, the diagnosis, prevention, or treatment of various diseases. The diagnosis means, for example, the judgment of a disease as being a target or the judgment of a condition of the target disease. The prevention means, for example, the inhibition of development, reduction in the risk of development, or the delay of development. The treatment means, for example, the amelioration of the target disease or condition or the suppression of progression thereof. The agent means a substance which is applied for the purpose of the procedure.

The compound of the present invention is represented by the formula (1):

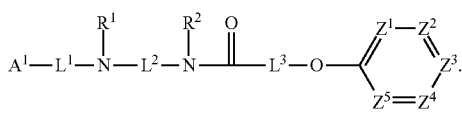
(1)

wherein $R^1$, $R^2$, $Z^1$, $Z^2$, $Z^3$, $Z^4$, $Z^5$, $L^1$, $L^2$, $L^3$, and $A^1$ are as defined above.

$A^1$ is a chelate group. The chelate group represented by $A^1$ is preferably a group having a polyazamacrocyclic structure, a group having a polyaminopolycarboxylic acid structure, or a group having a polyaminopolyphosphonic acid structure, more preferably a group having a polyaminopolycarboxylic acid structure, further preferably a group represented by the formula (5), (6), (7), (8), (9), (10), (11), or (12):

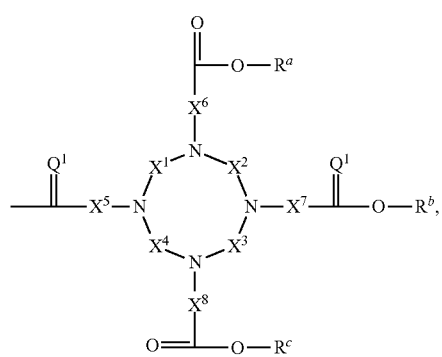
(5)

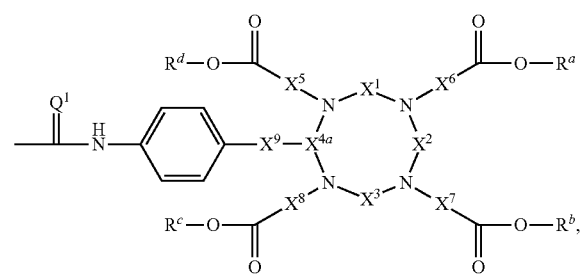
(6)

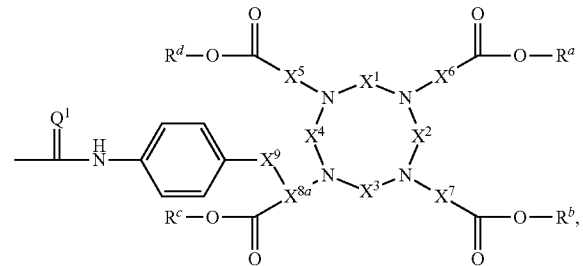
(7)

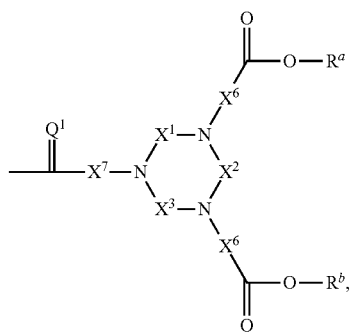
(8)

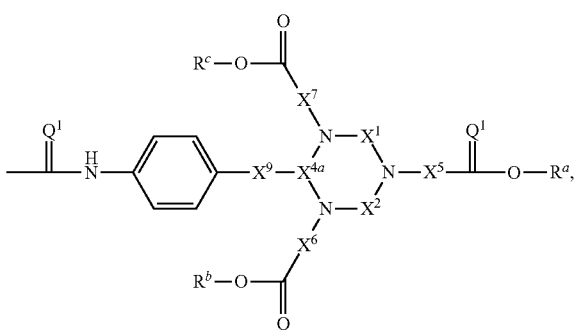
(9)

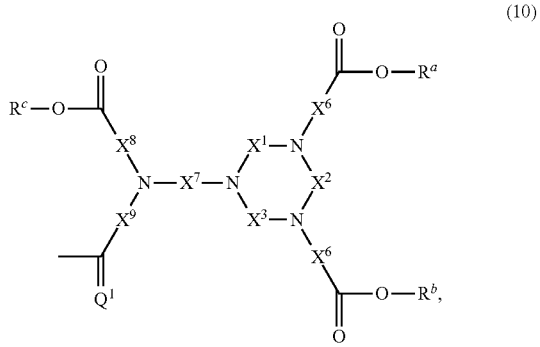
(10)

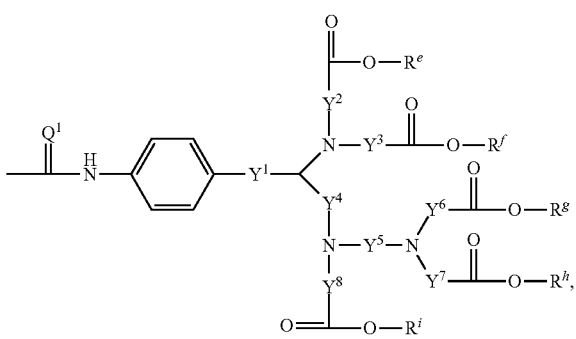
(11)

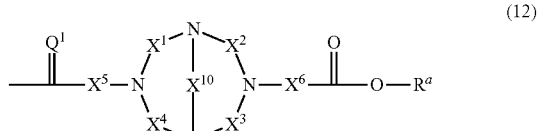
(12)

wherein $R^a$, $R^b$, $R^c$, $R^d$, $R^e$, $R^f$, $R^g$, $R^h$, $R^i$, $X^1$, $X^2$, $X^3$, $X^4$, $X^{4a}$, $X^5$, $X^6$, $X^7$, $X^8$, $X^9$, $X^{10}$, $Y^1$, $Y^2$, $Y^3$, $Y^4$, $Y^5$, $Y^6$, $Y^7$, $Y^8$, and $Q^1$ are as defined above, particularly preferably a group represented by the formula (5a), (6a), (7a), (8a), (8b), (8c), (9a), (10a), (10b), (11a), (11b), (11c), or (12a):
(5a)
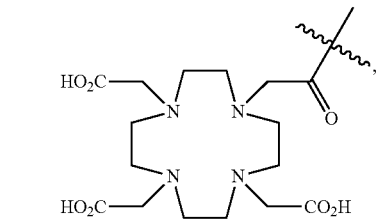
(6a)
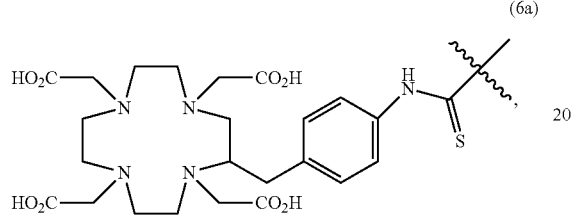
(7a)
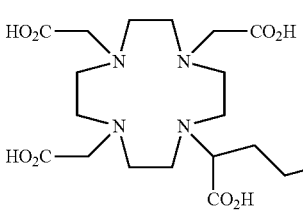
(8a)
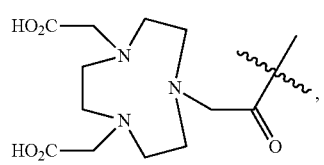
(8b)
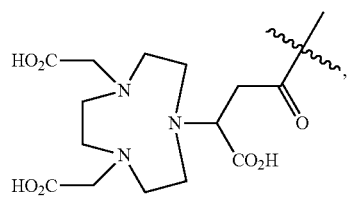
(8c)
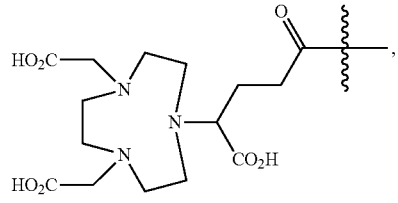
(9a)
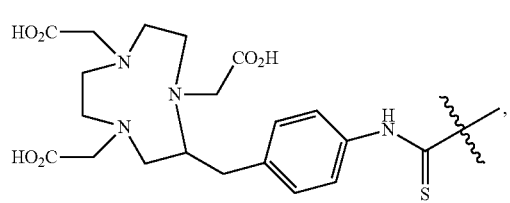
-continued
(10a)
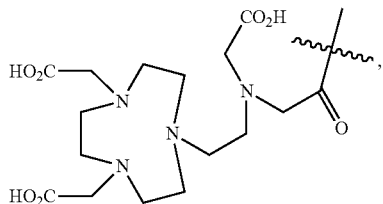
(10b)
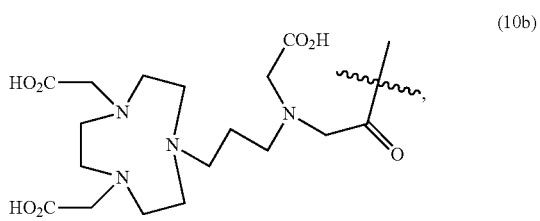
(11a)
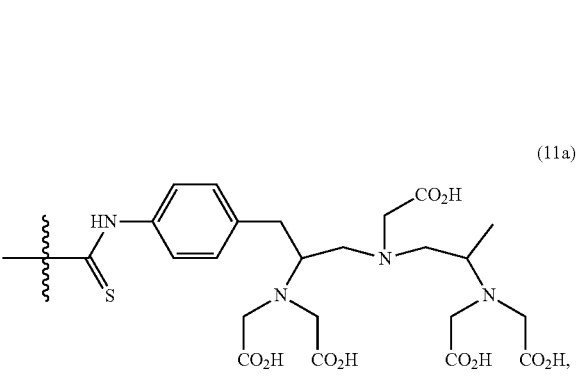
(11b)
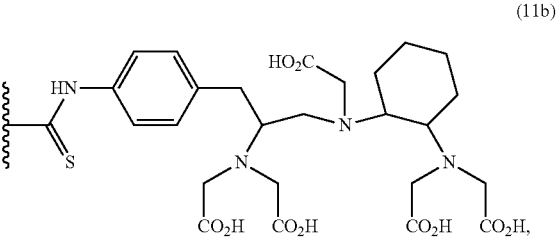
(11c)
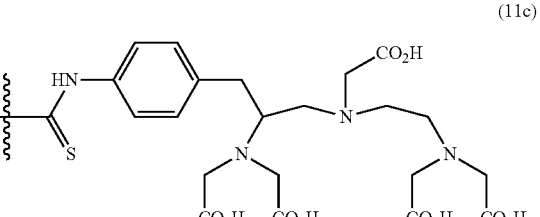
(12a)
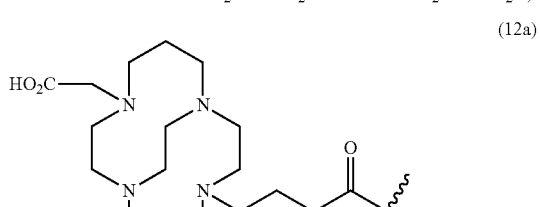

most preferably a group represented by the formula (5a), (8c), or (12a):

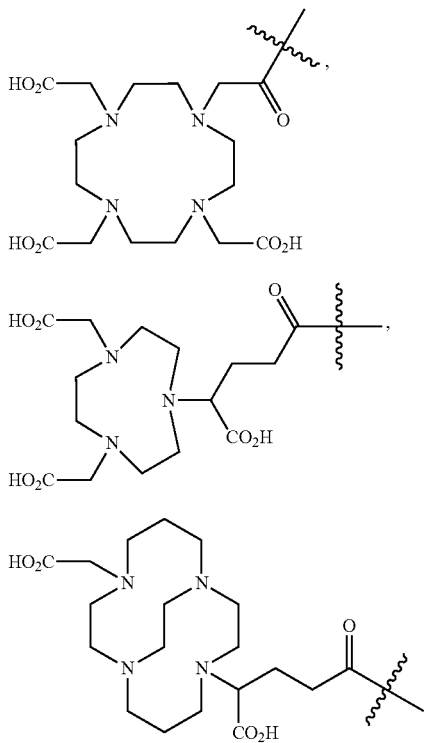

Each of $R^a$, $R^b$, $R^c$, $R^d$, $R^e$, $R^f$, $R^g$, $R^h$, and $R^i$ is a hydrogen atom or a carboxyl-protecting group. Each of $R^a$, $R^b$, $R^c$, $R^d$, $R^e$, $R^f$, $R^g$, $R^h$, and $R^i$ is preferably a hydrogen atom or a $C_{1-6}$ alkyl group, more preferably a hydrogen atom.

Each of $X^1$, $X^2$, $X^3$, $X^4$, $X^5$, $X^6$, $X^7$, $X^8$, $X^9$, $Y^1$, $Y^2$, $Y^3$, $Y^4$, $Y^5$, $Y^6$, $Y^7$, and $Y^8$ is an optionally substituted $C_{1-6}$ alkylene group or an optionally substituted $C_{3-8}$ cycloalkylene group. Each of $X^1$, $X^2$, $X^3$, $X^4$, $X^5$, $X^6$, $X^7$, $X^8$, $X^9$, $Y^1$, $Y^2$, $Y^3$, $Y^4$, $Y^5$, $Y^6$, $Y^7$, and $Y^8$ is preferably an optionally substituted $C_{1-4}$ alkylene group, more preferably a $C_{1-4}$ alkylene group, further preferably a methylene group, an ethylene group, or a propylene group. Examples of the substituent for the $C_{1-6}$ alkylene group or the $C_{3-8}$ cycloalkylene group represented by each of $X^1$, $X^2$, $X^3$, $X^4$, $X^5$, $X^6$, $X^7$, $X^8$, $X^9$, $Y^1$, $Y^2$, $Y^3$, $Y^4$, $Y^5$, $Y^6$, $Y^7$, and $Y^8$ include one or more groups selected from substituent group α.

Substituent group α: a halogen atom, a cyano group, a carbamoyl group, a sulfo group, an optionally protected amino group, an optionally protected hydroxyl group, an optionally protected carboxyl group, a $C_{1-6}$ alkyl group, a $C_{1-6}$ alkoxy group, an aryl group, a heterocyclic group, and an oxo group.

$X^{10}$ is an optionally substituted $C_{1-6}$ alkylene group. $X^{10}$ is preferably an optionally substituted $C_{1-4}$ alkylene group, more preferably a $C_{1-4}$ alkylene group, further preferably an ethylene group. Examples of the substituent for the $C_{1-6}$ alkylene group represented by $X^{10}$ include one or more groups selected from substituent group α.

Each of $X^{4a}$ and $X^{8a}$ is an optionally substituted $C_{1-6}$ alkanetriyl group. Each of $X^{4a}$ and $X^{8a}$ is preferably an optionally substituted $C_{1-4}$ alkanetriyl group, more preferably a $C_{1-4}$ alkanetriyl group. Examples of the substituent for the $C_{1-6}$ alkanetriyl group represented by each of $X^{4a}$ and $X^{8a}$ include one or more groups selected from substituent group α.

$R^1$ is a hydrogen atom, an optionally substituted $C_{1-6}$ alkyl group, or an amino-protecting group.

$R^1$ is preferably a hydrogen atom or an optionally substituted $C_{1-6}$ alkyl group, more preferably a hydrogen atom.

Examples of the substituent for the $C_{1-6}$ alkyl group represented by $R^1$ include one or more groups selected from substituent group α.

R is a hydrogen atom, an optionally substituted $C_{1-6}$-alkyl group, or an amino-protecting group. $R^2$ is preferably a hydrogen atom or an optionally substituted $C_{1-6}$ alkyl group, more preferably a hydrogen atom. Examples of the substituent for the $C_{1-6}$ alkyl group represented by $R^2$ include one or more groups selected from substituent group α.

Each of $Z^1$, $Z^2$, $Z^3$, $Z^4$, and $Z^5$ is a nitrogen atom or $CR^3$ wherein $R^3$ is as defined above, provided that at least one of $Z^1$, $Z^2$, $Z^3$, $Z^4$, and $Z^5$ is $CR^{3a}$ wherein $R^{3a}$ is as defined above.

$Z^1$ and $Z^5$ are the same or different and are each preferably $CR^3$ wherein $R^3$ is as defined above, more preferably $CR^{3b}$ wherein $R^{3b}$ is as defined above, further preferably $CR^{3d}$ wherein $R^{3d}$ represents a hydrogen atom or an optionally substituted $C_{1-6}$ alkyl group.

$Z^2$ is preferably a nitrogen atom or $CR^3$ wherein $R^3$ is as defined above, more preferably a nitrogen atom or $CR^{3b}$ wherein $R^{3b}$ is as defined above, further preferably $CR^{3b}$ wherein $R^{3b}$ is as defined above, particularly preferably $CR^{3d}$ wherein $R^{3d}$ is as defined above.

$Z^3$ is preferably $CR^3$ wherein $R^3$ is as defined above. When $Z^2$ is a nitrogen atom, $Z^3$ is preferably $CR^{3b}$ wherein $R^{3b}$ is as defined above. When $Z^2$ is $CR^3$ wherein $R^3$ is as defined above, $Z^3$ is preferably $CR^{3a}$ wherein $R^{3a}$ is as defined above. $Z^3$ is further preferably $CR^{3c}$ wherein $R^{3c}$ is as defined above, particularly preferably $CR^{3e}$ wherein $R^{3e}$ represents a group represented by the formula (2c):

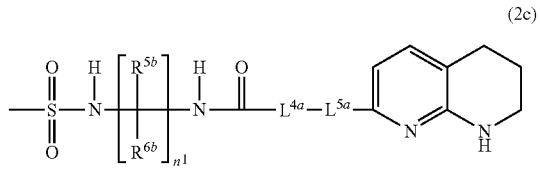

wherein $n^1 R^{5b}$ and $n^1 R^{6b}$ are the same or different and each represent a hydrogen atom or an optionally protected carboxyl group; $L^4a$ represents an optionally substituted divalent aromatic hydrocarbon group or a bond; $n^1$ represents 1 or 2; and $L^{5a}$ is as defined above.

$Z^4$ is preferably $CR^3$ wherein $R^3$ is as defined above. When $Z^2$ is a nitrogen atom, $Z^4$ is more preferably $CR^{3a}$ wherein $R^{3a}$ is as defined above. When $Z^2$ is $CR^3$ wherein $R^3$ is as defined above, $Z^4$ is more preferably $CR^{3b}$ wherein $R^{3b}$ is as defined above. $Z^4$ is further preferably $CR^{3b}$ wherein $R^{3b}$ is as defined above, particularly preferably $CR^{3d}$ wherein $R^{3d}$ is as defined above.

Preferred examples of the structure of the 6-membered ring having $Z^1$, $Z^2$, $Z^3$, $Z^4$, and $Z^5$ include the following structures:

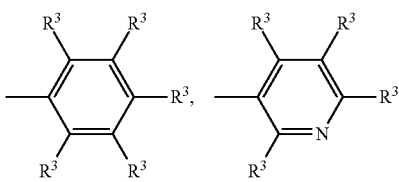

wherein $R^3$ is as defined above.

More preferred examples of the structure of the 6-membered ring having $Z^1$, $Z^2$, $Z^3$, $Z^4$, and $Z^5$ include the following structures:

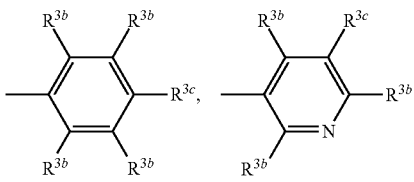

wherein $R^{3b}$ and $R^{3c}$ are as defined above.

Further preferred examples of the structure of the 6-membered ring having $Z^1$, $Z^2$, $Z^3$, $Z^4$, and $Z^5$ include the following structure:

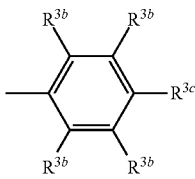

wherein $R^{3b}$ and $R^{3c}$ are as defined above.

$R^3$ is a hydrogen atom, a halogen atom, an optionally substituted $C_{1-6}$ alkyl group, an optionally substituted $C_{1-6}$ alkoxy group, or a group represented by the formula (2):

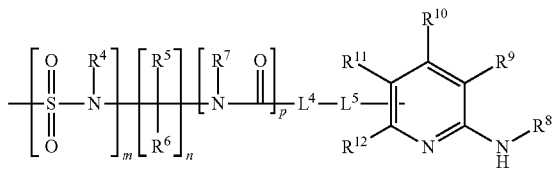

(2)

wherein $R^4$, $R^5$, $R^6$, $R^7$, $R^8$, $R^9$, $R^{10}$, $R^{11}$, $R^{12}$, $L^4$, $L^5$, m, n, and p are as defined above.

Examples of the substituent for the $C_{1-6}$ alkyl group or the $C_{1-6}$ alkoxy group represented by $R^3$ include one or more groups selected from substituent group α.

$R^{3b}$ is a hydrogen atom, a halogen atom, an optionally substituted $C_{1-6}$ alkyl group, or an optionally substituted $C_{1-6}$ alkoxy group. $R^{3b}$ is preferably a hydrogen atom or an optionally substituted $C_{1-6}$ alkyl group. Examples of the substituent for the $C_{1-6}$ alkyl group or the $C_{1-6}$ alkoxy group represented by $R^{3b}$ include one or more groups selected from substituent group α.

$R^{3c}$ is a group represented by the formula (2a):

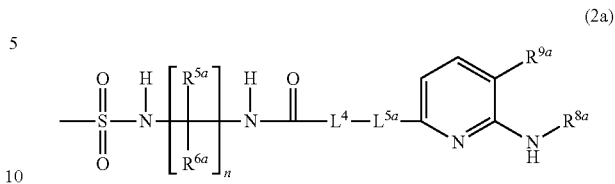

(2a)

wherein $R^{5a}$, $R^{6a}$, $R^{8a}$, $R^{9a}$, $L^4$, $L^{5a}$, and n are as defined above.

$R^{3c}$ is preferably a group represented by the formula (2b):

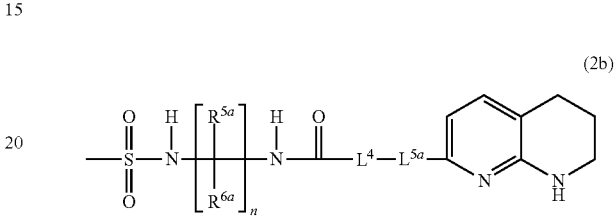

(2b)

wherein $R^{5a}$, $R^{6a}$, $L^4$, $L^{5a}$, and n are as defined above, more preferably a group represented by the formula (2c):

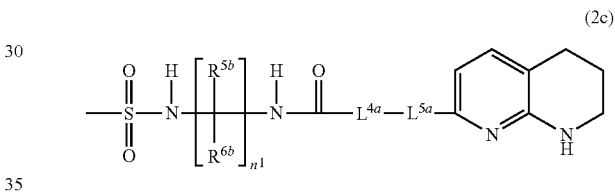

(2c)

wherein $R^{5b}$, $R^{6b}$, $L^4$, $L^{5a}$, and $n^1$ are as defined above.

$R^4$ is a hydrogen atom, an optionally substituted $C_{1-6}$ alkyl group, or an amino-protecting group. $R^4$ is preferably a hydrogen atom. Examples of the substituent for the $C_{1-6}$ alkyl group represented by $R^4$ include one or more groups selected from substituent group α.

n number of $R^5$ and n number of $R^6$ are the same or different and each represent a hydrogen atom, a halogen atom, an optionally substituted $C_{1-6}$ alkyl group, or an optionally protected carboxyl group. $R^5$ and $R^6$ are the same or different and are each preferably a hydrogen atom, an optionally substituted $C_{1-6}$ alkyl group, or an optionally protected carboxyl group. Examples of the substituent for the $C_{1-6}$ alkyl group represented by each of $R^5$ and $R^6$ include one or more groups selected from substituent group α.

n number of $R^{5a}$ and n number of $R^{6a}$ are the same or different and each represent a hydrogen atom, an optionally substituted $C_{1-6}$ alkyl group, or an optionally protected carboxyl group. $R^{5a}$ is preferably a hydrogen atom or an optionally protected carboxyl group. $R^{6a}$ is preferably a hydrogen atom or an optionally protected carboxyl group. Examples of the substituent for the $C_{1-6}$ alkyl group represented by each of $R^{5a}$ and $R^{6a}$ include one or more groups selected from substituent group α.

$n^1$ number of $R^{5b}$ and $n^1$ number of $R^{6b}$ are the same or different and each represent a hydrogen atom or an optionally protected carboxyl group. $R^{5b}$ is preferably a hydrogen atom. $R^{6b}$ is preferably a hydrogen atom.

$R^7$ is a hydrogen atom, an optionally substituted $C_{1-6}$ alkyl group, or an amino-protecting group. $R^7$ is preferably a hydrogen atom. Examples of the substituent for the $C_{1-6}$ alkyl group represented by $R^7$ include one or more groups selected from substituent group α.

$R^8$ is a hydrogen atom, an optionally substituted $C_{1-6}$ alkyl group, a bond with $L^5$, or an optionally substituted $C_{1-6}$ alkylene group together with $R^9$. $R^8$ is preferably a hydrogen atom, an optionally substituted $C_{1-6}$ alkyl group, or an optionally substituted $C_{1-6}$ alkylene group together with $R^9$, more preferably an optionally substituted $C_{1-6}$ alkylene group together with $R^9$. Examples of the substituent for the $C_{1-6}$ alkyl group represented by $R^8$ include one or more groups selected from substituent group α. Examples of the substituent for the $C_{1-6}$ alkylene group formed together with $R^9$ include one or more groups selected from substituent group β.

Substituent group β: a halogen atom, a cyano group, a carbamoyl group, a sulfo group, an optionally protected amino group, an optionally protected hydroxyl group, an optionally protected carboxyl group, a $C_{1-6}$ alkyl group, a $C_{1-6}$ alkoxy group, an aryl group, a $C_{1-6}$ alkylamino group, a di($C_{1-6}$ alkyl)amino group, a heterocyclic group, and an oxo group.

$R^{8a}$ is a hydrogen atom or an optionally substituted $C_{1-6}$ alkyl group; $R^{9a}$ is a hydrogen atom; or $R^{8a}$ and $R^{9a}$ together represent an optionally substituted $C_{1-6}$ alkylene group. Preferably, $R^{8a}$ and $R^{9a}$ together represent an optionally substituted $C_{1-6}$ alkylene group. Examples of the substituent for the $C_{1-6}$ alkyl group represented by $R^{8a}$ include one or more groups selected from substituent group α.

Examples of the substituent for the $C_{1-6}$ alkylene group formed together with $R^{9a}$ include one or more groups selected from substituent group β.

$R^9$ is a hydrogen atom, a halogen atom, an optionally protected amino group, an optionally substituted $C_{1-6}$ alkyl group, an optionally substituted $C_{1-6}$ alkylamino group, an optionally substituted di($C_{1-6}$alkyl)amino group, a bond with $L^5$, or an optionally substituted $C_{1-6}$alkylene group together with $R^8$. $R^9$ is preferably a hydrogen atom or an optionally substituted $C_{1-6}$ alkylene group together with $R^8$, more preferably an optionally substituted $C_{1-6}$ alkylene group together with $R^8$. Examples of the substituent for the $C_{1-6}$ alkyl group represented by $R^9$ include one or more groups selected from substituent group α. Examples of the substituent for the $C_{1-6}$ alkylene group formed together with $R^8$ include one or more groups selected from substituent group β.

$R^{10}$ and $R^{11}$ are the same or different and each represent a hydrogen atom, a halogen atom, an optionally protected amino group, an optionally substituted $C_{1-6}$ alkyl group, an optionally substituted $C_{1-6}$ alkylamino group, an optionally substituted di($C_{1-6}$ alkyl)amino group, or a bond with $L^5$. $R^{10}$ and $R^{11}$ are the same or different and are each preferably a hydrogen atom, a halogen atom, or an optionally substituted $C_{1-6}$ alkyl group, more preferably a hydrogen atom. Examples of the substituent for the $C_{1-6}$ alkyl group, the $C_{1-6}$ alkylamino group, or the di($C_{1-6}$alkyl)amino group represented by each of $R^{10}$ and $R^{11}$ include one or more groups selected from substituent group α.

$R^{12}$ is a hydrogen atom, a halogen atom, an optionally protected amino group, an optionally substituted $C_{1-6}$ alkyl group, an optionally substituted $C_{1-6}$ alkylamino group, an optionally substituted di($C_{1-6}$ alkyl)amino group, or a bond with $L^5$. $R^{12}$ is preferably a bond with $L^5$.

Examples of the substituent for the $C_{1-6}$ alkyl group, the $C_{1-6}$ alkylamino group, or the di($C_{1-6}$alkyl)amino group represented by $R^{12}$ include one or more groups selected from substituent group α.

Preferred examples of the structure of the 6-membered ring having $R^8$, $R^9$, $R^{10}$, $R^{11}$, and $R^{12}$ include the following structure:

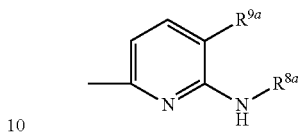

wherein $R^{8a}$ and $R^{9a}$ are as defined above.

More preferred examples of the structure of the 6-membered ring having $R^8$, $R^9$, $R^{10}$, $R^{11}$, and $R^{12}$ include the following structures:

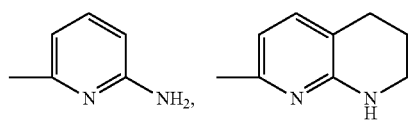

Further preferred examples of the structure of the 6-membered ring having $R^8$, $R^9$, $R^{10}$, $R^{11}$, and $R^{12}$ include the following structure:

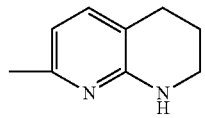

$L^4$ is an optionally substituted divalent aromatic hydrocarbon group, an optionally substituted divalent heterocyclic group, or a bond. $L^4$ is preferably a divalent aromatic hydrocarbon group, a divalent heterocyclic group, or a bond, more preferably an optionally substituted divalent aromatic hydrocarbon group or a bond, further preferably a phenylene group, an indolediol group, or a bond. Examples of the substituent for the divalent aromatic hydrocarbon group or the divalent heterocyclic group represented by $L^4$ include one or more groups selected from substituent group α.

$L^5$ is an optionally substituted $C_{1-6}$ alkylene group, an optionally substituted —O—$C_{1-6}$ alkylene group, or an optionally substituted —NH—$C_{1-6}$ alkylene group.

$L^5$ is preferably an optionally substituted $C_{1-6}$ alkylene group. Examples of the substituent for the $C_{1-6}$ alkylene group, the —O—$C_{1-6}$ alkylene group, or the —NH—$C_{1-6}$ alkylene group represented by $L^5$ include one or more groups selected from substituent group α.

$L^{5a}$ is an optionally substituted $C_{1-6}$ alkylene group. Examples of the substituent for the $C_{1-6}$ alkylene group represented by $L^{5a}$ include one or more groups selected from substituent group α.

m is 0 or 1. m is preferably 1.

n is an integer of 1 to 3. n is preferably 1 or 2.

p is 0 or 1. p is preferably 1.

$L^2$ is an optionally substituted $C_{1-6}$ alkylene group. $L^2$ is preferably a $C_{1-6}$ alkylene group, more preferably a $C_{1-4}$ alkylene group. Examples of the substituent for the $C_{1-6}$ alkylene group represented by $L^2$ include one or more groups selected from substituent group α.

$L^3$ is an optionally substituted $C_{1-6}$ alkylene group. L is preferably a $C_{1-6}$ alkylene group, more preferably a $C_{1-4}$alkylene group. Examples of the substituent for the $C_{1-6}$ alkylene group represented by L³ include one or more groups selected from substituent group α.

L¹ is a group represented by the formula (3):

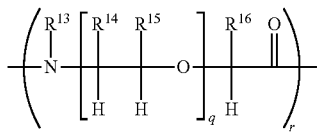

wherein $R^{13}$, $R^{14}$, $R^{15}$, $R^{16}$, q, and r are as defined above. L¹ is preferably a group represented by the formula (3a):

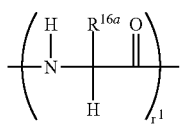

wherein $r^1$ number of $R^{16a}$ are the same or different and each represent an optionally sulfo group-substituted $C_{1-4}$ alkyl group; and $r^1$ represents 1 or 2.

r number of $R^{13}$ are the same or different and each represent a hydrogen atom, an optionally substituted $C_{1-6}$ alkyl group, or an amino-protecting group. Each of r number of $R^{13}$ is preferably a hydrogen atom or an amino-protecting group, more preferably a hydrogen atom. Examples of the substituent for the $C_{1-6}$ alkyl group represented by each of r number of $R^{13}$ include one or more groups selected from substituent group α.

q×r number of $R^{14}$ and q×r number of $R^{15}$ are the same or different and each represent a hydrogen atom or an optionally substituted $C_{1-6}$ alkyl group. Each of q×r number of $R^{14}$ and q×r number of $R^{15}$ is preferably a hydrogen atom or a $C_{1-6}$ alkyl group, more preferably a hydrogen atom. Examples of the substituent for the $C_{1-6}$ alkyl group represented by each of q×r number of $R^{14}$ and q×r number of $R^{15}$ include one or more groups selected from substituent group α.

r number of $R^{16}$ are the same or different and each represent a hydrogen atom, an optionally substituted $C_{1-6}$ alkyl group, or a group represented by the formula (4):

$R^{16}$ is preferably a hydrogen atom, an optionally substituted $C_{1-4}$ alkyl group, or a group represented by the formula (4), more preferably a hydrogen atom, an optionally sulfo group-substituted $C_{1-4}$ alkyl group, or a group represented by the formula (4), further preferably an optionally sulfo group-substituted $C_{1-4}$ alkyl group. Examples of the substituent for the $C_{1-6}$ alkyl group represented by $R^{16}$ include one or more groups selected from substituent group γ.

Substituent group γ: a halogen atom, a cyano group, a carbamoyl group, a sulfo group, a guanidino group, an optionally protected amino group, an optionally protected hydroxyl group, an optionally protected carboxyl group, an optionally protected mercapto group, a $C_{1-6}$ alkyl group, a $C_{1-6}$ alkoxy group, an aryl group, a $C_{1-6}$ alkylamino group, a di($C_{1-6}$alkyl)amino group, a $C_{1-6}$ alkylthio group, a heterocyclic group, and an oxo group.

s number of $R^{17}$ are the same or different and each represent a hydrogen atom or an optionally substituted $C_{1-6}$ alkyl group. $R^{17}$ is preferably a hydrogen atom or a $C_{1-6}$ alkyl group. Examples of the substituent for the $C_{1-6}$ alkyl group represented by $R^{17}$ include one or more groups selected from substituent group γ.

t number of $R^{18}$ are the same or different and each represent a hydrogen atom, an optionally substituted $C_{1-6}$ alkyl group, or an amino-protecting group. $R^{18}$ is preferably a hydrogen atom or an amino-protecting group. Examples of the substituent for the $C_{1-6}$ alkyl group represented by $R^{18}$ include one or more groups selected from substituent group α.

t number of $R^{19}$ are the same or different and each represent a hydrogen atom or an optionally substituted $C_{1-6}$alkyl group. $R^{19}$ is preferably a hydrogen atom or a $C_{1-6}$ alkyl group. Examples of the substituent for the $C_{1-6}$ alkyl group represented by $R^{19}$ include one or more groups selected from substituent group γ.

s is an integer of 1 to 3. s is preferably 1 or 2.

t is an integer of 0 to 3. t is preferably 1 or 2.

q is an integer of 0 to 3. r is an integer of 0 to 3. r is preferably an integer of 1 to 3.

The compound represented by the formula (1) or the salt thereof of the present invention is preferably a compound or a salt thereof wherein $A^1$ is a group having a polyaminopolycarboxylic acid structure; $R^1$ is a hydrogen atom or an optionally substituted $C_{1-6}$ alkyl group; $R^2$ is a hydrogen atom or an optionally substituted $C_{1-6}$ alkyl group; $Z^1$, $Z^2$, $Z^4$, and $Z^5$ are the same or different and each represent $CR^{3b}$ wherein $R^{3b}$ is as defined above; $Z^3$ is $CR^{3c}$ wherein $R^{3a}$ is as defined above; $L^2$ is an optionally substituted $C_{1-6}$ alkylene group; $L^3$ is an optionally substituted $C_{1-6}$ alkylene group; and $L^1$ is a group represented by the formula (3):

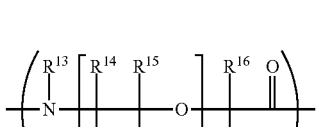

wherein $R^{13}$, $R^{14}$, $R^{15}$, $R^{16}$, q, and r are as defined above with the substituent for each group being the same as above.

The compound represented by the formula (1) or the salt thereof of the present invention is more preferably a compound or a salt thereof wherein $A^1$ is a group represented by the formula (5), (6), (7), (8), (9), (10), (11), or (12):

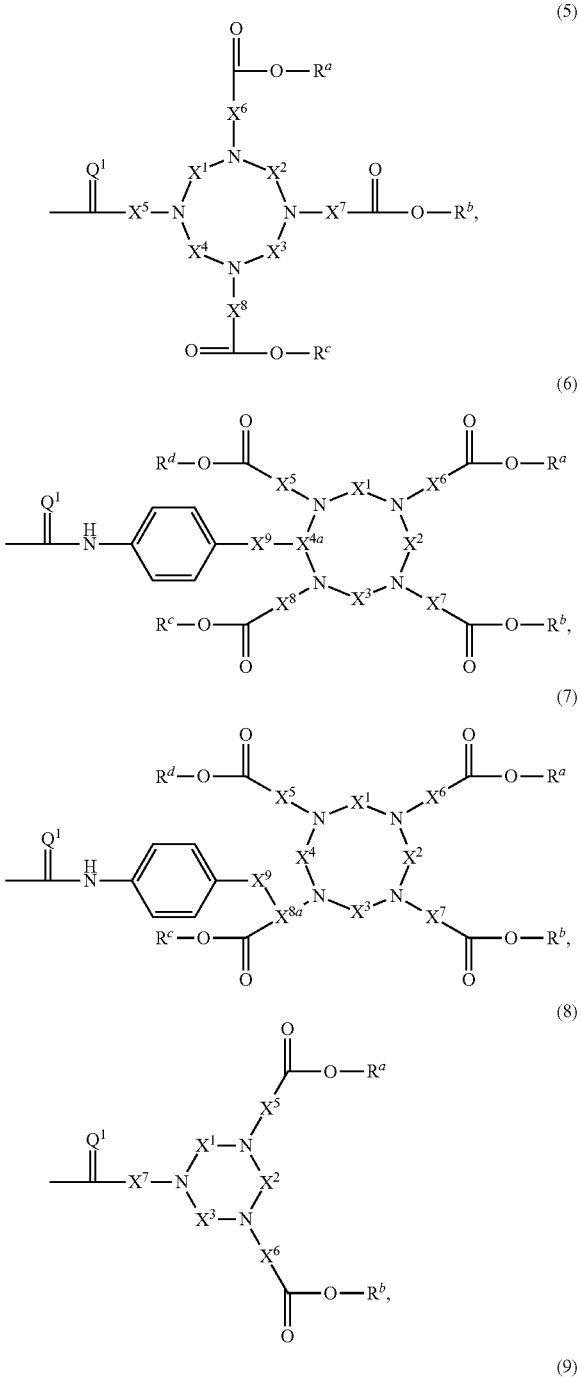

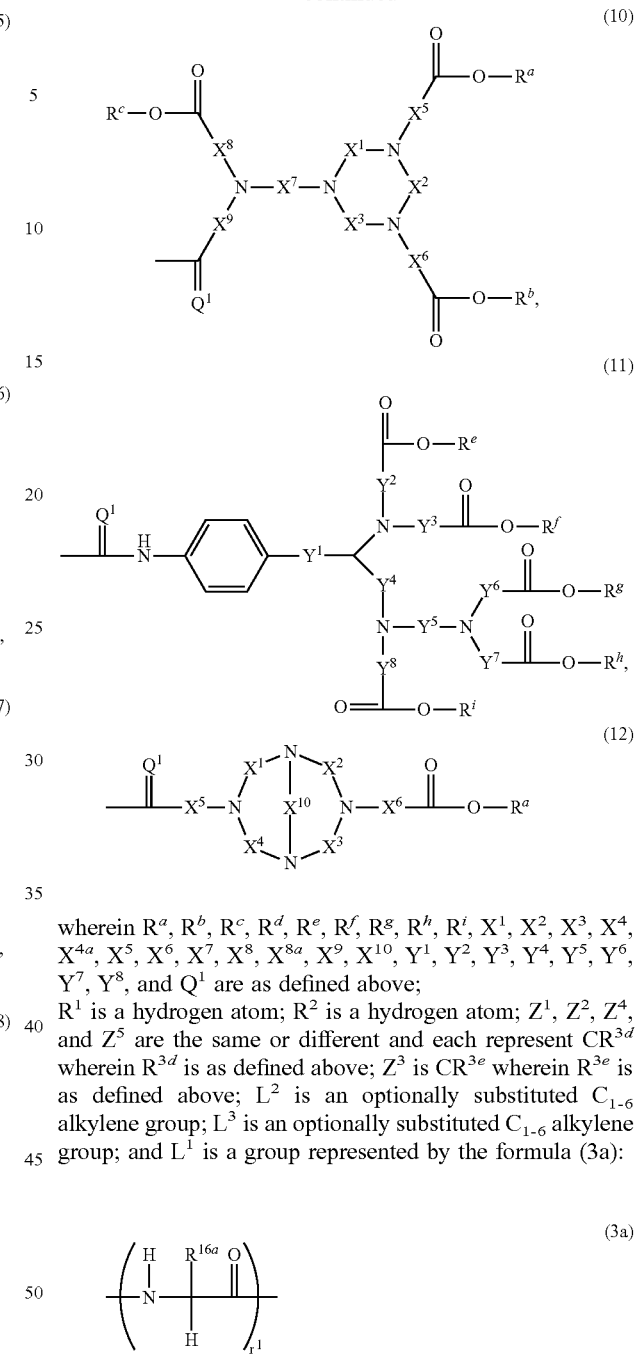

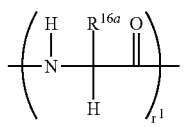

wherein $R^a$, $R^b$, $R^c$, $R^d$, $R^e$, $R^f$, $R^g$, $R^h$, $R^i$, $X^1$, $X^2$, $X^3$, $X^4$, $X^{4a}$, $X^5$, $X^6$, $X^7$, $X^8$, $X^{8a}$, $X^9$, $X^{10}$, $Y^1$, $Y^2$, $Y^3$, $Y^4$, $Y^5$, $Y^6$, $Y^7$, $Y^8$, and $Q^1$ are as defined above;

$R^1$ is a hydrogen atom; $R^2$ is a hydrogen atom; $Z^1$, $Z^2$, $Z^4$, and $Z^5$ are the same or different and each represent $CR^{3d}$ wherein $R^{3d}$ is as defined above; $Z^3$ is $CR^{3e}$ wherein $R^{3e}$ is as defined above; $L^2$ is an optionally substituted $C_{1-6}$ alkylene group; $L^3$ is an optionally substituted $C_{1-6}$ alkylene group; and $L^1$ is a group represented by the formula (3a):

$$\left(\!\!-\!\!\underset{H}{\overset{H}{N}}\!\!-\!\!\underset{}{\overset{R^{16a}}{\underset{}{|}}}\!\!-\!\!\underset{}{\overset{O}{\underset{}{\|}}}\!\!-\!\!\right)_{r^1} \quad (3a)$$

wherein $R^{16a}$ and $r^1$ are as defined above with the substituent for each group being the same as above.

The compound represented by the formula (1) or the salt thereof of the present invention is further preferably any of the following compounds or salts thereof described in Examples: 2,2′,2″-(10-((4R,7R)-16-(4-(N—((S)-1-carboxy-2-(4-(2-(5,6,7,8-tetrahydro-1,8-naphthyridin-2-yl)ethyl) benzamido)ethyl)sulfamoyl)-3,5-dimethylphenoxy)-2,5,8, 13-tetraoxo-4,7-bis(sulfomethyl)-3,6,9,12-tetraazahexadecyl)-1,4,7,10-tetraazacyclododecane-1,4,7-triyl)triacetic acid (Example 1, compound No. A8), 2,2′,2″-(10-(2-(((R)-1-((2-(4-(4-(N—((S)-1-carboxy-2-(4-(2-(5,6,7, 8-tetrahydro-1,8-naphthyridin-2-yl)ethyl)benzamido)ethyl)

sulfamoyl)-3,5-dimethylphenoxy)butanamido)ethyl) amino)-1-oxo-3-sulfopropan-2-yl)amino)-2-oxoethyl)-1,4, 7,10-tetraazacyclododecane-1,4,7-triyl)triacetic acid (Example 2, compound No. B2), 2,2',2''-(10-((4R,7R,10R)-19-(4-(N-((s)-1-carboxy-2-(4-(2-(5,6,7,8-tetrahydro-1,8-naphthyridin-2-yl)ethyl)benzamido)ethyl)sulfamoyl)-3,5-dimethylphenoxy)-2,5,8,11,16-pentaoxo-4,7,10-tris(sulfomethyl)-3,6,9,12,15-pentaazanonadecyl)-1,4,7,10-tetraazacyclododecane-1,4,7-triyl)triacetic acid (Example 3, compound No. C3), (S)-2,2',2'-(10-(19-(4-(N-(1-carboxy-2-(4-(2-(5,6,7,8-tetrahydro-1,8-naphthyridin-2-yl)ethyl)benzamido)ethyl)sulfamoyl)-3,5-dimethylphenoxy)-2,11,16-trioxo-6,9-dioxa-3,12,15-triazanonadecyl)-1,4,7,10-tetraazacyclododecane-1,4,7-triyl)triacetic acid (Example 4, compound No. D3), 2,2',2''-(10-((S)-4-(4-aminobutyl)-22-(4-(N-((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-2,5,14,19-tetraoxo-9,12-dioxa-3,6,15,18-tetraazadocosyl)-1,4,7,10-tetraazacyclododecane-1,4,7-triyl)triacetic acid (Example 5, compound No. E3), (S)-2,2',2''-(10-(28-(4-(N-(1-carboxy-2-(4-(2-(5,6,7,8-tetrahydro-1,8-naphthyridin-2-yl)ethyl)benzamido)ethyl)sulfamoyl)-3,5-dimethylphenoxy)-2,11,20,25-tetraoxo-6,9,15,18-tetraoxa-3,12,21,24-tetraazaoctacosyl)-1,4,7,10-tetraazacyclododecane-1,4,7-triyl)triacetic acid (Example 6, compound No. F3), 2,2',2''-(10-((R)-22-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-2,5,14,19-tetraoxo-4-(sulfomethyl)-9,12-dioxa-3,6,15,18-tetraazadocosyl)-1,4,7,10-tetraazacyclododecane-1,4,7-triyl)triacetic acid (Example 7, compound No. G3), 2,2',2''-(10-((9R)-18-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)-4-(((R)-1-((2-(4-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)butanamido)ethyl)amino)-1-oxo-3-sulfopropan-2-yl)carbamoyl)-2,7,10,15-tetraoxo-9-(sulfomethyl)-3,8,11,14-tetraazaoctadecyl)-1,4,7,10-tetraazacyclododecane-1,4,7-triyl)triacetic acid (Example 8, compound No. H9), 2,2',2'',2'''-(10-((4R,7R)-16-((5-(2-carboxy-1-(5-(2-(5,6,7,8-tetrahydro-1,8-naphthyridin-2-yl)ethoxy)-1H-indol-1-yl)ethyl)pyridin-3-yl)oxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid (Example 9, compound No. I21), 2,2',2''-(10-((4R,7R)-16-((5-(2-carboxy-1-(4-(2-(5,6,7,8-tetrahydro-1,8-naphthyridin-2-yl)ethyl)-1H-indol-1-yl)ethyl)pyridin-3-yl)oxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid (Example 10, compound No. J9), 2,2',2'-(10-(2-(((R)-1-((2-(4-(4-(N—((R)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid (Example 11, compound No. K8), 2,2',2''-(10-((4S,9R)-18-(4-(N—((S)-2-(4-(2-(6-aminopyridin-2-yl)ethyl)benzamido)-1-carboxyethyl)sulfamoyl)-3,5-dimethylphenoxy)-4-(((R)-1-((2-(4-(4-(4-(N—((S)-2-(4-(2-(6-aminopyridin-2-yl)ethyl)benzamido)-1-carboxyethyl)sulfamoyl)-3,5-dimethylphenoxy)butanamido)ethyl)amino)-1-oxo-3-sulfopropan-2-yl)carbamoyl)-2,7,10,15-tetraoxo-9-(sulfomethyl)-3,8,11,14-tetraazaoctadecyl)-1,4,7,10-tetraazacyclododecane-1,4,7-triyl)triacetic acid (Example 12, compound No. L10), 2,2',2''-(10-(2-(((R)-1-((2-(4-(4-(N—((S)-2-(4-(2-(6-aminopyridin-2-yl)ethyl)benzamido)-1-carboxyethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid (Example 13, compound No. M2), 2,2',2''-(10-((4R,7R)-16-(4-(N—((S)-2-(4-(2-(6-aminopyridin-2-yl)ethyl)benzamido)-1-carboxyethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid (Example 14, compound No. N3), 2,2',2''-(10-((4R,7R)-16-(4-(N—((S)-1-carboxy-2-(5-(5,6,7,8-tetrahydro-1,8-naphthyridin-2-yl)pentanamido)ethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid (Example 15, compound No. O10), 2,2',2'-(10-(2-(((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid (Example 16, compound No. P2), 2,2',2''-(10-((4R,7R)-16-(4-((S)-2-carboxy-1-(4-(2-(5,6,7,8-tetrahydro-1,8-naphthyridin-2-yl)ethyl)benzamido)ethyl)-2-fluorophenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid (Example 17, compound No. O12), 2,2'-((1-(((S)-2-(bis(carboxymethyl)amino)-3-(4-(3-((R)-1-(((R)-1-((2-(4-(4-(N—((S)-1-carboxy-2-(4-(2-(5,6,7,8-tetrahydro-1,8-naphthyridin-2-yl)ethyl)benzamido)ethyl)sulfamoyl)-3,5-dimethylphenoxy)butanamido)ethyl)amino)-1-oxo-3-sulfopropan-2-yl)amino)-1-oxo-3-sulfopropan-2-yl)thioureido)phenyl) propyl)(carboxymethyl)amino) propan-2-yl)azanediyl)diacetic acid (Example 18, compound No. R3), (S)-2,2',2''-(10-(2-((2-(4-4-(N-(1-carboxy-2-(4-(2-(5,6,7,8-tetrahydro-1,8-naphthyridin-2-yl)ethyl)benzamido)ethyl)sulfamoyl)-3,5-dimethylphenoxy)butanamido)ethyl)amino)-2-oxoethyl)-1,4,7,10-tetraazacyclododecane-1,4,7-triyl)triacetic acid (Example 19, compound No. S2) 2,2',2''',2''''-(2-(4-(3-((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)thioureido)benzyl)-1,4,7,10-tetraazacyclododecane-1,4,7,10-tetrayl)tetraacetic acid (Example 20, compound No. T2), 2,2'-((1-(((S)-2-(bis(carboxymethyl)amino)-3-(4-(3-((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)thioureido)phenyl) propyl)(carboxymethyl)amino)propan-2-yl)azanediyl)diacetic acid (Example 21, compound No. U1), 2,2',2''-(10-(2-(((R)-1-((2-(4-(4-(N—((S)-1-carboxy-2-(4-(5,6,7,8-tetrahydro-1,8-naphthyridin-2-yl)butanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid (Example 22, compound No. V8), 2,2',2''-(10-(2-(((R)-1-((2-(4-(4-(N—((S)-1-carboxy-2-(6-(5,6,7,8-tetrahydro-1,8-naphthyridin-2-yl) hexanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid (Example 23, compound No. W10), 2,2',2''-(10-((4R,7R)-16-(4-(N—((S)-1-carboxy-2-(5-(5,6,7,8-tetrahydro-1,8-naphthyridin-2-yl)ethyl)thiophene-2-carboxamido)ethyl)sulfamoyl)-3,5-dimethylphenoxy)-2,5,8,13-tetraoxo-4,7-bis (sulfomethyl)-3,6,9,12-tetraazahexadecyl)-1,4,7,10-tetraazacyclododecane-1,4,7-triyl)triacetic acid (Example 24, compound No. X9), 2,2',2"-(10-((4R,7R)-16-(4-(N—((S)-1-carboxy-2-(4-(2-(5,6,7,8-tetrahydro-1,8-naphthyridin-2-yl)ethyl)benzamido)ethyl)sulfamoyl)phenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid hexasodium salt (Example 25, compound No. Y13), 2,2',2"-(10-((4R,7R)-16-(4-(N—((S)-1-carboxy-2-(4-(3-(pyridin-2-ylamino)propyl)benzamido)ethyl)sulfamoyl)-3,5-dimethylphenoxy)-2,5,8,13-tetraoxo-4,7-bis(sulfomethyl)-3,6,9,12-tetraazahexadecyl)-1,4,7,10-tetraazacyclododecane-1,4,7-triyl)triacetic acid (Example 26, compound No. Z8), 2,2'-(7-(((R)-1-carboxy-4-(((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-4-oxobutyl)-1,4,7-triazonane-1,4-diyl)diacetic acid (Example 27, compound No. Aa7), and 5-(((R)-1-((2-(4-(4-(N—((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-(11-(carboxymethyl)-1,4,8,11-tetraazabicyclo[6.6.2]hexadecan-4-yl)-5-oxopentanoic acid (Example 28, compound Nos. Ab9-a and Ab9-b (Ab9-a and Ab9-b are stereoisomers)).

Next, methods for producing the compound represented by the formula (1) of the present invention will be described.

The compound represented by the formula (1) of the present invention is produced by the combination of methods known per se in the art and can be produced by, for example, production methods given below.

Production Method 1

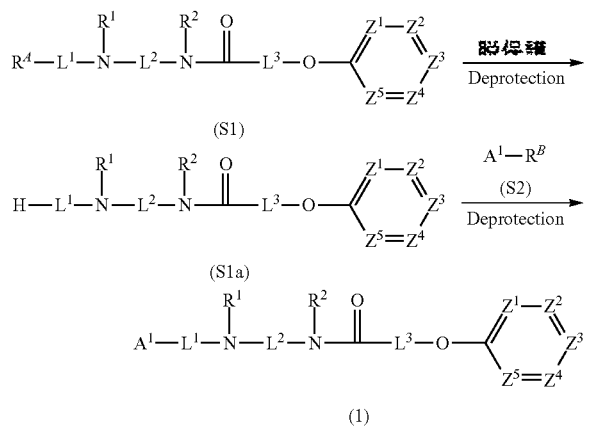

wherein R represents an amino-protecting group; and $R^1$, $R^2$, $R^B$, $Z^1$, $Z^2$, $Z^3$, $Z^4$, $Z^5$, $A^1$, $L^1$, $L^2$, and $L^3$ are as defined above.

(1) The compound represented by the formula (S1a) can be produced by deprotecting a compound represented by the formula (S1). This reaction can be carried out by a method described in, for example, T. W. Greene et al., Protective Groups in Organic Synthesis, Vol. 4, p. 696-926, 2007, John Wiley & Sons, INC.

(2) The compound represented by the formula (S2) is a compound known as a bifunctional chelate. For example, as the compound represented by the formula (S2), DOTA (1,4,7,10-tetraazacyclododecane-1,4,7,10-tetraacetic acid), TETA (1,4,8,11-tetraazacyclotetradecane-1,4,8,11-tetraacetic acid), DTPA (diethylenetriaminepentaacetic acid), and DOTA (1,4,7,10-tetraazacyclododecane-1,4,7,10-tetraacetic acid tri-tert-butyl ester and 1,4,7,10-tetraazacyclododecane-1,4,7,10-tetraacetic acid tribenzyl ester) having a protected carboxyl group are known.

(2-1) When $R^B$ in the formula (S2) is a hydroxyl group, the compound represented by the formula (1) can be produced by reacting the compound represented by the formula (S1a) with the compound represented by the formula (S2) in the presence of a condensing agent and in the presence or absence of a base. This reaction can be carried out by a method described in, for example, Bioconjugate Chem., Vol. 3, Issue 2, 1992 or Chemical Reviews, Vol. 97, p. 2243, 1997.

A solvent used in this reaction is not particularly limited as long as the solvent does not influence the reaction. Examples thereof include ethers, esters, halogenated hydrocarbons, nitriles, amides, alcohols, and water. These solvents may be used as a mixture. Preferred examples of the solvent include amides. N,N-Dimethylformamide and N,N-dimethylacetamide are more preferred. The amount of the solvent used is not particularly limited and may be 1 to 1,000 times (v/w) the amount of the compound represented by the formula (S1a).

Examples of the base used, if desired, in this reaction include inorganic bases and organic bases. The amount of the base used may be 1 to 50 times, preferably 1 to 10 times the mol of the compound represented by the formula (S1a).

Examples of the condensing agent used in this reaction include: carbodiimides such as N,N'-dicyclohexylcarbodiimide and 1-ethyl-3-(3-dimethylaminopropyl)carbodiimide; carbonyls such as carbonyldiimidazole; acid azides such as diphenylphosphorylazide; acid cyanides such as diethylphosphorylcyanide; 2-ethoxy-1-ethoxycarbonyl-1,2-dihydroquinoline; ureas such as O-benzotriazol-1-yl-1,1,3,3-tetramethyluronium=hexafluorophosphate and O-(7-azabenzotriazol-1-yl)-1,1,3,3-tetramethyluronium=hexafluorophosphate; and phosphonium salts such as benzotriazol-1-yloxy-trisdimethylaminophosphonium hexafluorophosphate and (benzotriazol-1-yloxy)tripyrrolidinophosphonium hexafluorophosphate. The condensation method can involve mixing the compound represented by the formula (S1a) and the compound represented by the formula (S2), followed by the addition of the condensing agent. Alternatively, the compound represented by the formula (S2) may be activated in advance with the condensing agent and then reacted with the compound represented by the formula (S1a). In addition, an active ester such as N-hydroxysuccinimide or pentafluorophenol can also be used.

The amount of the compound represented by the formula (S2) used is not particularly limited and may be 0.5 to 10 times (w/w) the amount of the compound represented by the formula (S1a). The reaction may be carried out at a temperature of −30 to 100° C., preferably 0 to 50° C. for 1 minute to 72 hours.

(2-2) When $R^B$ in the formula (S2) is a leaving group, the compound represented by the formula (1) can be produced by reacting the compound represented by the formula (S1a) with the compound represented by the formula (S2) in the presence of a base.

A solvent used in this reaction is not particularly limited as long as the solvent does not influence the reaction. Examples thereof include ethers, esters, halogenated hydrocarbons, nitriles, and amides. These solvents may be used as a mixture. The amount of the solvent used is not particularly limited and may be 1 to 1,000 times (v/w) the amount of the compound represented by the formula (S1a).

Examples of the base used in this reaction include inorganic bases and organic bases. The amount of the base used may be 1 to 50 times, preferably 1 to 10 times the mol of the compound represented by the formula (S1a).

The amount of the compound represented by the formula (82) used is not particularly limited and may be 0.5 to 10 times (w/w) the amount of the compound represented by the formula (S1a). The reaction may be carried out at a temperature of −30 to 100° C., preferably 0 to 50° C. for 1 minute to 72 hours.

Production Method 2

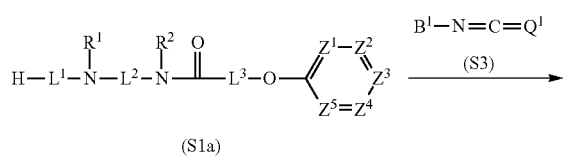

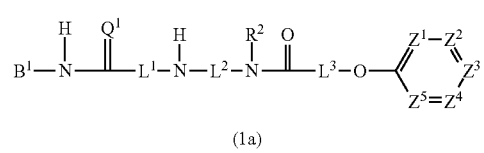

wherein $B^1$, $R^1$, $R^2$, $Z^1$, $Z^2$, $Z^3$, $Z^4$, $Z^5$, $L^1$, $L^2$, $L^3$, and $Q^1$ are as defined above.

For example, as the compound represented by the formula (S3), NCS-DOTA (2-(p-isothiocyanatobenzyl)-1,4,7,10-tetraazacyclododecane-1,4,7,10-tetraacetic acid) and MXDTPA (2-(p-isothiocyanatobenzyl)-5(6)-methyl-diethylenetriaminepentaacetic acid) are known. The compound represented by the formula (1a) can be produced by reacting the compound represented by the formula (S1a) with the compound represented by the formula (S3).

A solvent used in this reaction is not particularly limited as long as the solvent does not influence the reaction. Examples thereof include ethers, esters, halogenated hydrocarbons, nitriles, amides, alcohols, and water. These solvents may be used as a mixture. Preferred examples of the solvent include amides. N,N-Dimethylformamide and N,N-dimethylacetamide are more preferred. The amount of the solvent used is not particularly limited and may be 1 to 1,000 times (v/w) the amount of the compound represented by the formula (S1a).

Examples of the base used in this reaction include inorganic bases and organic bases. The amount of the base used may be 1 to 50 times, preferably 1 to 10 times the mol of the compound represented by the formula (S1a).

The amount of the compound represented by the formula (S3) used is not particularly limited and may be 0.5 to 10 times (w/w) the amount of the compound represented by the formula (S1a). The reaction may be carried out at a temperature of −30 to 100° C., preferably 0 to 50° C. for 1 minute to 72 hours.

Production Method 3

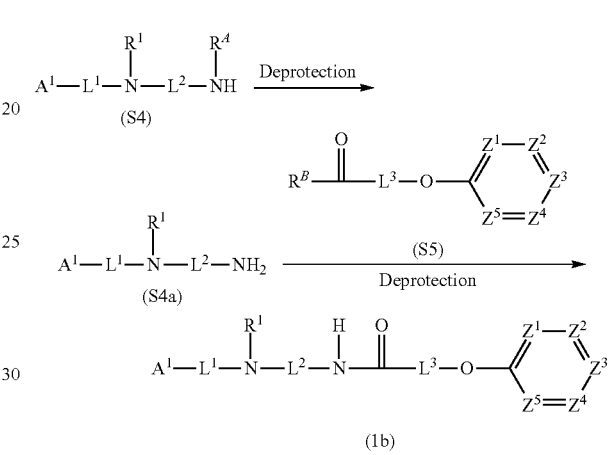

wherein $R^1$, $R^A$, $R^B$, $Z^1$, $Z^2$, $Z^3$, $Z^4$, $Z^5$, $L^1$, $L^2$, $L^3$, and $A^1$ are as defined above.

(1) The compound represented by the formula (S4a) can be produced by deprotecting a compound represented by the formula (S4). This reaction can be carried out according to production method 1(1).

(2) The compound represented by the formula (1b) can be produced by reacting the compound represented by the formula (S4a) with a compound represented by the formula (S5). This reaction can be carried out according to production method 1(2).

Next, methods for producing starting materials will be described.

Production Method A

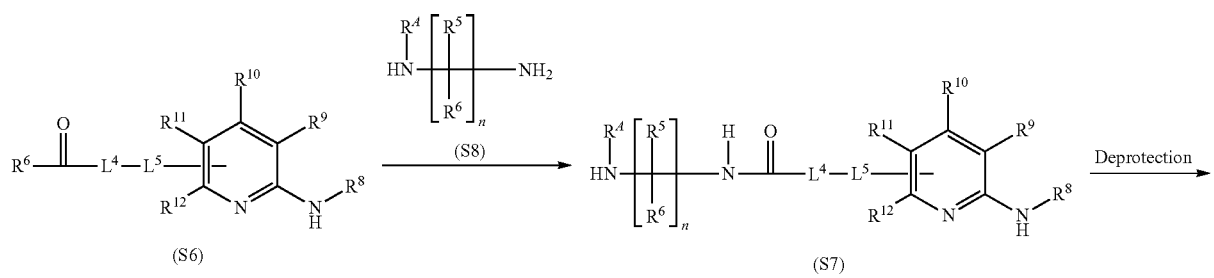

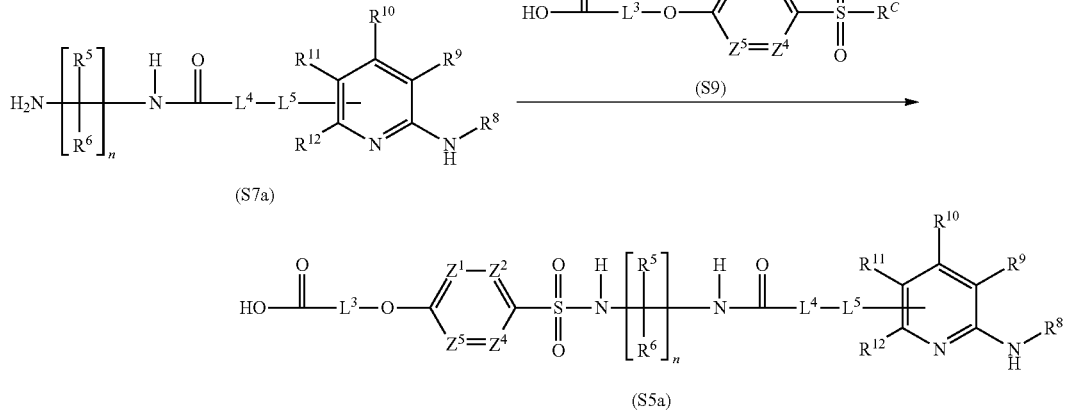

(S7a)

(S5a)

wherein $R^c$ represents a leaving group; and $R^5$, $R^6$, $R^8$, $R^9$, $R^{10}$, $R^{11}$, $R^{12}$, $R^A$, $R^B$, $Z^1$, $Z^2$, $Z^4$, $Z^5$, $L^3$, $L^4$, $L^5$, and n are as defined above.

(1) For example, as the compound represented by the formula (S6), 4-(2-(5,6,7,8-tetrahydro-1,8-naphthyridin-2-yl)ethyl)benzoic acid is known. For example, as the compound represented by the formula (S8), benzyl (2-aminoethyl)carbamate is known. The compound represented by the formula (S7) can be produced by reacting the compound represented by the formula (S6) with the compound represented by the formula (S8). This reaction can be carried out according to production method 1(2).

(2) The compound represented by the formula (S7a) can be produced by deprotecting the compound represented by the formula (S7). This reaction can be carried out according to production method 1(1).

(3) The compound represented by the formula (S5a) can be produced by reacting the compound represented by the formula (S7a) with a compound represented by the formula (S9) in the presence of a base. A solvent used in this reaction is not particularly limited as long as the solvent does not influence the reaction. Examples thereof include ethers, esters, halogenated hydrocarbons, nitriles, and amides. These solvents may be used as a mixture. Preferred examples of the solvent include halogenated hydrocarbons. Methylene chloride is more preferred. The amount of the solvent used is not particularly limited and may be 1 to 1,000 times (v/w) the amount of the compound represented by the formula (S7a).

Examples of the base used, if desired, in this reaction include inorganic bases and organic bases. The amount of the base used may be 1 to 50 times, preferably, 1 to 10 times the mol of the compound represented by the formula (S7a). The amount of the compound represented by the formula (S9) used is not particularly limited and may be 1 to 50 times, preferably 1 to 10 times the mol of the compound represented by the formula (S7a).

The reaction may be carried out at a temperature of −30 to 100° C., preferably 0 to 50° C. for 1 minute to 72 hours.

In this production method, the conversion of $Z^3$ is described. In the same way as this method, $Z^1$, $Z^2$, $Z^4$, or $Z^5$ can also be converted.

Production Method B

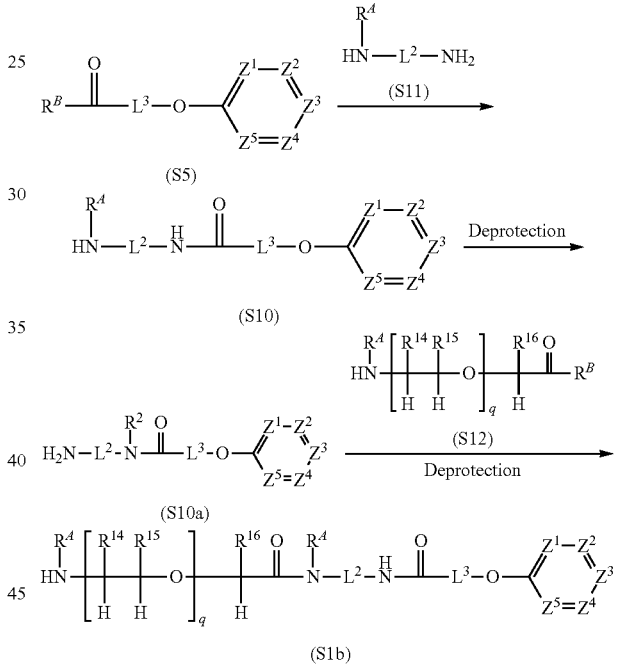

wherein $R^2$, $R^{14}$, $R^{15}$, $R^{16}$, $R^A$, $R^B$, $Z^1$, $Z^2$, $Z^3$, $Z^4$, $Z^5$, $L^2$, $L^3$, and q are as defined above.

(1) For example, as the compound represented by the formula (S11), benzyl (2-aminoethyl)carbamate is known. The compound represented by the formula (S10) can be produced by reacting the compound represented by the formula (S5) with the compound represented by the formula (S11). This reaction can be carried out according to production method 1(2).

(2) The compound represented by the formula (S10a) can be produced by deprotecting the compound represented by the formula (S10). This reaction can be carried out according to production method 1(1).

(3) For example, as the compound represented by the formula (S12), Fmoc-cysteic acid and Fmoc-8-amino-3,6-dioxaoctanoic acid are known. The compound represented by the formula (S1b) can be produced by reacting the compound represented by the formula (S10a) with the compound represented by the formula (S12). This reaction can be carried out according to production method 1(2).

Production Method C

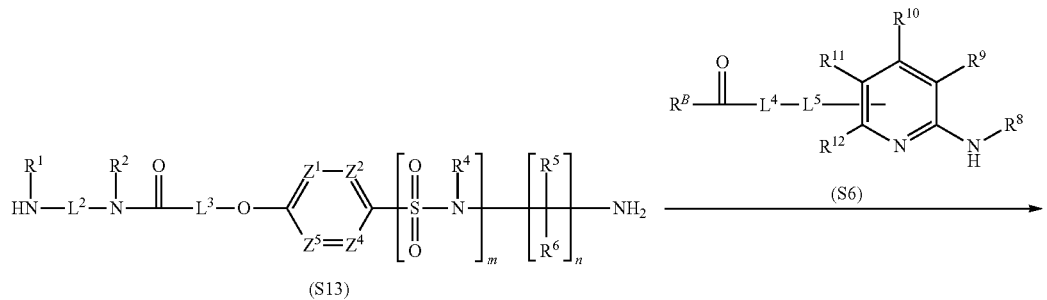

(S13)

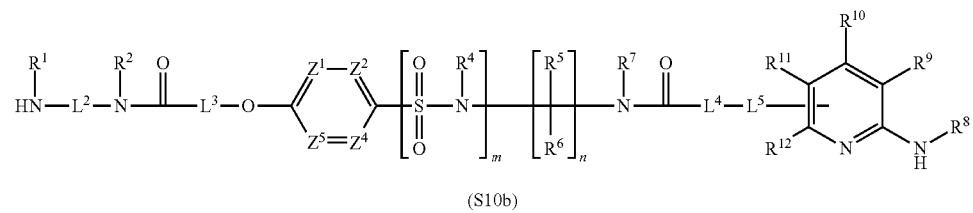

(S10b)

wherein $R^1$, $R^2$, $R^4$, $R^5$, $R^6$, $R^7$, $R^8$, $R^9$, $R^{10}$, $R^{11}$, $R^{12}$, $R^B$, $Z^1$, $Z^2$, $Z^4$, $Z^5$, $L^2$, $L^3$, $L^4$, $L^5$, m, and n are as defined above.

For example, as the compound represented by the formula (S6), 4-(2-(5,6,7,8-tetrahydro-1,8-naphthyridin-2-yl)ethyl)benzoic acid is known. For example, as the compound represented by the formula (S13), (S)-methyl 3-amino-2-(4-(4-((2-(((benzyloxy)carbonyl)amino)ethyl)amino)-4-oxobutoxy)-2,6-dimethylphenylsulfonamido)propanoate is known. The compound represented by the formula (S10b) can be produced by reacting the compound represented by the formula (S13) with the compound represented by the formula (S6). This reaction can be carried out according to production method 1(2).

In this production method, the conversion of $Z^3$ is described. In the same way as this method, $Z^1$, $Z^2$, $Z^4$, or $Z^5$ can also be converted.

Production Method D

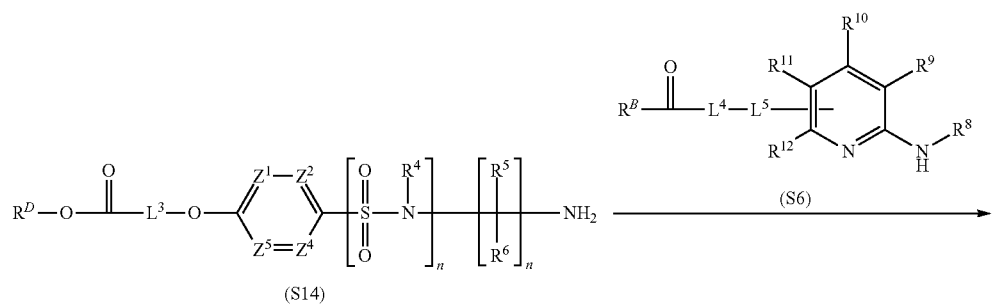

(S14)

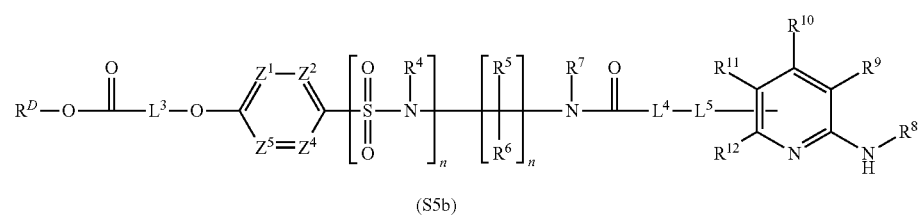

(S5b)

wherein $R^D$ represents a carboxyl-protecting group; and $R^4$, $R^5$, $R^6$, $R^7$, $R^8$, $R^9$, $R^{10}$, $R^{11}$, $R^{12}$, $R^B$, $Z^1$, $Z^2$, $Z^4$, $Z^5$, $L^3$, $L^4$, $L^5$, m, and n are as defined above.

The compound represented by the formula (S5b) can be produced by reacting a compound represented by the formula (S14) with the compound represented by the formula (S6). This reaction can be carried out according to production method 1(2).

In this production method, the conversion of $Z^3$ is described. In the same way as this method, $Z^1$, $Z^2$, $Z^4$, or $Z^5$ can also be converted.

Production Method E

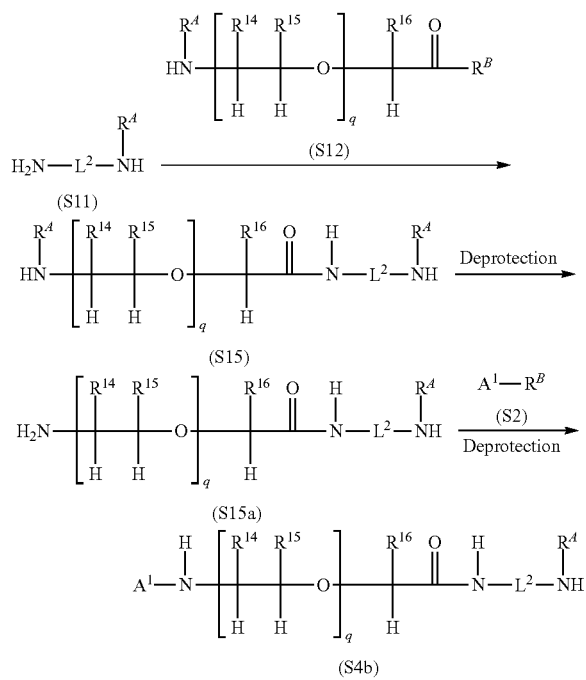

wherein $R^{14}$, $R^{15}$, $R^{16}$, $R^A$, $R^B$, $A^1$, $L^2$, and q are as defined above.

(1) The compound represented by the formula (S15) can be produced by reacting the compound represented by the formula (S11) with the compound represented by the formula (S12). This reaction can be carried out according to production method 1(2).

(2) The compound represented by the formula (S15a) can be produced by deprotecting the compound represented by the formula (S15). This reaction can be carried out according to production method 1(1).

(3) The compound represented by the formula (S4b) can be produced by reacting the compound represented by the formula (S15a) with the compound represented by the formula (S2). This reaction can be carried out according to production method 1(2).

Production Method F

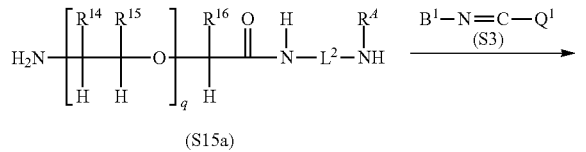

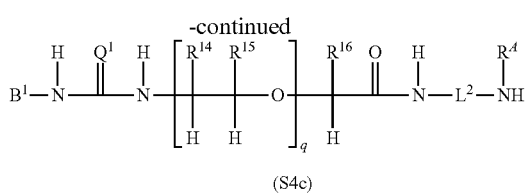

wherein $R^{14}$, $R^{15}$, $R^{16}$, $R^A$, $B^1$, $L^2$, $Q^1$, and q are as defined above.

The compound represented by the formula (S4c) can be produced by reacting the compound represented by the formula (S15a) with the compound represented by the formula (S3). This reaction can be carried out according to production method 2.

The compounds obtained by the production methods mentioned above can be converted to other compounds, for example, through a reaction known per se in the art such as condensation, addition, oxidation, reduction, dislocation, substitution, halogenation, dehydration, or hydrolysis or through an appropriate combination of these reactions.

The compounds obtained by the production methods mentioned above can be isolated and purified by an ordinary method such as extraction, crystallization, distillation, or column chromatography. Alternatively, the compounds obtained by the production methods mentioned above may be used directly in next reactions without being isolated.

The compounds obtained by the production methods mentioned above and their intermediates may have amino, hydroxyl, or carboxyl groups. In this case, the reactions can be carried out with their protective groups appropriately replaced. Also, two or more protective groups, if any, can each be deprotected selectively through a reaction known per se in the art.

The compounds used in the production methods mentioned above can also be used as salts, if these compounds can be in a form of salt. Examples of the salts include the same as those exemplified as the salt of the compound represented by the formula (1).

The compounds used in the production methods mentioned above may have isomers (e.g., optical isomers, geometric isomers, and tautomers). In this case, these isomers may be used. Alternatively, the compounds used in the production methods mentioned above may be any of solvates, hydrates, and crystals in various forms. In this case, these solvates, hydrates, and crystals in various forms can be used.

The complex of the compound represented by the formula (1) or the salt thereof with a metal can be produced, for example, as described below. The compound represented by the formula (1) or the salt thereof and a metal ion are mixed in the presence of a buffer solution to produce the complex. The buffer solution used in this reaction is not particularly limited as long as the buffer solution does not influence the reaction. Examples thereof include a sodium acetate buffer solution, an ammonium acetate buffer solution, a sodium citrate buffer solution, and an ammonium citrate buffer solution. The pH range of the buffer solution is preferably 3 to 6. The reaction temperature and the reaction time differ depending on the combination of the compound represented by the formula (1) or the salt thereof and a radioactive metal and may be 0 to 150° C. and 5 to 60 minutes. The complex obtained by this production method can be isolated and purified by an ordinary method such as extraction, crystallization, distillation, or column chromatography. When the metal is a radioactive metal, the complex can also be produced according to this production method. However, the radioactive metal emits radiation, and the radioactive metal is in a trace amount. In consideration of these factors, the following things must be noted. Unnecessary prolongation of the reaction time is not preferred because of the possibility of causing the decomposition of a compound by radiation. Usually, a labeled compound can be obtained at a radiochemical yield exceeding 80%. If a higher purity is necessary, the compound can be purified by a method such as preparative liquid chromatography, preparative TLC, dialysis, solid-phase extraction, and/or ultrafiltration. Also, a metal fluoride complex, which is a conjugate of a fluoride and a metal, can be regarded as a metal and reacted with the compound represented by the formula (1) or the salt thereof to produce the complex. This reaction can be carried out by a method described in, for example, JP-B-5388355. For suppressing decomposition by radiation, it is preferred to add an additive such as gentisic acid, ascorbic acid, benzyl alcohol, tocopherol, gallic acid, gallic acid ester, or α-thioglycerol.

The complex of the compound represented by the formula (1) or the salt thereof with a metal of the present invention has high accumulation and persistence in integrin-expressing cells and exhibits fast blood clearance. Therefore, the complex is useful as an agent for the diagnosis or treatment, etc., of a disease involving an integrin.

In the case of using the compound represented by the formula (1) or the salt thereof of the present invention as an agent for diagnosis or treatment, etc., the compound or the salt is preferably used as a metal complex. Examples of such a metal complex include the following complexes on a use basis.

Examples of the complex useful as an agent for nuclear magnetic resonance diagnosis or the like include complexes containing a metal ion exhibiting paramagnetism (e.g., a paramagnetic ion of a metal selected from the group consisting of Co, Mn, Cu, Cr, Ni, V, Au, Fe, Eu, Gd, Dy, Tb, Ho, and Er) as a metal component.

Examples of the complex useful as an agent for x-ray diagnosis or the like include complexes containing a metal ion absorbing x-rays (e.g., an ion of a metal selected from the group consisting of Re, Sm, Ho, Lu, Pm, Y, Bi, Pb, Os, Pd, Gd, La, Au, Yb, Dy, Cu, Rh, Ag, and Ir) as a metal component.

Examples of the complex useful as an agent for radiodiagnosis, radiotherapy, or the like include complexes containing a radioactive metal ion (e.g., an ion of a radioactive metal selected from the group consisting of $^{18}$F aluminum complex, $^{18}$F gallium complex, $^{18}$F indium complex, $^{18}$F lutetium complex, $^{18}$F thallium complex, $^{44}$Sc, $^{47}$Sc, $^{51}$Cr, $^{52m}$Mn, $^{55}$Co, $^{57}$Co, $^{58}$Co, $^{52}$Fe, $^{59}$Fe, $^{60}$Co, $^{62}$Cu, $^{64}$Cu, $^{67}$Cu, $^{67}$Ga, $^{68}$Ga, $^{72}$As, $^{72}$Se, $^{73}$Se, $^{75}$Se, $^{76}$As, $^{82}$Rb, $^{82}$Sr, $^{85}$Sr, $^{89}$Sr, $^{89}$Zr, $^{86}$Y, $^{87}$Y, $^{90}$Tc, $^{99m}$Tc, $^{103}$Ru, $^{103}$Pd, $^{105}$Rh, $^{109}$Pd, $^{111}$In, $^{114m}$In, $^{171m}$Sn, $^{111}$Ag, $^{113m}$In, $^{140}$La, $^{149}$Pm, $^{149}$Tb, $^{152}$Tb, $^{155}$Tb, $^{161}$Tb, $^{153}$Sm, $^{159}$Gd, $^{165}$Dy, $^{166}$Dy, $^{166}$Ho, $^{165}$Er, $^{169}$Yb, $^{175}$Yb, $^{177}$Lu, $^{186}$Re, $^{188}$Re, $^{192}$Ir, $^{197}$Hg, $^{198}$Au, $^{199}$Au, $^{201}$Tl, $^{203}$Hg, $^{211}$At, $^{212}$Bi, $^{212}$Pb, $^{213}$Bi, $^{217}$Bi, $^{223}$Ra, $^{225}$Ac and $^{227}$Th) as a metal component.

The radioactive metal is preferably a cytotoxic radioactive metal for use in an agent for treatment or the like, and is preferably a noncytotoxic radioactive metal for use in an agent for diagnosis or the like.

Examples of the noncytotoxic radioactive metal for use in an agent for diagnosis or the like include gamma ray-emitting nuclides and positron-emitting nuclides (e.g., $^{18}$F aluminum complex, $^{18}$F gallium complex, $^{18}$F indium complex, $^{18}$F lutetium complex, $^{18}$F thallium complex, $^{99m}$Tc, $^{111}$In, $^{113m}$In, $^{114m}$In, $^{67}$Ga, $^{68}$Ga, $^{82}$Rb, $^{86}$Y, $^{87}$Y, $^{152}$Tb, $^{155}$Tb, $^{201}$Tl, $^{51}$Cr, $^{52}$Fe, $^{57}$Co, $^{58}$Co, $^{60}$Co, $^{82}$Sr, $^{85}$Sr, $^{197}$Hg, $^{44}$Sc, $^{62}$Cu, $^{64}$Cu or $^{89}$Zr). $^{18}$F aluminum complex, $^{111}$In, $^{67}$Ga, $^{68}$Ga, $^{64}$Cu, or $^{89}$Zr is preferred from the viewpoint of half-life, radiation energy, and easy labeling reaction, etc.

Examples of the cytotoxic radioactive metal for use in an agent for treatment or the like include alpha ray-emitting nuclides and beta ray-emitting nuclides. Specific examples thereof include $^{90}$Y, $^{114m}$In, $^{117}$Sn, $^{186}$Re, $^{188}$Re, $^{64}$Cu, $^{67}$Cu, $^{59}$Fe, $^{89}$Sr, $^{198}$Au, $^{203}$Hg, $^{212}$Pb, $^{165}$Dy, $^{103}$Ru, $^{149}$Tb, $^{161}$Tb, $^{212}$Bi, $^{166}$Ho, $^{165}$Er, $^{153}$Sm, $^{177}$Lu, $^{213}$Bi, $^{223}$Ra, $^{225}$Ac or $^{227}$Th. Among these radioactive metals, $^{64}$Cu, $^{67}$Cu, $^{90}$Y, $^{153}$Sm, $^{166}$Ho, $^{177}$Lu, or $^{225}$Ac is preferred from the viewpoint of half-life, radiation energy, easy labeling reaction, and stability of the complex.

The agent for diagnosis or treatment, etc., of the present invention may be provided by any of a method for providing an already labeled preparation containing the complex of the compound represented by the formula (1) or the salt thereof with a metal and a method for providing a kit preparation containing the compound represented by the formula (1) or the salt thereof. When the agent for diagnosis or treatment is provided as an already labeled preparation, the agent containing the already labeled complex can be used directly in administration. When the agent is provided as a kit preparation, the agent is labeled with a desired radioactive metal in clinical settings and then used in administration. The kit preparation is provided in the form of an aqueous solution or a freeze-dried preparation. Use of the kit preparation eliminates the need of a special purification step, and a reaction solution can be prepared just before use as a dosing solution by merely performing reaction by the addition of a radioactive metal obtained from a generator stocked regularly in clinical settings or a radioactive metal provided by a drug manufacturer aside from or in set with the kit preparation.

The agent for treatment, etc., of the present invention may be used in combination with another anticancer agent. Examples of such anticancer agent include alkylating agents, antimetabolites, microtubule inhibitors, anticancer antibiotics, topoisomerase inhibitors, platinum preparations, molecular targeting drugs, hormones, and biologics. Examples of the alkylating agents include nitrogen mustard anticancer agents such as cyclophosphamide, nitrosourea anticancer agents such as ranimustine, and dacarbazine. Examples of the antimetabolites include 5-FU, UFT, carmofur, capecitabine, tegafur, TS-1, gemcitabine, and cytarabine. Examples of the microtubule inhibitors include alkaloid anticancer agents such as vincristine, and taxane anticancer agents such as docetaxel and paclitaxel. Examples of the anticancer antibiotics include mitomycin C, doxorubicin, epirubicin, daunorubicin, and bleomycin. Examples of the topoisomerase inhibitors include irinotecan and nogitecan having a topoisomerase I inhibitory effect, and etoposide having a topoisomerase II inhibitory effect. Examples of the platinum preparations include cisplatin, Paraplatin, nedaplatin, and oxaliplatin. Examples of the molecular targeting drugs include trastuzumab, rituximab, imatinib, gefitinib, erlotinib, bevacizumab, cetuximab, panitumumab, bortezomib, sunitinib, sorafenib, crizotinib, and regorafenib. Examples of the hormones include dexamethasone, finasteride, and tamoxifen. Examples of the biologics include interferons α, β, and γ and interleukin 2.

The agent for treatment, etc., of the present invention may be used in combination with a cancer therapy and can be used in combination with surgical operation as well as radiotherapy (including gamma knife therapy, cyberknife therapy, boron neutron capture therapy, proton radiation therapy, and heavy particle radiotherapy), MR-guided focused ultrasound surgery, cryotherapy, radiofrequency ablation, percutaneous ethanol injection therapy, arterial embolization, or the like.

Examples of the disease targeted by the agent for diagnosis or treatment, etc., of the present invention include mammalian (including humans) diseases involving an integrin. Examples of the diseases involving an integrin include cancer, ischemic disease, thrombosis, myocardial infarction, arteriosclerosis, angina pectoris, inflammation, osteolysis, osteoporosis, diabetic retinopathy, macular degeneration, myopia, ocular histoplasmosis, rheumatoid arthritis, osteoarthropathy, rubeotic glaucoma, ulcerative colitis, Crohn's disease, multiple sclerosis, psoriasis, and restenosis. The type of the cancer is not particularly limited. Examples thereof include rectal cancer, colon cancer, large intestine cancer, familial polyposis colorectal cancer, hereditary non-polyposis colorectal cancer, esophageal cancer, oral cancer, lip cancer, laryngeal cancer, hypopharyngeal cancer, tongue cancer, salivary gland cancer, stomach cancer, adenocarcinoma, medullary thyroid cancer, papillary thyroid carcinoma, kidney cancer, renal parenchyma cancer, ovary cancer, neck cancer, uterine body cancer, endometrial cancer, choriocarcinoma, pancreatic cancer, prostate cancer, testis cancer, breast cancer, ureteral cancer, skin cancer, melanoma, brain tumor, glioblastoma, astrocytoma, meningioma, medulloblastoma, peripheral neuroectodermal tumor, Hodgkin's lymphoma, non-Hodgkin's lymphoma, Burkitt's lymphoma, acute lymphatic leukemia (ALL), chronic lymphatic leukemia (CLL), acute myeloid leukemia (AML), chronic myeloid leukemia (CML), adult T-cell leukemia, hepatocellular cancer, gallbladder cancer, bile duct cancer, biliary cancer, bronchial cancer, lung cancer (small-cell lung cancer, non-small cell lung cancer, etc.), multiple myeloma, basalioma, teratoma, retinoblastoma, neuroblastoma, choroidal melanoma, seminoma, rhabdomyosarcoma, craniopharyngioma, osteosarcoma, chondrosarcoma, myosarcoma, liposarcoma, fibrosarcoma, Ewing sarcoma, and plasmacytoma. The agent for diagnosis or treatment, etc., of the present invention is preferably used for the suppression of solid cancer, preferably head and neck cancer, colorectal cancer, breast cancer, small-cell lung cancer, non-small cell lung cancer, glioblastoma, malignant melanoma, pancreatic cancer, or prostate cancer.

The agent for treatment, etc., of the present invention can be used for suppressing cancer by administering an effective amount thereof to a mammal including a human. In the case of using the agent as an anticancer agent, its effect has the broadest sense including both of a prophylactic effect of preventing, for example, cancer occurrence, metastasis or implantation, or recurrence, and a therapeutic effect of inhibiting cancer progression or ameliorating symptoms by suppressing the growth of cancer cells or reducing the size of tumor, and should not be interpreted restrictively in any case.

For pharmaceutical use of the complex of the compound represented by the formula (1) or the salt thereof with a metal of the present invention, usually, the complex may be appropriately mixed with a pharmacologically acceptable additive. Examples of the additive include excipients, disintegrants, binders, lubricants, corrigents, colorants, flavoring agents, surfactants, coating agents, stabilizers, and plasticizers. Examples of the excipients include: sugar alcohols such as erythritol, mannitol, xylitol, and sorbitol; saccharides such as saccharose, powder sugar, lactose, and glucose; cyclodextrins such as α-cyclodextrin, β-cyclodextrin, γ-cyclodextrin, hydroxypropyl β-cyclodextrin, and sulfobutyl ether β-cyclodextrin sodium; celluloses such as crystalline cellulose and microcrystalline cellulose; and starches such as corn starch, potato starch, and pregelatinized starch. Examples of the disintegrants include carmellose, carmellose calcium, croscarmellose sodium, carboxymethyl starch sodium, crospovidone, low-substituted hydroxypropylcellulose, and partly pregelatinized starch. Examples of the binders include hydroxypropylcellulose, carmellose sodium, and methylcellulose. Examples of the lubricants include stearic acid, magnesium stearate, calcium stearate, talc, hydrated silicon dioxide, light anhydrous silicic acid, and sucrose fatty acid ester. Examples of the corrigents include aspartame, saccharine, stevia, thaumatin, and acesulfame potassium. Examples of the colorants include titanium dioxide, red ferric oxide, yellow ferric oxide, black iron oxide, Food Red No. 102, Food Yellow No. 4, and Food Yellow No. 5. Examples of the flavoring agents include: essential oils such as orange oil, lemon oil, peppermint oil, and pine oil; extracts such as orange extract and peppermint extract; flavors such as cherry flavor, vanilla flavor, and fruit flavor; powder flavors such as apple micron, banana micron, peach micron, strawberry micron, and orange micron; vanillin; and ethylvanillin. Examples of the surfactants include sodium lauryl sulfate, sodium dioctyl sulfosuccinate, polysorbate, and polyoxyethylene hydrogenated castor oil. Examples of the coating agents include hydroxypropylmethylcellulose, aminoalkyl methacrylate copolymer E, aminoalkyl methacrylate copolymer RS, ethylcellulose, cellulose acetate phthalate, hydroxypropylmethylcellulose phthalate, methacrylic acid copolymer L, methacrylic acid copolymer LD, and methacrylic acid copolymer S. Examples of the stabilizers include gentisic acid, ascorbic acid, benzyl alcohol, tocopherol, gallic acid, gallic acid ester, and α-thioglycerol. Examples of the plasticizers include triethyl citrate, macrogol, triacetin, and propylene glycol. Any one of these additives or two or more thereof in combination may be used. These additives are not particularly limited by their contents and can be appropriately contained so as to adequately exert their effects according to each purpose. Such a preparation can be administered orally or parenterally in a form such as a tablet, a capsule, powders, a syrup, granules, a pill, a suspension, an emulsion, a solution, a powder preparation, a suppository, eye drops, nasal drops, eardrops, a patch, an ointment, or an injection according to a routine method. The administration, the dose, and the number of doses can be appropriately selected according to the age, body weight, and symptoms of a patient. Usually, the preparation can be administered orally or parenterally (e.g., through injection, through an intravenous drip, and by administration to a rectal site) to an adult.

In the case of using the radioactive metal, examples of its type can include alpha ray-emitting nuclides, beta ray-emitting nuclides, gamma ray-emitting nuclides, and positron-emitting nuclides. A beta ray-emitting nuclide (i.e., a nuclide which emits R rays) is preferred for the agent for treatment, etc.

The agent for diagnosis, etc., of the present invention can be used in the imaging of integrin expression. In the presence of a tumor or a neovessel expressing the integrin protein in the body, the complex of the compound represented by the formula (1) or the salt thereof with a metal of the present invention accumulates in the tumor or the like. Thus, the tumor can be imaged by the detection of radiation using an instrument such as a single photon emission computed tomography (SPECT) apparatus, a positron emission tomography (PET) apparatus, or a scintillation camera. Before treatment, integrin expression or the presence or absence of abnormal integrin accumulation at normal tissues is confirmed by the administration of the diagnostic drug. As a result, the applicability of a therapeutic drug can be determined, or the therapeutic drug can be presumed to be more effective for the imaged tumor having higher accumulation. Also, the complex of the compound represented by the formula (1) or the salt thereof with a metal of the present invention can be used in the determination of a therapeutic effect. The diagnostic drug of the present invention is administered to a patient who has received the therapeutic drug of the present invention or any of other treatments so that a tumor is imaged. Decrease or increase in tumor size can be determined by observing change in accumulation over time.

The dose of the agent for treatment, etc., of the present invention differs depending on the age, sex, and symptoms of a patient, an administration route, the number of doses, and a dosage form. In general, the dose of the pharmaceutical composition can be selected, for example, within the range of 0.0000001 mg to 100 mg per kg of body weight for one dose, though the dose according to the present invention is not limited thereto. One dose in an adult can be 18.5 MBq to 7400 MBq in terms of the amount of radioactivity.

The dose of the agent for diagnosis, etc., of the present invention also differs depending on the age, sex, and symptoms of a patient, an administration route, the number of doses, and a dosage form. In general, the dose of the pharmaceutical composition can be selected, for example, within the range of 0.0000001 mg to 100 mg per kg of body weight for one dose, though the dose according to the present invention is not limited thereto. One dose in an adult can be 111 MBq to 740 MBq in terms of the amount of radioactivity.

EXAMPLES

Next, the present invention will be described in more detail with reference to Reference Examples, Examples, and Test Examples. However, the present invention is not intended to be limited by them.

The carrier used in silica gel column chromatography was silica gel 60N (spherical/neutral) 63 to 210 μm (Kanto Chemical Co., Inc.), unless otherwise specified. A mixing ratio for an eluent is a volume ratio. For example, "hexane/ethyl acetate=90/10 to 50/50" means that an eluent of "hexane:ethyl acetate=90:10" was changed to an eluent of "hexane:ethyl acetate=50:50".

$^1$H-NMR spectra were measured using tetramethylsilane as an internal standard and Bruker AV300 (Bruker Corp.) or JEOL JNM-AL400 model (JEOL Ltd.), and δ values were indicated by ppm.

For HPLC analysis, measurement was carried out using Nexera HPLC System (Shimadzu Corp.) (column: TSKgel ODS-100Z (Tosoh Corp.), solvent: solution A=0.1% formic acid/water, solution B=0.1% formic acid/methanol/acetonitrile (4:1), gradient cycle: 0.0 min (solution A/solution B=90/10), 30 min (solution A/solution B=0/100), 40 min (solution A/solution B=0/100), flow rate: 1.0 mL/min) or Waters 600E system (Waters Corp.) (column: SunFire C18OBD 4.6×150 mm (Waters Corp.) and CAPCELL PAK C18MG 4.6×150 mm (Shiseido Japan Co., Ltd.), gradient cycle: 0.0 min (solution A/solution B=80/20), 10 min (solution A/solution B=0/100), 15 min (solution A/solution B=0/100), flow rate: 1.0 mL/min), unless otherwise specified. If different analysis conditions were used for optical isomer separation or the like, the conditions were described in Examples. Preparative HPLC was carried out using Waters 600E system (Waters Corp.) (column: SunFire Prep C18 OBD 30×150 mm (Waters Corp.) or SunFire Prep C18 OBD 19×150 mm (Waters Corp.), solvent: solution A=0.11 formic acid/water, solution B=0.1% formic acid/methanol:acetonitrile (4:1) or solvent: solution A=10 mmol/L aqueous ammonium acetate solution, solution B=10 mmol/L ammonium acetate/methanol:acetonitrile (4:1)), unless otherwise specified. TLC analysis was conducted using silica gel 60F$_{254}$ (Merck KGaA) or RP-18F$_{254}$ (Merck KGaA), unless otherwise specified.

For MS and LC/MS analysis, measurement was carried out using LCMS-2010EV (Shimadzu Corp.) (column: SunFire C18 4.6×150 mm (Waters Corp.), solvent: solution A=0.1% formic acid/water, solution B=0.1% formic acid/methanol:acetonitrile (4:1), gradient cycle: 0.0 min (solution A/solution B=80/20), 10.0 min (solution A/solution B=0/100), 15.0 min (solution A/solution B=0/100), flow rate: 1 mL/min) or ACQUITY SQD LC/MS System (Waters Corp.) (column: BEHC18 2.1×30 mm (Waters Corp.), solution A=0.1% formic acid/water, solution B=0.1% formic acid/acetonitrile, gradient cycle: 0.0 min (solution A/solution B=0.95/5), 2.0 min (solution A/solution B=5/95), 3.0 min (solution A/solution B=5/95), flow rate: 0.5 mL/min). Retention time (min) was indicated by rt (min), and ESI positive and negative ion peaks were detected. The MS spectra of some high-molecular-weight compounds were measured using Q-TOF Premier (Waters Corp.).

Each abbreviation has the following meaning: Bn: benzyl, Boc: tert-butoxycarbonyl, $^t$Bu: tert-butyl, DIEA: N,N-diisopropylethylamine, DMAc: N,N-dimethylacetamide, DMAP: 4-dimethylaminopyridine, DMF: N,N-dimethylformamide, DMFDA: N,N-dimethylformamide dimethyl acetal, DMSO: dimethyl sulfoxide, Et: ethyl, Fmoc: 9-fluorenylmethyloxycarbonyl, HATU: O-(7-azabenzotriazol-1-yl)-1,1,3,3-tetramethyluronium hexafluorophosphate, HBTU: O-benzotriazol-1-yl 1,1,3,3-tetramethyluronium hexafluorophosphate, NMP: N-methylpyrrolidone, TBS: tert-butyldimethylsilyl, TFA: trifluoroacetic acid, THF: tetrahydrofuran, and Z: benzyloxycarbonyl

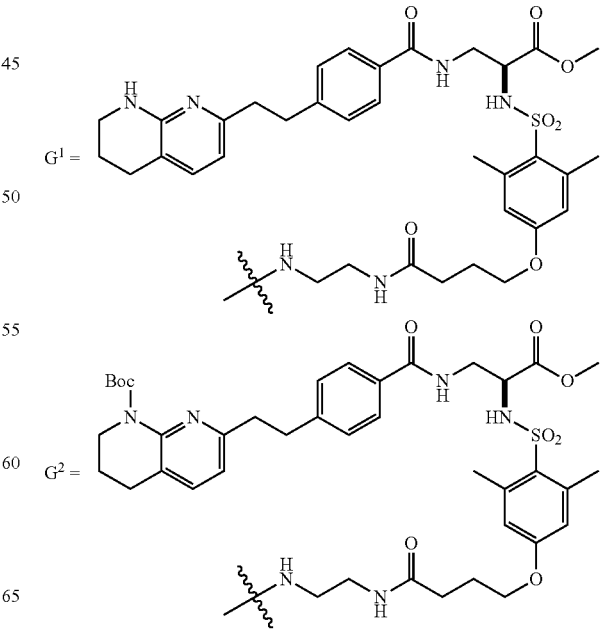

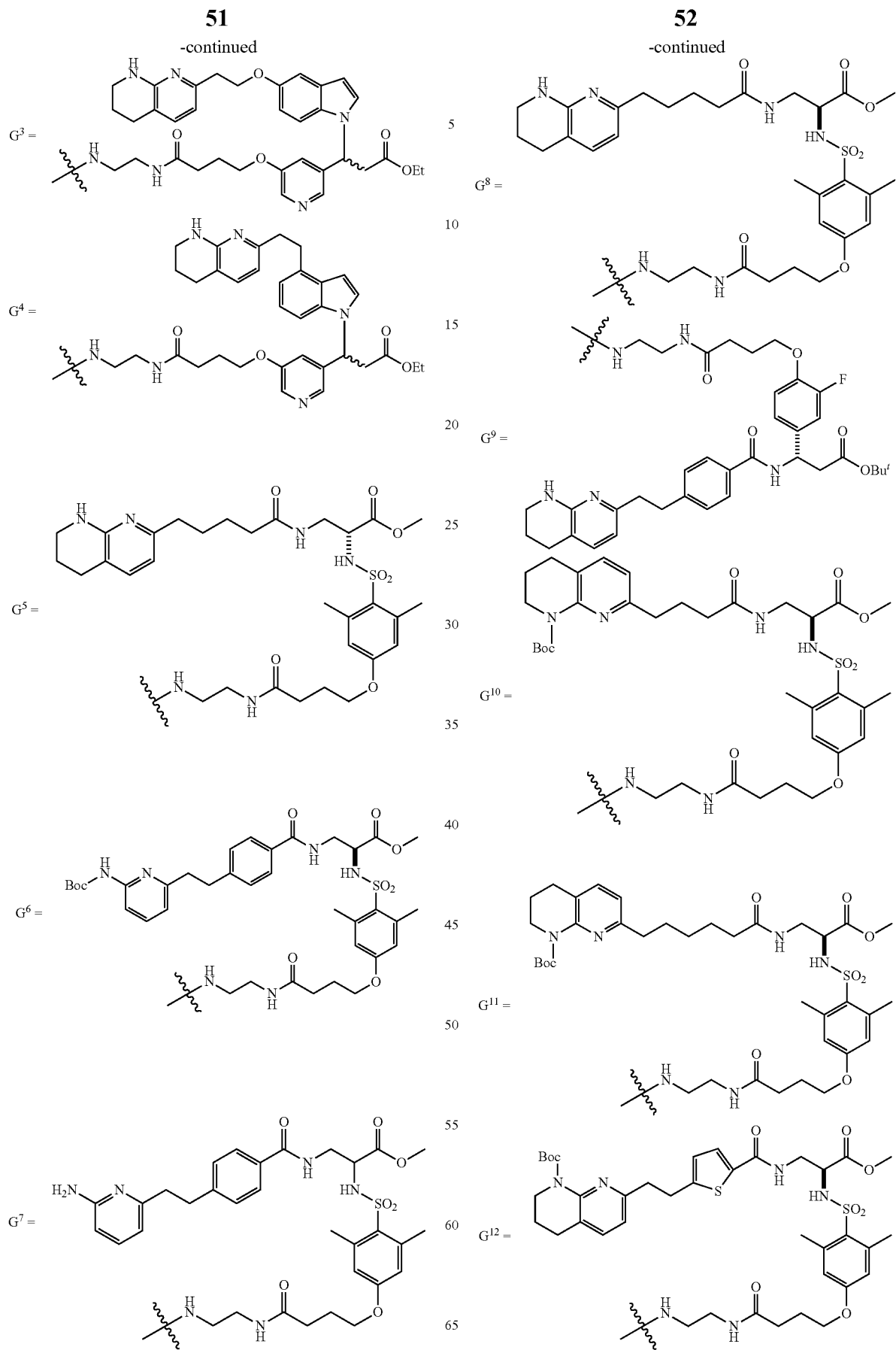

-continued
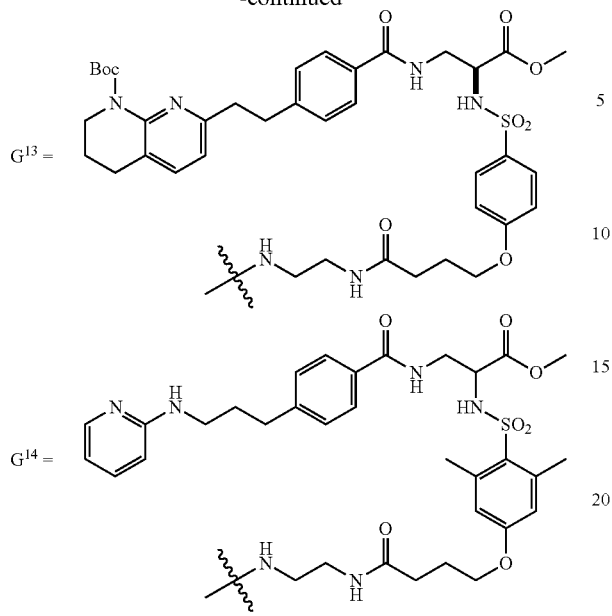
Reference Example 1
(A1)
Compound (A1) was obtained according to the method described in Journal of Medicinal Chemistry, 2000, Vol. 43, p. 3736-3745.
Reference Example 2
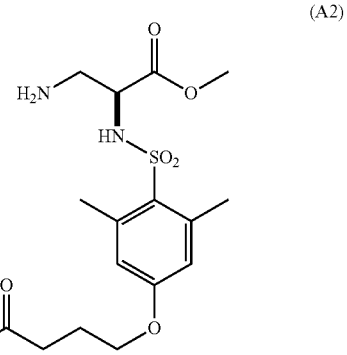
Compound (A2) was obtained according to the method described in Bioconjugate chemistry, 2006, Vol. 17, p. 1294-1313.
Example 1
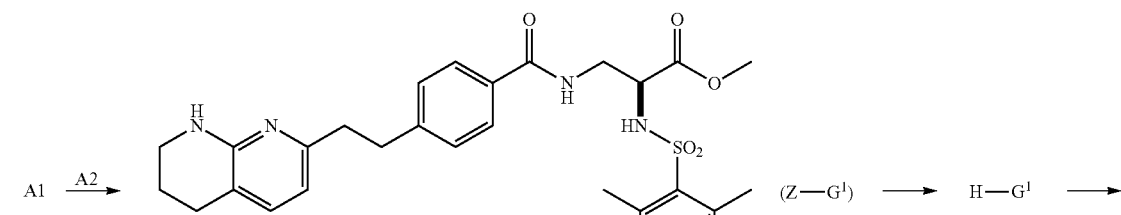
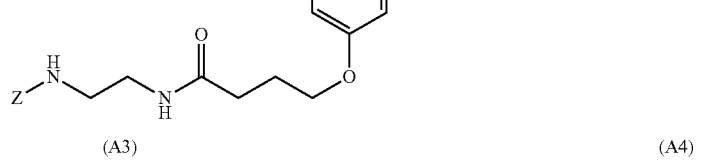
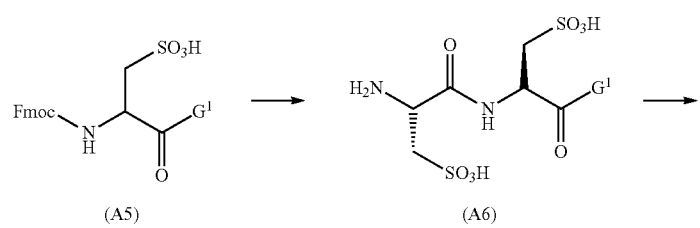

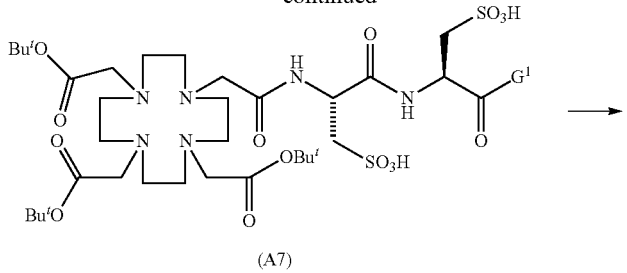

(A7)

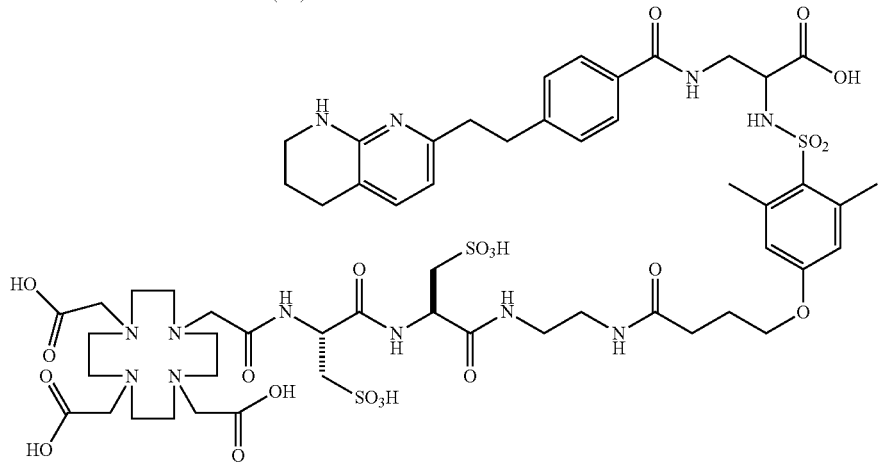

(A8)

(1) To a solution of compound (A2) (130 mg), compound (A1) (57.0 mg), and DIEA (250 μL) in DMF (2 mL), a solution of HBTU (85.5 mg) in DMF (0.5 mL) was added, and the mixture was stirred at room temperature for 1 hour. Water (500 μL) and acetonitrile (2 mL) were added thereto, and the mixture was purified by preparative HPLC to obtain compound (A3) (152 mg). LC/MS (SunFire) rt (min): 9.43 MS (ESI, m/z): 829.10 [M+H]$^+$, 827.15 [M−H]$^−$ (2) Compound (A3) (27.8 mg), methanol (10 mL), and 10% Pd/C (10 mg) were placed in a sealed tube and stirred for 3 hours in a 0.5 MPa hydrogen atmosphere. Insoluble matter was filtered off, and the solvent was distilled off under reduced pressure to obtain compound (A4) (20.8 mg). LC/MS (SunFire) rt (min): 6.09 MS (ESI, m/z): 695.10 [M+H]$^+$, 693.10 [M−H]$^−$ (3) To a solution of compound (A4) (58.5 mg), Fmoc-cysteic acid (65.9 mg), and DIEA (100 μL) in DMF (0.8 mL), a solution of HBTU (63.7 mg) in DMF (0.3 mL) was added, and the mixture was stirred at room temperature for 1 hour. Water (100 μL) was added thereto, and the mixture was purified by preparative HPLC to obtain compound (A5) (43.4 mg). LC/MS (ACQUITY) rt (min): 1.32 MS (ESI, m/z): 1068.6 [M+H]$^+$, 1066.6 [M−H]$^−$ (4) To a solution of compound (A5) (26.5 mg) in DMF (0.5 mL), diethylamine (0.5 mL) was added, and the mixture was stirred at room temperature for 1 hour. The solvent was distilled off under reduced pressure. To the obtained oil, Fmoc-cysteic acid (19.4 mg), DMF (0.6 mL), and DIEA (100 μL) were added, then, a solution of HBTU (18.8 mg) in DMF (150 μL) was added, and the mixture was stirred at room temperature for 70 minutes. Water (100 μL) was added thereto, and the solvent was distilled off under reduced pressure. Then, DMF (0.5 mL) and diethylamine (0.5 mL) were added to the residue, and the mixture was stirred at room temperature for 1 hour. The solvent was distilled off under reduced pressure, and then, insoluble matter was filtered off. A 50% aqueous acetonitrile solution (300 μL) was added to the residue, and the mixture was purified by preparative HPLC to obtain compound (A6) (15.6 mg). LC/MS (SunFire) rt (min): 9.56 MS (ESI, m/z): 997.15 [M+H]$^+$, 995.20 [M−H]$^−$ (5) To a solution of tri-tert-butyl 1,4,7,10-tetraazacyclododecane-1,4,7,10-tetraacetate (14.0 mg) and DIEA (50 μL) in DMF (200 μL), a solution of HBTU (9.0 mg) in DMF (100 μL) was added, and the mixture was stirred at room temperature for 5 minutes. Then, the reaction mixture was added to a solution of compound (A6) (15.6 mg) and DIEA (10 μL) in DMF (200 μL), and the mixture was stirred at room temperature for 1 hour. Water (100 μL) and acetonitrile (100 μL) were added thereto, and the mixture was purified by preparative HPLC to obtain compound (A7) (10.5 mg). LC/MS (SunFire) rt (min): 10.74 MS (ESI, m/z): 685.15 [M+2H]$^{2+}$ (6) A mixture of compound (A7) (5.4 mg), THF (450 μL), water (100 μL), and a 3 mol/L aqueous lithium hydroxide solution (100 μL) was stirred at room temperature for 75 minutes. TFA was added thereto, and the solvent was distilled off under reduced pressure. To the obtained residue, TFA/triethylsilane (95/5) (1 mL) was added, and the mixture was stirred for 1.5 hours. Then, the solvent was distilled off under reduced pressure. To the obtained residue, a 50% aqueous acetonitrile solution (200 μL) and TFA (10 μL) were added, and the mixture was purified by preparative HPLC to obtain compound (A8) (4.2 mg). LC/MS (SunFire) rt (min): 10.74 MS (ESI, m/z): 685.15 [M+2H]$^{2+}$

Example 2

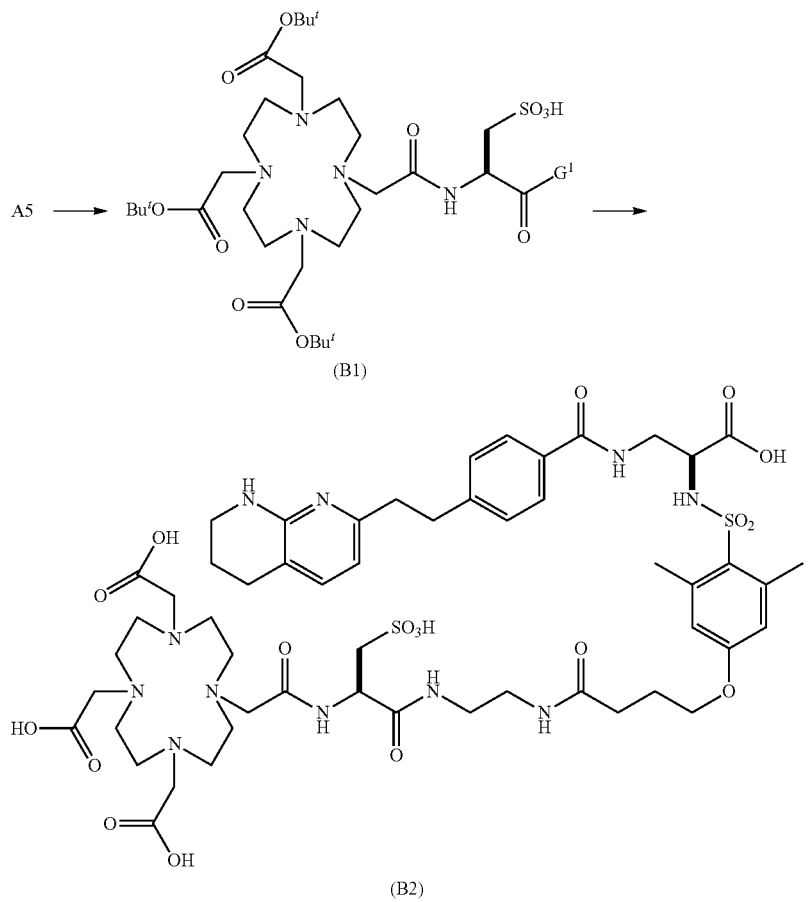

(1) To a solution of compound (A5) (8.8 mg) in DMF (0.5 mL), diethylamine (0.5 mL) was added, and the mixture was stirred at room temperature for 150 minutes. The solvent was distilled off under reduced pressure. To the residue, DMF (0.2 mL) and DIEA (10 μL) were added, then a solution of tri-tert-butyl 1,4,7,10-tetraazacyclododecane-1,4,7,10-tetraacetate (7.1 mg), DMF (0.1 mL), DIEA (20 μL), and HBTU (4.5 mg) in DMF (45 μL) was added, and the mixture was stirred at room temperature for 3 hours. Tri-tert-butyl 1,4,7,10-tetraazacyclododecane-1,4,7,10-tetraacetate (7.0 mg), DMF (50 μL), DIEA (20 μL), HBTU (4.5 mg), and DMF (50 μL) were added thereto, and the mixture was stirred for 30 minutes. Water (100 μL) and a 50% aqueous acetonitrile solution (400 μL) were added thereto, and the mixture was purified by preparative HPLC to obtain compound (B1) (10.0 mg). LC/MS (SunFire) rt (min): 8.89 MS (ESI, m/z): 701.25 [M+2H]$^{2+}$, 1399.20 [M−H]$^{-}$ (2) To compound (E1) (2.4 mg), THF (0.7 mL), water (0.1 mL), and a 3 mol/L aqueous lithium hydroxide solution (100 μL) were added, and the mixture was stirred at room temperature for 1.5 hours. TFA was added thereto, and the solvent was distilled off under reduced pressure. TFA/triethylsilane (95/5) (1 mL) was added to the residue, and the mixture was stirred at room temperature for 1 hour. TFA was distilled off under reduced pressure. A 20% aqueous acetonitrile solution (1.2 mL) was added to the residue, and the mixture was purified by preparative HPLC to obtain compound (B2) (1.8 mg). LC/MS (SunFire) rt (min): 8.14 MS (ESI, m/z): 609.90 [M+2H]$^{2+}$, 1217.05 [M−H]$^{-}$

Example 3

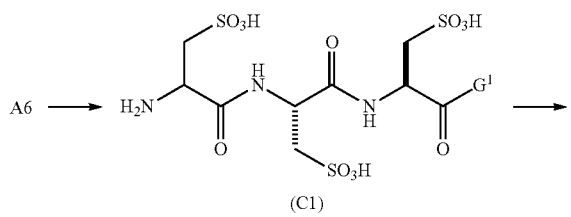

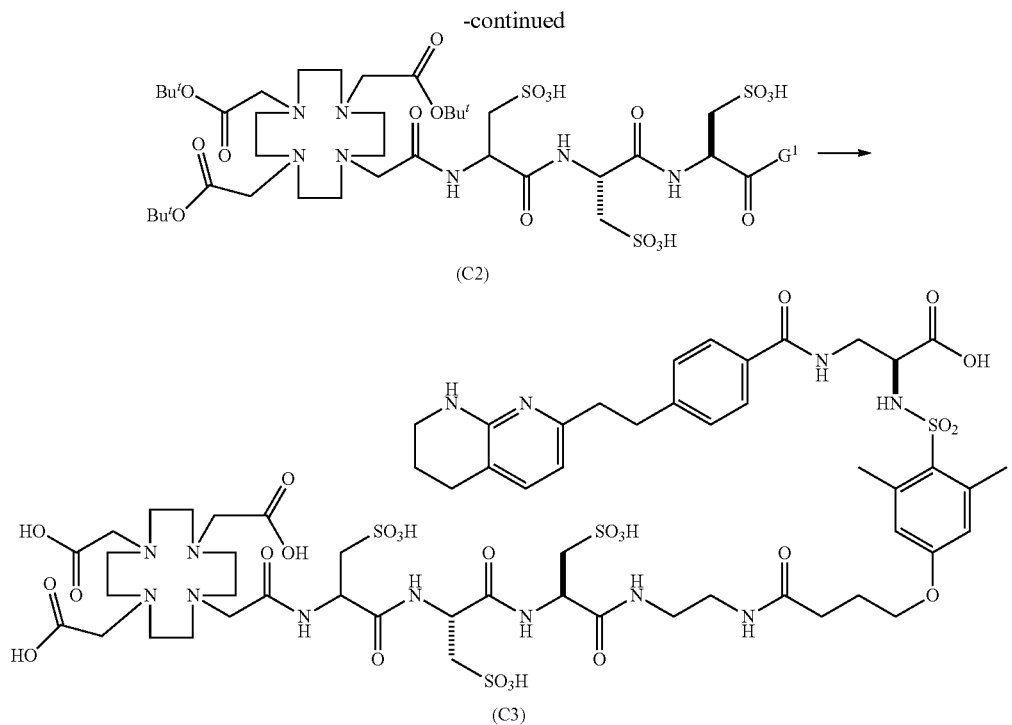

(1) To compound (A6) (21.5 mg), Fmoc-cysteic acid (21.1 mg), DMF (0.8 mL), and DIEA (30 μL) were added, then a solution of HBTU (19.7 mg) in DMF (200 μL) was added, and the mixture was stirred at room temperature for 70 minutes. Water (200 μL) and diethylamine (0.5 mL) were added thereto, and the mixture was stirred at room temperature for 1 hour. The solvent was distilled off under reduced pressure, and then, a 50% aqueous acetonitrile solution (0.6 mL) was added to the residue. Insoluble matter was filtered off, and the residue was purified by preparative HPLC to obtain compound (C1) (15.0 mg). LC/MS (ACQUITY) rt (min): 0.91 MS (ESI, m/z): 1148.4 [M+H]$^+$, 1146.4 [M−H]$^−$ (2) To compound (C1) (7.2 mg), a 50% aqueous methanol solution (300 μL) and a 4 mol/L solution of hydrogen chloride in dioxane (20 μL) were added, and the solvent was distilled off under reduced pressure. To the obtained residue, tri-tert-butyl 1,4,7,10-tetraazacyclododecane-1,4,7,10-tetraacetate (12.6 mg), DMF (400 μL), and DIEA (20 μL) were added, then a solution of HBTU (7.2 mg) in DMF (200 μL) was added, and the mixture was stirred at room temperature for 1 hour. HBTU (10.0 mg) was added thereto, and the mixture was stirred for 1 hour, followed by the addition of water (300 μL). The mixture was purified by preparative HPLC to obtain compound (C2) (4.1 mg). LC/MS (ACQUITY) rt (min): 1.16 MS (ESI, m/z): 852.3 [M+2H]$^{2+}$, 850.3[M−2H]$^{2−}$ (3) A mixture of compound (C2) (4.1 mg), THF (1.3 mL), water (150 μL), and a 3 mol/L aqueous lithium hydroxide solution (150 μL) was stirred at room temperature for 140 minutes. TFA was added thereto, and the solvent was distilled off under reduced pressure. To the obtained residue, TFA/triethylsilane (95/5) (1 mL) was added, and the mixture was stirred for 2 hours. Then, TFA was distilled off under reduced pressure. A 10 mmol/L aqueous ammonium acetate solution (800 μL) was added to the residue, and then, the mixture was purified by preparative HPLC to obtain compound (C3) (2.3 mg). LC/MS (ACQUITY) rt (min): 0.93 MS (ESI, m/z): 759.7 [M−2H]$^{2−}$ Example 4

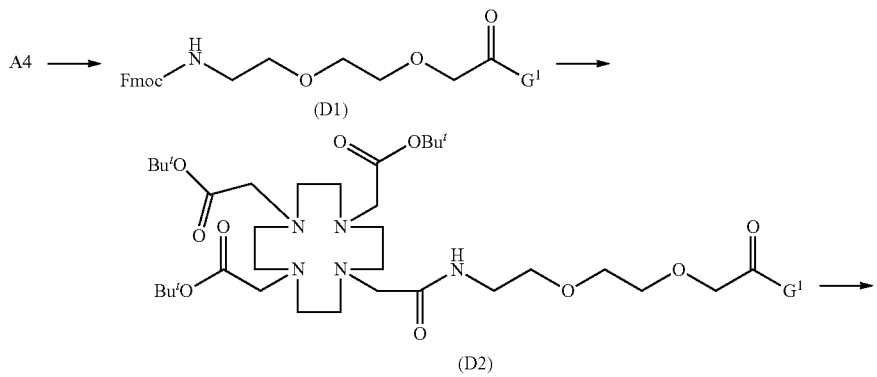

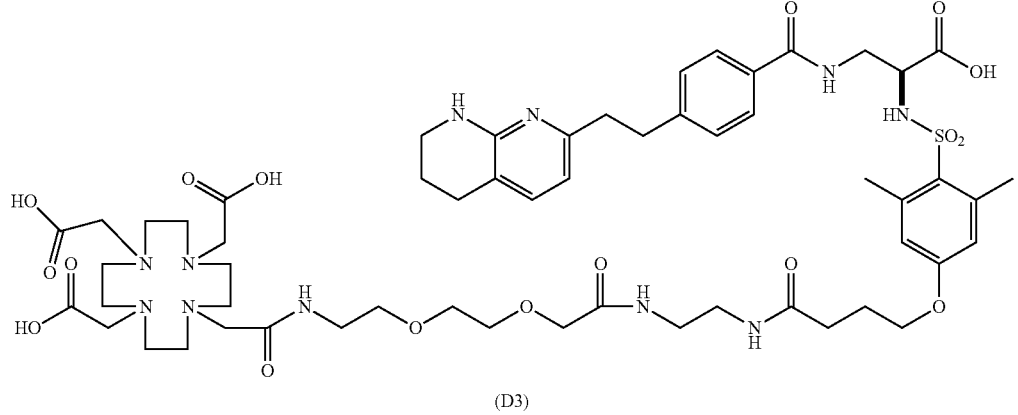

(D3)

(1) To a solution of Fmoc-8-amino-3,6-dioxaoctanoic acid (31.0 mg), compound (A4) (20.8 mg), and DIEA (50 μL) in DMF (400 μL), a solution of HBTU (22.7 mg) in DMF (100 μL) was added, and the mixture was stirred at room temperature for 1 hour. Water (100 μL) and acetonitrile (100 μL) were added thereto, and the mixture was purified by preparative HPLC to obtain compound (D1) (22.8 mg). LC/MS (SunFire) rt (min): 9.81 MS (ESI, m/z): 531.95 [M+2H]$^{2+}$ (2) To a solution of compound (D1) (7.5 mg) in DMF (0.5 mL), diethylamine (0.5 mL) was added, and the mixture was stirred at room temperature for 1 hour. Then, the solvent was distilled off under reduced pressure. To the obtained residue, tri-tert-butyl 1,4,7,10-tetraazacyclododecane-1,4,7,10-tetraacetate (8.1 mg), DMF (200 μL), and DIEA (40 μL) were added, then a solution of HBTU (5.3 mg) in DMF (100 μL) was added, and the mixture was stirred at room temperature for 1 hour. Water (100 μL) and acetonitrile (200 μL) were added thereto, and the mixture was purified by preparative HPLC to obtain a fraction containing compound (D2). LC/MS (SunFire) rt (min): 8.36 MS (ESI, m/z): 698.10 [M+2H]$^{2+}$, 1392.50 [M−H]$^{-}$ (3) The solvent in the fraction containing compound (D2) obtained in the step (2) was distilled off under reduced pressure. Then, THF (350 μL), water (50 μL), and a 3 mol/L aqueous lithium hydroxide solution (50 μL) were added to the residue, and the mixture was stirred at room temperature for 1.5 hours. TFA was added thereto, and the solvent was distilled off under reduced pressure. To the obtained residue, TFA/triethylsilane (95/5) (1 mL) was added, and the mixture was stirred for 1.5 hours. The solvent was distilled off under reduced pressure. A 50% aqueous acetonitrile solution (600 μL) was added to the residue, and the mixture was purified by preparative HPLC to obtain compound (D3) (1.8 mg). LC/MS (SunFire) rt (min): 7.66 MS (ESI, m/z): 606.85 [M+2H]$^{2+}$, 404.95 [M+3H]$^{3+}$ Example 5

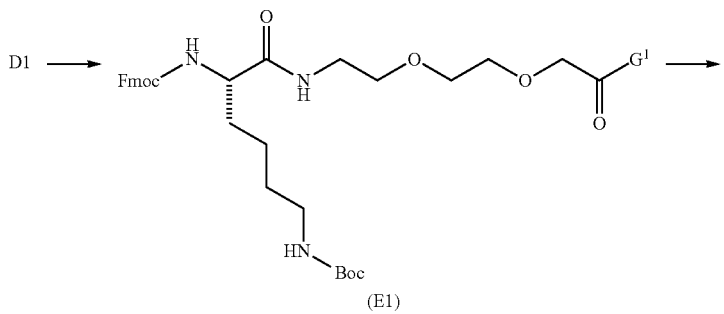

(E1)

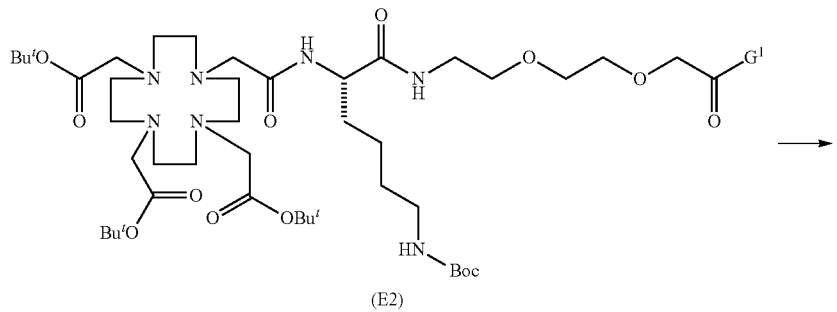

(E2)

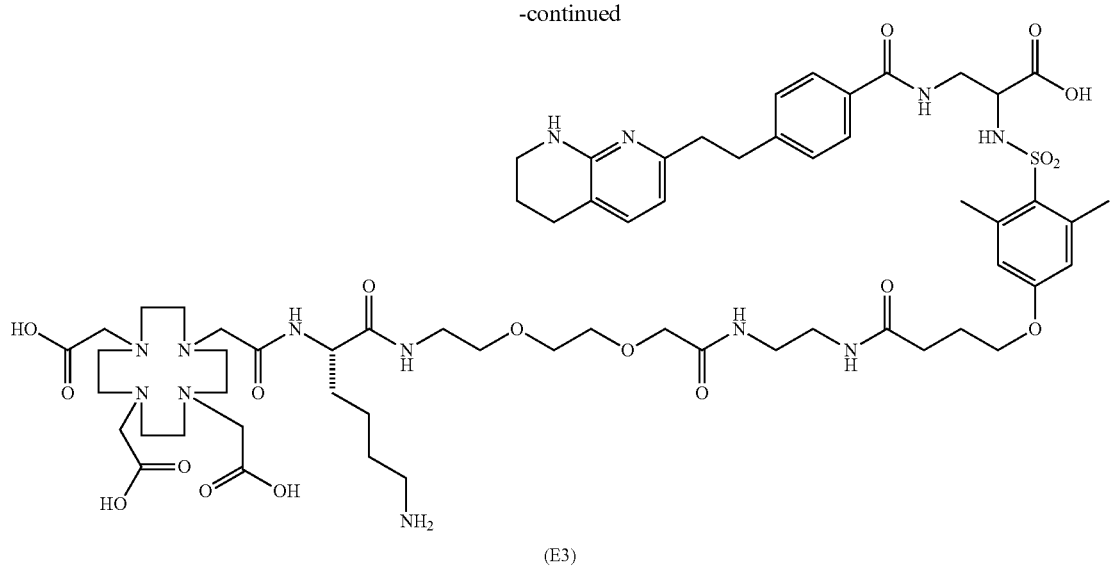

(E3)

(1) To a solution of compound (D1) (29.8 mg) in DMF (0.5 mL), diethylamine (0.5 mL) was added, and the mixture was stirred at room temperature for 2.5 hours. Then, the solvent was distilled off under reduced pressure. To the obtained residue, DMF (0.4 mL) and DIEA (10 μL) were added, then a solution of Fmoc-Lys(BOC)-OH (39.4 mg), DMF (150 μL), DIEA (20 μL), and HBTU (26.5 mg) in DMF (150 μL) was added, and the mixture was stirred at room temperature for 1 hour. Water (100 μL) was added thereto, and the mixture was purified by preparative HPLC to obtain compound (E1) (4.4 mg). LC/MS (SunFire) rt (min): 10.56 MS (ESI, m/z): 645.85 [M+2H]$^{2+}$, 430.35 [M+3H]$^{3+}$, 1288.45 [M−H]$^{−}$ (2) To a solution of compound (E1) (4.4 mg) in DMF (0.5 mL), diethylamine (0.5 mL) was added, and the mixture was stirred at room temperature for 8 hours. The solvent was distilled off under reduced pressure. DMF (0.4 mL) and DIEA (10 μL) were added to the residue, and the mixture was stirred. Then, a solution of tri-tert-butyl 1,4,7,10-tetraazacyclododecane-1,4,7,10-tetraacetate (7.8 mg), DMF (0.1 mL), DIEA (10 μL), and HBTU (5.2 mg) in DMF (100 μL) was added thereto, and the mixture was stirred at room temperature for 1 hour. Water (100 μL) was added thereto, and then, the mixture was purified by preparative HPLC to obtain compound (E2) (4.4 mg). LC/MS (SunFire) rt (min): 8.21 MS (ESI, m/z): 812.35 [M+2H]$^{2+}$ (3) To compound (E2) (4.4 mg), THF (0.7 mL), water (0.1 mL), and a 3 mol/L aqueous lithium hydroxide solution (0.1 mL) were added, and the mixture was stirred at room temperature for 1.5 hours. TFA was added thereto, and the solvent was distilled off under reduced pressure. TFA/triethylsilane (95/5) (1 mL) was added to the residue, and the mixture was stirred at room temperature for 1.5 hours. The solvent was distilled off under reduced pressure. A 20% aqueous acetonitrile solution (1 mL) and methanol (0.6 mL) were added to the residue, and the mixture was purified by preparative HPLC to obtain compound (E3) (2.5 mg). LC/MS (SunFire) rt (min): 6.19 MS (ESI, m/z): 670.75 [M+2H]$^{2+}$, 447.60 [M+3H]$^{3+}$ Example 6

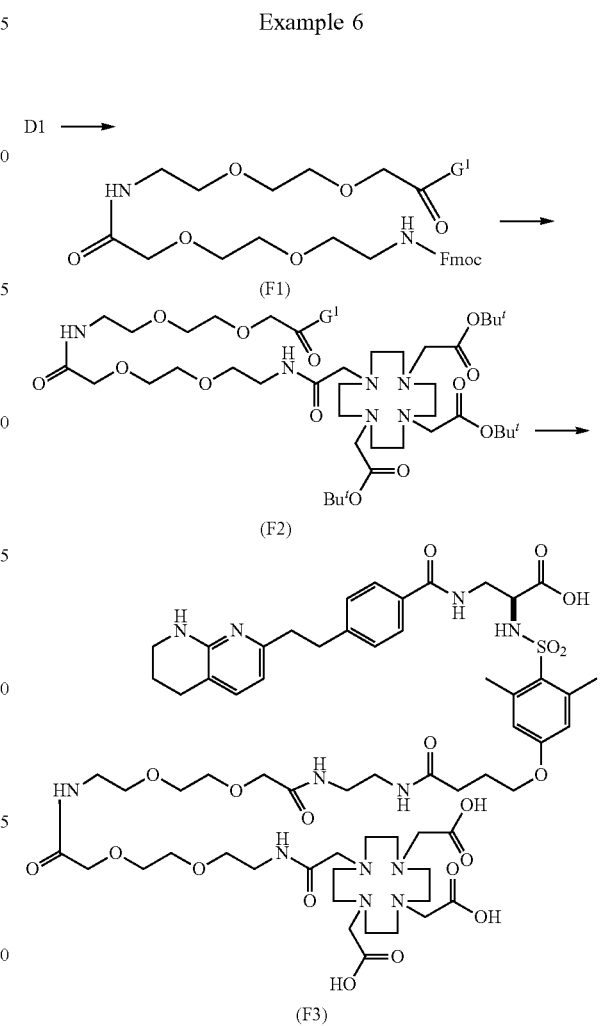

(1) To a solution of compound (D1) (30.9 mg) in DMF (0.5 mL), diethylamine (0.5 mL) was added, and the mixture was stirred at room temperature for 50 minutes. The solvent was distilled off under reduced pressure. To the residue, DMF (0.3 mL) and DIEA (15 μL) were added, then a solution of Fmoc-8-amino-3,6-dioxaoctanoic acid (23.0 mg), DMF (150 μL), DIEA (15 μL), and HBTU (22.0 mg) in DMF (150 μL) was added, and the mixture was stirred at room temperature 50 minutes. Water (100 μL) was added thereto, and then, the mixture was purified by preparative HPLC to obtain compound (F1) (10.9 mg). LC/MS (ACQUITY) rt (min): 1.29 MS (ESI, m/z): 1207.7 [M+H]$^+$, 604.7 [M+2H]$^{2+}$, 1205.7 [M−H]$^−$ (2) To a solution of compound (F1) (10.9 mg) in DMF (0.5 mL), diethylamine (0.5 mL) was added, and the mixture was stirred at room temperature for 1 hour. The solvent was distilled off under reduced pressure. To the residue, DMF (0.4 mL) and DIEA (15 μL) were added, then a solution of tri-tert-butyl 1,4,7,10-tetraazacyclododecane-1,4,7,10-tetraacetate (15.5 mg), DMF (100 μL), DIEA (15 μL), and HBTU (9.6 mg) in DMF (100 μL) was added, and the mixture was stirred at room temperature for 30 minutes. Water (100 μL) was added thereto, and the mixture was purified by preparative HPLC. The solvent was distilled off under reduced pressure to obtain a fraction containing compound (F2) (12.4 mg). LC/MS (SunFire) rt (min): 7.80 MS (ESI, m/z): 514.10 [M+3H]$^{3+}$, 1537.80 [M−H]$^−$ (3) To compound (F2) (10.4 mg), THF (0.7 mL), water (0.1 mL), and a 3 mol/L aqueous lithium hydroxide solution (0.1 mL) were added, and the mixture was stirred at room temperature for 1.5 hours. TFA was added thereto, and the solvent was distilled off under reduced pressure. TFA/triethylsilane (95/5) (1 mL) was added to the residue, and the mixture was stirred at room temperature for 80 minutes. TFA was distilled off under reduced pressure. A 20% aqueous acetonitrile solution (2.1 mL) was added to the residue, and the mixture was purified by preparative HPLC to obtain compound (F3) (4.0 mg). LC/MS (SunFire) rt (min): 7.17 MS (ESI, m/z): 679.45 [M+2H]$^{2+}$, 453.35 [M+3H]$^{3+}$ Example 7

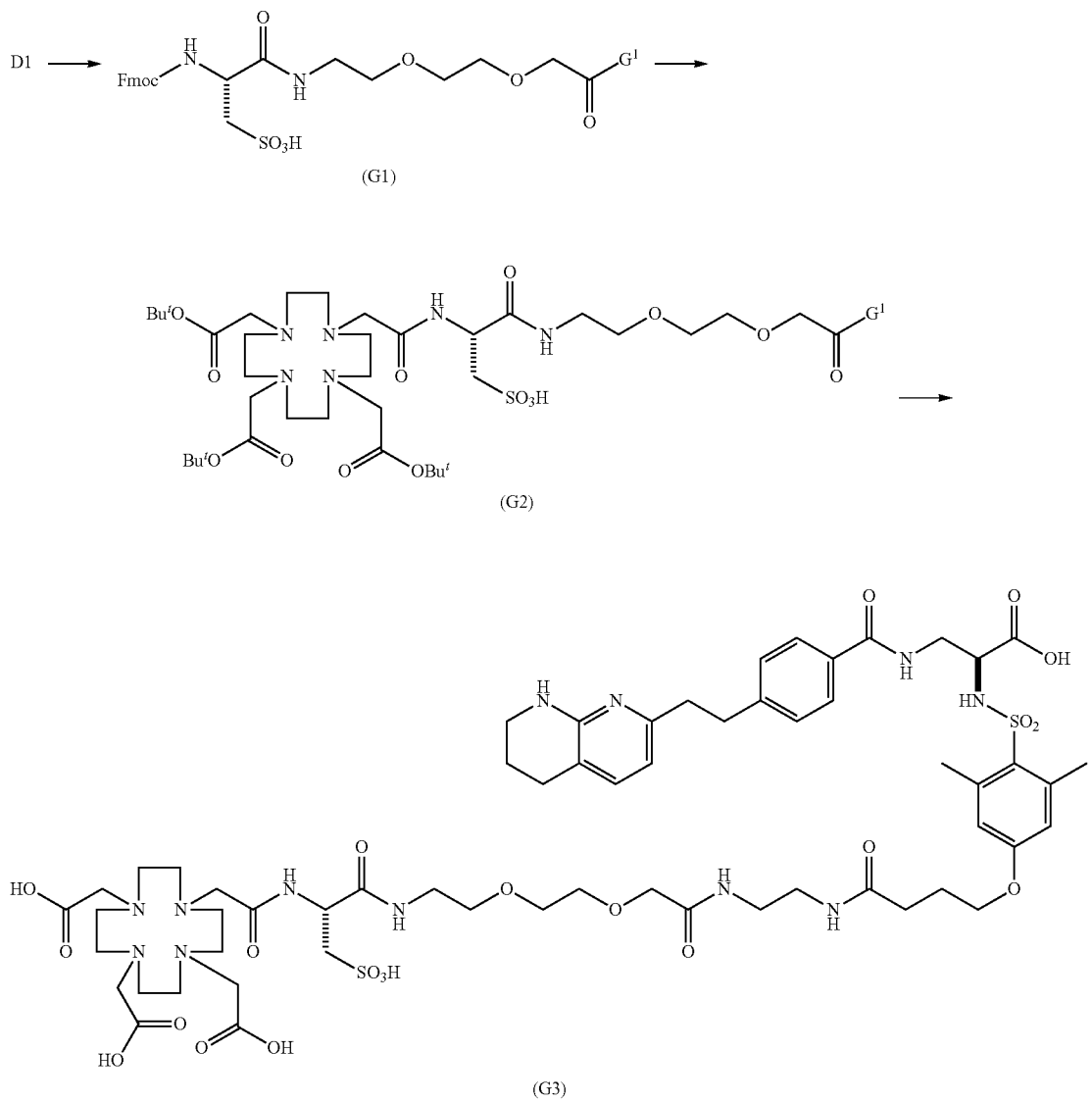

(1) To a solution of compound (D1) (27.3 mg) in DMF (0.5 mL), diethylamine (0.5 mL) was added, and the mixture was stirred at room temperature for 1 hour. Then, the solvent was distilled off under reduced pressure. To the obtained residue, Fmoc-cysteic acid (20.1 mg), DMF (0.7 mL), and DIEA (20 µL) were added, then a solution of HBTU (19.5 mg) in DMF (200 µL) was added, and the mixture was stirred at room temperature for 10 minutes. Water (0.5 mL) and ethyl acetate (2 mL) were added to the reaction mixture. The aqueous layer was separated and purified by preparative HPLC to obtain compound (G1) (11.2 mg). LC/MS (SunFire) rt (min): 11.78 MS (ESI, m/z): 1235.35 [M+Na]$^+$, 629.40 [M+2Na]$^{2+}$, 1212.40 [M−H]$^-$ (2) To a solution of compound (G1) (11.2 mg) in DMF (0.5 mL), diethylamine (0.5 mL) was added, and the mixture was stirred at room temperature for 1.5 hours. The solvent was distilled off under reduced pressure. To the obtained residue, DMF (0.2 mL) and DIEA (10 µL) were added, and the mixture was stirred. A solution of tri-tert-butyl 1,4,7,10-tetraazacyclododecane-1,4,7,10-tetraacetate (15.5 mg), DMF (200 µL), DIEA (10 µL), and HBTU (10.5 mg) in DMF (100 µL) was added to the reaction mixture, and the mixture was stirred at room temperature for 30 minutes. To the reaction mixture, water (100 µL) was added, then a 50% aqueous acetonitrile solution (1.2 mL) was added, and then, the mixture was purified by preparative HPLC to obtain compound (G2) (7.6 mg). LC/MS (SunFire) rt (min): 8.26 MS (ESI, m/z): 1545.80 [M+H]$^+$, 773.90 [M+2H]$^{2+}$, 1543.85 [M−H]$^-$ (3) To compound (G2) (7.6 mg), THF (1 mL), water (140 µL), and a 3 mol/L aqueous lithium hydroxide solution (140 µL) were added, and the mixture was stirred at room temperature for 1.5 hours. TFA was added thereto, and the solvent was distilled off under reduced pressure. TFA/triethylsilane (95/5) (1 mL) was added to the residue, and the mixture was stirred at room temperature for 100 minutes. TFA was distilled off under reduced pressure. A 50% aqueous acetonitrile solution (1.2 mL) and water (500 µL) were added to the residue, and the mixture was purified by preparative HPLC to obtain compound (G3) (5.1 mg). LC/MS (SunFire) rt (min): 8.30 MS (ESI, m/z): 682.50 [M+2H]$^{2+}$ Example 8

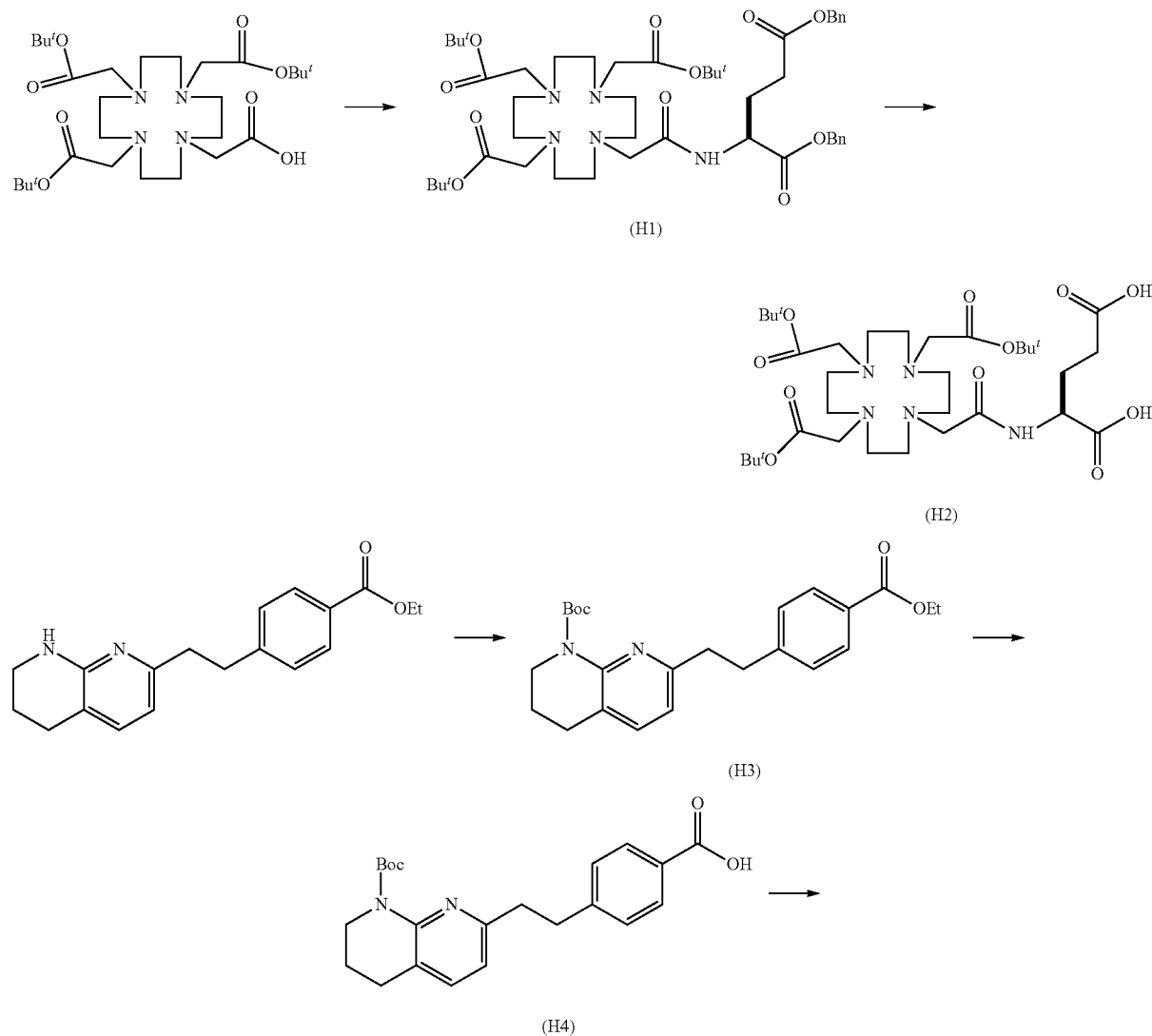

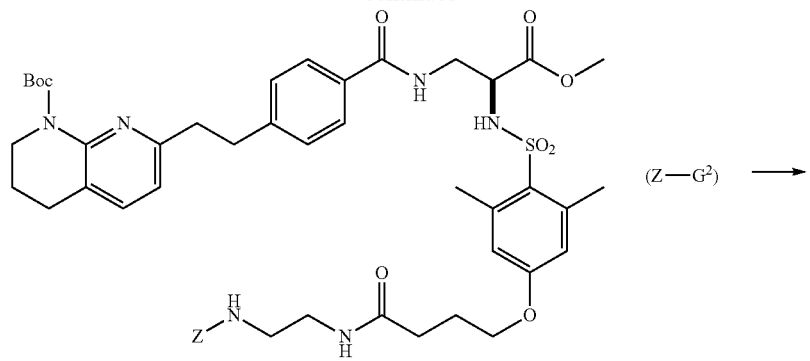
(H5)
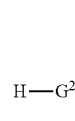 → 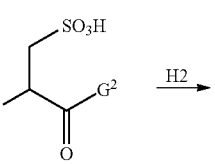
(H6) (H7)
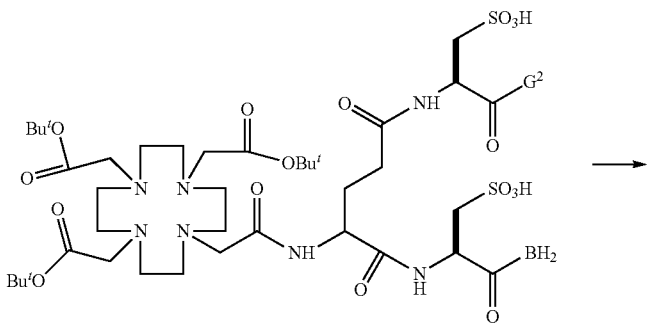
(H8)
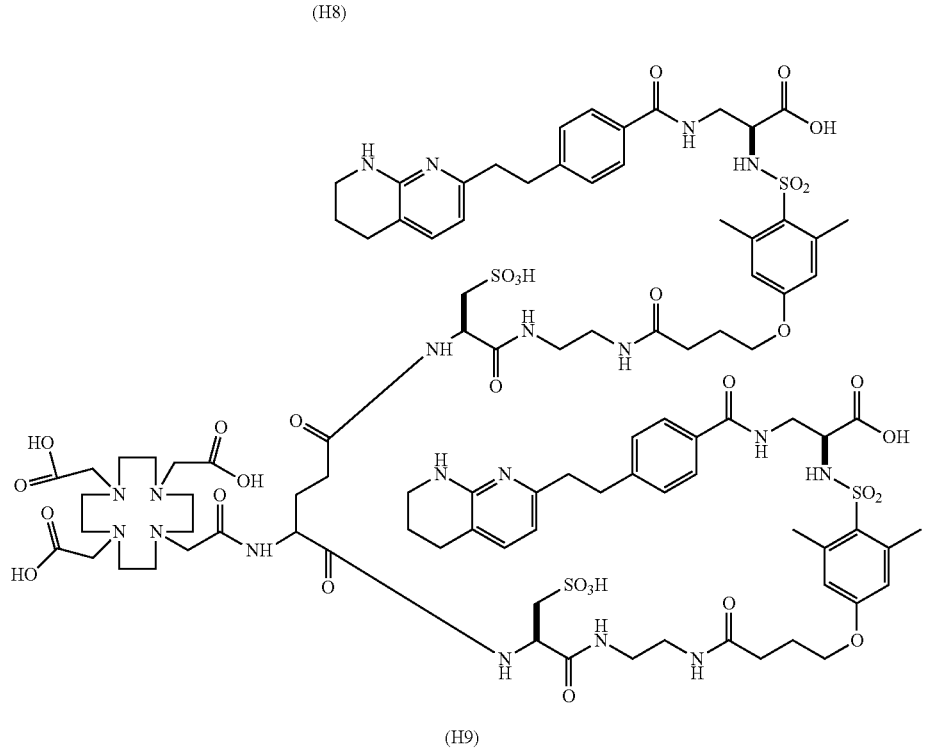
(H9)

(1) To a mixture of L-glutamic acid dibenzyl ester hydrochloride (86.9 mg), tri-tert-butyl 1,4,7,10-tetraazacyclododecane-1,4,7,10-tetraacetate (114 mg), DMF (2 mL), and DIEA (100 μL), HBTU (83 mg) was added, and the resulting mixture was stirred at room temperature for 30 minutes. The solvent was distilled off under reduced pressure, and ethyl acetate (5 mL) and a saturated aqueous solution of sodium chloride (3 mL) were added to the residue. The organic layer was separated, and the aqueous layer was subjected to extraction with ethyl acetate (5 mL) five times. The combined organic layers were dried over anhydrous magnesium sulfate and purified by silica gel column chromatography (ethyl acetate) to obtain compound (H1) (96 mg). TLC Rf: 0.58 (ethyl acetate/methanol=5/1) MS (ESI, m/z): 904.8 [M+Na]$^+$ (2) Compound (H1) (90.0 mg), methanol (10 mL), and 10% Pd/C (50 mg) were placed in a sealed tube and stirred for 3 hours in a 0.4 MPa hydrogen atmosphere. Insoluble matter was filtered off, and the solvent was distilled off under reduced pressure to obtain compound (H2) (80 mg). LC/MS (SunFire) rt (min): 9.50 MS (ESI, m/z): 702.20 [M+H]$^+$, 700.35 [M−H]$^-$ (3) A mixture of ethyl 4-(2-(5,6,7,8-tetrahydro-1,8-naphthyridin-2-yl)ethyl)benzoate (2.76 g), THF (70 mL), DIEA (4.7 mL), and di-tert-butyl dicarbonate (4.1 mL) was refluxed for 19 hours. Di-tert-butyl dicarbonate (4 mL) and DIEA (5 mL) were added thereto, and the mixture was refluxed for 6 hours. The solvent was distilled off under reduced pressure. The obtained residue was dissolved in ethyl acetate (200 mL), and the solution was washed with water and a saturated aqueous solution of sodium chloride. The obtained product was purified by silica gel column chromatography (hexane/ethyl acetate=5/1 to 2/1) to obtain compound (H3) (1.47 g). MS (ESI, m/z): 411.43 [M+H]$^+$ (4) To a solution of compound (H3) (213 mg) in THF (15 mL) and methanol (5 mL), a 2 mol/L aqueous lithium hydroxide solution (3 mL) was added, and the mixture was stirred at room temperature for 1 hour and then left overnight. Water (10 mL) was added thereto, and the mixture was adjusted to pH 4 by the addition of sodium bisulfate, followed by extraction with ethyl acetate (20 mL) three times. The extract was washed three times with a saturated aqueous solution of sodium chloride (30 mL) and dried over anhydrous sodium sulfate, and the solvent was distilled off under reduced pressure to obtain compound (H4) (202 mg). MS (ESI, m/z): 383.3 [M+H]$^+$, 381.4 [M−H]$^-$ (5) To a solution of compound (A2) (266 mg) and compound (H4) (150 mg) in DMF (5 mL) and DIEA (0.6 mL), HBTU (178 mg) was added, and the mixture was stirred at room temperature for 1 hour. The solvent was distilled off under reduced pressure, and ethyl acetate (10 mL) and a saturated aqueous solution of sodium bicarbonate (10 mL) were added to the residue, followed by extraction with ethyl acetate (20 mL) twice. The combined organic layers were washed twice with a saturated aqueous solution of sodium chloride (20 mL), then dried over anhydrous sodium sulfate, and purified by silica gel column chromatography (ethyl acetate/methanol=40/1) to obtain compound (H5) (187 mg). LC/MS (SunFire) rt (min): 12.25 MS (ESI, m/z): 929.25 [M+H]$^+$, 927.25 [M−H]$^-$ (6) Compound (H5) (180 mg), methanol (10 mL), and 10% Pd/C (50 mg) were placed in a sealed tube and stirred for 5 hours in a 0.5 MPa hydrogen atmosphere. Insoluble matter was filtered off, and the solvent was distilled off under reduced pressure to obtain compound (H6) (131 mg). MS (ESI, m/z): 795.7 [M+H]$^+$, 695.5 [M−BOC]$^+$, 793.2 [M−H]$^-$ (7) To a solution of compound (H6) (130 mg) and Fmoc-cysteic acid (77.0 mg) in DMF (4 mL) and DIEA (200 μL), HBTU (68.4 mg) was added, and the mixture was stirred at room temperature for 1 hour. A saturated aqueous solution of sodium chloride (5 mL), ethyl acetate (5 mL), and water (5 mL) were added thereto. The organic layer was separated, and the aqueous layer was subjected to extraction with ethyl acetate (10 mL) six times. The organic layers were combined, and the solvent was distilled off under reduced pressure. The obtained residue was purified by silica gel column chromatography (ethyl acetate/methanol=5/1) to obtain compound (H7) (66.6 mg). LC/MS (SunFire) gradient cycle: 0.0 min (solution A/solution B=30/70), 10.0 min (solution A/solution B=0/100), 15.0 min (solution A/solution B=0/100) rt (min): 11.55 MS (ESI, m/z): 1166.40 [M−H]$^-$ (8) To a solution of compound (H7) (55 mg) in DMF (4 mL), diethylamine (2 mL) was added, and the mixture was stirred at room temperature for 150 minutes. The solvent was distilled off under reduced pressure. To the obtained residue, compound (H2) (11.0 mg), DMF (0.5 mL), and DIEA (50 μL) were added, then HBTU (15.1 mg) was added, and the mixture was stirred at room temperature for 20 minutes. DIEA (20 μL) was added thereto, and the mixture was stirred at room temperature for 2 hours. The solvent was distilled off under reduced pressure. The obtained residue was purified by preparative HPLC to obtain compound (H8) (3.2 mg). LC/MS (SunFire) gradient cycle: 0.0 min (solution A/solution B=60/40), 30.0 min (solution A/solution B=0/100) rt (min): 17.12 MS (ESI, m/z): 853.45 [M+3H]$^{3+}$, 819.85 [M+3H−BOC]$^{3+}$, 786.70 [M+3H−2BOC]$^{3+}$ (9) A mixture of compound (H8) (3.2 mg), THF (350 μL), water (50 μL), and a 3 mol/L aqueous lithium hydroxide solution (35 μL) was stirred at room temperature for 90 minutes. TFA was added thereto, and the solvent was distilled off under reduced pressure. To the obtained residue, TFA/triethylsilane (95/5) (1 mL) was added, and the mixture was stirred for 90 minutes. Then, TFA was distilled off under reduced pressure. To the obtained residue, a 50% aqueous acetonitrile solution (800 μL) was added, and the mixture was purified by preparative HPLC to obtain compound (H9) (2.7 mg). LC/MS (SunFire) rt (min): 10.25 MS (ESI, m/z): 721.30 [M+3H]$^{3+}$, 1078.80 [M−2H]$^{2-}$ Example 9

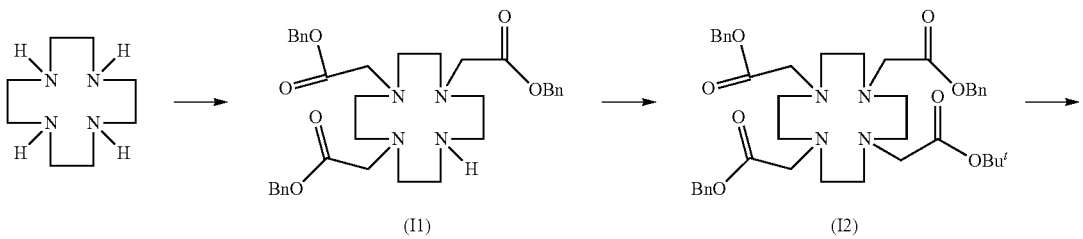

-continued
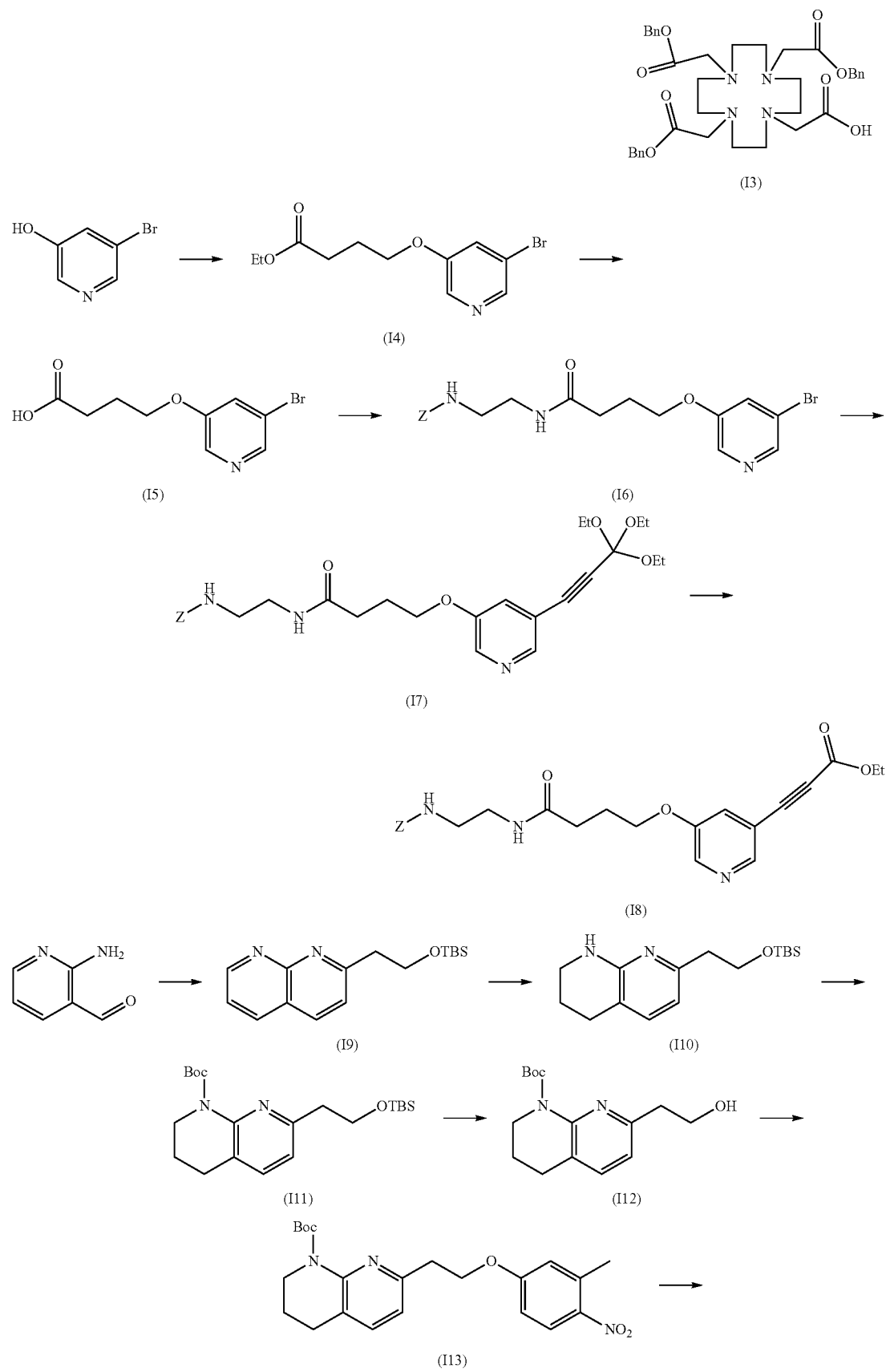

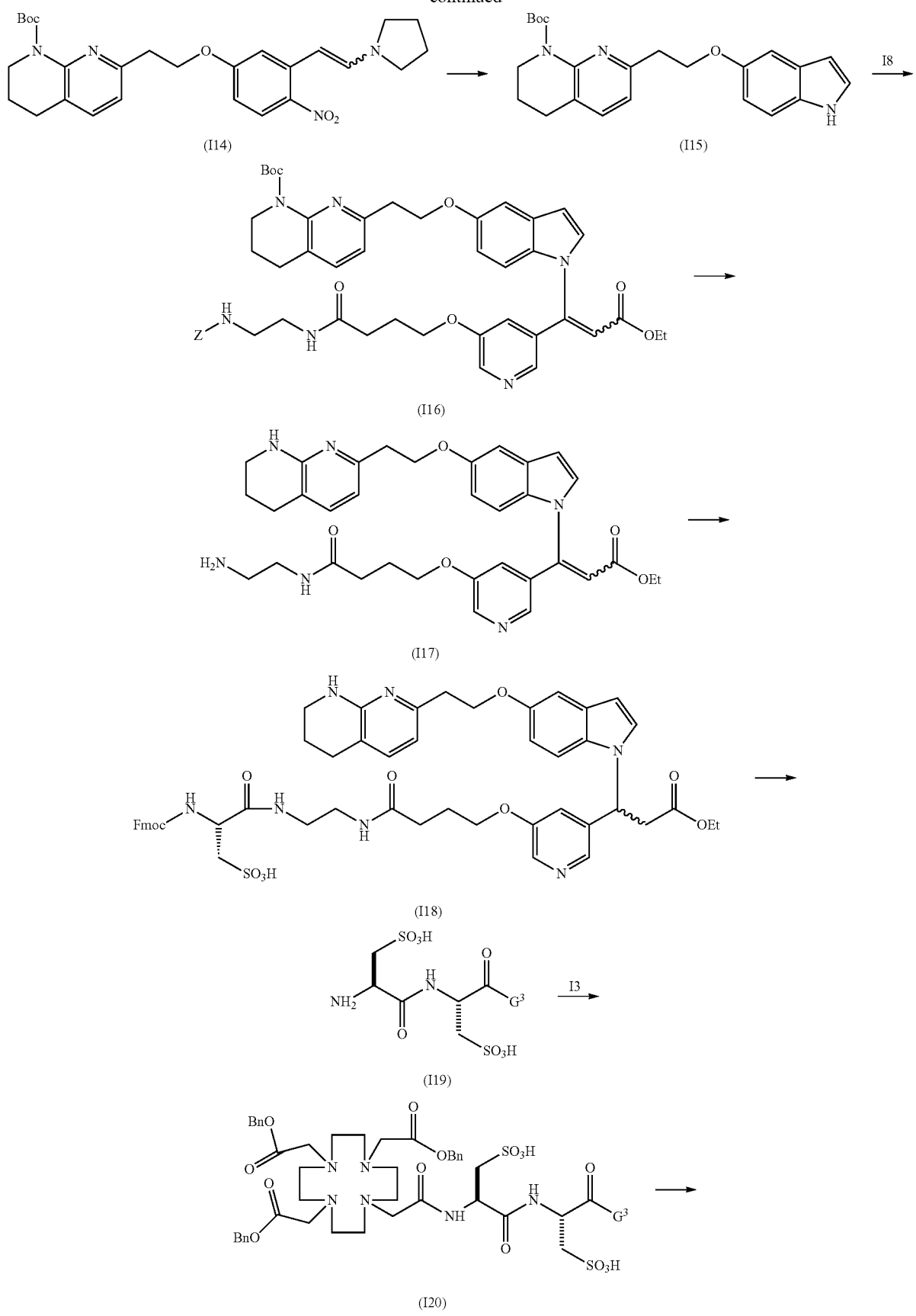

-continued

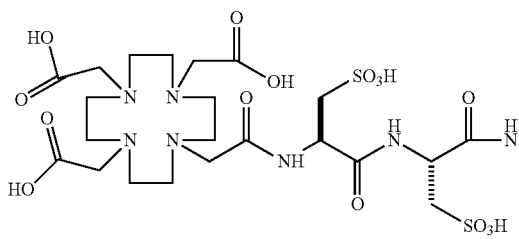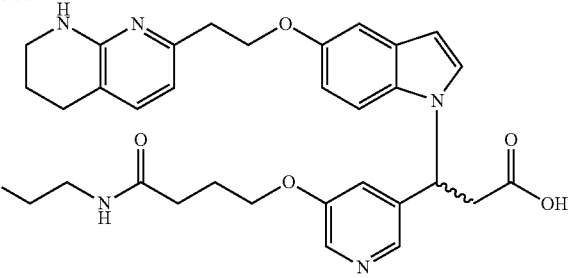

(I21)

(1) To a suspension of 1,4,7,10-tetraazacyclododecane (5.0 g), sodium acetate trihydrate (13.0 g), and DMAc (40 mL), a solution of benzyl bromoacetate (22 g) in DMAc (20 mL) was added dropwise at 20° C. or lower over 20 minutes, and then, the mixture was stirred at room temperature for 20 hours. Ethyl acetate (500 mL) was added to the reaction mixture, and the mixture was washed three times with water (300 mL), then dried over anhydrous sodium sulfate, and purified by silica gel column chromatography (ethyl acetate/methanol=5/1 to 1/1) to obtain compound (I11) (2.0 g). TLC Rf: 0.07 (ethyl acetate/methanol=5/1)

(2) To a mixture of compound (I11) (0.650 g), acetonitrile (8 mL), and potassium carbonate (160 mg), tert-butyl bromoacetate (156 µL) was added, and the resulting mixture was stirred at room temperature for 24 hours. Ethyl acetate (100 mL) and a saturated aqueous solution of sodium bicarbonate (50 mL) were added thereto. The organic layer was separated, then washed with a saturated aqueous solution of sodium chloride, and dried over anhydrous sodium sulfate, and the solvent was distilled off under reduced pressure. The obtained residue was purified by silica gel column chromatography (ethyl acetate/methanol=3/1) to obtain compound (I2) (319 mg). TLC Rf: 0.48 (acetonitrile/water=9/1) MS (ESI, m/z): 753.5 [M+Na]$^+$ (3) To compound (I2) (130 mg), a 4 mol/L solution of hydrogen chloride in dioxane (4 mL) was added, and the mixture was stirred at room temperature for 22 hours. The solvent was distilled off under reduced pressure. To the obtained residue, a 50% aqueous acetonitrile solution (2 mL) was added, and the mixture was purified by preparative HPLC to obtain compound (I3) (39.2 mg). LC/MS (SunFire) rt (min): 9.44 MS (ESI, m/z): 675.10 [M+H]$^+$, 673.25 [M−H]$^-$ (4) To a mixture of 5-bromo-3-hydroxypyridine (2.98 g), potassium carbonate (3.75 g), and DMF (35 mL), ethyl 4-bromobutanoate (3.9 mL) was added, and the resulting mixture was stirred at 40° C. for 2 hours. A saturated aqueous solution of ammonium chloride (30 mL) and ethyl acetate (100 mL) were added to the reaction mixture. The organic layer was separated, and the aqueous layer was subjected to extraction with ethyl acetate (100 mL) twice. The organic layers were combined, then washed with a saturated aqueous solution of sodium chloride, and dried over anhydrous sodium sulfate, and the solvent was distilled off under reduced pressure. The obtained residue was purified by silica gel column chromatography (hexane/ethyl acetate=10/1 to 7/1) to obtain compound (I4) (4.13 g). $^1$H-NMR (400 MHz, CDCl$_3$) δ: 8.28 (1H, brs), 8.22 (1H, brs), 7.35 (1H, dd, J=2.16, 2.24 Hz), 4.17 (2H, q, J=7.16 Hz), 4.06 (2H, t, J=6.12 Hz), 2.52 (2H, t, J=7.24 Hz), 2.13 (2H, tt, J=6.12, 7.24 Hz), 1.27 (3H, t, J=7.12 Hz)

(5) To a solution of compound (I4) (1.89 g) in methanol (20 mL) and THF (20 mL), a 5 mol/L aqueous sodium hydroxide solution (3 mL) was added, and the mixture was stirred at room temperature for 2 hours. Concentrated hydrochloric acid (2 mL) was added thereto, and the solvent was distilled off under reduced pressure. Then, water (50 mL) was added to the residue, followed by extraction with ethyl acetate (50 mL) four times. The organic layers were combined and dried over anhydrous sodium sulfate, and the solvent was distilled off under reduced pressure to obtain compound (I5) (1.76 g). TLC Rf: 0.19 (hexane/ethyl acetate=1/1) HPLC (SunFire) rt (min): 11.97 MS (ESI, m/z): 259.9 [M+H]$^+$ (6) To a mixture of compound (I5) (1.76 g), Z-ethylenediamine hydrochloride (1.87 g), DMF (40 mL), and DIEA (2.8 mL), HBTU (2.64 g) was added, and the resulting mixture was stirred at room temperature for 2.5 hours. Ethyl acetate (250 mL) and water (100 mL) were added thereto. The organic layer was separated, then washed twice with water (300 mL) and once with a saturated aqueous solution of sodium chloride (300 mL), and dried over anhydrous sodium sulfate. The solvent was distilled off under reduced pressure. The obtained residue was recrystallized from ethyl acetate to obtain compound (I6) (1.73 g). TLC Rf: 0.58 (ethyl acetate) HPLC (SunFire) rt (min): 13.60

(7) To a mixture of compound (I6) (1.70 g), 3,3,3-triethoxy-1-propyne (1.1 g), acetonitrile (20 mL), triethylamine (25 mL), and DMF (20 mL), dichlorobis(triphenylphosphine)palladium(II) (250 mg) and copper(I) iodide (38 mg) were added, and the resulting mixture was stirred at 70° C. for 3 hours in a nitrogen atmosphere and then left all night and all day at room temperature. The solvent was distilled off under reduced pressure. The obtained residue was dissolved in ethyl acetate (100 mL), and the solution was washed three times with water (100 mL) and once with a saturated aqueous solution of sodium chloride (100 mL) and dried over anhydrous sodium sulfate. Then, the solvent was distilled off under reduced pressure. The obtained residue was purified by silica gel column chromatography (ethyl acetate/methanol=0/10 to 2/8) to obtain compound (I7) ((1.7 g). TLC Rf 0.26 (hexane/ethyl acetate=1/2) HPLC (SunFire) rt (min): 14.65 MS (ESI, m/z): 550.3 [M+Na]$^+$ (8) To a solution of compound (I7) (1.70 g) in acetonitrile (25 mL), 2 mol/L hydrochloric acid (2 mL) was added, and the mixture was stirred at room temperature for 30 minutes. Ethyl acetate (100 mL) was added thereto, and the mixture was washed with a saturated aqueous solution of sodium bicarbonate and a saturated aqueous solution of sodium chloride, then dried over anhydrous sodium sulfate, and then purified by silica gel column chromatography (ethyl acetate/methanol=0/10 to 2/8) to obtain compound (I8) (1.3 g). TLC Rf: 0.26 (hexane/ethyl acetate=1/2) HPLC (SunFire) rt (min): 13.74 MS (ESI, m/z): 454.1 [M+H]$^+$ (9) A mixture of 4-((tert-butyldimethylsilyl)oxy)butan-2-one (22.0 g), 2-aminonicotinaldehyde (9.62 g), proline (4.6 g), and ethanol (120 mL) was refluxed for 10 hours. 4-((tert-Butyldimethylsilyl)oxy)butan-2-one (10 g) was added thereto, and the mixture was refluxed for 10 hours. The solvent was distilled off under reduced pressure, and the residue was purified by silica gel column chromatography (hexane/ethyl acetate=2/1 to 3/1) to obtain compound (I9) (2.57 g). LC/MS (SunFire) rt (min): 13.94 MS (ESI, m/z): 289.40 [M+H]$^+$

(10) Compound (I9) (2.50 g), methanol (75 mL), ethanol (75 mL), and 10% Pd/C (450 mg) were placed in an autoclave and stirred for 4 hours in a 4 MPa hydrogen atmosphere. Insoluble matter was filtered off, and the solvent was distilled off under reduced pressure to obtain compound (I10) (2.5 g). HPLC (SunFire) rt (min): 10.19

(11) A mixture of compound (I10) (2.5 g), THF (25 mL), DIEA (7.5 mL), and di-tert-butyl dicarbonate (6 mL) was stirred at 70° C. for 11 hours. The solvent was distilled off under reduced pressure. The obtained residue was purified by silica gel column chromatography (hexane/ethyl acetate=10/1) to obtain compound (I11) (1.85 g). TLC Rf: 0.85 (hexane/ethyl acetate=1/2)

(12) To a solution of compound (I11) (1.85 g) in THF (25 mL), a 1 mol/L solution of tetrabutyl ammonium fluoride in THF (8 mL) was added, and the mixture was stirred at room temperature for 3 hours. Then, ethyl acetate (50 mL) and a saturated aqueous solution of ammonium chloride (50 mL) were added thereto. The organic layer was separated, and the aqueous layer was subjected to extraction with ethyl acetate (100 mL) twice. The organic layers were combined, then washed with a saturated aqueous solution of sodium chloride, and then dried over anhydrous sodium sulfate, and the solvent was distilled off under reduced pressure. The obtained residue was purified by silica gel column chromatography (hexane/ethyl acetate=80/20 to 30/70) to obtain compound (I12) (1.17 g). LC/MS (ACQUITY) rt (min): 0.79 MS (ESI, m/z): 279.4 [M+H]$^+$

(13) To a solution of compound (I12) (1.17 g), triphenylphosphine (1.32 g), and 3-methyl-4-nitrophenol (837 mg) in THF (15 mL), diisopropyl azodicarboxylate (1.5 mL) was added dropwise over 5 minutes, and the mixture was stirred at room temperature for 3.5 hours. Ethyl acetate (100 mL) and a saturated aqueous solution of sodium bicarbonate (100 mL) were added thereto. The organic layer was separated and washed with a saturated aqueous solution of sodium chloride. After drying over anhydrous sodium sulfate, the solvent was distilled off under reduced pressure. The obtained residue was purified by silica gel column chromatography (hexane/ethyl acetate=85/15 to 60/40) to obtain a fraction containing compound (I13). The solvent was distilled off under reduced pressure. To the obtained residue, DMF (30 mL), benzyl bromide (3 mL), and cesium carbonate (7.6 g) were added, and the mixture was stirred at room temperature for 30 minutes. Ethyl acetate (300 mL) and water (100 mL) were added thereto. The organic layer was separated and dried over anhydrous sodium sulfate, and then, the solvent was distilled off under reduced pressure. The obtained residue was purified by silica gel column chromatography (hexane/ethyl acetate=80/20 to 60/40) to obtain compound (I13) (1.53 g). LC/MS (ACQUITY) rt (min): 1.27 MS (ESI, m/z): 414.5 [M+H]$^+$

(14) To a solution of compound (I13) (1.53 g) in DMF (15 mL), DMFDA (2.5 mL) and pyrrolidine (1.4 mL) were added, and the mixture was stirred at 80° C. for 5 hours. Water (50 mL) and ethyl acetate (150 mL) were added thereto. The organic layer was separated, then washed with water and a saturated aqueous solution of sodium chloride, and dried over anhydrous sodium sulfate. The solvent was distilled off under reduced pressure. The obtained residue was purified by silica gel column chromatography (hexane/ethyl acetate=70/30 to 40/60) to obtain compound (I14) (0.93 g). MS (ESI, m/z):495.3 [M+H]$^+$

(15) Compound (I14) (930 mg), methanol (20 mL), and 10% Pd/C (200 mg) were placed in a sealed tube and stirred for 3 hours in a 0.5 MPa hydrogen atmosphere. Insoluble matter was filtered off, and the solvent was distilled off under reduced pressure. The obtained residue was purified by silica gel column chromatography (hexane/ethyl acetate=75/25 to 70/30) to obtain compound (I15) (571 mg). TLC Rf: 0.36 (hexane/ethyl acetate=1/1) LC/MS (SunFire) rt (min): 9.15 MS (ESI, m/z): 394.10 [M+H]$^+$

(16) To compound (I15) (152.4 mg), compound (I8) (240 mg), and cesium fluoride (53 mg), DMF (2.5 mL) was added, and the mixture was stirred at 70° C. for 5 hours. Ethyl acetate (30 mL) was added thereto, and the mixture was washed with water and a saturated aqueous solution of sodium chloride. The solvent was distilled off under reduced pressure. The obtained residue was purified by silica gel column chromatography (ethyl acetate/methanol=100/0 to 90/10) to obtain compound (I16) (159 mg). LC/MS (SunFire) rt (min): 10.85,11.17 MS (ESI, m/z): 847.20 [M+H]$^+$

(17) Compound (I16) (159 mg), methanol (15 mL), and 10% Pd/C (80 mg) were placed in a sealed tube and stirred for 6 hours in a 0.5 MPa hydrogen atmosphere. Insoluble matter was filtered off, and the solvent was distilled off under reduced pressure. The residue was purified by preparative HPLC to obtain compound (I17) (44.6 mg). LC/MS (SunFire) rt (min): 5.92 MS (ESI, m/z): 615.15 [M+H]$^+$

(18) To a solution of compound (I17) (27.4 mg) and Fmoc-cysteic acid (39.3 mg) in DMF (0.8 mL) and DIEA (30 μL), a solution of HBTU (37.4 mg) in DMF (0.2 mL) was added, and the mixture was stirred at room temperature for 1 hour. Water (0.1 mL) were added thereto, and the mixture was purified by preparative HPLC to obtain compound (I18) (12.0 mg). LC/MS (SunFire) rt (min): 11.97 MS (ESI, m/z): 494.90 [M+2H]$^{2+}$, 986.15 [M−H]$^−$

(19) To a solution of compound (I18) (6.7 mg) in DMF (0.5 mL), diethylamine (0.5 mL) was added, and the mixture was stirred at room temperature for 11 hours.

The solvent was distilled off under reduced pressure. To the obtained residue, Fmoc-cysteic acid (10.6 mg), DMF (0.4 mL), and DIEA (20 μL) were added, then a solution of HBTU (9.5 mg) in DMF (0.1 mL) was added, and the mixture was stirred at room temperature for 1 hour. Water (0.2 mL) was added thereto, and the mixture was stirred for 20 minutes. Then, pyrrolidine (0.3 mL) was added thereto, and the mixture was stirred for 30 minutes. The reaction mixture was concentrated under reduced pressure, and the residue was purified by preparative HPLC to obtain compound (I19) (4.5 mg). LC/MS (SunFire) rt (min): 8.90 MS (ESI, m/z): 917.20 [M+H]$^+$, 459.30 [M+2H]$^{2+}$, 915.10 [M−H]$^−$

(20) To a solution of compound (I3) (11.4 mg) in DMF (200 μL) and DIEA (10 μL), a solution of HBTU (6.4 mg) in DMF (100 μL) was added, then the mixture was added to a solution of compound (I19) (4.5 mg) in DMF (200 μL) and DIEA (10 μL), and the resulting mixture was stirred at room temperature for 45 minutes. Water (100 μL) was added thereto, and the mixture was purified by preparative HPLC to obtain compound (I20) (5.2 mg). LC/MS (SunFire) rt (min): 10.43 MS (ESI, m/z): 787.60 [M+2H]$^{2+}$

(21) A mixture of compound (I20) (5.2 mg), THF (1 mL), water (140 μL), and a 3 mol/L aqueous lithium hydroxide solution (100 μL) was stirred at room temperature for 3 hours. The solvent was distilled off under reduced pressure. Then, a 50% aqueous acetonitrile solution (400 μL) and formic acid (14 μL) were added to the residue, and the mixture was purified by preparative HPLC to obtain compound (I21) (1.5 mg). LC/MS (SunFire) rt (min): 8.01 MS (ESI, m/z): 638.45 $[M+2H]^{2+}$, 425.65 $[M+3H]^{3+}$ Example 10

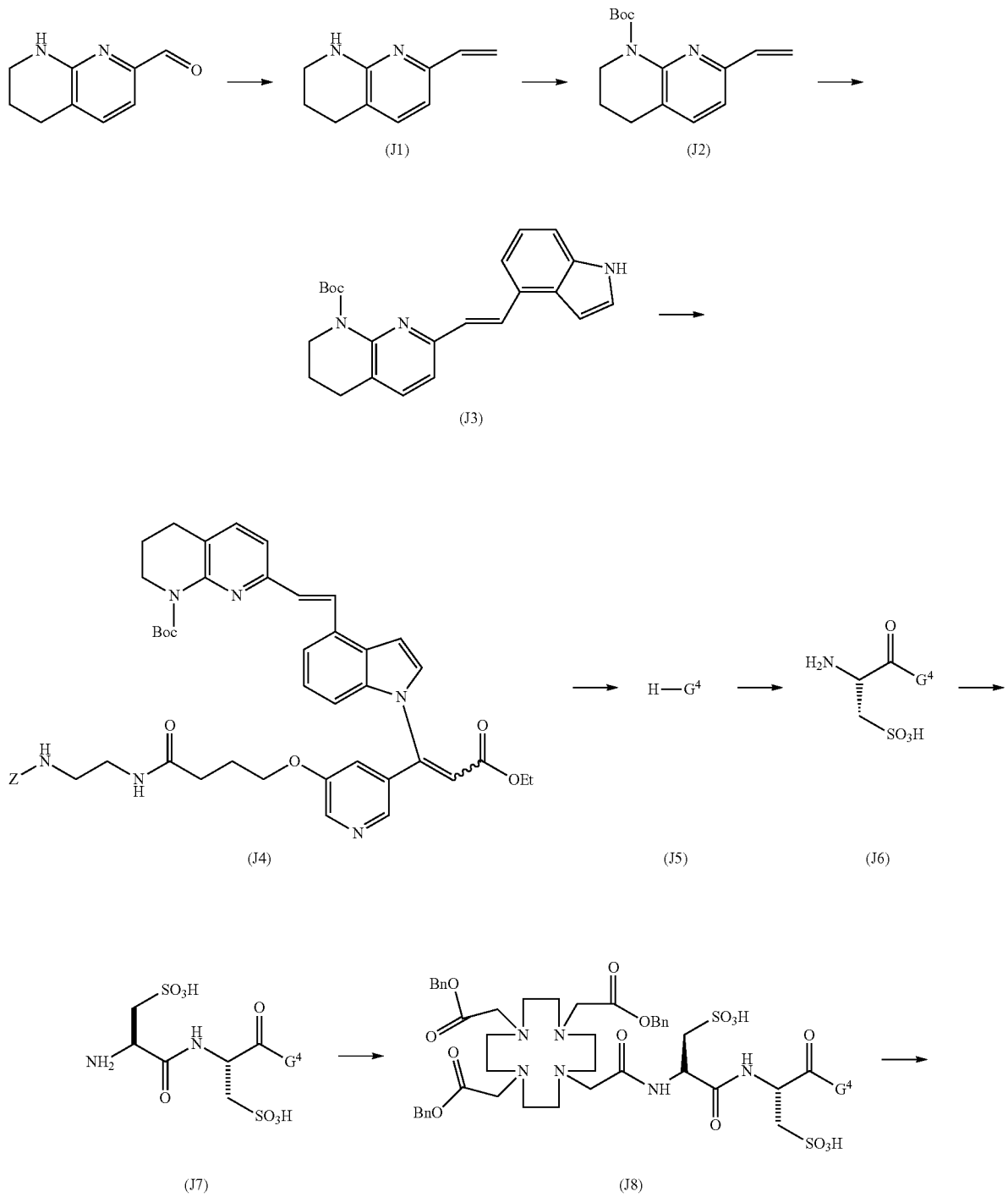

-continued

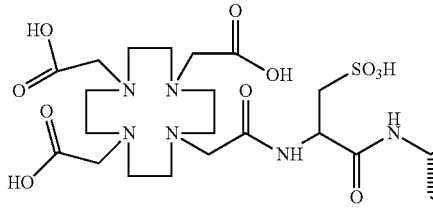 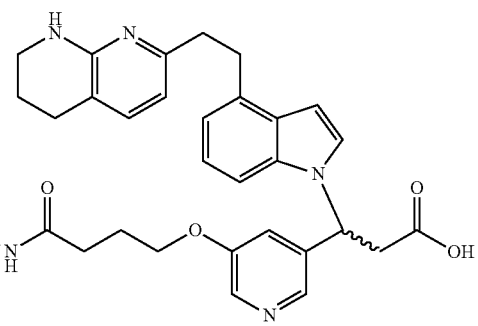

(J9)

(1) To sodium hydride (60% suspension in mineral oil, 1.65 g), DMSO (40 mL) was added, and the mixture was heated to 80° C. and then cooled to room temperature. Methyl triphenylphosphonium bromide (14.7 g) was added thereto, and the mixture was stirred for 10 minutes. Then, a solution of 5,6,7,8-tetrahydro-1,8-naphthyridine-2-carbaldehyde (2.46 g) in DMSO (25 mL) was added thereto, and the mixture was stirred at room temperature for 30 minutes. Water (600 mL) and ethyl acetate (300 mL) were added thereto. Then, the organic layer was separated, and the aqueous layer was subjected to extraction with ethyl acetate (300 mL). The organic layers were combined, then washed with a saturated aqueous solution of sodium chloride (300 mL), and dried over anhydrous sodium sulfate, and then, the solvent was distilled off under reduced pressure. The obtained residue was purified by silica gel column chromatography (hexane/ethyl acetate=4/1) to obtain compound (J1) (1.13 g). TLC Rf: 0.19 (hexane/ethyl acetate=2/1)

(2) To compound (J1) (1.37 g), di-tert-butyl dicarbonate (3.9 mL), DIEA (3.3 mL), and THF (15 mL) were added, and the mixture was refluxed for 3 days. The solvent was distilled off under reduced pressure, and ethyl acetate (50 mL) and a saturated aqueous solution of sodium chloride (50 mL) were added to the residue. The organic layer was separated, and the aqueous layer was subjected to extraction with ethyl acetate (50 mL). The organic layers were combined, then washed with a saturated aqueous solution of sodium chloride (50 mL), and dried over anhydrous magnesium sulfate, and then, the solvent was distilled off under reduced pressure. The obtained residue was purified by silica gel column chromatography (hexane/ethyl acetate=8/1 to 7/1) to obtain compound (J2) (1.71 g). TLC Rf: 0.51 (hexane/ethyl acetate=2/1) $^1$H-NMR (400 MHz, CDCl$_3$) δ: 7.34 (1H, d, J=10.2 Hz), 6.96 (1H, d, J=10.2 Hz), 6.73 (1H, dd, 14.2, 23.1 Hz), 6.22 (1H, dd, 2.2, 23.1 Hz), 5.39 (1H, dd, 2.2, 14.2 Hz), 3.77 (2H, t, J=8.6 Hz), 2.75 (2H, t, J=8.8 Hz), 1.93 (2H, tt, J=8.6, 8.8 Hz), 1.47 (9H, s)

(3) To a mixture of compound (J2) (1.71 g), 4-bromoindole (824 μL), DMF (25 mL), and triethylamine (4 mL), palladium(II) acetate (147 mg) and (2-biphenyl)di-tert-butylphosphine (392 mg) were added, and the resulting mixture was stirred at 110° C. for 20 hours. Ethyl acetate (300 mL) and water (100 mL) were added thereto. The organic layer was separated, then washed twice with a saturated aqueous solution of sodium chloride (100 mL), and dried over anhydrous magnesium sulfate, and then, the solvent was distilled off under reduced pressure. The obtained residue was purified by silica gel column chromatography (hexane/ethyl acetate=9/1 to 5/1) to obtain compound (J3) (1.18 g). TLC Rf: 0.31 (hexane/ethyl acetate=2/1) MS (ESI, m/z): 376.2 [M+H]$^+$ (4) To compound (J3) (150 mg), compound (I8) (180 mg), and cesium fluoride (60 mg), DMF (1.5 mL) was added, and the mixture was stirred at 60° C. for 20 hours. Ethyl acetate (10 mL) was added thereto, and the mixture was washed with water and a saturated aqueous solution of sodium chloride and dried over anhydrous sodium sulfate. Then, the solvent was distilled off under reduced pressure. The obtained residue was purified by silica gel column chromatography (ethyl acetate/methanol=10/0 to 9/1) to obtain compound (J4) (130 mg). TLC Rf: 0.2 (ethyl acetate) LC/MS (SunFire) rt (min): 12.15, 12.68 MS (ESI, m/z): 415.25 [M+2H]$^{2+}$ (5) Compound (J4) (130 mg), methanol (20 mL), and 10% Pd/C (100 mg) were placed in a sealed tube and stirred for 9 hours in a 0.5 MPa hydrogen atmosphere. Insoluble matter was filtered off, and the solvent was distilled off under reduced pressure. The residue was purified by preparative HPLC to obtain compound (J5) (29.0 mg). HPLC (SunFire) rt (min): 7.42 LC/MS (SunFire) rt (min): 6.66 MS (ESI, m/z): 599.35 [M+H]$^+$ (6) To a solution of compound (J5) (29.0 mg) and Fmoc-cysteic acid (48.0 mg) in DMF (1 mL) and DIEA (60 μL), a solution of HBTU (45.9 mg) in DMF (0.4 mL) was added, and the mixture was stirred at room temperature for 1 hour. Water (1 mL) was added thereto, and the solvent was distilled off under reduced pressure. To the obtained residue, DMF (1 mL) and diethylamine (1 mL) were added, and the mixture was left at room temperature for 13 hours. The solvent was distilled off under reduced pressure. To the obtained residue, a 50% aqueous acetonitrile solution was added, and the mixture was purified by preparative HPLC to obtain compound (J6). HPLC (SunFire) rt (min): 9.80

(7) To compound (J6) obtained in the step (6), a solution of Fmoc-cysteic acid (48.0 mg), DMF (0.6 mL), DIEA (60 μL), and HBTU (45.9 mg) in DMF (0.4 mL) was added, and the mixture was stirred at room temperature for 1.5 hours. Water (0.5 mL) was added thereto, and the mixture was stirred for 5 minutes. Then, pyrrolidine (0.5 mL) was added thereto, and the mixture was stirred at room temperature for 30 minutes. The solvent was distilled off under reduced pressure. The obtained residue was purified by preparative HPLC to obtain compound (J7) (8.0 mg). HPLC (SunFire) rt (min): 9.17 LC/MS (SunFire) rt (min): 9.23 MS (ESI, m/z): 901.10 [M+H]$^+$, 451.35 [M+2H]$^{2+}$, 899.00 [M−H]$^-$ (8) To a solution of compound (I3) (16.9 mg) in DMF (200 μL) and DIEA (20 μL), a solution of HBTU (9.5 mg) in DMF (60 μL) was added, then the mixture was added to a solution of compound (J7) (8.0 mg) in DMF (200 μL) and DIEA (10 μL), and the resulting mixture was stirred at room temperature for 2 hours. Water (100 μL) was added thereto, and then, the mixture was purified by preparative HPLC to obtain compound (J8) (6.9 mg). LC/MS (SunFire) rt (min): 10.46 MS (ESI, m/z): 779.65 [M+2H]$^{2+}$ (9) A mixture of compound (J8) (4.2 mg), THF (0.7 mL), water (0.1 mL), and a 3 mol/L aqueous lithium hydroxide solution (70 μL) was stirred at room temperature for 4 hours. The solvent was distilled off under reduced pressure. To the obtained residue, a 50% aqueous acetonitrile solution (400 μL) and formic acid (10 μL) were added, and the mixture was purified by preparative HPLC to obtain compound (J9) (1.2 mg). LC/MS (SunFire) rt (min): 8.62 MS (ESI, m/z): 630.45 [M+2H]$^{2+}$, 628.05 [M−2H]$^{2−}$ Example 11

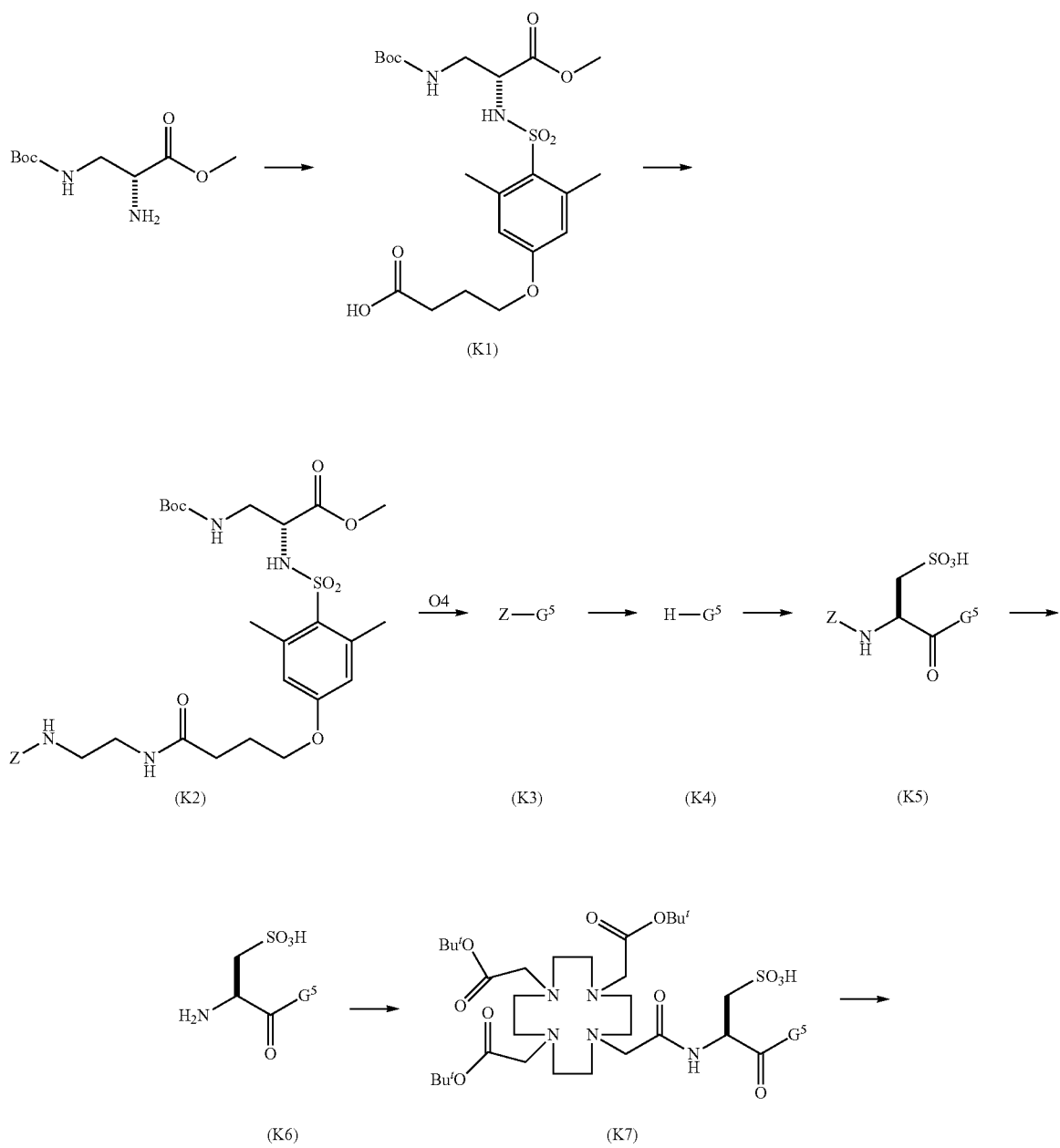

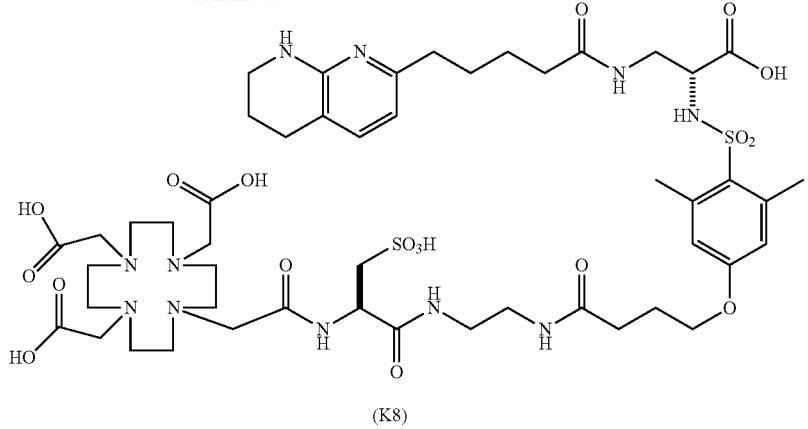

(K8)

(1) To a mixture of (R)-methyl 2-amino-3-((tert-butoxycarbonyl)amino) propanoate hydrochloride (3.92 g), acetonitrile (39 mL), and potassium carbonate (6.4 g), 4-(4-(chlorosulfonyl)-3,5-dimethylphenyloxy) butanoic acid (4.32 g) was added in 4 divided portions every 30 minutes, and then, the resulting mixture was stirred at room temperature for 9 hours. Water (150 mL) and ethyl acetate (50 mL) were added thereto. The aqueous layer was separated, and sodium chloride (20 g) and ethyl acetate (50 mL) were added thereto. The reaction mixture was neutralized with concentrated hydrochloric acid, and the separated organic layer was washed twice with a saturated aqueous solution of sodium chloride (100 mL) and then dried over anhydrous sodium sulfate. The solvent was distilled off under reduced pressure to obtain compound (K1) (3.13 g). HPLC (CAPCELL PAK MG) rt (min): 14.28 LC/MS (ACQUITY) rt (min): 1.31 MS (ESI, m/z): 487.4 [M−H]−

(2) To a mixture of compound (K1) (3.13 g), DMF (13 mL), Z-ethylenediamine hydrochloride (1.48 g), and DIEA (2.3 mL), HBTU (2.55 g) was added, and the resulting mixture was stirred at room temperature for 1 hour. Water (16 mL) was added dropwise thereto, and the mixture was stirred for 2 hours. Then, water (16 mL) was added thereto, and the solid was collected by filtration to obtain compound (K2) (3.40 g). HPLC (CAPCELL PAK MG) rt (min): 14.98 LC/MS (ACQUITY) rt (min): 1.46 MS (ESI, m/z): 665.5 [M+H]+, 663.6 [M−H]−

(3) To a solution of compound (K2) (3.04 g) in dichloromethane (10 mL), TFA (10 mL) was added, and the mixture was stirred at room temperature for 1.5 hours. The solvent was distilled off under reduced pressure, and a 4 mol/L solution of hydrogen chloride in dioxane (10 mL) was added to the residue. The solvent was distilled off under reduced pressure. To the obtained residue, compound (O4) (1.04 g), DMF (16 mL), DIEA (2.4 mL), and HBTU (1.91 g) were added, and the mixture was stirred at room temperature for 1.5 hours. A 5% aqueous sodium bicarbonate solution (80 mL) and ethyl acetate (80 mL) were added thereto, and the mixture was stirred at room temperature for 10 minutes. The organic layer was separated, then washed twice with a saturated aqueous solution of sodium chloride (50 mL), and dried over anhydrous sodium sulfate, and then, the solvent was distilled off under reduced pressure. Ethyl acetate (16 mL) was added to the residue, and the solid was collected by filtration to obtain compound (K3) (2.52 g). LC/MS (ACQUITY) rt (min): 1.16 MS (ESI, m/z): 781.7 [M+H]+

(4) A mixture of 10% Pd/C (0.40 g), methanol (25 mL), and compound (K3) (1.90 g) was stirred at room temperature for 17 hours in a hydrogen atmosphere. Insoluble matter was filtered off, and the solvent was distilled off under reduced pressure to obtain compound (K4) (1.72 g). LC/MS (ACQUITY) rt (min): 0.79 MS (ESI, m/z): 647.6 [M+H]+, 645.6 [M−H]−

(5)

To a mixture of compound (K4) (183 mg), Z-cysteic acid (85.8 mg), DMF (2 mL), and DIEA (172 μL), HBTU (113 mg) was added, and the resulting mixture was stirred at room temperature for 1 hour. Water (10 mL) and acetic acid (0.5 mL) were added thereto. The organic layer was separated and washed with water (10 mL), and the solvent was distilled off under reduced pressure. The obtained residue was purified by silica gel column chromatography (chloroform/methanol=95/5 to 65/35) to obtain compound (K5) (110 mg). LC/MS (ACQUITY) rt (min): 1.05 MS (ESI, m/z): 932.8 [M+H]+, 930.9 [M−H]−

(6) A mixture of compound (K5) (110 mg), 10% Pd/C (50 mg), and methanol/water (9/1) (14 mL) was stirred at room temperature for 2.5 hours in a hydrogen atmosphere. Insoluble matter was filtered off, and the solvent was distilled off under reduced pressure to obtain compound (K6) (84.3 mg). LC/MS (ACQUITY) rt (min): 0.80 MS (ESI, m/z): 798.7 [M+H]+, 796.8 [M−H]−

(7) To a mixture of compound (K6) (84.3 mg), tri-tert-butyl 1,4,7,10-tetraazacyclododecane-1,4,7,10-tetraacetate (60.7 mg), DMF (1 mL), and DIEA (50 μL), HBTU (40.2 mg) was added, and the resulting mixture was stirred at room temperature for 30 minutes. Water (1 mL), methanol (0.5 mL), and formic acid (200 μL) were added thereto, and the mixture was purified by preparative HPLC to obtain compound (K7) (61.9 mg). LC/MS (ACQUITY) rt (min): 1.12 MS (ESI, m/z): 677.4 [M+2H]$^{2+}$, 1351.3 [M−H]−

(8) To compound (K7) (29 mg), concentrated hydrochloric acid (2 mL) was added, and the mixture was stirred at room temperature for 3 days. The solvent was distilled off under reduced pressure. A 50% aqueous acetonitrile solution (2 mL) was added to the residue, and the mixture was purified by preparative HPLC to obtain compound (K8) (11.0 mg). LC/MS (ACQUITY) rt (min): 0.75 MS (ESI, m/z): 586.1 [M+2H]$^{2+}$, 584.0 [M−2H]$^{2−}$ Example 12
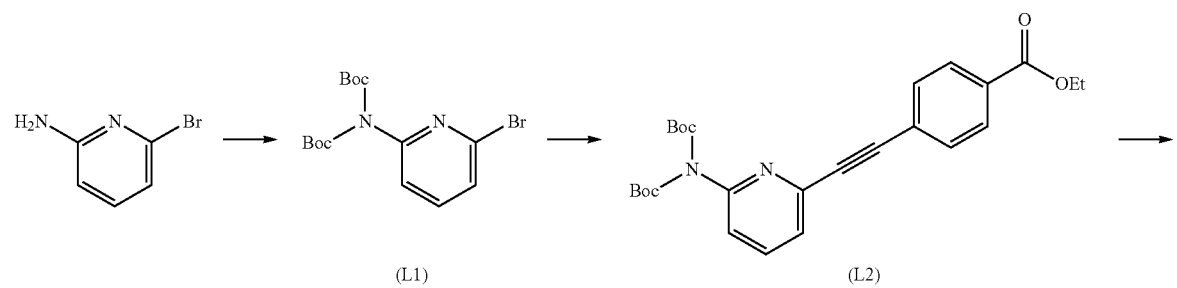
(L1) (L2)
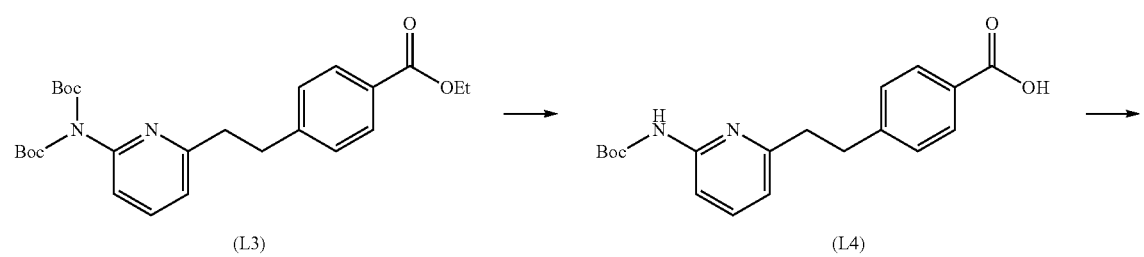
(L3) (L4)
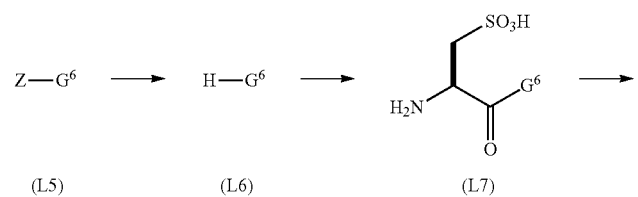
(L5) (L6) (L7)
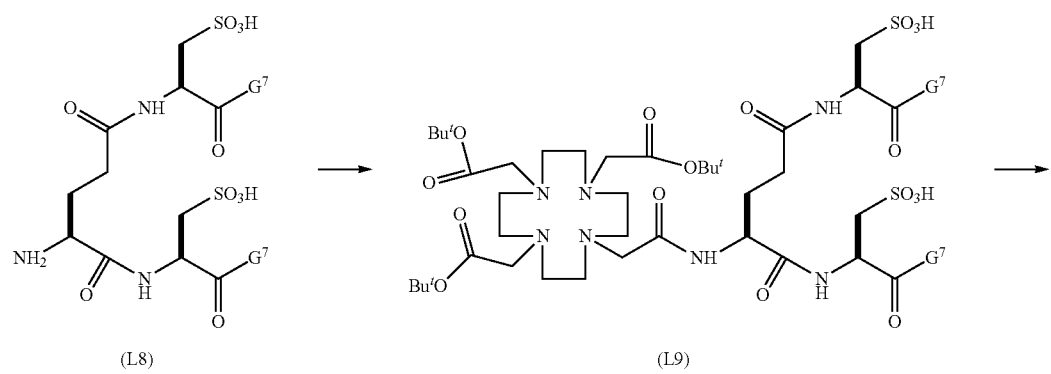
(L8) (L9)

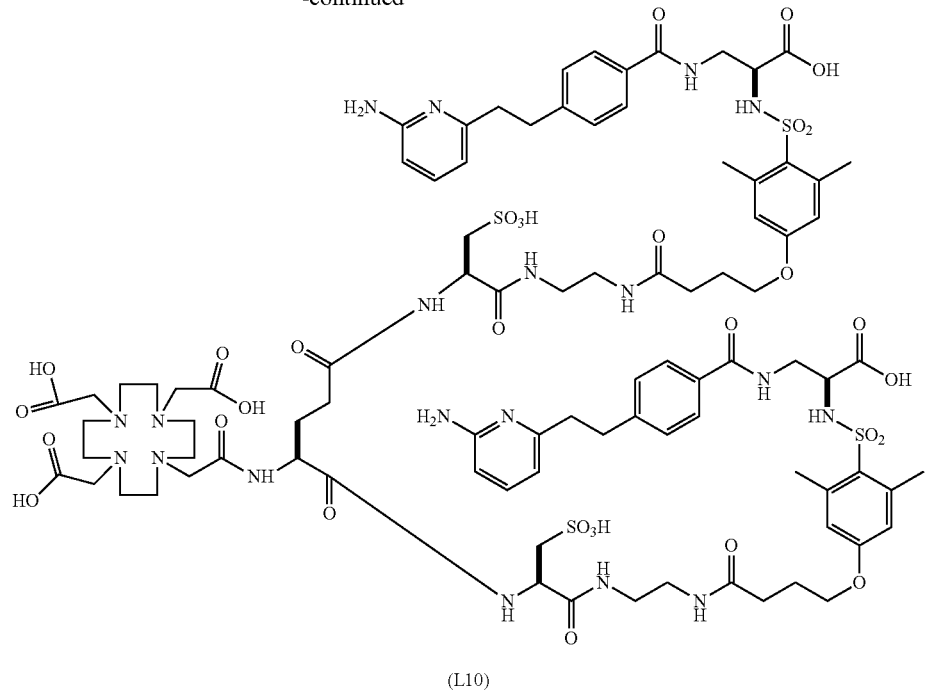

(L10)

(1) To a mixture of 2-amino-6-bromopyridine (1.73 g), THF (20 mL), DMAP (120 mg), and DIEA (7 mL), di-tert-butyl dicarbonate (4.6 mL) was added, and the resulting mixture was stirred at room temperature for 3 hours. The solvent was distilled off under reduced pressure. The obtained residue was purified by silica gel column chromatography (hexane/ethyl acetate=3/1) to obtain compound (L1) (3.09 g). $^1$H-NMR (400 MHz, CDCl$_3$) δ: 7.55-7.59 (1H, m), 7.37-7.39 (1H, m), 7.27 (1H, m), 1.46 (18H, s)

(2) To a mixture of ethyl 4-ethynylbenzoate (0.97 g), compound (L1) (1.44 g), acetonitrile (20 mL), and triethylamine (10 mL), dichlorobis(triphenylphosphine)palladium (II) (78.2 mg) and copper(I) iodide (32 mg) were added, and the resulting mixture was heated at 70° C. for 200 minutes. After cooling to room temperature, ethyl acetate (30 mL) and water (30 mL) were added thereto. The organic layer was separated, and the aqueous layer was subjected to extraction with ethyl acetate (30 mL). The organic layers were combined, then washed with water and a saturated aqueous solution of sodium chloride, and dried over anhydrous magnesium sulfate, and then, the solvent was distilled off under reduced pressure. The obtained residue was purified by silica gel column chromatography (hexane/acetone=20/1 to 10/1) to obtain compound (L2) (1.22 g). TLC Rf: 0.63 (hexane/ethyl acetate=2/1) LC/MS (SunFire) rt (min): 14.63 MS (ESI, m/z): 467.10 [M+H]$^+$ (3) Compound (L2) (1.10 g), methanol (150 mL), and 10% Pd/C (300 mg) were placed in an autoclave and stirred for 8 hours in a 3 MPa hydrogen atmosphere. Insoluble matter was filtered off, and the solvent was distilled off under reduced pressure to obtain compound (L3) (1.17 g). TLC Rf: 0.59 (hexane/ethyl acetate=2/1) LC/MS (SunFire) rt (min): 14.53 MS (ESI, m/z): 493.10 [M+Na]$^+$ (4) To a solution of compound (L3) (610 mg) in methanol (15 mL), a solution of sodium hydroxide (0.29 g) in water (1 mL) was added, and the mixture was stirred at room temperature for 1 hour. Sodium hydroxide (0.40 g), water (5 mL), and THF (5 mL) were added thereto, and the mixture was stirred for 4 hours. About half the amount of the solvent was distilled off under reduced pressure. Water (20 mL) was added to the residue, and the mixture was adjusted to pH 4 by the addition of sodium bisulfate. Ethyl acetate (30 mL) and water (30 mL) were added thereto. The organic layer was separated, and the aqueous layer was subjected to extraction with ethyl acetate (50 mL). The organic layers were combined, then washed with a saturated aqueous solution of sodium chloride, and dried over anhydrous sodium sulfate, and the solvent was distilled off under reduced pressure to obtain compound (L4) (0.51 g). TLC Rf: 0.24 (hexane/ethyl acetate=2/1) MS (ESI, m/z): 343.1 [M+H]$^+$, 341.2 [M−H]$^-$ (5) To a mixture of compound (A2) (390 mg), compound (L4) (208 mg), DMF (5 mL), and DIEA (0.6 mL), a solution of HBTU (235 mg) in DMF (2 mL) was added, and the resulting mixture was stirred at room temperature for 1 hour. Ethyl acetate (50 mL) and water (30 mL) were added thereto. The organic layer was separated, then washed with a saturated aqueous solution of sodium chloride, and dried over anhydrous sodium sulfate. The solvent was distilled off under reduced pressure. The obtained residue was purified by silica gel column chromatography (hexane/ethyl acetate=40/60 to 0/100) to obtain compound (L5) (599 mg). LC/MS (SunFire) rt (min): 13.67 MS (ESI, m/z): 889.40 [M+H]$^+$, 887.35 [M−H]$^-$ (6) Compound (L5) (599 mg), methanol (30 mL), and 10% Pd/C (100 mg) were placed in a sealed tube and stirred for 6 hours in a 0.5 MPa hydrogen atmosphere. Insoluble matter was filtered off, and the solvent was distilled off under reduced pressure to obtain compound (L6) (476 mg). LC/MS (SunFire) rt (min): 9.64 MS (ESI, m/z): 755.35 [M+H]$^+$, 753.40 [M−H]$^-$ (7) To a solution of compound (L6) (129 mg) and Fmoc-cysteic acid (145 mg) in DMF (1 mL) and DIEA (70 μL), a solution of HBTU (138 mg) in DMF (1 mL) was added, and the mixture was stirred at room temperature for 30 minutes. DIEA (0.1 mL) was added thereto, and the mixture was stirred for 2 hours. Water (0.1 mL) was added thereto, and the solvent was distilled off under reduced pressure. To the obtained residue, DMF (0.8 mL) and diethylamine (0.8 mL) were added, and the mixture was stirred at room temperature for 15 minutes. Then, the solvent was distilled off under reduced pressure. The obtained residue was purified by preparative HPLC to obtain compound (L7) (77.8 mg). LC/MS (SunFire) rt (min): 11.59 MS (ESI, m/z): 906.25 $[M+H]^+$, 904.20 $[M-H]^-$ (8) To a mixture of compound (L7) (51.6 mg) and (S)-bis(2,5-dioxopyrrolidin-1-yl) 2-((tert-butoxycarbonyl)amino)pentanedioate (12.5 mg), DMF (0.4 mL) and DIEA (30 μL) were added, and the resulting mixture was stirred at room temperature for 24 hours. Water (0.1 mL) was added thereto, and then, the solvent was distilled off under reduced pressure. TFA/triethylsilane (95/5) (1 mL) was added to the residue, and the mixture was stirred at room temperature for 1 hour. TFA was distilled off under reduced pressure. A 50% aqueous acetonitrile solution (1.5 mL) was added to the residue, and the mixture was purified by preparative HPLC to obtain compound (L8) (24.8 mg). LC/MS (SunFire) rt (min): 7.86 MS (ESI, m/z): 862.05 $[M+2H]^{2+}$, 859.95 $[M-2H]^{2-}$ (9) To a solution of tri-tert-butyl 1,4,7,10-tetraazacyclododecane-1,4,7,10-tetraacetate (5.2 mg) in DMF (0.1 mL) and DIEA (10 μL), a solution (75 μL) of HBTU (4.4 mg) in DMF (100 μL) was added, then the mixture was added to a solution of compound (L8) (9.6 mg) in DMF (200 μL) and DIEA (20 μL), and the resulting mixture was stirred at room temperature for 50 minutes. Water (200 μL) was added thereto, and the mixture was purified by preparative HPLC to obtain compound (L9) (7.2 mg). LC/MS (SunFire) rt (min): 8.98 MS (ESI, m/z): 1139.70 $[M+2H]^{2+}$, 760.15 $[M+3H]^{3+}$, 1137.35 $[M-2H]^{2-}$

(10) To compound (L9) (7.6 mg), THF (0.3 mL), water (0.1 mL), and a 3 mol/L aqueous lithium hydroxide solution (70 μL) were added, and the mixture was stirred at room temperature for 1.5 hours. TFA was added thereto, and then, the solvent was distilled off under reduced pressure. To the obtained residue, TFA/triethylsilane (95/5) (1 mL) was added, and the mixture was stirred at room temperature for 1.5 hours. TFA was distilled off under reduced pressure. A 50% aqueous acetonitrile solution (0.2 mL) was added to the residue, and the mixture was purified by preparative HPLC to obtain compound (L10) (2.3 mg). LC/MS (SunFire) rt (min): 8.61 MS (ESI, m/z): 1041.55 $[M+2H]^{2+}$, 694.55 $[M+3H]^{3+}$, 1039.35 $[M-2H]^{2-}$ Example 13

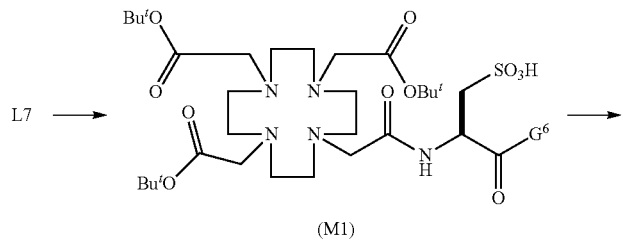

(M1)

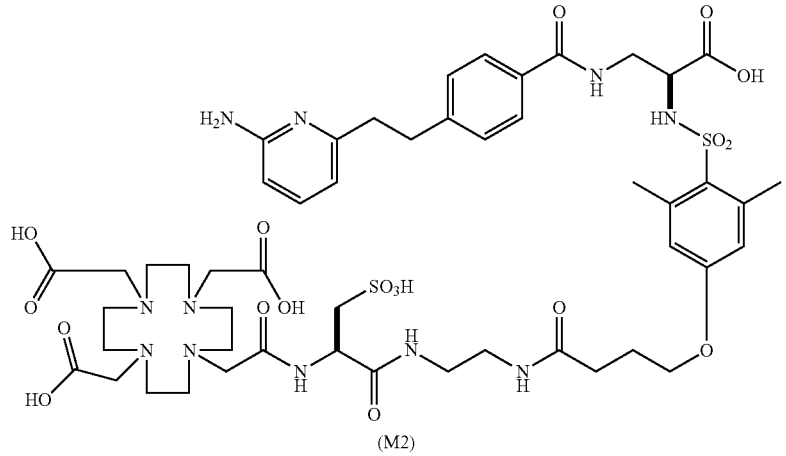

(M2)

(1) To a solution of tri-tert-butyl 1,4,7,10-tetraazacyclododecane-1,4,7,10-tetraacetate (24.8 mg) in DMF (0.2 mL) and DIEA (17 μL), a solution of HBTU (17.0 mg) in DMF (100 μL) was added, then the mixture was added to a solution of compound (L7) (13.1 mg) in DMF (200 μL) and DIEA (10 μL), and the resulting mixture was stirred at room temperature for 1 hour. Water (200 μL) was added thereto, and the mixture was purified by preparative HPLC to obtain compound (M1) (12.3 mg). LC/MS (SunFire) rt (min): 11.05 MS (ESI, m/z): 730.95 $[M+2H]^{2+}$, 1459.05 $[M-H]^{-}$ (2) To compound (M1) (7.8 mg), THF (0.7 mL), water (0.1 mL), and a 3 mol/L aqueous lithium hydroxide solution (70 μL) were added, and the mixture was stirred at room temperature for 1.5 hours. TFA was added thereto, and the solvent was distilled off under reduced pressure. TFA/triethylsilane (95/5) (1 mL) was added to the residue, and the mixture was stirred at room temperature for 2 hours. TFA was distilled off under reduced pressure. A 50% aqueous acetonitrile solution (0.8 mL) was added to the residue, and the mixture was purified by preparative HPLC to obtain compound (M2) (1.9 mg). LC/MS (SunFire) rt (min): 7.34 MS (ESI, m/z): 590.10 $[M+2H]^{2+}$, 588.25 $[M-2H]^{2-}$ Example 14

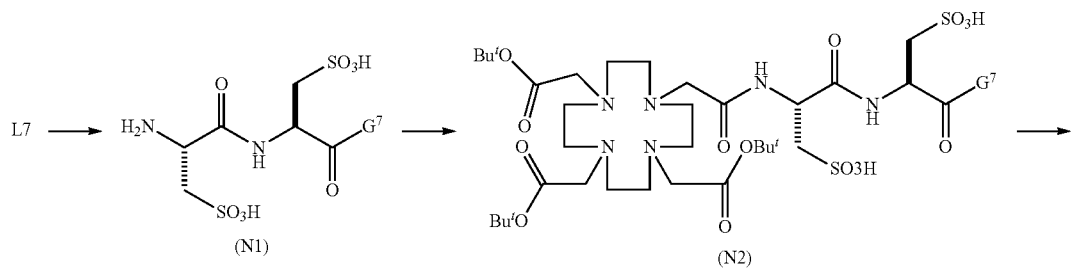

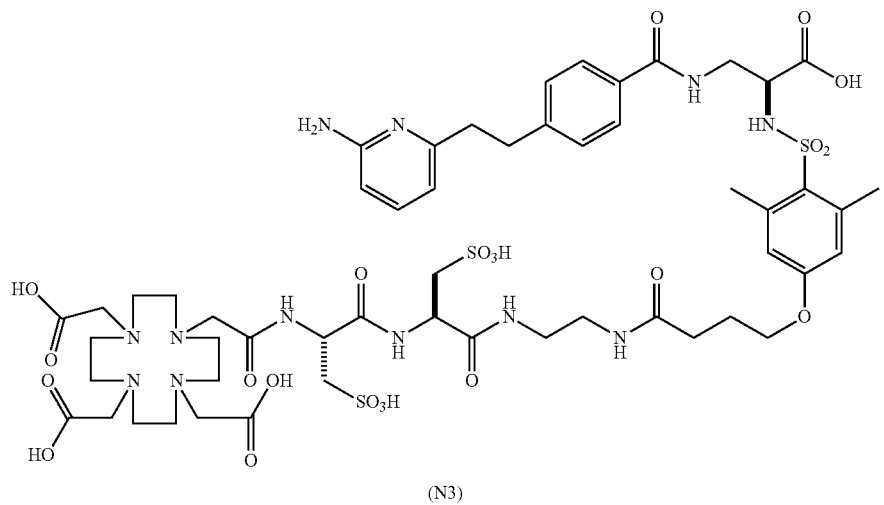

(1) To a solution of Fmoc-cysteic acid (22.0 mg) in DMF (0.2 mL) and DIEA (20 µL), a solution of HBTU (21.0 mg) in DMF (100 µL) was added, then the mixture was added to a solution of compound (L7) (16.3 mg) in DMF (0.4 mL) and DIEA (20 µL), and the resulting mixture was stirred at room temperature for 1 hour. Water (0.1 mL) was added thereto, and the solvent was distilled off under reduced pressure. DMF (0.5 mL) and diethylamine (0.5 mL) were added to the residue, and the mixture was left at room temperature for 15 hours. The solvent was distilled off under reduced pressure. TFA/triethylsilane (95/5) (1 mL) was added to the residue, and the mixture was stirred at room temperature for 20 minutes. TFA was distilled off. The obtained residue was purified by preparative HPLC to obtain compound (N1) (9.6 mg). LC/MS (SunFire) rt (min): 8.93 MS (ESI, m/z): 957.10 [M+H]$^+$, 955.15 [M−H]$^−$ (2) To a solution of tri-tert-butyl 1,4,7,10-tetraazacyclododecane-1,4,7,10-tetraacetate (8.3 mg) in DMF (0.1 mL) and DIEA (10 µL), a solution of HBTU (5.5 mg) in DMF (100 µL) was added, then the mixture was added to a solution of compound (N1) (4.6 mg) in DMF (200 µL) and DIEA (20 µL), and the resulting mixture was stirred at room temperature for 1.5 hours. Water (100 µL) was added thereto, and the mixture was purified by preparative HPLC to obtain compound (N2) (3.5 mg). LC/MS (SunFire) rt (min): 9.69 MS (ESI, m/z): 756.70 [M+2H]$^+$, 1509.45 [M−H]$^−$ (3) To compound (N2) (3.5 mg), THF (0.7 mL), water (0.1 mL), and a 3 mol/L aqueous lithium hydroxide solution (70 µL) were added, and the mixture was stirred at room temperature for 2 hours. TFA was added thereto, and the solvent was distilled off under reduced pressure. TFA/triethylsilane (95/5) (1 mL) was added to the residue, and the mixture was stirred at room temperature for 1 hour. TFA was distilled off under reduced pressure. A 50% aqueous acetonitrile solution (0.4 mL) was added to the residue, and the mixture was purified by preparative HPLC to obtain compound (N3) (0.9 mg). LC/MS (SunFire) rt (min): 10.28 MS (ESI, m/z): 665.15 [M+2H]$^{2+}$ Example 15

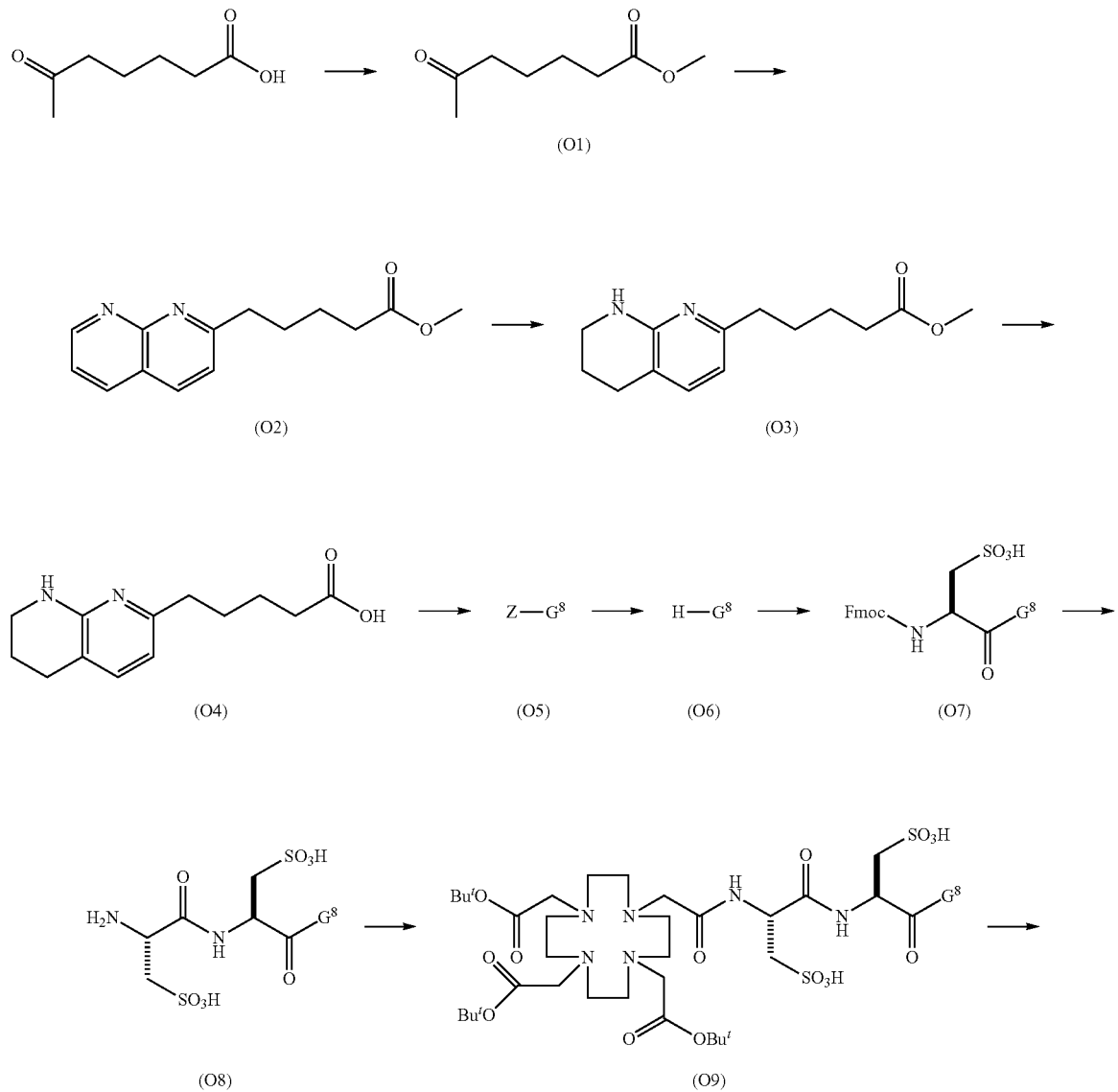

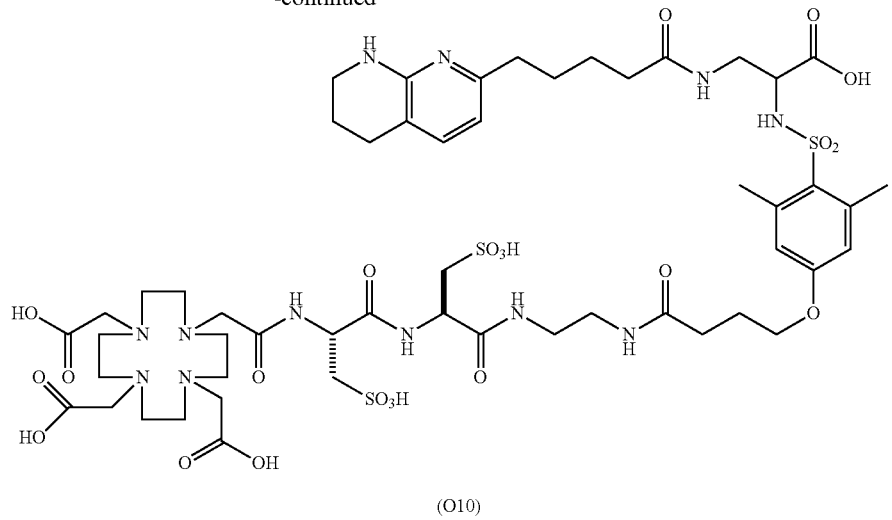

(O10)

(1) To a solution of 6-oxoheptanoic acid (99.2 g) in methanol (1 L), concentrated sulfuric acid (20 mL) was added, and the mixture was heated to reflux for 4 hours. The reaction mixture was cooled to room temperature, and then, the solvent was distilled off under reduced pressure. Water (1 L) and ethyl acetate (600 mL) were added to the residue. The organic layer was separated and washed with a 5% aqueous sodium bicarbonate solution (600 mL) and a saturated aqueous solution of sodium chloride (600 mL), and the solvent was distilled off under reduced pressure to obtain compound (O1) (95.2 g). TLC Rf: 0.45 (hexane/ethyl acetate=2/1)

(2) To a mixture of 2-aminonicotinaldehyde (133 g) and methanol (500 mL), compound (O1) (189 g) and methanol (600 mL) were added, then pyrrolidine (100 mL) was added, and the resulting mixture was heated to reflux for 8 hours. The reaction mixture was cooled to room temperature, and the solvent was distilled off under reduced pressure. Then, toluene (100 mL) was added to the residue, and the solvent was distilled off under reduced pressure. To the obtained residue, toluene (150 mL) was added, and the mixture was stirred at 50° C. for 2 hours and then stirred at room temperature for 3 hours. The solid was collected by filtration to obtain compound (O2) (149 g). TLC Rf: 0.56 (ethyl acetate/methanol=5/1) LC/MS (ACQUITY) rt (min): 0.73 MS (ESI, m/z): 245.2 [M+H]$^+$ (3) 10% Pd/C (10.0 g), compound (O2) (97.5 g), and methanol (250 mL) were placed in an autoclave and stirred for 8 hours in a 5 MPa hydrogen atmosphere. Insoluble matter was filtered off, and the solvent was distilled off under reduced pressure. To the obtained residue, acetonitrile (100 mL) was added, and the solid was collected by filtration to obtain compound (O3) (71.5 g). P HPLC (CAPCEL PAK MG) rt (min): 8.06 $^1$H-NMR (300 MHz, CDCl$_3$) δ: 7.05 (1H, d, J=7.5 Hz), 6.34 (1H, d, 7.5 Hz), 4.74 (1H, brs), 3.66 (3H, s), 3.37-3.42 (2H, m), 2.68 (2H, t, J=6.0 Hz), 2.52-2.57 (2H, m), 2.30-2.37 (2H, m), 1.90 (2H, tt, J=5.7, 6.0 Hz), 1.63-1.70 (4H, m)

(4) To compound (O3) (70.0 g), methanol (210 mL) was added. After dissolution by heating at 40° C., a mixture of sodium hydroxide (16.9 g) and water (105 mL) was added dropwise to the solution over 15 minutes, and the resulting mixture was stirred at 40° C. for 1 hour. The solvent was distilled off under reduced pressure. Water (210 mL) was added to the residue, and the mixture was heated to 40° C. Concentrated hydrochloric acid was added dropwise thereto such that the temperature was kept at 50° C. or lower until the pH reached 5. Water (50 mL) was added thereto, and the mixture was cooled to room temperature and left all night and all day. The solid matter was collected by filtration to obtain compound (O4) (62.2 g). HPLC (CAPCEL PAK MG) rt (min): 7.03 LC/MS (ACQUITY) rt (min): 0.62 MS (ESI, m/z): 235.2 [M+H]$^+$ (5) To a mixture of compound (A2) (7.40 g), compound (O4) (3.37 g), DMF (50 mL), and DIEA (3.86 mL), HBTU (4.98 g) was added in small portions, and the resulting mixture was stirred at room temperature for 2 hours. A 5% aqueous sodium bicarbonate solution (200 mL) and ethyl acetate (200 mL) were added to the reaction mixture, and the mixture was stirred at room temperature for 10 minutes. The organic layer was separated, then washed three times with a saturated aqueous solution of sodium chloride, and dried over anhydrous sodium sulfate, and then, the solvent was distilled off under reduced pressure. To the obtained residue, ethyl acetate (50 mL) was added, and the solid matter was collected by filtration to obtain compound (O5) (9.20 g). LC/MS (ACQUITY) rt (min): 1.12 MS (ESI, m/z): 781.5 [M+H]$^+$, 779.6 [M−H]$^−$ (6) To compound (O5) (7.20 g) and 10% Pd/C (300 mg), methanol (40 mL) was added, and the mixture was stirred at room temperature for 3 hours in a hydrogen atmosphere. Insoluble matter was filtered off, and the solvent was distilled off under reduced pressure. To the obtained residue, toluene (50 mL) was added, and the solvent was distilled off under reduced pressure to obtain compound (O6) (5.45 g). LC/MS (ACQUITY) rt (min): 0.73 MS (ESI, m/z): 647.4 [M+H]$^+$ (7) To a solution of compound (O6) (120 mg) and Fmoc-cysteic acid (145 mg) in DMF (2 mL) and DIEA (140 μL), a solution of HBTU (141 mg) in DMF (1.5 mL) was added, and the mixture was stirred at room temperature for 20 minutes. Water (2 mL) was added thereto, and the mixture was purified by preparative HPLC to obtain compound (O7) (87.7 mg). LC/MS (SunFire) rt (min): 11.83 MS (ESI, m/z): 1020.25 [M+H]$^+$, 1018.50 [M−H]$^−$ (8) To a solution of compound (O7) (29.8 mg) in DMF (0.5 mL), diethylamine (0.5 mL) was added, and the mixture was stirred at room temperature for 80 minutes. The solvent was distilled off under reduced pressure. To the obtained residue, Fmoc-cysteic acid (22.8 mg), DMF (0.7 mL), and DIEA (22 μL) were added, then a solution of HBTU (22.2 mg) in DMF (200 μL) was added, and the mixture was stirred at room temperature for 30 minutes. Water (0.5 mL) was added thereto, and the solvent was distilled off under reduced pressure. Then, DMF (0.5 mL) and diethylamine (0.5 mL) were added to the residue, and the mixture was stirred at room temperature for 70 minutes. The solvent was distilled off under reduced pressure. Then, water (2 mL) was added to the residue, and the mixture was washed three times with hexane/ethyl acetate (1/1) (2 mL) and purified by preparative HPLC to obtain compound (O8) (13.2 mg). LC/MS (SunFire) rt (min): 8.47 MS (ESI, m/z): 949.15 [M+H]$^+$, 947.20 [M−H]$^-$ (9) To a solution of tri-tert-butyl 1,4,7,10-tetraazacyclododecane-1,4,7,10-tetraacetate (23.9 mg) in DMF (200 μL) and DIEA (20 μL), a solution of HBTU (15.8 mg) in DMF (100 μL) was added, then the mixture was added to a solution of compound (O8) (13.2 mg) in DMF (300 μL) and DIEA (20 μL), and the resulting mixture was stirred at room temperature for 1 hour. Water (200 μL) was added thereto, and the mixture was purified by preparative HPLC to obtain compound (O9) (9.5 mg). LC/MS (SunFire) rt (rain): 9.19 MS (ESI, m/z): 752.70 [M+2H]$^{2+}$, 1501.45 [M−H]$^-$

(10) A mixture of compound (O9) (6.2 mg), THF (700 μL), water (100 μL), and a 3 mol/L aqueous lithium hydroxide solution (100 μL) was stirred at room temperature for 2 hours. TFA was added to the reaction mixture, and the solvent was distilled off under reduced pressure. TFA/triethylsilane (95/5) (0.5 mL) was added to the residue, and the mixture was stirred for 1.5 hours. Then, the solvent was distilled off under reduced pressure. To the obtained residue, a 20% aqueous acetonitrile solution (600 μL) and methanol (300 μL) were added, and the mixture was purified by preparative HPLC to obtain compound (O10) (1.6 mg). LC/MS (SunFire) rt (min): 11.49 MS (ESI, m/z): 661.35 [M+2H]$^{2+}$, 1319.35 [M−H]$^-$, 659.45 [M−2H]$^{2-}$ Example 16

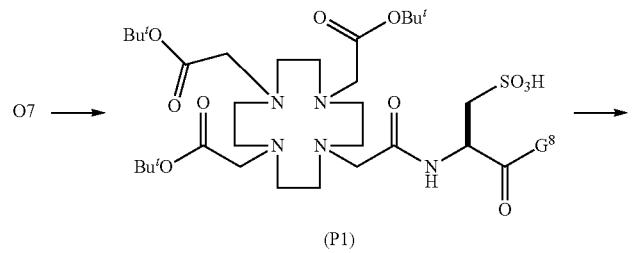

(P1)

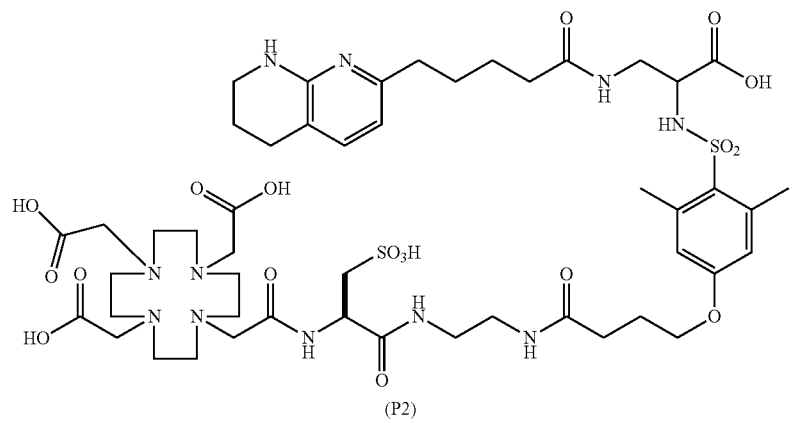

(P2)

(1) To a solution of compound (O7) (28.1 mg) in DMF (0.5 mL), diethylamine (0.5 mL) was added, and the mixture was stirred at room temperature for 1.5 hours. The solvent was distilled off under reduced pressure. To the residue, DMF (400 µL) and DIEA (20 µL) were added, then a solution of tri-tert-butyl 1,4,7,10-tetraazacyclododecane-1,4,7,10-tetraacetate (31.6 mg), DMF (150 µL), DIEA (20 µL), and HBTU (20.9 mg) in DMF (150 mL) was added, and the mixture was stirred at room temperature for 45 minutes. Water (500 µL) was added thereto, followed by extraction with hexane/ethyl acetate (1/1) (0.5 mL) three times. Then, the extract was purified by preparative HPLC to obtain compound (P1) (19.6 mg). HPLC (SunFire) rt (min): 9.71 LC/MS (ACQUITY) rt (min): 1.12 MS (ESI, m/z): 1352.5 [M+H]$^+$, 1350.6 [M−H]$^-$ (2) To compound (P1) (11.8 mg), THF (1.4 mL), water (200 µL), and a 3 mol/L aqueous lithium hydroxide solution (200 µL) were added, and the mixture was stirred at room temperature for 1.5 hours. TFA was added thereto, and the solvent was distilled off under reduced pressure. To the obtained residue, TFA/triethylsilane (95/5) (1 mL) was added, and the mixture was stirred at room temperature for 100 minutes. The solvent was distilled off under reduced pressure. Water/acetonitrile (2/1) (1.8 mL) and formic acid (1.8 µL) were added to the residue, and the mixture was purified by preparative HPLC to obtain compound (P2) (8.9 mg). HPLC (SunFire) rt (min): 8.75 LC/MS (ACQUITY) rt (min): 0.75 MS (ESI, m/z): 1170.4 [M+H]$^+$, 585.9 [M+2H]$^{2+}$, 1168.4 [M−H]$^-$ Example 17

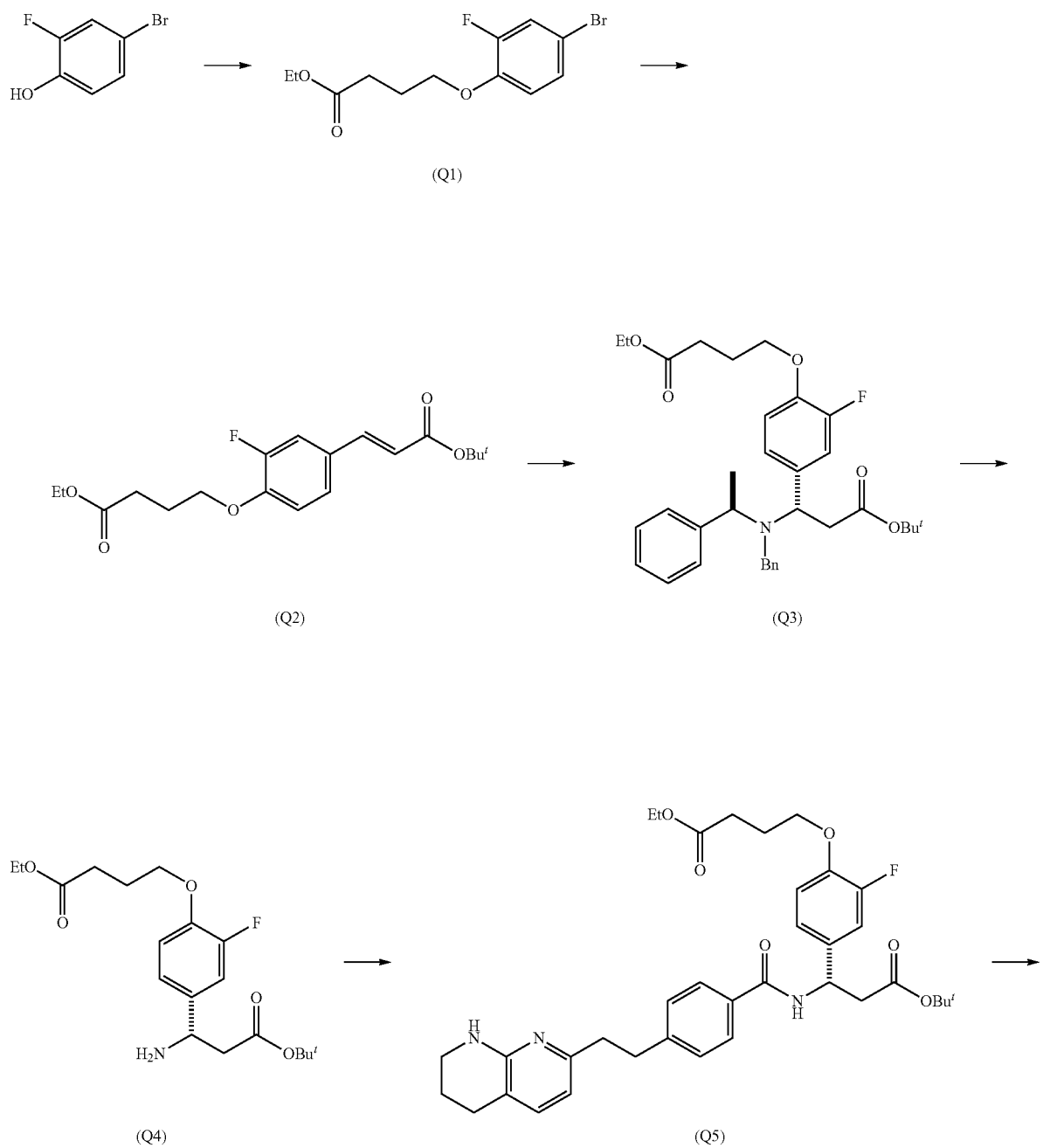

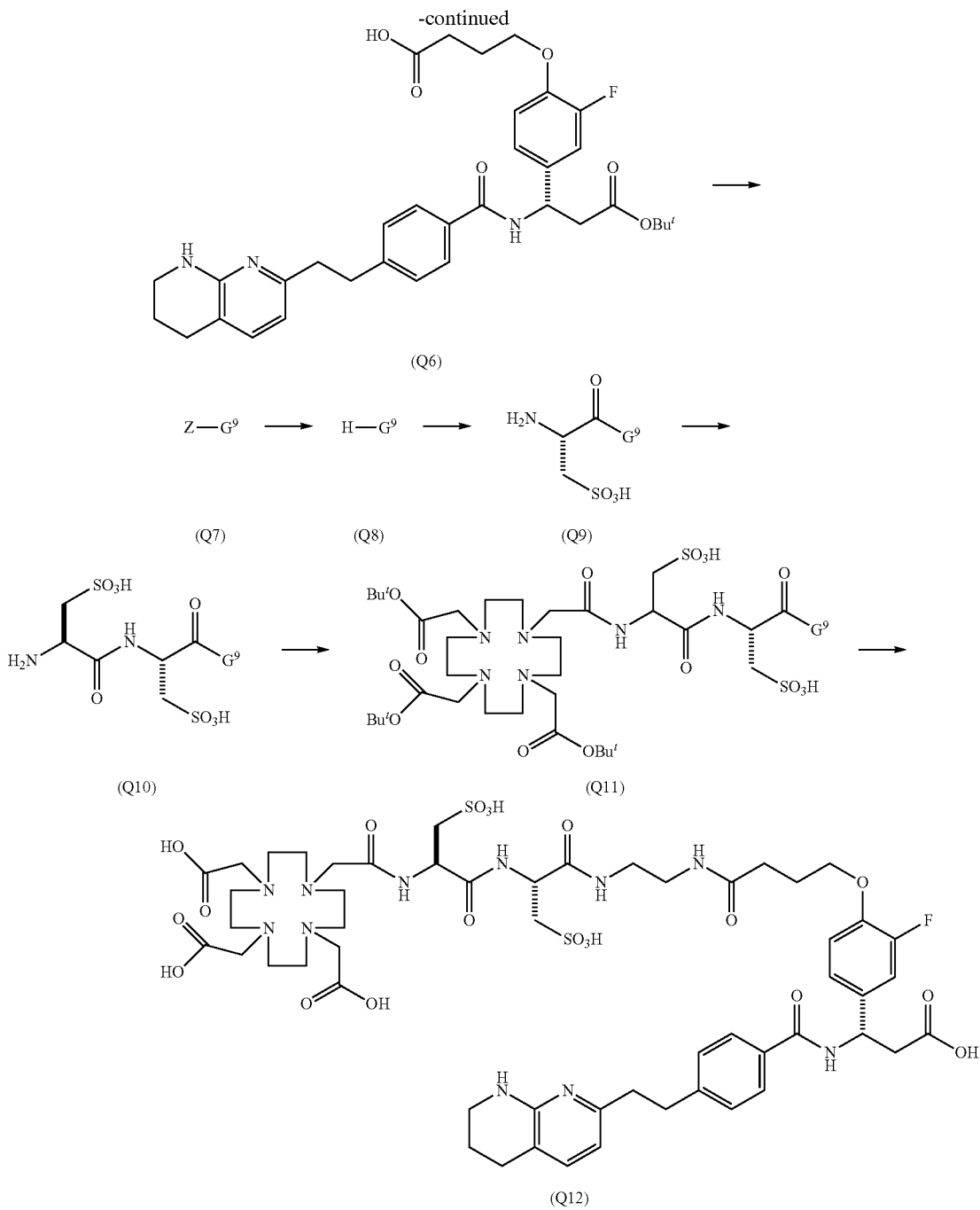

(1) To a mixture of 4-bromo-2-fluorophenol (4.71 g), NMP (25 mL), and potassium carbonate (5.1 g), ethyl 4-bromobutanoate (4.2 mL) was added at 90° C., and the resulting mixture was stirred at the same temperature as above for 5.5 hours. The reaction mixture was cooled to room temperature, and ethyl acetate and water were added thereto. The organic layer was separated, then washed with 4% hydrochloric acid, and then dried over anhydrous magnesium sulfate. The obtained residue was purified by silica gel column chromatography (hexane/ethyl acetate=9/1 to 7/3) to obtain compound (Q1) (7.3 g). TLC Rf: 0.48 (hexane/ethyl acetate=4/1) $^1$H-NMR (300 MHz, CDCl$_3$) δ: 7.15-7.25 (2H, m), 6.83 (1H, t, J=9.0 Hz), 4.15 (2H, q, J=7.2 Hz), 4.06 (2H, t, J=6.0 Hz), 2.52 (2H, t, J=7.5 Hz), 2.15 (2H, tt, J=7.5, 6.0 Hz), 1.27 (3H, t, J=7.2 Hz)

(2) To a mixture of compound (Q1) (7.0 g), tert-butyl acrylate (15 mL), NMP (20 mL), and triethylamine (20 mL), palladium(II) acetate (224 mg) and tri(o-tolyl)phosphine (609 mg) were added in a nitrogen atmosphere, and the resulting mixture was stirred at 110° C. for 8 hours. The reaction mixture was cooled to room temperature. Insoluble matter was filtered off, and the residue was washed with ethyl acetate (200 mL). The organic layers were combined, then washed twice with water (300 mL), then washed with a saturated aqueous solution of sodium chloride (300 mL), and dried over anhydrous sodium sulfate. The solvent was distilled off under reduced pressure. The obtained residue was purified by silica gel column chromatography (hexane/ethyl acetate=9/1 to 4/1) to obtain compound (Q2) (5.38 g). TLC Rf: 0.40 (hexane/ethyl acetate=4/1) $^1$H-NMR (300 MHz, CDCl$_3$) δ: 7.48 (1H, d, J=15.6 Hz), 7.17-7.26 (2H, m), 6.91 (1H, t, J=5.1 Hz), 6.22 (1H, d, J=15.6 Hz), 4.16 (2H, q, J=7.2 Hz), 4.11 (2H, t, J=6.0 Hz), 2.54 (2H, t, J=7.2 Hz), 2.15 (2H, tt, J=6.0, 7.2 Hz), 1.55 (9H, s), 1.26 (3H, t, J=7.2 Hz) LC/MS (ACQUITY) rt (min): 1.94 MS (ESI, m/z): 297.1 [M−tBu]$^+$ (3) A solution of (R)-(+)-N-benzyl-1-phenylethylamine (5.13 g) in THF (50 mL) was cooled to −70° C., and butyllithium (1.62 mol/L solution in hexane, 13 mL) was added dropwise over 15 minutes such that the temperature was kept at −65° C. or lower. The temperature of the mixture was raised to −30° C. over 50 minutes. Then, the reaction mixture was cooled to −70° C., and a solution of compound (Q2) (4.21 g) in THF (20 mL) was added dropwise thereto over 15 minutes. The mixture was stirred at the same temperature as above for 2 hours, and a saturated aqueous solution of ammonium chloride (100 mL) was added thereto. Ethyl acetate (300 mL) and water (200 mL) were added to the mixture. The organic layer was separated, and the aqueous layer was subjected to extraction with ethyl acetate (200 mL). The organic layer and the extract were combined, then washed once with a 10% aqueous acetic acid solution (300 mL) and twice with a saturated aqueous solution of sodium chloride (300 mL), and dried over anhydrous sodium sulfate. The solvent was distilled off under reduced pressure. The obtained residue was recrystallized from IPA/hexane to obtain compound (Q3) (3.03 g). The filtrate of recrystallization was purified by silica gel column chromatography (hexane/ethyl acetate=10/0 to 9/1) to obtain compound (Q3) (2.75 g). TLC Rf: 0.52 (hexane/ethyl acetate=4/1) LC/MS (ACQUITY) rt (min): 2.32 MS (ESI, m/z): 564.3 [M+H]$^+$ (4) Compound (Q3) (434 mg), ethanol (5 mL), acetic acid (0.4 mL), water (40 μL), and 10% Pd/C (100 mg) were placed in a sealed tube and stirred for 5 hours in a 0.5 MPa hydrogen atmosphere. Insoluble matter was filtered off, and the reaction mixture was neutralized with a saturated aqueous solution of sodium bicarbonate (50 mL), followed by extraction with ethyl acetate (100 mL) twice. The extract was washed with a saturated aqueous solution of sodium chloride and dried over anhydrous sodium sulfate to obtain compound (Q4) (290 m). TLC Rf: 0.15 (hexane/ethyl acetate=5/1) LC/MS (ACQUITY) rt (min): 1.15 MS (ESI, m/z): 370.2 [M+H]$^+$ (5) To a solution of compound (Q4) (220 mg) and compound (A1) (140 mg) in DMF (7 mL) and DIEA (420 μL), HBTU (228 mg) was added, and the mixture was stirred at room temperature for 40 minutes. The solvent was distilled off under reduced pressure. The obtained residue was purified by silica gel column chromatography (ethyl acetate/methanol=10/0 to 9/1) to obtain compound (Q5) (310 mg). TLC Rf: 0.74 (ethyl acetate/methanol=5/1) LC/MS (ACQUITY) rt (min): 1.39 MS (ESI, m/z): 634.4 [M+H]$^+$ (6) To a mixture of compound (Q5) (289 mg), THF (2.8 mL), methanol (2 mL), and water (0.4 mL), a 2 mol/L aqueous lithium hydroxide solution (460 μL) was added, and the resulting mixture was stirred at room temperature for 2.5 hours. To the reaction mixture, water (10 mL) was added, and then, citric acid (300 mg) was added, followed by extraction with chloroform (15 mL) four times. The extract was dried over anhydrous sodium sulfate, and the solvent was distilled off under reduced pressure to obtain compound (Q6) (181 mg). LC/MS (ACQUITY) rt (min): 1.20 MS (ESI, m/z): 606.3 [M+H]$^+$, 604.3 [M−H]$^-$ (7) To a mixture of compound (Q6) (181 mg), z-ethylenediamine hydrochloride (89.6 mg), DMF (2 mL), and DIEA (200 μL), HBTU (147 mg) was added, and the resulting mixture was stirred at room temperature for 20 minutes. Ethyl acetate (60 mL) and water (10 mL) were added to the reaction mixture. The organic layer was separated, then washed twice with water (30 mL), then washed with a saturated aqueous solution of sodium chloride (30 mL), and dried over anhydrous sodium sulfate. The solvent was distilled off under reduced pressure. The obtained residue was purified by silica gel column chromatography (ethyl acetate/methanol=10/0 to 9/1) to obtain compound (Q7) (135 mg). LC/MS (ACQUITY) rt (min): 1.32 MS (ESI, m/z): 782.4 [M+H]$^+$ (8) To a mixture of compound (Q7) (130 mg), ethanol (10 mL), and 10% Pd/C (50 mg), 1,4-cyclohexadiene (0.4 mL) was added at 60° C., and the resulting mixture was stirred at the same temperature as above for 2 hours. The reaction mixture was cooled to room temperature. Insoluble matter was filtered off, and the solvent was distilled off under reduced pressure to obtain compound (Q8) (108 mg). LC/MS (ACQUITY) rt (min): 1.02 MS (ESI, m/z): 648.3 [M+H]$^+$, 324.7 [M+2H]$^{2+}$ (9) To a solution of compound (O8) (108 mg) and Fmoc-cysteic acid (78.2 mg) in DMF (3 mL) and DIEA (70 μL), HBTU (75.9 mg) was added, and the mixture was stirred at room temperature for 25 minutes. To the reaction mixture, water (0.1 mL) were added, then diethylamine (2 mL) was added, and the mixture was stirred at room temperature for 1.5 hours. Diethylamine was distilled off. Then, water (1 mL) was added to the residue, and the mixture was washed three times with ethyl acetate (2 mL) and then purified by preparative HPLC to obtain compound (Q9) (63.2 mg). HPLC (SunFire) solvent: solution A=10 mmol/L aqueous ammonium acetate solution, solution B=10 mmol/L ammonium acetate/methanol:acetonitrile (4:1)), gradient cycle: 0.0 min (solution A/solution B=80/20), 10 min (solution A/solution B=0/100), 15 min (solution A/solution B=0/100), flow rate: 1.0 mL/min) rt (min): 12.92 LC/MS (ACQUITY) rt (min): 1.08 MS (ESI, m/z): 799.3 [M+H]$^+$, 797.3 [M−H]$^-$

(10) To a solution of compound (Q9) (34.2 mg) and Fmoc-cysteic acid (33.5 mg) in DMF (0.6 mL) and DIEA (30 DL), a solution of HBTU (32.5 mg) in DMF (400 μL) was added, and the mixture was stirred at room temperature for 1 hour. To the reaction mixture, water (0.5 mL) was added, then diethylamine (1 mL) was added, and the mixture was stirred at room temperature for 1 hour. Diethylamine was distilled off. Then, water (1 mL) was added to the residue, and the mixture was washed three times with ethyl acetate (2 mL) and then purified by preparative HPLC to obtain compound (Q10) (13.9 mg). HPLC (SunFire) solvent: solution A=10 mmol/L aqueous ammonium acetate solution, solution B=10 mmol/L ammonium acetate/methanol:acetonitrile (4:1)), gradient cycle: 0.0 min (solution A/solution B=80/20), 10 min (solution A/solution B=0/100), 15 min (solution A/solution B=0/100), flow rate: 1.0 mL/min) rt (min): 12.16 LC/MS (ACQUITY) rt (min): 1.07 MS (ESI, m/z): 950.4 [M+H]$^+$

(11) To a solution of tri-tert-butyl 1,4,7,10-tetraazacyclododecane-1,4,7,10-tetraacetate (25.1 mg) in DMF (150 μL) and DIEA (30 μL), a solution of HBTU (16.7 mg) in DMF (150 μL) was added, then the mixture was added to a solution of compound (Q10) (13.9 mg) in DMF (400 μL) and DIEA (20 μL), and the resulting mixture was stirred at room temperature for 45 minutes. Water (300 μL) was added thereto, and the mixture was purified by preparative HPLC to obtain compound (Q11) (11.1 mg). HPLC (SunFire) rt (min): 10.80 LC/MS (ACQUITY) rt (min): 1.24 MS (ESI, m/z): 1504.6 [M+H]$^+$, 1502.6 [M−H]$^−$

(12) To compound (Q11) (5.2 mg), TFA/triethylsilane (95/5) (1 mL) was added, and the mixture was stirred at room temperature for 1 hour. The solvent was distilled off under reduced pressure. To the obtained residue, water (1 mL) and a 50% aqueous acetonitrile solution (0.2 mL) were added, and the mixture was purified by preparative HPLC to obtain compound (Q12) (3.7 mg). HPLC (SunFire) rt (min): 19.61 LC/MS (ACQUITY) rt (min): 0.80 MS (ESI, m/z): 1280.2 [M+H]$^+$, 1278.4 [M−H]$^−$ Example 18

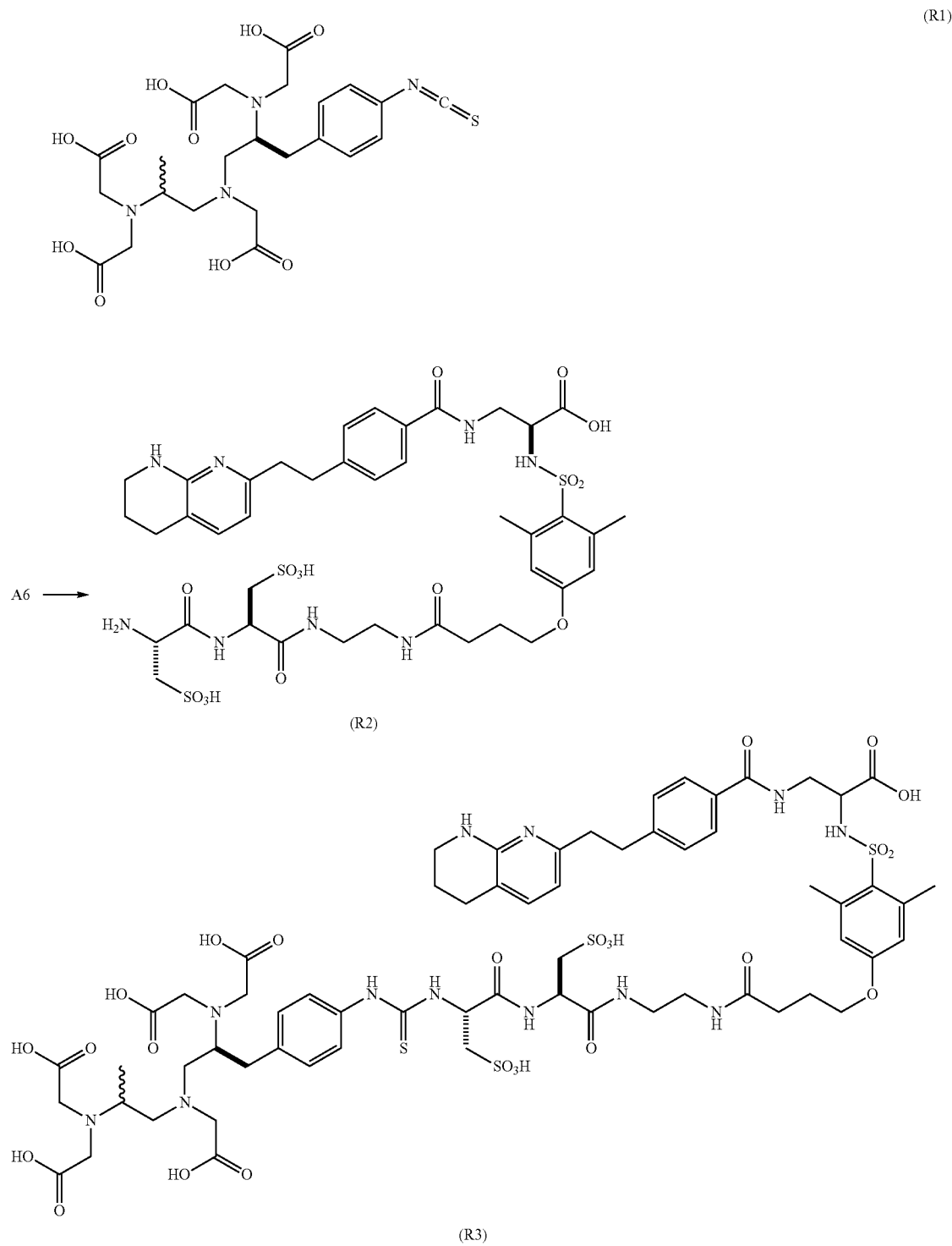

(1) Compound (R1) was obtained according to the method described in Bioconjugate Chemistry, 1991, Vol. 2, p. 187-194 and Bioconjugate Chemistry, 1991, Vol. 2, p. 180-186.

(2) A mixture of compound (A6) (12.4 mg), THF (1.4 mL), water (400 μL), and a 3 mol/L aqueous lithium hydroxide solution (200 μL) was stirred at room temperature for 2 hours. Formic acid (50 μL) was added to the reaction mixture, and the solvent was distilled off under reduced pressure. Water (1 mL) was added to the residue, and the mixture was purified by preparative HPLC to obtain compound (R2) (6.9 mg). HPLC (SunFire) rt (min): 9.85 LC/MS (ACQUITY) rt (min): 0.83 MS (ESI, m/z): 983.4 [M+H]$^+$ 981.3 [M−H]$^−$, 490.1 [M−2H]$^{2−}$ (3) To a mixture of compound (R2) (6.9 mg), compound (R1) (10.1 mg), DMF (800 μL), and DIEA (10 μL), water (300 μL) was added, and the resulting mixture was stirred at room temperature for 2 days. Water (400 μL) was added thereto, and the mixture was purified by preparative HPLC to obtain compound (R3) (7.5 mg). HPLC (SunFire) solvent: solution A=10 mmol/L aqueous ammonium acetate solution, solution B=10 mmol/L ammonium acetate/methanol:acetonitrile (4:1)), gradient cycle: 0.0 min (solution A/solution B=80/20), 10 min (solution A/solution B=0/100), 15 min (solution A/solution B=0/100), flow rate: 1.0 mL/min) rt (min): 7.26 LC/MS (ACQUITY) rt (min): 0.83 MS (ESI, m/z): 769.4 [M+2H]$^{2+}$, 513.4 [M+3H]$^{3+}$, 767.4 [M−2H]$^{2−}$ Example 19

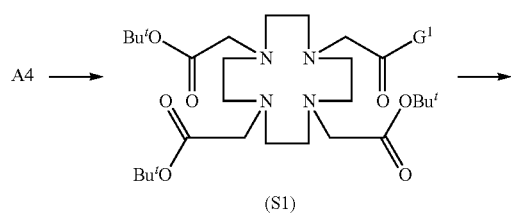

(1) To a mixture of tri-tert-butyl 1,4,7,10-tetraazacyclododecane-1,4,7,10-tetraacetate (24.7 mg), DMF (150 μL), and DIEA (30 μL), a solution of HBTU (16.4 mg) in DMF (150 μL) was added, then the resulting mixture was added to a solution of compound (A4) (14.7 mg) in DMF (400 μL) and DIEA (20 μL), and the resulting mixture was stirred at room temperature for 50 minutes. Water (200 μL) was added thereto, and the mixture was purified by preparative HPLC to obtain compound (S1) (15.7 mg). HPLC (SunFire) rt (min): 8.87 LC/MS (ACQUITY) rt (min): 1.44 MS (ESI, m/z): 1249.6 [M+H]$^+$, 1247.6 [M−H]$^−$ (2) To compound (S1) (12.8 mg), THF (1 mL), water (200 μL), and a 3 mol/L aqueous lithium hydroxide solution (200 μL) were added, and the mixture was stirred at room temperature for 1.5 hours. TFA was added thereto, and then, the solvent was distilled off under reduced pressure. TFA/triethylsilane (95/5) (1 mL) was added to the residue, and the mixture was stirred at room temperature for 2 hours. TFA was distilled off. Water/acetonitrile (2/1) (1.8 mL) and formic acid (1.8 μL) were added to the residue, and the mixture was purified by preparative HPLC to obtain compound (S2) (9.2 mg). HPLC (SunFire) rt (min): 7.76 LC/MS (ACQUITY) rt (min): 0.79 MS (ESI, m/z): 534.4 [M+2H]$^{2+}$, 1065.4 [M−H]$^−$

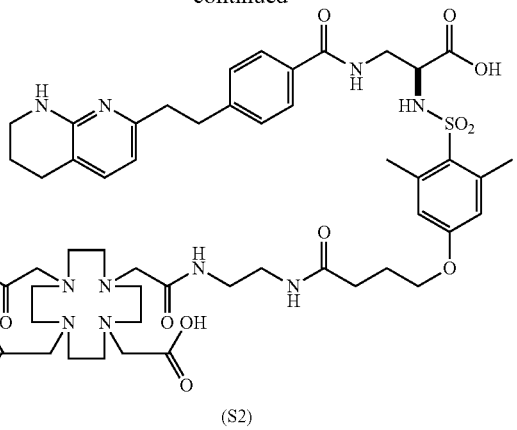

Example 20

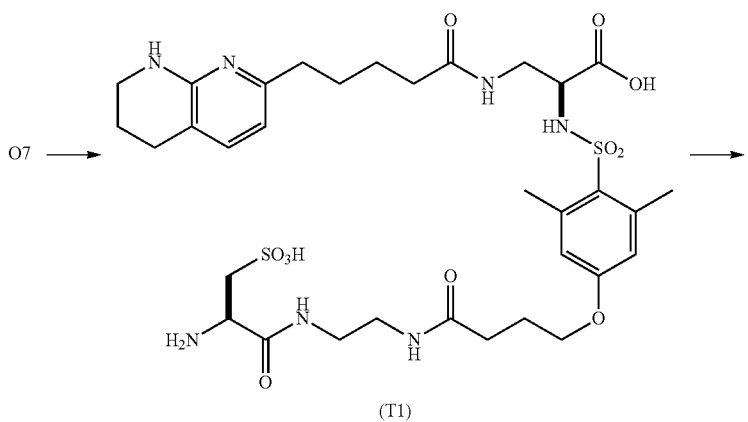

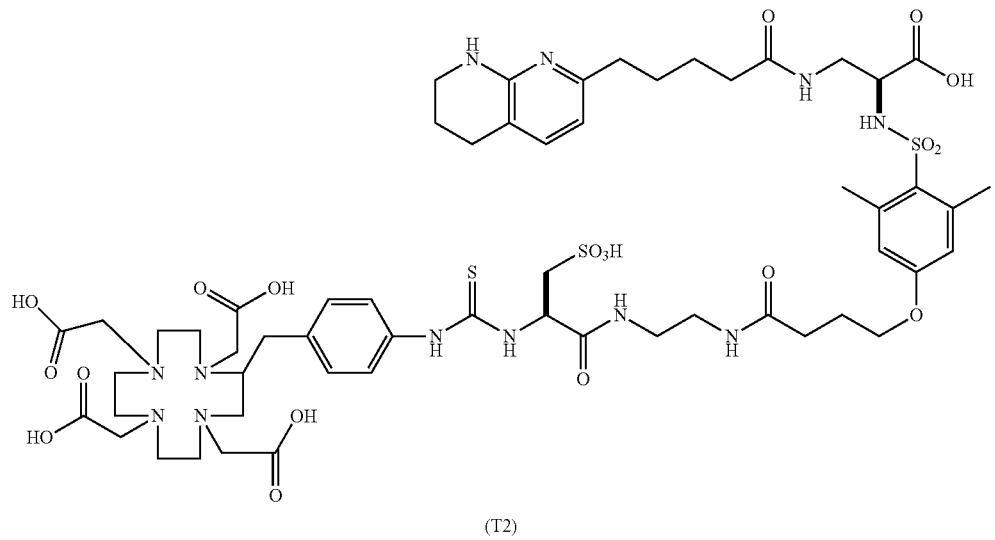

(T2)

(1) To a solution of compound (O7) (120 mg) in DMF (1 mL), diethylamine (1 mL) was added, and the mixture was stirred at room temperature for 1 hour. The solvent was distilled off under reduced pressure. Water (1 mL) and a 3 mol/L aqueous lithium hydroxide solution (100 µL) were added to the residue, and the mixture was stirred at room temperature for 14 hours. A 50% aqueous acetonitrile solution (1 mL) and water (1 mL) were added thereto, and the mixture was washed with ethyl acetate (3 mL) and then purified by preparative HPLC to obtain compound (T1) (69.8 mg). HPLC (SunFire) rt (min): 8.10 LC/MS (ACQUITY) rt (min): 0.76 MS (ESI, m/z): 784.4 [M+H]$^+$, 782.4 [M−H]$^−$ (2) To a mixture of compound (T1) (19.2 mg), DMF (200 µL), and DIEA (10 µL), 2,2',2'',2'''-(2-(4-isothiocyanatobenzyl)-1,4,7,10-tetraazacyclododecane-1,4,7,10-tetrayl)tetraacetic acid (13.5 mg) was added, and the resulting mixture was stirred. DMF (600 µL), water (300 µL), and DIEA (30 µL) were added thereto, and the mixture was stirred at room temperature for 2 days. Water (1.1 mL) and formic acid (100 µL) were added thereto, and the mixture was purified by preparative HPLC to obtain compound (T2). HPLC (CAPCEL PAK MG) rt (min): 9.90 LC/MS (ACQUITY) rt (min): 0.80 MS (ESI, m/z): 1335.7 [M+H]$^+$, 668.5 [M+2H]$^{2+}$, 1333.7 [M−H]$^−$ Example 21

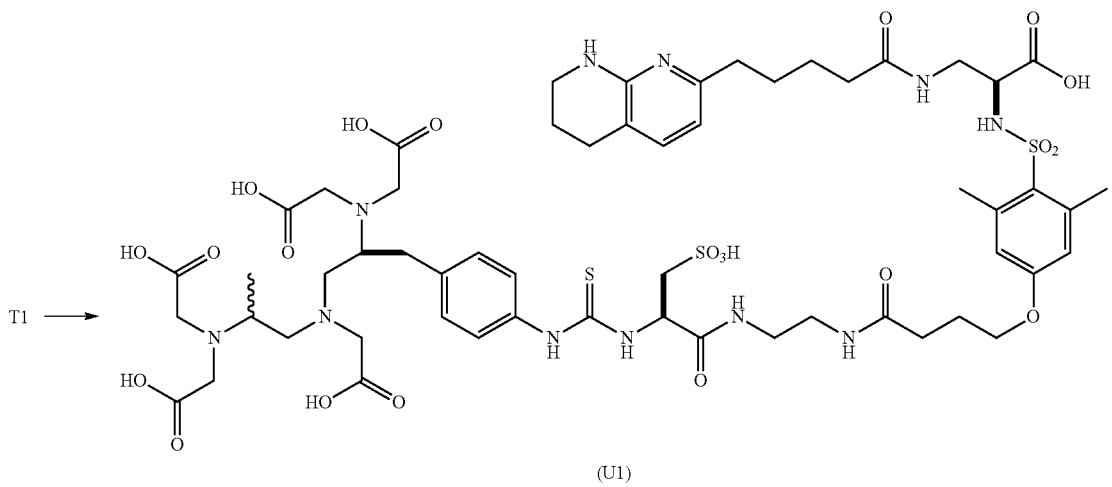

(U1)

(1) To a mixture of compound (T1) (17.5 mg), DMF (200 μL), and DIEA (10 μL), compound (R1) (22.4 mg) was added, and the resulting mixture was stirred. DMF (600 DL), water (300 μL), and DIEA (30 μL) were added thereto, and the mixture was stirred at room temperature for 2 days. The obtained product was purified by preparative HPLC to obtain compound (U1). HPLC (SunFire) solvent: solution A=10 mmol/L aqueous ammonium acetate solution, solution B=10 mmol/L ammonium acetate/methanol:acetonitrile (4:1)), solution A/solution B=70/30, flow rate: 1.0 mL/min rt (min): 6.65 LC/MS (ACQUITY) rt (min): 0.93 MS (ESI, m/z): 669.7 [M+2H]$^+$ Example 22

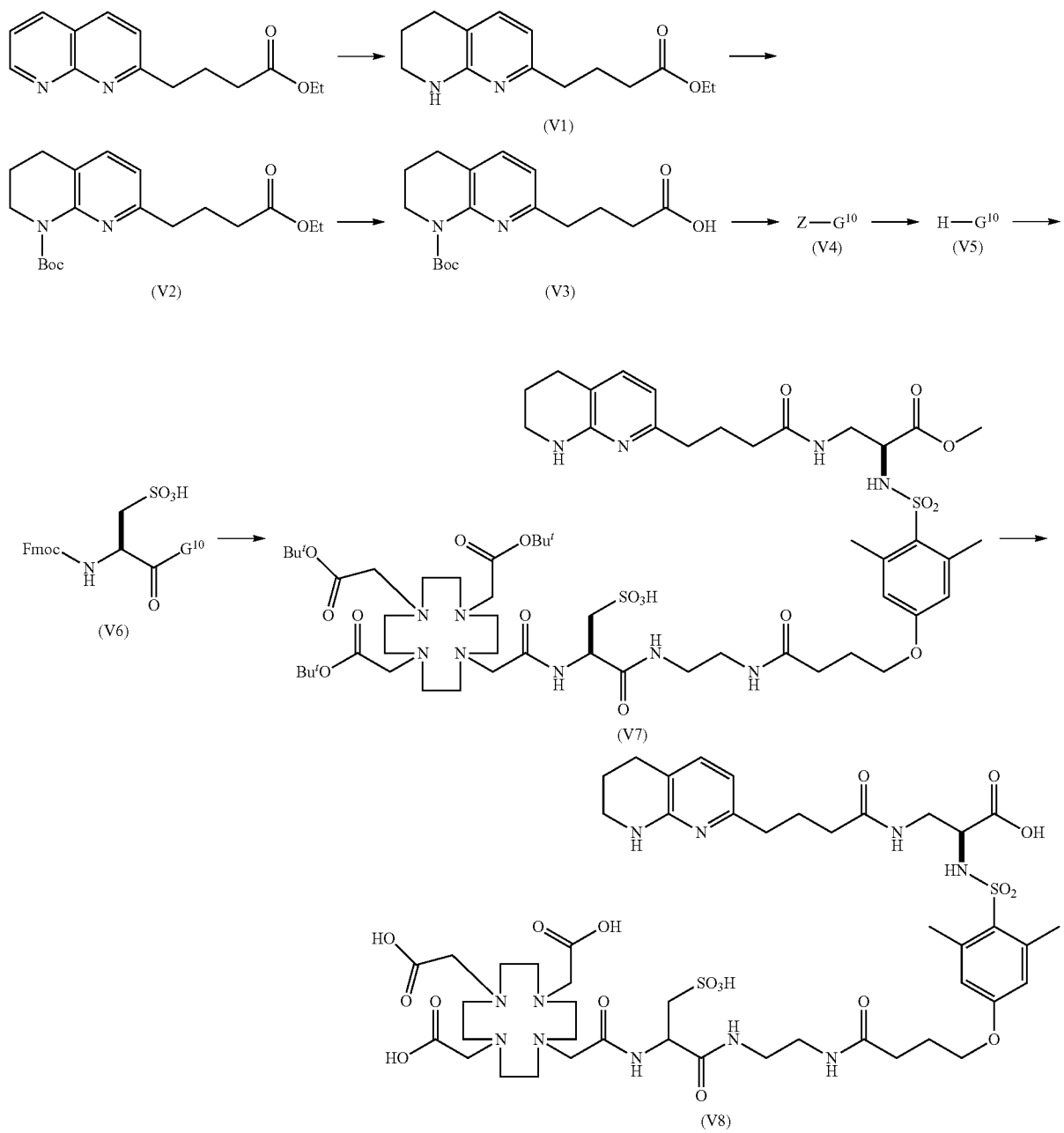

(1) A mixture of ethyl 4-(1,8-naphthyridin-2-yl)butanoate (1.24 g), methanol (30 mL), and 10% Pd/C (205 mg) was stirred at room temperature for 16 hours in a hydrogen atmosphere. Insoluble matter was filtered off, and the residue was purified by silica gel column chromatography (ethyl acetate) to obtain compound (V1) (961 mg). TLC Rf: 0.43 (dichloromethane/methanol=95/5) MS (ESI, m/z): 249.3 [M+H]$^+$ (2) To a mixture of compound (V1) (961 mg), THF (10 mL), and DIEA (1.8 mL), di-tert-butyl dicarbonate (1.8 mL) was added, and the resulting mixture was heated to reflux for 19 hours. The reaction mixture was cooled to room temperature, and ethyl acetate and water were added thereto. The organic layer was separated, then dried over anhydrous sodium sulfate, and then purified by silica gel column chromatography (dichloromethane to hexane/ethyl acetate=4/1) to obtain compound (V2) (1.09 g). TLC Rf: 0.50 (dichloromethane/methanol=100/1) MS (ESI, m/z): 349.3 [M+H]$^+$ (3) To a solution of compound (V2) (1.1 g) in THF (8 mL) and methanol (8 mL), a 1 mol/L aqueous lithium hydroxide solution (5.3 mL) was added, and the mixture was stirred at room temperature for 14 hours. The reaction mixture was neutralized with hydrochloric acid, followed by extraction with ethyl acetate. The extract was dried over anhydrous sodium sulfate, and the solvent was distilled off under reduced pressure to obtain compound (V3) (982 mg). TLC Rf: 0.52 (dichloromethane/methanol=9/1) MS (ESI, m/z): 321.3 [M+H]$^+$ (4) To a solution of compound (V3) (130 mg) and compound (A2) (245 mg) in dichloromethane (7 mL) and DIEA (91 µL), HOBt (126 mg) and EDC·HCl (203 rag) were added, and the mixture was stirred at room temperature for 2 hours. Dichloromethane and water were added thereto. The organic layer was separated, then dried over anhydrous sodium sulfate, and then purified by silica gel column chromatography (dichloromethane/methanol=95/5) to obtain compound (V4) (255 mg). TLC Rf: 0.22 (dichloromethane/methanol=95/5) MS (ESI, m/z): 867.5 [M+H]$^+$ (5) A mixture of compound (V4) (255 mg), methanol (8 mL), and 10% Pd/C (121 mg) was stirred at room temperature for 14 hours in a hydrogen atmosphere. Insoluble matter was filtered off, and the residue was purified by silica gel column chromatography (chloroform/ethanol/ammonia water=7/3/0.5) to obtain compound (V5) (163 mg). TLC Rf: 0.05 (dichloromethane/methanol=10/1) MS (ESI, m/z): 733.5 [M+H]$^+$ (6) To a mixture of disodium Fmoc-cysteinate (100 mg) and DMF (3 mL), methanesulfonic acid (22 µL) was added, and the resulting mixture was stirred for 5 minutes. DMF (5 mL), DIEA (200 µL), and compound (V5) (163 mg) were added thereto, and the mixture was stirred for 5 minutes. Then, HBTU (187 mg) was added thereto, and the mixture was stirred at room temperature for 2 hours. The solvent was distilled off under reduced pressure, and the residue was purified by silica gel column chromatography (chloroform/ethanol/ammonia water=7/3/0.5) to obtain compound (V6) (172 mg). TLC Rf: 0.25 (chloroform/ethanol/ammonia water=7/3/0.5) MS (ESI, m/z): 1104.2 [M–H]$^-$ (7) To compound (V6) (108 mg), TFA (1 mL) was added, and the mixture was stirred at room temperature for 45 minutes. Then, the solvent was distilled off under reduced pressure. To the obtained residue, acetonitrile/methanol (9/1) (3 mL) and diethylamine (0.5 mL) were added, and the mixture was stirred for 1 hour. The solvent was distilled off under reduced pressure, and a 50% aqueous acetonitrile solution (3 mL), toluene (3 mL), and hexane (3 mL) were added to the residue. The aqueous layer was separated, and the solvent was distilled off under reduced pressure. To the obtained residue, DMF (1 mL) and DIEA (60 µL) were added, then a solution of tri-tert-butyl 1,4,7,10-tetraazacyclododecane-1,4,7,10-tetraacetate (89.2 mg), DMF (300 µL), DIEA (20 µL), and HBTU (59.1 mg) in DMF (300 µL) was added, and the mixture was stirred at room temperature for 80 minutes. Water (2 mL) was added thereto, and then, the mixture was purified by preparative HPLC to obtain compound (V7) (25.9 mg). HPLC (SunFire) rt (min): 8.76 LC/MS (ACQUITY) rt (min): 1.28 MS (ESI, m/z): 670.2 [M+2H]$^{2+}$, 1337.0 [M–H]$^-$ (8) To compound (V7) (20.9 mg), TFA (1 mL) was added, and the mixture was stirred at room temperature for 5 hours. Then, the solvent was distilled off under reduced pressure. To the obtained residue, acetonitrile (1 mL) and TBME (1 mL) were added, and the solvent was distilled off under reduced pressure. To the obtained residue, water (0.6 mL) and a 3 mol/L aqueous lithium hydroxide solution (100 µL) were added, and the mixture was stirred at room temperature for 1 hour. Then, formic acid (20 µL) was added thereto, and the mixture was purified by preparative HPLC to obtain compound (V8) (9.6 mg). HPLC (SunFire) rt (min): 8.36 LC/MS (ACQUITY) rt (min): 0.71 MS (ESI, m/z): 1156.7 [M+H]$^+$ Example 23

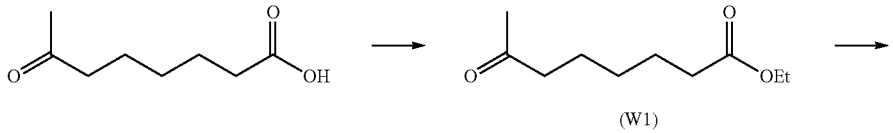

(W1)

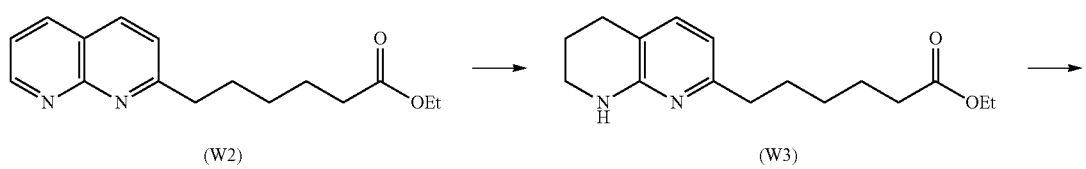

(W2)     (W3)

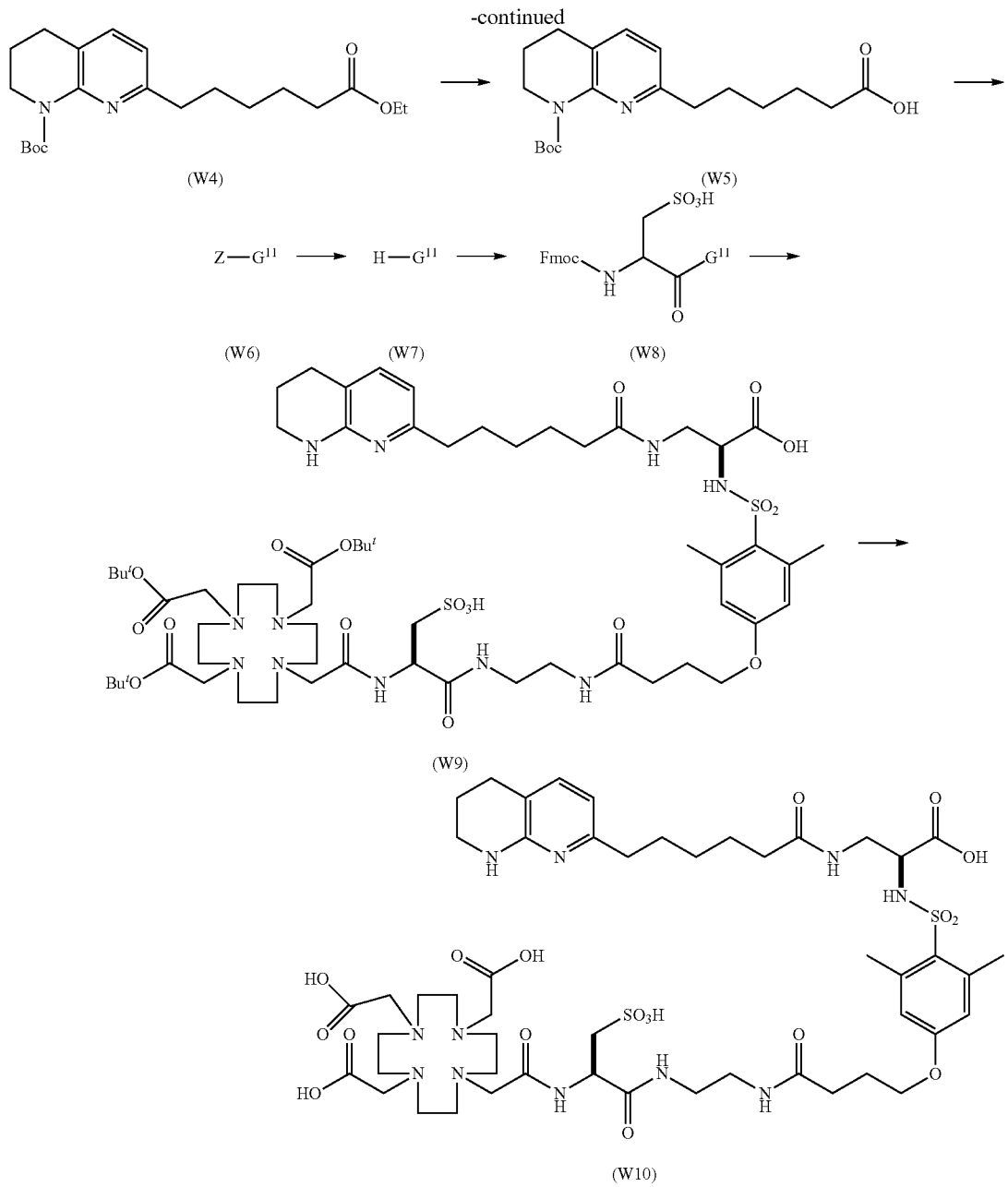

(1) A mixture of 7-oxooctanoic acid (158 mg), ethanol (35 mL), and concentrated sulfuric acid (500 μL) was refluxed for 17 hours. The solvent was distilled off under reduced pressure, and then, a saturated aqueous solution of sodium bicarbonate and dichloromethane were added to the residue. The organic layer was separated and dried over anhydrous sodium sulfate, and the solvent was distilled off under reduced pressure to obtain compound (W1) (180 mg). MS (ESI, m/z): 187.2 [M+H]$^+$ (2) A mixture of 2-aminonicotinaldehyde (118 mg), compound (W1) (180 mg), proline (56 mg), and methanol (10 mL) was refluxed for 18 hours. The solvent was distilled off under reduced pressure, and the residue was purified by silica gel column chromatography (ethyl acetate) to obtain compound (W2) (90 mg). MS (ESI, m/z): 273.2 [M+H]$^+$ (3) A mixture of compound (W2) (946 mg), methanol (20 mL), and 10% Pd/C (140 mg) was stirred at room temperature for 16 hours in a hydrogen atmosphere. Insoluble matter was filtered off, and the solvent was distilled off under reduced pressure to obtain compound (W3) (904 mg). MS (ESI, m/z): 277.3 [M+H]$^+$ (4) To a solution of compound (W3) (900 mg) in THF (10 mL) and DIEA (1.5 mL), di-tert-butyl dicarbonate (1.5 mL) was added, and the mixture was refluxed for 25 hours. Ethyl acetate and water were added thereto. The organic layer was separated, then dried over anhydrous sodium sulfate, and then purified by silica gel column chromatography (dichloromethane/methanol=100/3) to obtain compound (W4) (904 mg). TLC Rf: 0.33 (dichloromethane/methanol=100/1) MS (ESI, m/z): 377.2 [M+H]$^+$ (5) To a solution of compound (W4) (1.05 g) in THF (18 mL) and methanol (9 mL), a 1 mol/L aqueous lithium hydroxide solution (5 mL) was added, and the mixture was stirred at room temperature for 3 hours. The reaction mixture was neutralized with hydrochloric acid, followed by extraction with ethyl acetate. The extract was dried over anhydrous sodium sulfate, and the solvent was distilled off under reduced pressure to obtain compound (W5) (970 mg). TLC Rf: 0.47 (dichloromethane/methanol=9/1) MS (ESI, m/z): 349.3 [M+H]$^+$ (6) To a solution of compound (W5) (209 mg) and compound (A2) (265 mg) in dichloromethane (4 mL) and DIEA (120 μL), HOBt (122 mg) and EDC·HCl (233 mg) were added, and the mixture was stirred at room temperature for 3 hours. Dichloromethane and water were added thereto. The organic layer was separated, then dried over anhydrous sodium sulfate, and then purified by silica gel column chromatography (dichloromethane/methanol=95/5) to obtain compound (W6) (300 mg). TLC Rf: 0.12 (dichloromethane/methanol=95/5) MS (ESI, m/z): 895.7 [M+H]$^+$ (7) A mixture of compound (W6) (300 mg), methanol (8 mL), and 10% Pd/C (126 mg) was stirred at room temperature for 16 hours in a hydrogen atmosphere. Insoluble matter was filtered off, and the residue was purified by silica gel column chromatography (chloroform/ethanol/ammonia water=7/3/0.5) to obtain compound (W7) (194 mg). TLC Rf: 0.05 (dichloromethane/methanol=10/1) MS (ESI, m/z): 761.5 [M+H]$^+$ (8) To a mixture of disodium Fmoc-cysteinate (120 mg) and DMF (3 mL), methanesulfonic acid (40 μL) was added, and the resulting mixture was stirred for 5 minutes. DMF (7 mL), DIEA (250 μL), and compound (W7) (194 mg) were added thereto, and the mixture was stirred for 5 minutes. Then, HBTU (201 mg) was added thereto, and the mixture was stirred at room temperature for 15 hours. The solvent was distilled off under reduced pressure, and the residue was purified by silica gel column chromatography (chloroform/ethanol/ammonia water=7/3/0.5) to obtain compound (W8) (216 mg). TLC Rf: 0.31 (chloroform/ethanol/ammonia water=7/3/0.5) MS (ESI, m/z): 1132.2 [M−H]$^-$ (9) To compound (W8) (103 mg), TFA (1 mL) was added, and the mixture was stirred at room temperature for 45 minutes. Then, the solvent was distilled off under reduced pressure. To the obtained residue, acetonitrile/methanol (9/1) (3 mL) and diethylamine (0.5 mL) were added, and the mixture was stirred for 1 hour. The solvent was distilled off under reduced pressure, and a 50% aqueous acetonitrile solution (3 mL), toluene (3 mL), and hexane (3 mL) were added to the residue. The aqueous layer was separated, and the solvent was distilled off under reduced pressure. To the obtained residue, DMF (1 mL) and DIEA (60 μL) were added, then a solution of tri-tert-butyl 1,4,7,10-tetraazacyclododecane-1,4,7,10-tetraacetate (90.1 mg), DMF (300 μL)., DIEA (60 μL), and HBTU (59.5 mg) in DMF (300 μL) was added, and the mixture was stirred at room temperature for 25 minutes. Water (2 mL) was added thereto, and the mixture was purified by preparative HPLC to obtain compound (W9) (57.7 mg). HPLC (SunFire) rt (min): 8.93 LC/MS (ACQUITY) rt (min): 1.26 MS (ESI, m/z): 1367.0 [M+H]$^+$, 1365.0 [M−H]$^-$

(10) To compound (W9) (21.6 mg), TFA (1 mL) was added, and the mixture was stirred at room temperature for 4 hours. Then, the solvent was distilled off under reduced pressure. To the obtained residue, acetonitrile (1 mL) and TBME (1 mL) were added, and the solvent was distilled off under reduced pressure. To the obtained residue, water (0.6 mL) and a 3 mol/L aqueous lithium hydroxide solution (100 μL) were added, and the mixture was stirred at room temperature for 1 hour. Then, formic acid (20 μL) was added thereto, and the mixture was purified by preparative HPLC to obtain compound (W10) (11.0 mg). HPLC (SunFire) rt (min): 8.94 LC/MS (ACQUITY) rt (min): 0.79 MS (ESI, m/z): 1184.8 [M+H]$^+$ Example 24

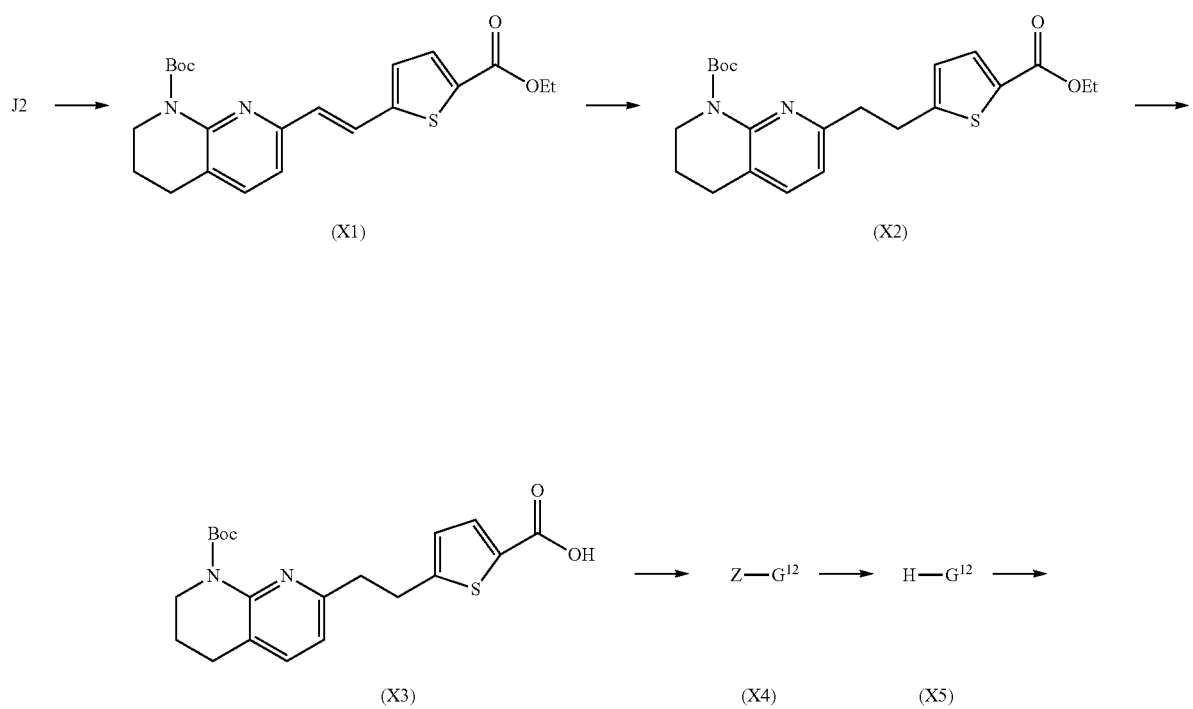

-continued
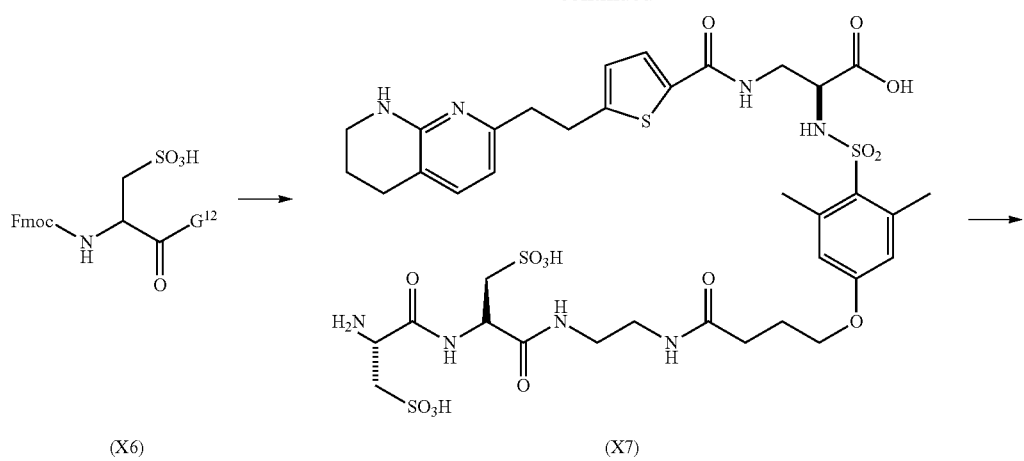
(X6) (X7)
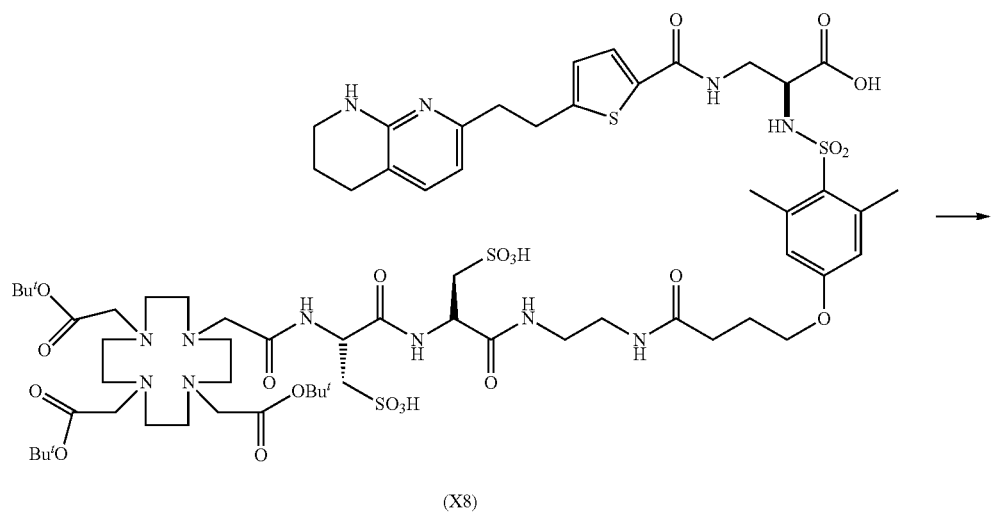
(X8)
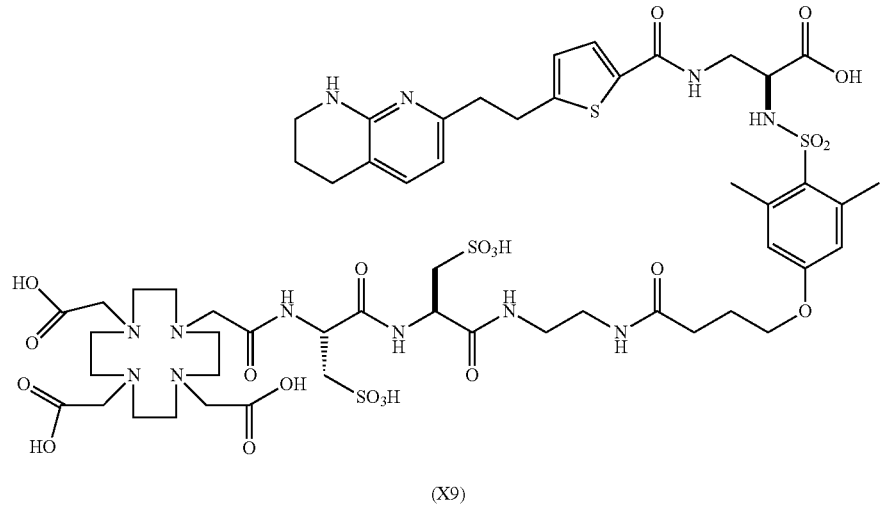
(X9)

(1) To a mixture of compound (J2) (1.5 g), ethyl 5-bromothiophene-2-carboxylate (1.42 g), triethylamine (3.5 mL), and DMF (22 mL), palladium(II) acetate (133 mg) and (2-(di-tert-butylphosphino)biphenyl (352 mg) were added, and the resulting mixture was stirred at 110° C. for 17 hours. The reaction mixture was cooled to room temperature, and ethyl acetate and water were added thereto. The organic layer was separated, then dried over anhydrous sodium sulfate, and then purified by silica gel column chromatography (hexane/ethyl acetate=9/1 to 5/1) to obtain compound (X1) (564 mg). TLC Rf: 0.55 (hexane/ethyl acetate=2/1) MS (ESI, m/z): 415.3 [M+H]$^+$ (2) Compound (X1) (564 mg), methanol (20 mL), and 10% Pd/C (198 mg) were placed in a sealed tube and stirred at room temperature for 17 hours in a hydrogen atmosphere. Insoluble matter was filtered off, and the residue was purified by silica gel column chromatography (hexane/ethyl acetate=8/2) to obtain compound (X2) (498 mg). TLC Rf: 0.47 (hexane/ethyl acetate=2/1) MS (ESI, m/z): 417.3 [M+H]$^+$ (3) To a solution of compound (X2) (498 mg) in THF (8 mL) and methanol (4 mL), a 1 mol/L aqueous lithium hydroxide solution (2 mL) was added, and the mixture was stirred at room temperature for 24 hours. To the reaction mixture, water (10 mL) were added, and then acetic acid was added until the solution became whitish. After extraction with ethyl acetate, the extract was dried over anhydrous sodium sulfate and then purified by silica gel column chromatography (dichloromethane/ethanol=9/1) to obtain compound (X3) (394 mg). TLC Rf: 0.49 (dichloromethane/methanol=9/1) $^1$H-NMR (400 MHz, CDCl$_3$) δ: 7.64 (1H, d, J=4.0 Hz), 7.31 (1H, d, J=8.8 Hz), 6.79 (1H, d, 4.0 Hz), 6.78 (1H, d, J=8.0 Hz), 3.78 (2H, t, J=6.4 Hz), 3.29 (2H, t, J=7.2 Hz), 3.10 (2H, t, J=7.2 Hz), 2.73 (2H, t, J=6.8 Hz), 1.93 (2H, tt, J=6.8, 6.4 Hz), 1.52 (9H, s) MS (ESI, m/z): 389.3 [M+H]$^+$ (4) To a mixture of compound (A2) (415 mg), compound (X3) (238 mg), DMF (5 mL), and DIEA (540 µL), HBTU (290 mg) was added, and the resulting mixture was stirred at room temperature for 1 hour. Ethyl acetate and water were added to the reaction mixture. The organic layer was separated, then dried over anhydrous sodium sulfate, and purified by silica gel column chromatography (dichloromethane/methanol=95/5) to obtain compound (X4) (570 mg). TLC Rf: 0.41 (ethyl acetate) MS (ESI, m/z): 935.5 [M+H]$^+$ (5) Compound (X4) (187 mg), methanol (15 mL), and 10% Pd/C (61 mg) were placed in a sealed tube and stirred for 18 hours in a hydrogen atmosphere. Insoluble matter was filtered off, and the solvent was distilled off under reduced pressure. The residue was purified by silica gel column chromatography (dichloromethane/methanol=95/5 to chloroform/ethanol/ammonia water=7/3/0.5) to obtain compound (X5) (87 mg). TLC Rf: 0.27 (chloroform/ethanol/ammonia water=8/2/0.3) MS (ESI, m/z): 801.4 [M+H]$^+$ (6) A mixture of disodium Fmoc-cysteinate (48 mg), DMF (1 mL), and methanesulfonic acid (8.5 µL) was stirred at room temperature for 30 minutes. DIEA (91 µL), DMF (2 mL), compound (X5) (87 mg), and HBTU (85 mg) were added thereto, and the mixture was stirred at room temperature for 1 hour. The solvent was distilled off under reduced pressure. The obtained residue was purified by silica gel column chromatography (chloroform/ethanol/ammonia water=7/3/0.5) to obtain compound (X6) (106 mg). TLC Rf: 0.26 (chloroform/ethanol/ammonia water=7/3/0.5) MS (ESI, m/z): 1172.1 [M−H]$^-$ (7) To a solution of compound (X6) (80 mg) in DMF (0.5 mL), diethylamine (0.5 mL) was added, and the mixture was stirred at room temperature for 80 minutes. The solvent was distilled off under reduced pressure. To the obtained oil, DMF (1 mL), DIEA (60 µL), Fmoc-cysteic acid (65.4 mg), and HBTU (63.3 mg) were added, and the mixture was stirred at room temperature for 20 minutes. To the reaction mixture, water (1 mL) was added, then diethylamine (2 mL) was added, and the mixture was stirred at room temperature for 30 minutes. Water (2 mL) was added thereto, and the mixture was washed twice with ethyl acetate (2 mL) and then purified by preparative HPLC to obtain compound (X7) (66.8 mg). HPLC (SunFire) rt (min): 9.36 LC/MS (ACQUITY) rt (min): 0.79 MS (ESI, m/z): 989.5 [M+H]$^+$, 987.4 [M−H]$^-$ (8) To a solution of tri-tert-butyl 1,4,7,10-tetraazacyclododecane-1,4,7,10-tetraacetate (39.0 mg) in DMF (150 µL) and DIEA (25 µL), a solution of HBTU (24.8 mg) in DMF (100 µL) was added, then the mixture was added to a solution of compound (X7) (27.3 mg) in DMF (0.3 mL) and DIEA (10 µL), and the resulting mixture was stirred at room temperature for 30 minutes. Water (0.5 mL) and acetonitrile (0.2 mL) were added thereto, and the mixture was purified by preparative HPLC to obtain compound (X8) (19.0 mg). HPLC (SunFire) rt (min): 9.89 LC/MS (ACQUITY) rt (min): 1.03 MS (ESI, m/z): 1543.7 [M+H]$^+$, 1541.7 [M−H]$^-$ (9) To compound (X8) (9.6 mg), TFA/triethylsilane (95/5) (1 mL) was added, and the mixture was stirred at room temperature for 1 hour. The solvent was distilled off under reduced pressure. A 50% aqueous acetonitrile solution (1.2 mL) was added to the residue, and the mixture was purified by preparative HPLC to obtain compound (X9) (3.6 mg). HPLC (SunFire) rt (min): 10.08 LC/MS (ACQUITY) rt (min): 0.78 MS (ESI, m/z): 688.4 [M+2H]$^{2+}$, 1373.5 [M−H]$^-$, 686.5 [M−2H]$^{2-}$ Example 25

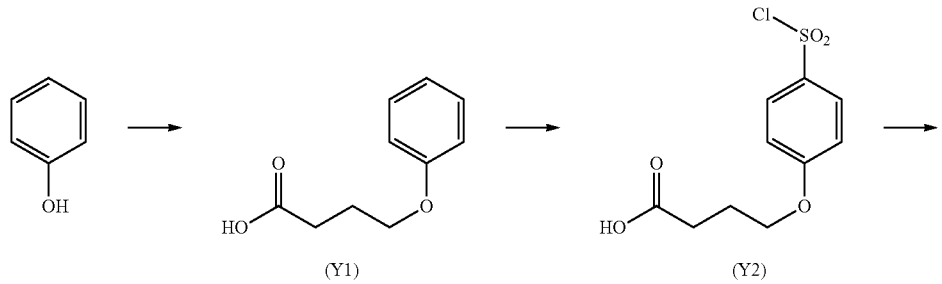

-continued
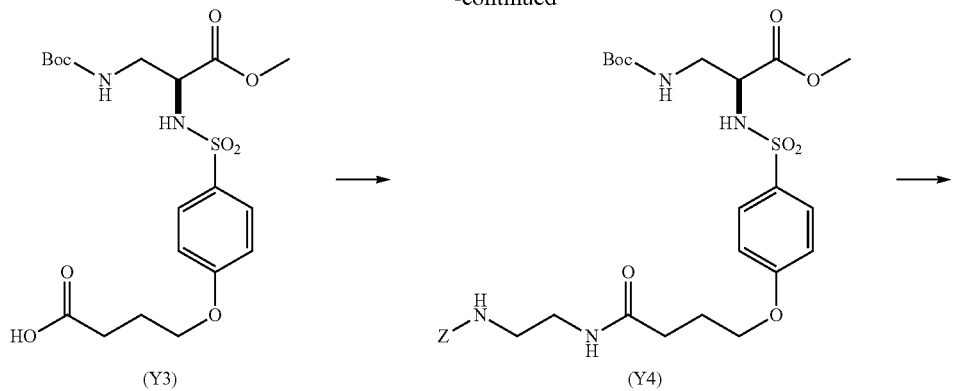
(Y3) (Y4)
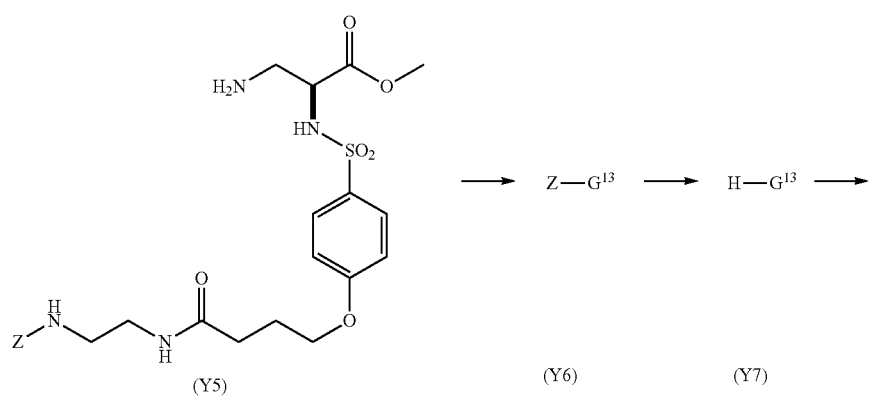
(Y5) (Y6) (Y7)
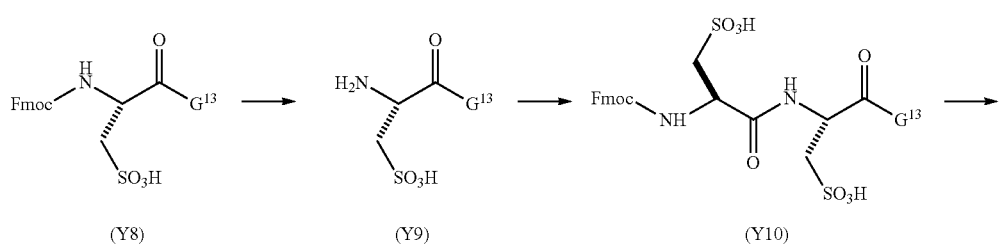
(Y8) (Y9) (Y10)
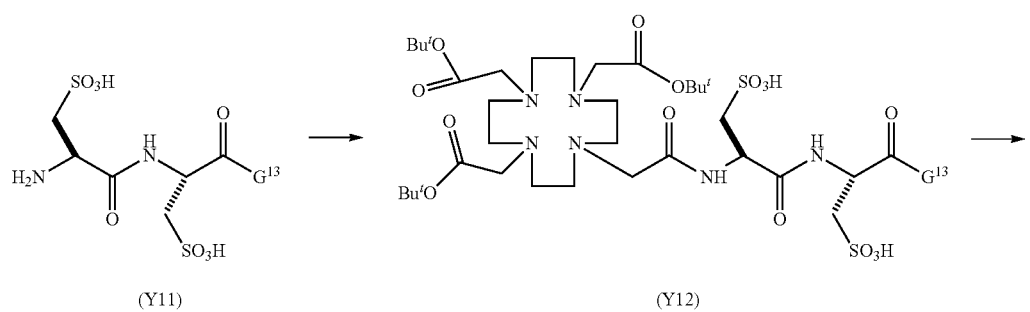
(Y11) (Y12)

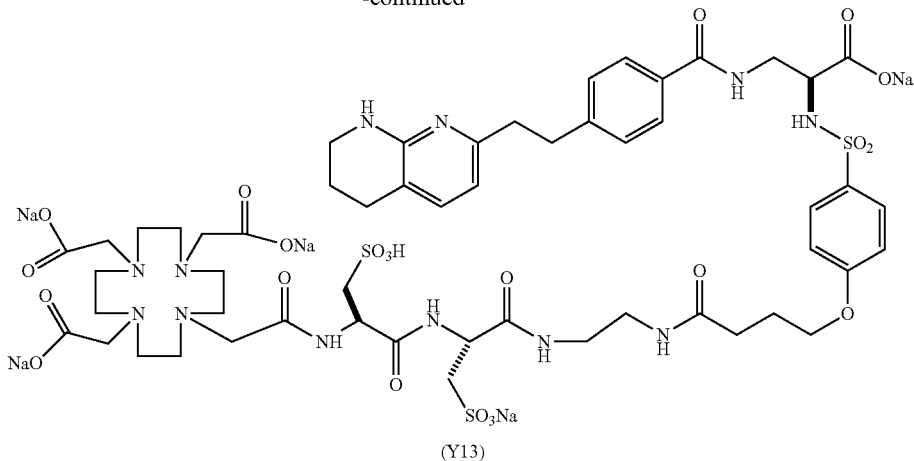

(Y13)

(1) To a mixture of phenol (2.84 g), DMF (40 mL), and potassium carbonate (7.9 g), ethyl 4-bromobutanoate (4.8 mL) was added, and the resulting mixture was stirred at room temperature for 22 hours. Ethyl acetate and water were added thereto. The organic layer was separated, and the solvent was distilled off under reduced pressure. To the obtained residue, ethanol (80 mL), water (20 mL), and sodium hydroxide (4.7 g) were added, and the mixture was stirred at room temperature for 4 hours. The solvent was distilled off under reduced pressure. The obtained residue was washed with hexane and then dissolved in water, and the solution was adjusted acidic with concentrated hydrochloric acid, followed by extraction with ethyl acetate. The organic layer was dried over anhydrous sodium sulfate, and the solvent was distilled off under reduced pressure to obtain compound (Y1) (5.08 g). TLC Rf: 0.38 (ethyl acetate)

(2) To a solution of compound (Y1) (5.08 g) in chloroform (30 mL), chlorosulfonic acid (10 mL) was added dropwise at 0° C. or lower over 30 minutes, and the mixture was stirred at 0° C. for 15 minutes. The reaction mixture was added to ice water, and the solid matter was collected by filtration to obtain compound (Y2) (4.25 g). TLC Rf: 0.38 (dichloromethane/methanol=95/5)

(3) To a mixture of (S)-2-amino-3-((tert-butoxycarbonyl)amino)propanoic acid methyl hydrochloride (1.0 g), dichloromethane (10 mL), and DIEA (1.4 mL), a solution of compound (Y2) (1.25 g) in dichloromethane (35 mL) was added, and the resulting mixture was stirred at room temperature for 70 hours. Water was added thereto. The organic layer was separated and dried over anhydrous sodium sulfate, and the solvent was distilled off under reduced pressure. The residue was purified by silica gel column chromatography (dichloromethane/methanol=95/5) to obtain compound (Y3) (938 mg). TLC Rf: 0.16 (dichloromethane/methanol=95/5)

(4) To a mixture of compound (Y3) (938 mg), Z-ethylenediamine hydrochloride (517 mg), DMF (14 mL), and DIEA (1.4 mL), HATU (877 mg) was added, and the resulting mixture was stirred at room temperature for 1 hour. Dichloromethane and water were added to the reaction mixture. The organic layer was separated, then dried over anhydrous sodium sulfate, and then purified by silica gel column chromatography (ethyl acetate) to obtain compound (Y4) (1.11 g). TLC Rf: 0.25 (dichloromethane/methanol=95/5)

(5) To a solution of compound (Y4) (1.11 g) in dichloromethane (10 mL), TFA (10 mL) was added, and the mixture was stirred at room temperature for 1 hour. The solvent was distilled off under reduced pressure, and a saturated aqueous solution of sodium bicarbonate and dichloromethane were added to the residue. The organic layer was separated and dried over anhydrous sodium sulfate to obtain compound (Y5) (894 mg). TLC Rf: 0.20 (dichloromethane/methanol=9/1)

(6) To a solution of compound (Y5) (894 mg) and compound (H4) (640 mg) in DMF (15 mL) and DIEA (1.46 mL), HATU (673 mg) was added, and the mixture was stirred at room temperature for 2 hours. Ethyl acetate and water were added thereto. The organic layer was separated, then dried over anhydrous sodium sulfate, and then purified by silica gel column chromatography (ethyl acetate/methanol=100/5) to obtain compound (Y6) (1.47 g). TLC Rf: 0.51 (dichloromethane/methanol=9/1)

(7) Compound (Y6) (225 mg), methanol (10 mL), and 10% Pd/C (62 mg) were placed in a sealed tube and stirred for 17 hours in a hydrogen atmosphere. Insoluble matter was filtered, and the solvent was distilled off under reduced pressure. The residue was purified by silica gel column chromatography (chloroform/ethanol/ammonia water=7:3:0.5) to obtain compound (Y7) (126 mg). TLC Rf: 0.69 (chloroform/ethanol/ammonia water=7/3/0.5)

(8) A mixture of disodium Fmoc-cysteinate (40 mg), DMF (0.5 mL), and methanesulfonic acid (7.2 µL) was stirred at room temperature for 30 minutes, and then, DIEA (77 µL), DMF (1.5 mL), and compound (Y7) (69 mg) were added thereto. HBTU (48 mg) was added thereto, and the mixture was stirred at room temperature for 2.5 hours, followed by the addition of chloroform and water. The organic layer was separated, then dried over anhydrous sodium sulfate, and purified by silica gel column chromatography (chloroform/ethanol/ammonia water=7/3/0.5) to obtain compound (Y8) (76 mg). TLC Rf: 0.35 (chloroform/ethanol/ammonia water=7/3/0.5)

(9) A mixture of compound (Y8) (140 mg), DMF (2 mL), and diethylamine (200 µL) was stirred at room temperature for 80 minutes. The solvent was distilled off under reduced pressure, and the residue was purified by silica gel column chromatography (chloroform/ethanol/ammonia water=7/3/0.5) to obtain compound (Y9) (100 mg). TLC Rf: 0.10 (chloroform/ethanol/ammonia water=7/3/0.5)

(10) A mixture of disodium Fmoc-cysteinate (46 mg), DMF (1 mL), and methanesulfonic acid (8.3 μL) was stirred at room temperature for 30 minutes. Then, DIEA (89 μL), DMF (1.5 mL), compound (Y9) (100 mg), and HBTU (58 mg) were added thereto, and the mixture was stirred at room temperature for 1.5 hours. Chloroform and water were added to the reaction mixture. The organic layer was separated, then dried over anhydrous sodium sulfate, and purified by silica gel column chromatography (chloroform/ethanol/ammonia water=6/4/1) to obtain compound (Y10) (155 mg). TLC Rf: 0.19 (chloroform/ethanol/ammonia water=6/4/1)

(11) A mixture of compound (Y10) (142 mg), DMF (2 mL), and diethylamine (200 μL) was stirred at room temperature for 1 hour. The solvent was distilled off under reduced pressure, and the residue was purified by silica gel column chromatography (chloroform/ethanol/ammonia water=5/5/1.5) to obtain compound (Y11) (89 mg). TLC Rf: 0.21 (chloroform/ethanol/ammonia water=5/5/1.5) MS (ESI, m/z): 1013.3 [M−BOC+2Na]$^+$, 1067.3 [M−H]$^-$, 533.2 [M−2H]$^{2-}$

(12) To a mixture of compound (Y11) (26 mg), tri-tert-butyl 1,4,7,10-tetraazacyclododecane-1,4,7,10-tetraacetate (16 mg), DMF (500 μL), and DIEA (21 μL), HATU (23 mg) was added, and the resulting mixture was stirred at room temperature for 5 minutes. The solvent was distilled off under reduced pressure, and the residue was purified by silica gel column chromatography (chloroform/ethanol/ammonia water=7/3/0.5) to obtain compound (Y12) (25 mg). TLC Rf: 0.22 (chloroform/ethanol/ammonia water=7/3/0.5)

(13) To compound (Y12) (45 mg), TFA (2 mL) was added, and the mixture was stirred at room temperature for 22 hours. The solvent was distilled off under reduced pressure. To the obtained residue, DMF (2 mL) and sodium hydroxide (17 mg) were added, and the mixture was stirred at room temperature for 47 hours. The solvent was distilled off under reduced pressure, and the residue was purified on a reversed-phase silica gel (Sep-Pak C18, water/methanol=5/95 to 10/90) to obtain compound (Y13) (40 mg). Reversed-phase TLC Rf: 0.68 (water/acetonitrile=95/5)

Example 26

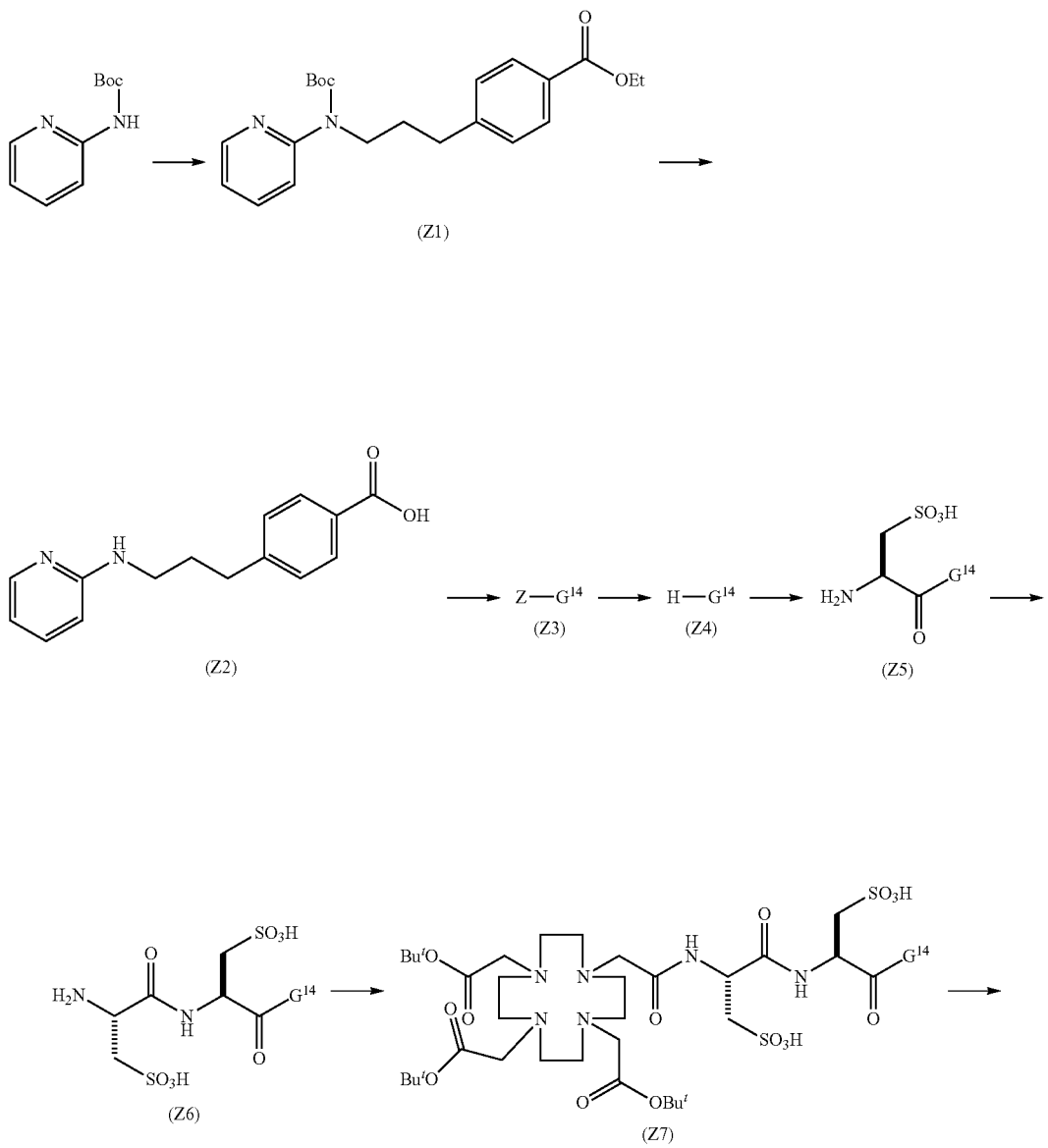

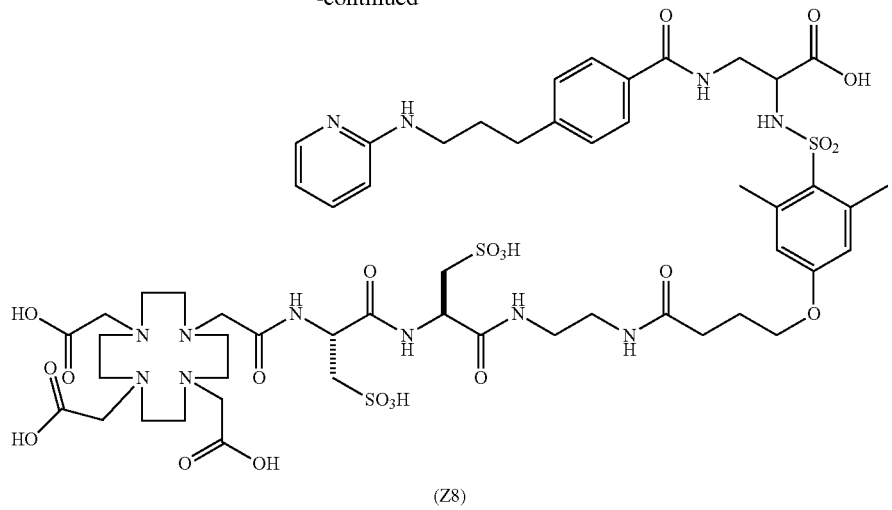

(Z8)

(1) A solution of 2-(tert-butoxycarbonylamino)pyridine (1.07 g) in DMF (6 mL) was ice-cold. Sodium hydride (60% dispersion in mineral oil, 221 mg) was added thereto over 10 minutes, and the mixture was stirred at the same temperature as above for 15 minutes and then added to a solution of ethyl 4-(3-bromopropyl)benzoate (1.5 g) in DMF (6 mL), followed by stirring at room temperature for 3 hours. The reaction mixture was added to 2% hydrochloric acid, followed by extraction with ethyl acetate. The extract was washed with a saturated aqueous solution of sodium carbonate and a saturated aqueous solution of sodium chloride in this order. The resultant was dried over anhydrous magnesium sulfate, and the solvent was distilled off under reduced pressure. The obtained residue was purified by silica gel column chromatography (hexane/ethyl acetate) to obtain compound (Z1) (1.8 g). $^1$H-NMR (300 MHz, CDCl$_3$) δ: 8.37 (1H, dd, J=2.1, 4.2 Hz), 7.94 (2H, d, J=7.2 Hz), 7.54-7.65 (2H, m), 7.22 (2H, d, J=7.2 Hz), 6.99-7.03 (1H, m), 4.36 (2H, q, J=7.2 Hz), 3.98 (2H, t, J=7.2 Hz), 2.69 (2H, t, J=7.2 Hz), 1.93-2.03 (2H, m), 1.48 (9H, s), 1.38 (3H, t, J=7.2 Hz)

(2) To compound (Z1) (1.5 g), concentrated hydrochloric acid (5 mL) was added, and the mixture was stirred at 70° C. for 3 hours. Concentrated hydrochloric acid (2 mL) was added thereto, and the mixture was stirred at room temperature for 12 hours. A saturated aqueous solution of sodium bicarbonate was added thereto until the pH reached 4, followed by extraction with ethyl acetate. The solvent was distilled off under reduced pressure to obtain compound (Z2) (300 mg). LC/MS (ACQUITY) rt (min): 0.66 MS (ESI, m/z): 257.1 [M+H]$^+$ (3) To a mixed solution of compound (A2) (750 mg), compound (Z2) (200 mg), DMF (3 mL), and DIEA (0.68 mL), HBTU (296 mg) was added, and the mixture was stirred at room temperature for 1 hour. Ethyl acetate and water were added thereto. The organic layer was separated and dried over anhydrous magnesium sulfate, and then, the solvent was distilled off under reduced pressure. The obtained residue was purified by silica gel column chromatography (chloroform/methanol) to obtain compound (Z3) (480 mg). LC/MS (ACQUITY) rt (min): 1.16 MS (ESI, m/z): 803.5 [M+H]$^+$ (4) Compound (Z3) (480 mg), methanol (30 mL), and 10% Pd/C (100 mg) were placed in a sealed tube and stirred for 5 hours in a hydrogen atmosphere. Insoluble matter was filtered off, and the solvent was distilled off under reduced pressure to obtain compound (Z4) (510 mg).

(5) A mixture of disodium Fmoc-cysteinate (73.4 mg), THF (1 mL), and methanesulfonic acid (11 μL) was stirred at room temperature for 30 minutes. To the reaction mixture, DIEA (29 μL), NMP (1 mL), and compound (Z4) (94 mg) were added, then HBTU (64 mg) was added, and the mixture was stirred at room temperature for 2.5 hours. Methanol was added thereto. Insoluble matter was filtered off, and the solvent was distilled off under reduced pressure. The residue was washed twice with water. THF (2 mL), NMP (0.3 mL), and diethylamine (2 mL) were added thereto, and the mixture was stirred at room temperature for 3 hours. The solvent was distilled off under reduced pressure, and the residue was washed with toluene to obtain compound (Z5) (74 mg). LC/MS (ACQUITY) rt (min): 0.78 MS (ESI, m/z): 820.4 [M+H]$^+$ (6) A mixture of disodium Fmoc-cysteinate (45.9 mg), THF (2 mL), and methanesulfonic acid (6.8 μL) was stirred at room temperature for 1 hour. Then, compound (Z5) (74 mg), NMP (0.7 mL), DIEA (18 μL), and HBTU (40.0 mg) were added thereto, and the mixture was stirred at room temperature for 2.5 hours. Methanol was added thereto. The solvent was distilled off under reduced pressure, and the residue was washed with ethyl acetate. NMP (1 mL) and diethylamine (1 mL) were added to the residue, and the mixture was stirred at room temperature for 3 hours. The solvent was distilled off under reduced pressure. The obtained residue was purified by preparative HPLC to obtain compound (Z6) (6.7 mg). LC/MS (ACQUITY) rt (min): 0.83 MS (ESI, m/z): 971.5 [M+H]$^+$, 486.4 [M+2H]$^{2+}$, 969.5 [M−H]$^−$ (7) To a solution of tri-tert-butyl 1,4,7,10-tetraazacyclododecane-1,4,7,10-tetraacetate (5.9 mg) and compound (Z6) (6.7 mg) in NMP (200 μL) and DIEA (20 μL), HBTU (5.2 mg) was added, and the mixture was stirred at room temperature for 50 minutes. Methanol (100 μL) was added thereto, and then, the mixture was purified by preparative HPLC to obtain compound (Z7) (3.9 mg). LC/MS (ACQUITY) rt (min): 1.08 MS (ESI, m/z): 763.9 [M+2H]$^{2+}$ (8) A mixture of compound (Z7) (3.9 mg), THF (200 μL), water (20 μL), 2-propanol (20 μL), and a 4 mol/L aqueous lithium hydroxide solution (27 μL) was stirred at room temperature for 4 hours. TFA was added thereto, and the solvent was distilled off under reduced pressure. TFA/triethylsilane (95/5) (100 μL) was added to the residue, and the mixture was stirred for 2 hours. Then, the solvent was distilled off under reduced pressure. The obtained residue was purified by preparative HPLC to obtain compound (Z8) (1.8 mg). LC/MS (ACQUITY) rt (min): 0.76 MS (ESI, m/z): 672.6 [M+2H]$^{2+}$, 670.6 [M−2H]$^{2−}$ Example 27
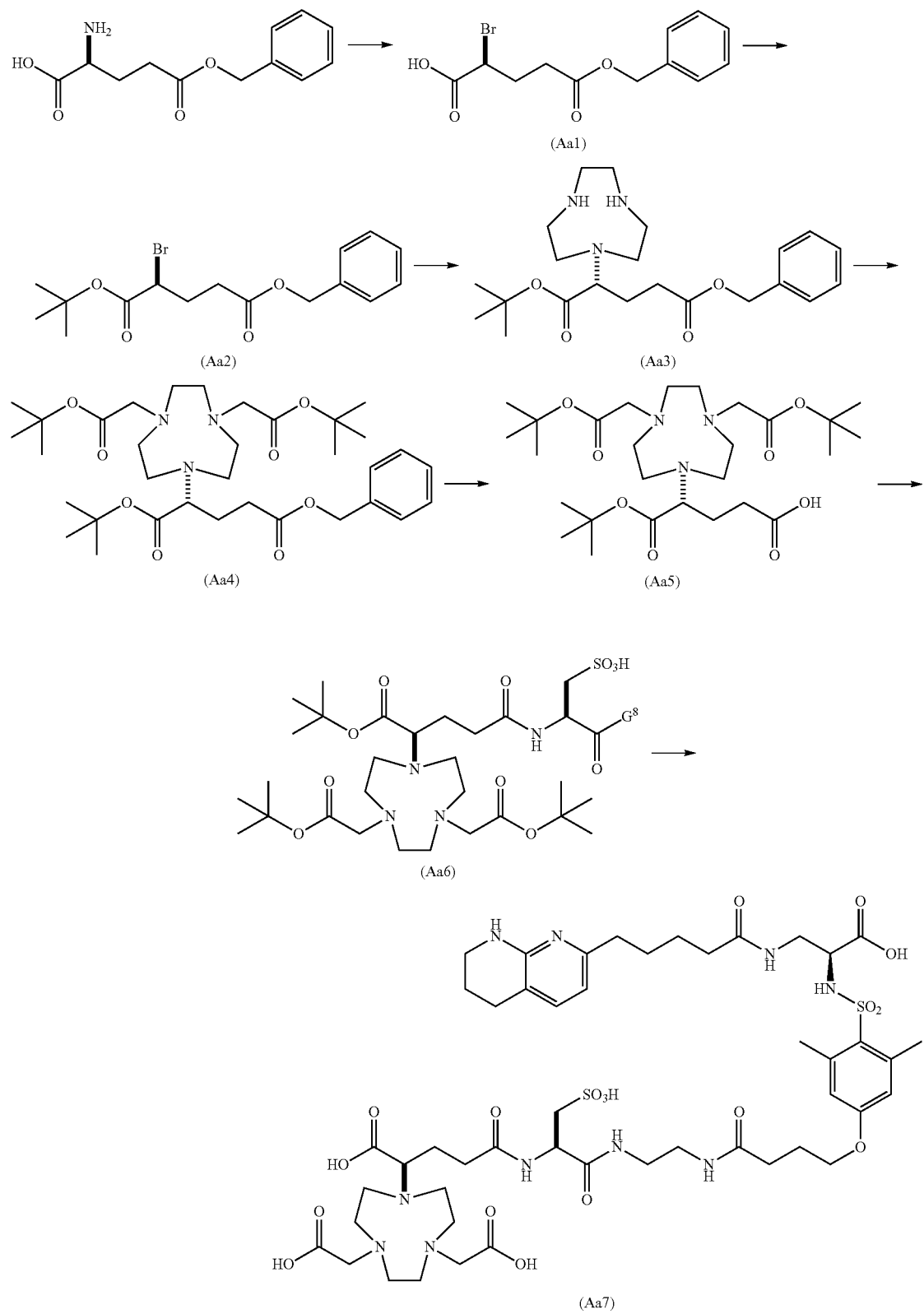

(1) To a mixture of L-glutamic acid γ benzyl ester (5.0 g), water (10 mL), sodium bromide (7.6 g), and hydrobromic acid (6 mL), sodium nitrite (2.6 g) was added at 5° C. or lower over 10 minutes, and the resulting mixture was stirred at 5° C. for 2 hours. Diisopropyl ether and concentrated sulfuric acid (2 mL) were added to the reaction mixture. The organic layer was separated, then washed with water and a saturated aqueous solution of sodium chloride in this order, and then dried over anhydrous sodium sulfate. The solvent was distilled off under reduced pressure. Then, the obtained residue was purified by silica gel column chromatography (hexane/ethyl acetate=1/1) to obtain compound (Aa1) (3.1 g). LC/MS (ACQUITY) rt (min): 1.32 MS (ESI, m/z): 301.1 [M+H]1H-NMR (300 MHz, CDCl$_3$) δ: 7.31-7.38 (5H, m), 5.1 (2H, s), 4.41 (1H, dd, J=6.0, 7.8 Hz), 2.58-2.63 (2H, m), 2.25-2.50 (2H, m)

(2) To a solution of compound (Aa1) (3.1 g) in chloroform (15 mL), a mixture of tert-butyl 2,2,2-trichloroacetimidate (4.3 mL) and hexane (12 mL) was added at room temperature over 20 minutes. DMAc (1.5 mL) and BF$_3$·OEt$_2$ (220 μL) were added thereto, and the mixture was stirred at room temperature for 40 hours. Then, the solvent was distilled off under reduced pressure, and the residue was purified by silica gel column chromatography (hexane/ethyl acetate=95/5 to 85/15) to obtain compound (Aa2) (2.84 g). $^1$H-NMR (300 MHz, CDCl$_3$) δ: 7.31-7.38 (5H, m), 5.14 (2H, s), 4.24 (1H, dd, J=6.0, 8.7 Hz), 2.53-2.59 (2H, m), 2.19-2.43 (2H, m), 1.47 (9H, a)

(3) To a solution of 1,4,8,11-tetraazacyclotetradecane (1.84 g) in chloroform (60 mL), a solution of compound (Aa2) (1.70 g) in chloroform (50 mL) was added over 90 minutes, and the mixture was stirred at room temperature for 3 days. The solvent was distilled off under reduced pressure, and the residue was purified by silica gel column chromatography (hexane/ethyl acetate=50/50 to 0/100 and then ethyl acetate/methanol=80/20) to obtain compound (Aa3) (0.76 g). LC/MS (ACQUITY) rt (min): 0.91 MS (ESI, m/z): 406.5 [M+H]$^+$ (4) To a mixture of compound (Aa3) (0.76 g), DMAc (7 mL), and potassium carbonate (607 mg), tert-butyl bromoacetate (580 μL) was added, and the resulting mixture was stirred at room temperature for 2 hours. Ethyl acetate (30 mL) and water (30 mL) were added thereto. The organic layer was separated, then washed twice with water (30 mL) and once with a saturated aqueous solution of sodium chloride (30 mL) in this order, and dried over anhydrous sodium sulfate. The solvent was distilled off under reduced pressure. The obtained residue was purified by silica gel column chromatography (hexane/ethyl acetate=95/5 to 60/40) to obtain compound (Aa4) (1.04 g). LC/MS (ACQUITY) rt (min): 1.63 MS (ESI, m/z): 634.7 [M+H]$^+$ (5) Compound (Aa4) (0.28 g), isopropyl alcohol (20 mL), water (0.5 mL), and 10% Pd/C (0.10 g) were placed in a sealed tube and stirred for 7 hours in a 0.5 MPa hydrogen atmosphere. Insoluble matter was filtered off, and the solvent was distilled off under reduced pressure to obtain compound (Aa5) (0.24 g). LC/MS (ACQUITY) rt (min): 1.34 MS (ESI, m/z): 544.7 [M+H]$^+$ (6) To a mixture of compound (Aa5) (94.9 mg), (R)-2-amino-3-((2-(4-(4-(N—((S)-1-methoxy-1-oxo-3-(5-(5,6,7,8-tetrahydro-1,8-naphthyridin-2-yl)pentanamido)propan-2-yl)sulfamoyl)-3,5-dimethylphenoxy)butanamido)ethyl) amino)-3-oxopropane-1-sulfonic acid (104 mg), DMF (0.8 mL), and N,N-diisopropylethylamine (61 μL), HBTU (64.5 mg) was added, and the resulting mixture was stirred at room temperature for 35 minutes. Water (1.1 mL) and acetonitrile (0.8 mL) were added thereto, and the mixture was stirred and then purified by preparative HPLC to obtain compound (Aa6) (151 mg). HPLC (CAPCELL PAK MG) rt (min): 11.82 LC/MS (ACQUITY) rt (min): 1.28 MS (ESI, m/z): 1324.2 [M+H]$^+$, 1322.2 [M−H]$^-$ (7) To compound (Aa6) (73 mg), concentrated hydrochloric acid (2.5 mL) was added, and the mixture was stirred at room temperature for 2 days and then concentrated under reduced pressure. The concentrate was diluted with acetonitrile containing 50% water (2 mL) and then purified by preparative HPLC to obtain compound (Aa7) (33.3 mg). HPLC (CAPCELL PAK MG) rt (min): 9.37 LC/MS (ACQUITY) rt (min): 0.77 MS (ESI, m/z): 1141.8 [M+H]$^+$, 1139.8 [M−H]$^-$ Example 28

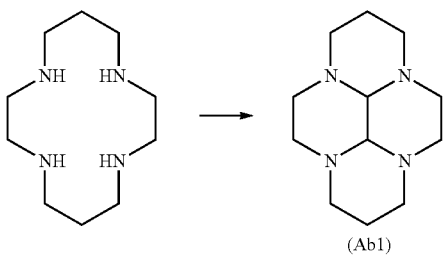

(Ab1)

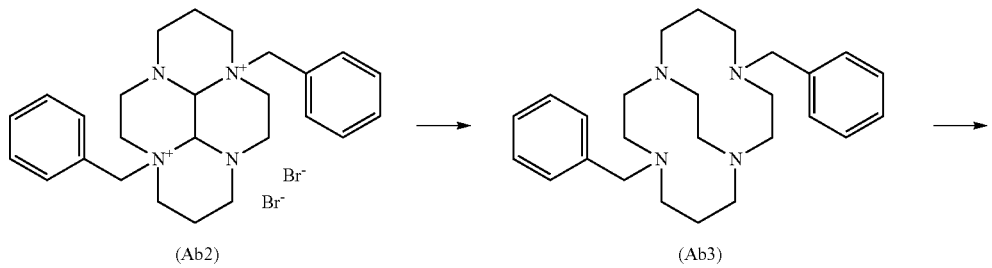

(Ab2)  (Ab3)

-continued
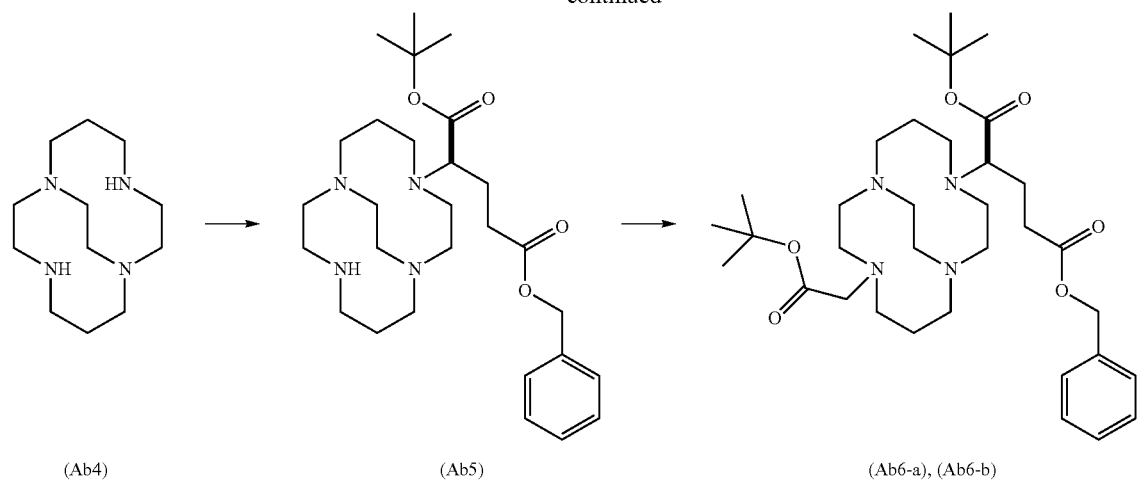
(Ab4) (Ab5) (Ab6-a), (Ab6-b)
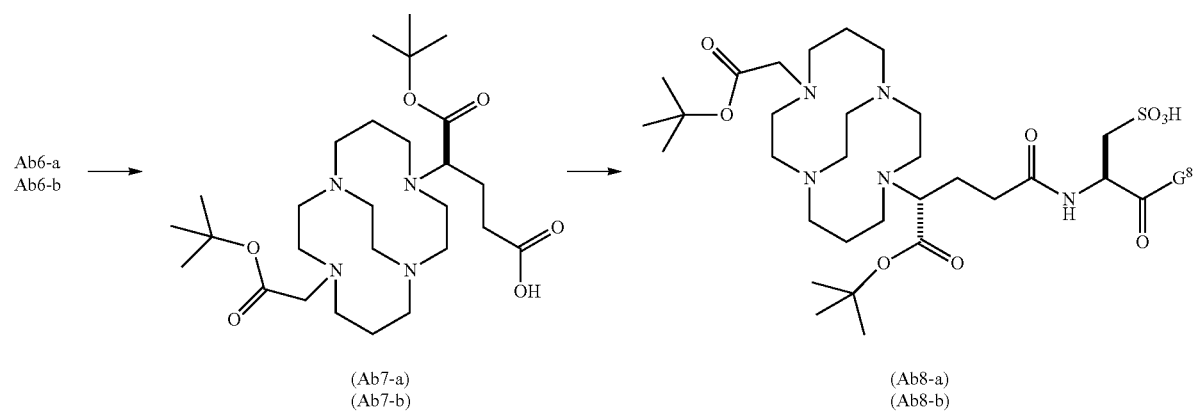
Ab6-a
Ab6-b
(Ab7-a)
(Ab7-b)
(Ab8-a)
(Ab8-b)
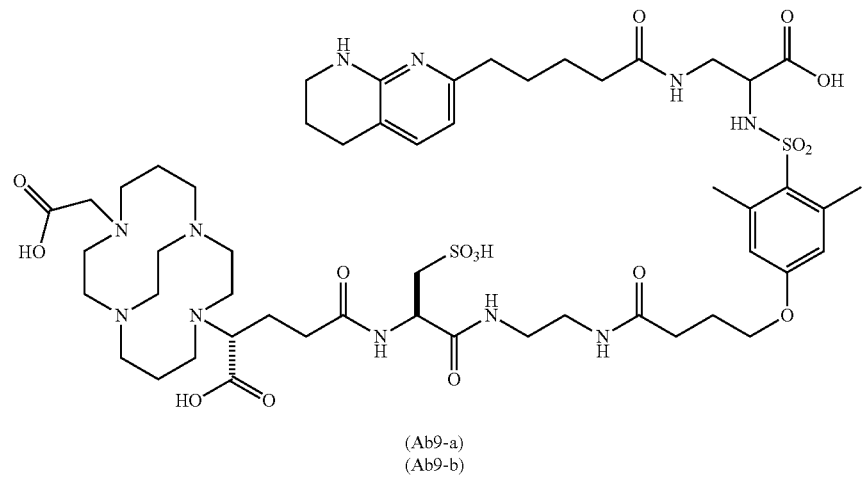
(Ab9-a)
(Ab9-b)

(1) To a solution of 1,4,8,11-tetraazacyclotetradecane (5.35 g) in acetonitrile (450 mL), 39% glyoxal (4.5 mL) was added, and the mixture was stirred at room temperature for 1.5 hours and then stirred at 50° C. for 2 hours. The solvent was distilled off under reduced pressure. Diisopropyl ether (100 mL) was added to the residue, and the mixture was stirred at room temperature for 1 hour. Then, the obtained solid was collected by filtration to obtain compound (Ab1) (2.46 g). $^1$H-NMR (300 MHz, CDCl$_3$) δ: 3.49-3.57 (2H, m), 3.08 (2H, s), 2.93-2.97 (6H, m), 2.74 (2H, d, J=11.1 Hz), 2.01-2.35 (8H, m), 1.19-1.26 (2H, m)

(2) To a solution of compound (Ab1) (2.40 g) in acetonitrile (40 mL), benzyl bromide (18 mL) was added, and the mixture was stirred at room temperature for 15 days. The deposited solid was collected by filtration and washed with acetonitrile and dichloromethane to obtain compound (Ab2) (4.0 g). LCMS (ACQUITY) rt (min): 0.46 MS (ESI, m/z): 313.4 [M−Bn]$^+$ (3) To a mixture of compound (Ab2) (4.0 g), ethanol (180 mL), and water (9 mL), sodium borohydride (4 g) was added in 4 divided portions every 15 minutes, and the resulting mixture was stirred at room temperature for 3 days. After addition of 3M hydrochloric acid (80 mL) and water (100 mL) in this order under cooling, the reaction mixture was neutralized with sodium hydroxide, followed by extraction with toluene (200 mL) twice. The extract was dried over anhydrous sodium sulfate, and then, the solvent was distilled off under reduced pressure to obtain compound (Ab3) (1.9 g). LC/MS (ACQUITY) rt (min): 0.73 MS (ESI, m/z): 407.6 [M+H]$^+$ (4) Compound (Ab3) (0.90 g), acetic acid (25 mL), and 10% Pd/C (230 mg) were placed in a sealed tube and stirred for 11 hours in a hydrogen atmosphere. Insoluble matter was filtered off, and the solvent was distilled off under reduced pressure. Then, water (30 mL), sodium hydroxide (2 g), and a saturated aqueous solution of sodium chloride (10 mL) were added to the residue, followed by extraction with toluene (50 mL) three times. The solvent was distilled off under reduced pressure to obtain compound (Ab4) (509 mg). LC/MS (ACQUITY) rt (min): 0.20 MS (ESI, m/z): 227.4 [M+H]$^+$ $^1$H-NMR (300 MHz, CDCl$_3$) δ: 3.73 (1H, brs), 3.11 (2H, ddd, J=2.7, 9.9, 13.2 Hz), 2.59-2.94 (14H, m), 2.34-2.46 (4H, m), 2.26 (1H, brs), 1.85-1.99 (2H, m), 1.25-1.36 (2H, m)

(5) To a mixture of compound (Ab4) (509 mg), acetonitrile (8 mL), and potassium carbonate (930 mg), a solution of compound (Aa2) (880 mg) in acetonitrile (3 mL) was added, and the resulting mixture was stirred at room temperature for 1 day. Insoluble matter was filtered off, and the solvent was distilled off under reduced pressure. The residue was purified by silica gel column chromatography (ethyl acetate/isopropylamine=100/5 to 100/10) to obtain compound (Ab5) (467 mg). LC/MS (ACQUITY) rt (min): 0.92 MS (ESI, m/z): 503.6 [M+H]$^+$ (6) To a mixture of compound (Ab5) (383 mg), DMAc (3 mL), and potassium carbonate (250 mg), tert-butyl bromoacetate (123 HL) was added, and the resulting mixture was stirred at room temperature for 2 hours. Ethyl acetate (20 mL), water (10 mL), and a saturated aqueous solution of sodium chloride (20 mL) were added thereto. The organic layer was separated and dried over anhydrous sodium sulfate, and the solvent was distilled off under reduced pressure. The residue was purified by silica gel column chromatography (chloroform/methanol=9/1, ethyl acetate/isopropylamine=10/1) and preparative HPLC in this order to obtain compounds (Ab6-a) (76 mg) and (Ab6-b) (50 mg) ((Ab6-a) and (Ab6-b) were stereoisomers). (Ab6-a) LC/MS (ACQUITY) rt (min): 1.19 MS (ESI, m/z): 617.7 [M+H]$^+$ (Ab6-b) LC/MS (ACQUITY) rt (min): 1.64 MS (ESI, m/z): 617.7 [M+H]$^+$ (7-a) Compound (Ab6-a) (76 g), THF (2 mL), water (2 mL), and 10% Pd/C (10 mg) were placed in a sealed tube and stirred for 6 hours in a hydrogen atmosphere. Insoluble matter was filtered off, and the solvent was distilled off under reduced pressure to obtain compound (Ab7-a) (64 mg). LC/MS (ACQUITY) rt (min): 0.82 MS (ESI, m/z): 527.5 [M+H]$^+$ (7-b) Compound (Ab6-b) (50 g), THF (2 mL), water (2 mL), and 10% Pd/C (10 mg) were placed in a sealed tube and stirred for 6 hours in a hydrogen atmosphere. Insoluble matter was filtered off, and the solvent was distilled off under reduced pressure to obtain compound (Ab7-b) (45 mg). LC/MS (ACQUITY) rt (min): 1.30 MS (ESI, m/z): 527.5 [M+H]$^+$ (8-a) To a mixture of compound (Ab7-a) (60.9 mg), (R)-2-amino-3-((2-(4-(4-(N—((S)-1-methoxy-1-oxo-3-(5-(5,6,7,8-tetrahydro-1,8-naphthyridin-2-yl)pentanamido)propan-2-yl)sulfamoyl)-3,5-dimethylphenoxy)butanamido)ethyl)amino)-3-oxopropane-1-sulfonic acid (92.6 mg), DMF (0.8 mL), and N,N-diisopropylethylamine (50 μL), HBTU (48.4 mg) was added, and the resulting mixture was stirred at room temperature for 15 minute. Water (0.5 mL) and a 50% aqueous acetonitrile solution (0.6 mL) were added thereto, and the mixture was stirred and then purified by preparative HPLC to obtain compound (Ab8-a) (74 mg). HPLC (CAPCELL PAK MG) rt (min): 9.74 LC/MS (ACQUITY) rt (min): 0.91 MS (ESI, m/z): 1307.0 [M+H]$^+$, 654.3 [M+2H]$^{2+}$, 1305.0 [M−H]$^−$ (8-b) To a mixture of compound (Ab7-b) (40.2 mg), (R)-2-amino-3-((2-(4-(4-(N—((S)-1-methoxy-1-oxo-3-(5-(5,6,7,8-tetrahydro-1,8-naphthyridin-2-yl)pentanamido)propan-2-yl)sulfamoyl)-3,5-dimethylphenoxy)butanamido)ethyl)amino)-3-oxopropane-1-sulfonic acid (60.6 mg), DMF (0.8 mL), and N,N-diisopropylethylamine (35 μL), HBTU (31.7 mg) was added, and the resulting mixture was stirred at room temperature for 15 minutes. Water (0.5 mL) and a 50% aqueous acetonitrile solution (0.6 mL) were added thereto, and the mixture was stirred and then purified by preparative HPLC to obtain compound (Ab8-b) (69 mg). HPLC (CAPCELL PAK MG) rt (min): 11.88 LC/MS (ACQUITY) rt (min): 1.22 MS (ESI, m/z): 1307.0 [M+H]$^+$, 654.3 [M+2H]$^{2+}$, 1305.1 [M−H]$^−$ (9-a) To compound (Ab8-a) (69.5 mg), concentrated hydrochloric acid (2.5 mL) was added, and the mixture was stirred at room temperature for 2 days and then concentrated under reduced pressure. The concentrate was diluted with acetonitrile containing 50% water (2.4 mL) and then purified by preparative HPLC to obtain compound (Ab9-a) (44.1 mg). HPLC (CAPCELL PAK MG) rt (min): 8.95 LC/MS (ACQUITY) rt (min): 0.75 MS (ESI, m/z): 1180.8 [M+H]$^+$, 590.9 [M+2H]$^{2+}$, 1178.8 [M−H]$^−$ (9-b) To compound (Ab8-b) (64.4 mg), concentrated hydrochloric acid (2.5 mL) was added, and the mixture was stirred at room temperature for 2 days and then concentrated under reduced pressure. The concentrate was diluted with acetonitrile containing 50% water (2.4 mL) and then purified by preparative HPLC to obtain compound (Ab9-b) (33.1 mg). HPLC (CAPCELL PAK MG) rt (min): 9.19 LC/MS (ACQUITY) rt (min): 0.75 MS (ESI, m/z): 1180.8 [M+H]$^+$, 591.0 [M+2H]$^{2+}$, 1178.7 [M−H]$^−$ Example 29

(1)

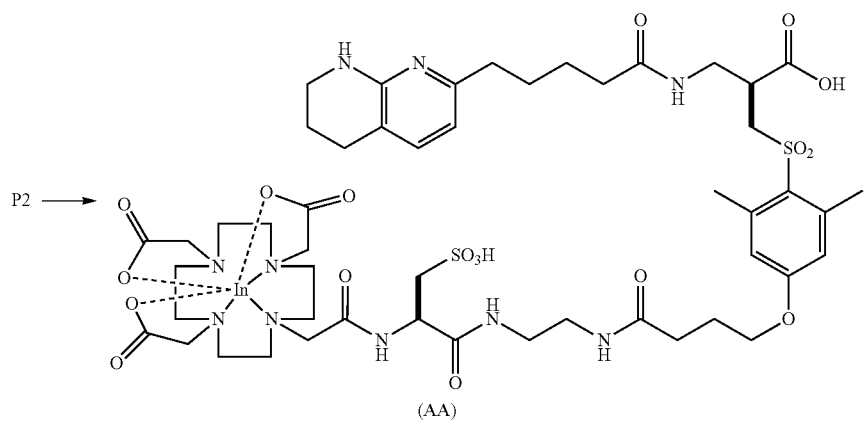
(AA)

To a mixture of compound (P2) (112 mg), water (1 mL), a 1 mol/L aqueous ammonium acetate solution (1 mL), and acetic acid (300 µL), a solution of indium chloride tetrahydrate (129 mg) in water (0.5 mL) was added, and the resulting mixture was stirred at 110° C. for 10 minutes. A 50% aqueous acetonitrile solution (3 mL) was added thereto, and the mixture was purified by preparative HPLC to obtain compound (AA) (118 mg). HPLC (CAPCELL PAK MG) rt (min): 9.35 LC/MS (ACQUITY) rt (min): 0.75 MS (ESI, m/z): 1280.9 [M−H]⁻

(2)

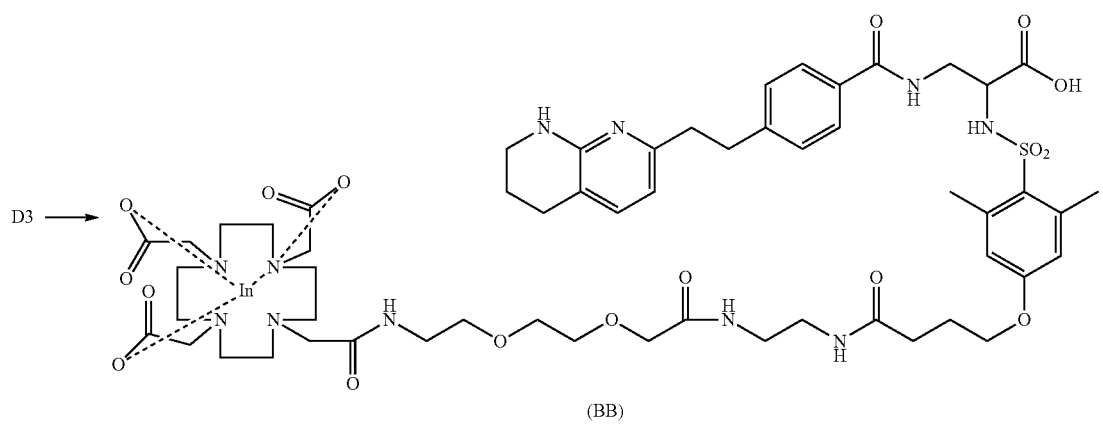
(BB)

To a mixture of compound (D3) (2.4 mg), water (80 μL), a 0.5 mol/L aqueous ammonium acetate solution (100 μL), acetic acid (10 μL), and gentisic acid (0.4 mg), a mixture (50 μL) of indium chloride tetrahydrate (15.6 mg) and water (156 μL) was added, and the resulting mixture was heated at 100° C. for 10 minutes. A 50% aqueous acetonitrile solution (500 μL) was added thereto, and the mixture was purified by preparative HPLC to obtain compound (BB) (1.6 mg). HPLC (SunFire) rt (min): 7.89 LC/MS (SunFire) rt (min): 7.76 MS (ESI, m/z): 662.75 [M+2H]$^{2+}$, 442.15 [M+3H]$^{3+}$ (3)

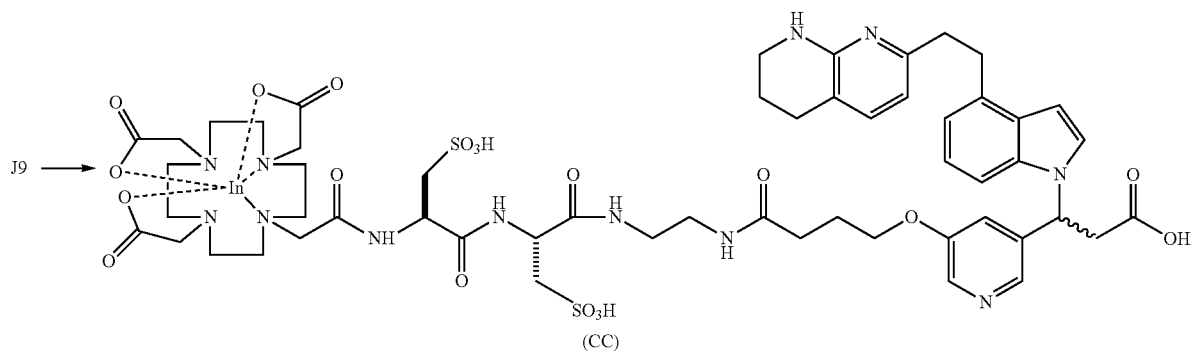

(CC)

Compound (CC) (1.2 mg) was obtained in the same way as in Example 29(1) using compound (J9) (1.3 mg). HPLC (SunFire) rt (min): 10.93 LC/MS (SunFire) rt (min): 10.25 MS (ESI, m/z): 686.30 [M+2H]$^{2+}$, 684.15 [M−2H]$^{2-}$ Example 30

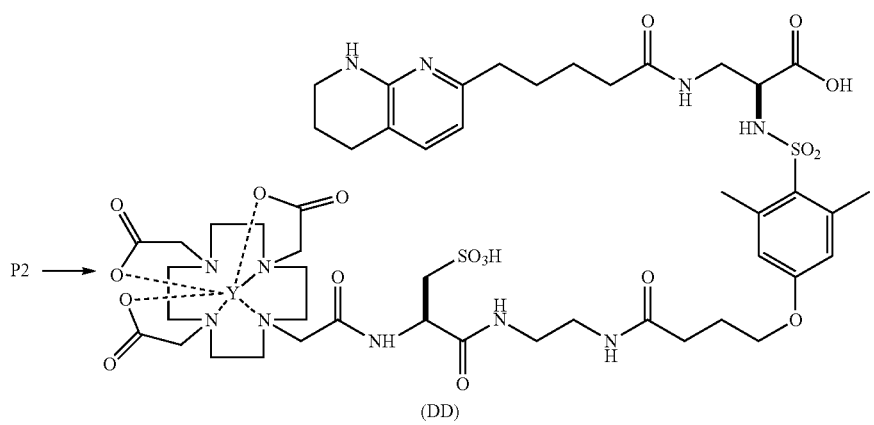

(DD)

To a mixture of compound (P2) (140 mg), water (1 mL), a 1 mol/L aqueous ammonium acetate solution (1 mL), and acetic acid (300 μL), a solution of yttrium chloride hexahydrate (143 mg) in water (0.5 mL) was added, and the resulting mixture was stirred at 110° C. for 10 minutes. A 50% aqueous acetonitrile solution (3 mL) was added thereto, and the mixture was purified by preparative HPLC to obtain compound (DD) (111 mg). HPLC (CAPCELL PAK MG) rt (min): 9.71 LC/MS (ACQUITY) rt (min): 0.75 MS (ESI, m/z): 1256.6 [M+H]$^+$, 1254.6 [M−H]$^−$ Example 31

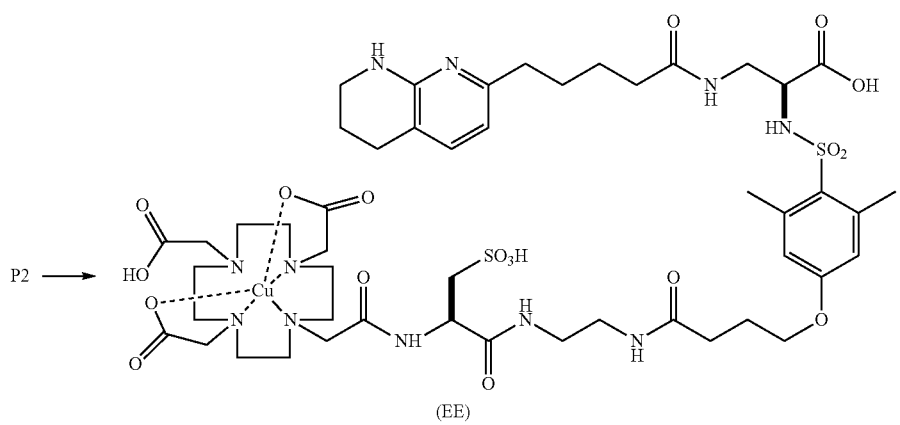

A mixture of compound (P2) (36.8 mg), a 0.5 mol/L aqueous sodium acetate solution/water/acetic acid (10/10/1) (1.2 mL), and copper(II) chloride (4.4 mg) was stirred at 110° C. for 10 minutes. The reaction mixture was purified on SepPak C18 (water/methanol=1/1) to obtain compound (EE) (39.1 mg). HPLC (MG) rt (min): 9.23 LC/MS (ACQUITY) rt (min): 0.75 MS (ESI, m/z): 1231.6 [M+H]$^+$, 1229.6 [M−H]$^−$ Example 32

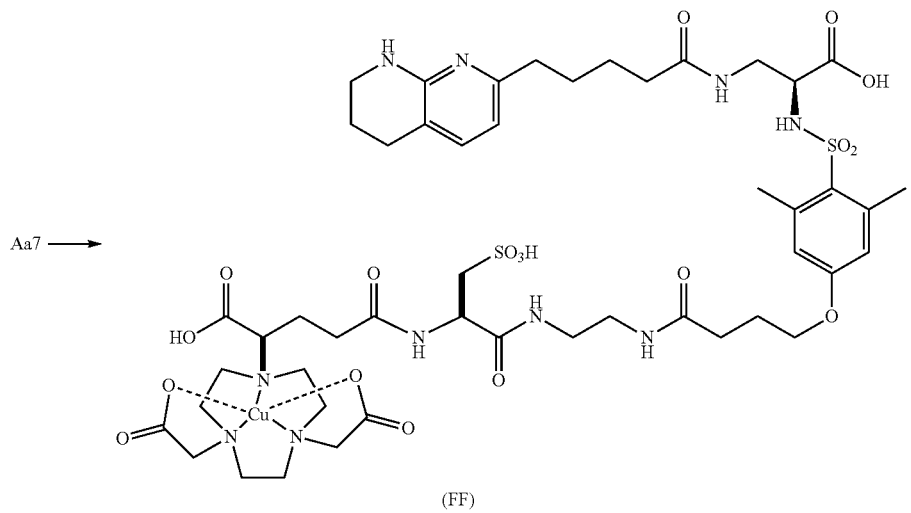

A mixture of compound (Aa7) (16.9 mg), a 0.5 mol/L aqueous sodium acetate solution/water/acetic acid (10/10/1) (0.4 mL), and copper(II) chloride (3.2 mg) was stirred at 110° C. for 5 minutes and then purified on SepPak C18 (water/methanol=1/1) to obtain compound (FF) (14.4 mg). HPLC (CAPCELL PAK MG) rt (min): 9.80 LC/MS (ACQUITY) rt (min): 0.79 MS (ESI, m/z): 1202.5 [M+H]$^+$, 601.9 [M+2H]$^{2+}$, 1200.5 [M−H]$^-$ Example 33

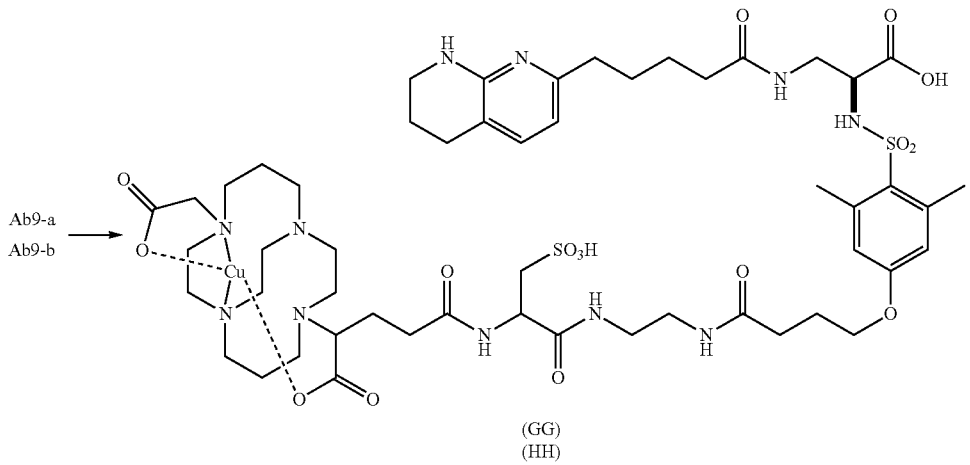

(GG)
(HH)

A mixture of compound (Ab9-a) (16.2 mg), a 0.5 mol/L aqueous sodium acetate solution/water/acetic acid (80/80/1) (0.4 mL), and copper(II) chloride (3.1 mg) was stirred at 110° C. for 10 minutes and then purified by preparative HPLC to obtain compound (GG) (16.0 mg). HPLC (CAPCELL PAK MG) rt (min): 9.52 LC/MS (ACQUITY) rt (min): 0.79 MS (ESI, m/z): 1241.7 [M+H]$^+$, 621.5 [M+2H]$^{2+}$, 1239.7 [M−H]$^-$ A mixture of compound (Ab9-b) (13.6 mg), a 0.5 mol/L aqueous sodium acetate solution/water/acetic acid (80/80/1) (0.4 mL), and copper(II) chloride (3.1 mg) was stirred at 110° C. for 10 minutes and then purified by preparative HPLC to obtain compound (HH) (13.3 mg). HPLC (CAPCELL PAK MG) rt (min): 9.59 LC/MS (ACQUITY) rt (min): 0.79 MS (ESI, m/z): 1241.7 [M+H]$^+$, 621.5 [M+2H]$^{2+}$, 1239.7 [M−H]$^-$ Example 34

(1) Labeling Method A

To a mixed solution of compound (P2) (8.5 µg) and a 0.2 mol/L sodium acetate buffer solution (pH 4.0) (1.5 mL), a [$^{111}$In] indium chloride solution (80 MBq, 100 µL) was added. The mixture was heated at 100° C. for 15 minutes and then left at room temperature for 5 minutes to obtain radiolabeled compound [$^{111}$In]-(P2). As a result of analysis by reversed-phase TLC (Whatman, KC18F, development solvent: methanol/0.5 mol/L aqueous ammonium acetate solution (50/50)); the radiolabeled compound had an Rf value of 0.4. Its radiochemical purity was 95% or more both immediately after preparation and after standing at room temperature for 24 hours.

(2) Labeling Method B

To a mixed solution of compound (P2) (79 µg), gentisic acid (1.8 mg), a 0.6 mol/L sodium acetate buffer solution (pH 4.0, 120 µL), and a 0.4 mol/L aqueous sodium hydroxide solution (24 µL), a [$^{90}$Y] yttrium chloride solution (700 MBq, 240 µL) was added. The mixture was heated at 100° C. for 20 minutes and then left at room temperature for 5 minutes to obtain radiolabeled compound [$^{90}$Y]-(P2). As a result of analysis by reversed-phase TLC (Whatman, KC18F, development solvent: methanol/0.5 mol/L aqueous ammonium acetate solution (50/50)), the radiolabeled compound had an Rf value of 0.4. Its radiochemical purity was 95% or more both immediately after preparation and after standing at room temperature for 24 hours.

(3) Labeling Method C

To a mixed solution of compound (P2) (5.8 g) and a 0.2 mol/L sodium acetate buffer solution (pH 4.0, 219 µL), a [$^{64}$Cu] copper chloride solution (pH 5, 35 MBq, 55 µL) was added. The mixture was heated at 100° C. for 15 minutes and then left at room temperature for 5 minutes to obtain radiolabeled compound [$^{64}$Cu]-(P2). As a result of analysis by reversed-phase TLC (Whatman, KC18F, development solvent: methanol/0.5 mol/L aqueous ammonium acetate solution (50/50)), the radiolabeled compound had an Rf value of 0.4. Its radiochemical purity was 90% or more both immediately after preparation and after standing at room temperature for 22 hours.

(4) to (27)

Radiolabeled compounds were synthesized in the same way as in (1) and (2).

(28) Labeling Method D

To a mixed solution of compound (Aa7) (4.2 µg), gentisic acid (1 mg), and a 0.2 mol/L sodium acetate buffer solution (pH 4.0) (5.0 μL), [$^{64}$Cu] copper chloride in a 0.2 mol/L sodium acetate buffer solution (pH 4.0) (40 MBq, 155 μL) was added. The mixture was heated at 100° C. for 15 minutes and then left at room temperature for 5 minutes to obtain radiolabeled compound [$^{64}$Cu]-(Aa7). As a result of analysis by reversed-phase TLC (Merck KGaA, RP-8 F$_{254}$s, development solvent: methanol/0.5 mol/L aqueous ammonium acetate solution (50/50)), the radiolabeled compound had an Rf value of 0.4. Its radiochemical purity was 90% or more both immediately after preparation and after standing at room temperature for 24 hours.

(29) and (30)

Radiolabeled compounds were synthesized in the same way as in (28).

The results about (4) to (30) are shown below.

TABLE 1

| Example No. | Labeling precursor | Labeling method | Radiolabeled compound | Rate of labeling (%) | Rf value | Developing solvent: (methanol)/(0.5 mol/L aqueous ammonium acetate solution) |
|---|---|---|---|---|---|---|
| 34-(4) | D3 | A | [$^{111}$In]-(D3) | >80 | 0.4 | 65/35 |
| 34-(5) | A8 | A | [$^{111}$In]-(A8) | >95 | 0.4 | 50/50 |
| 34-(6) | H9 | A | [$^{111}$In]-(H9) | >95 | 0.4 | 65/35 |
| 34-(7) | I21 | A | [$^{111}$In]-(I21) | >90 | 0.5 | 60/40 |
| 34-(8) | J9 | A | [$^{111}$In]-(J9) | >80 | 0.5 | 60/40 |
| 34-(9) | N3 | A | [$^{111}$In]-(N3) | >90 | 0.5 | 50/50 |
| 34-(10) | L10 | A | [$^{111}$In]-(L10) | >95 | 0.4 | 60/40 |
| 34-(11) | M2 | A | [$^{111}$In]-(M2) | >90 | 0.5 | 60/40 |
| 34-(12) | B2 | A | [$^{111}$In]-(B2) | >95 | 0.4 | 60/40 |
| 34-(13) | E3 | A | [$^{111}$In]-(E3) | >90 | 0.3 | 75/25 |
| 34-(14) | F3 | A | [$^{111}$In]-(F3) | >90 | 0.4 | 75/25 |
| 34-(15) | G3 | A | [$^{111}$In]-(G3) | >95 | 0.4 | 60/40 |
| 34-(16) | O10 | A | [$^{111}$In]-(O10) | >95 | 0.4 | 50/50 |
| 34-(17) | Z8 | A | [$^{111}$In]-(Z8) | >95 | 0.3 | 50/50 |
| 34-(18) | C3 | A | [$^{111}$In]-(C3) | >90 | 0.5 | 60/40 |
| 34-(19) | Q12 | A | [$^{111}$In]-(Q12) | >95 | 0.6 | 50/50 |
| 34-(20) | R3 | A | [$^{111}$In]-(R3) | >90 | 0.6 | 50/50 |
| 34-(21) | S2 | A | [$^{111}$In]-(S2) | >90 | 0.3 | 50/50 |
| 34-(22) | X9 | A | [$^{111}$In]-(X9) | >95 | 0.6 | 50/50 |
| 34-(23) | V8 | A | [$^{111}$In]-(V8) | >95 | 0.4 | 50/50 |
| 34-(24) | W10 | A | [$^{111}$In]-(W10) | >95 | 0.4 | 60/40 |
| 34-(25) | K8 | A | [$^{111}$In]-(K8) | >95 | 0.4 | 50/50 |
| 34-(26) | A8 | B | [$^{90}$Y]-(A8) | >95 | 0.4 | 50/50 |
| 34-(27) | N3 | B | [$^{90}$Y]-(N3) | >90 | 0.5 | 50/50 |
| 34-(28) | Aa7 | D | [$^{64}$Cu]-(Aa7) | >90 | 0.4 | 50/50 |
| 34-(29) | Ab9-a | D | [$^{64}$Cu]-(Ab9-a) | >90 | 0.4 | 70/30 |
| 34-(30) | Ab9-b | D | [$^{64}$Cu]-(Ab9-b) | >90 | 0.4 | 70/30 |

Test Example 1

Integrin $\alpha_v\beta_3$ Binding Affinity Test 0.2 g/mL $\alpha_v\beta_3$ (Chemicon International, Inc.) was immobilized on each well of a 96-well plate (Corning Inc.). Each well was blocked with a 1% Block Ace (DS Pharma Biomedical Co., Ltd) solution and then washed with T-PBS (PBS containing 0.05% Tween 20). Evaluation compound solutions having a 2-fold concentration (10 concentrations of 3.16-fold dilutions from 0.3 μmol/L, buffer (20 mM Tris-HCl pH 7.5, 150 mM NaCl, 1 mM CaCl$_2$, 1 mM MgCl$_2$, and 1 mM MnCl$_2$)) and a 4 μg/mL biotinylated vitronectin solution (vitronectin (Upstate Biotechnology Inc.) was labeled with EZ-Link Sulfo-NHS-Biotinylation Kit (Pierce/Thermo Fisher Scientific Inc.) and then concentration-adjusted) were each added at 50 μL/well, and the plate was shaken at room temperature for 2 hours. After washing with T-PBS, a 0.2 μg/mL avidin peroxidase (Pierce/Thermo Fisher Scientific Inc.) solution was added thereto, and the plate was shaken at room temperature for 1 hour. After washing with T-PBS, color was developed by an o-phenylenediamine (Sigma-Aldrich Inc.) solution (the reaction was terminated by the addition of 4 mol/L sulfuric acid), and the absorbance was measured (490 nm, Reference: 595 nm). The IC$_{50}$ value was calculated using XLfit 3.0 (ID Business Solutions Ltd.). RGDfV (Bachem AG) was measured in duplicate as a QC sample for each plate.

Test Example 2

Integrin $\alpha_v\beta_5$ Binding Affinity Test 0.2 g/mL $\alpha_v\beta_5$ (Chemicon International, Inc.) was immobilized on each well of a 96-well plate (Corning Inc.). Each well was blocked with a 1% Block Ace (DS Pharma Biomedical Co., Ltd) solution and then washed with PBST (10 mM Na$_2$HPO$_4$ pH 7.5, 150 mM NaCl, and 0.01% Tween 20). Evaluation compound solutions having a 2-fold concentration (10 concentrations of 3.16-fold dilutions from 0.3 μmol/L, buffer (20 mM Tris-HCl pH 7.5, 150 mM NaCl, 1 mM $CaCl_2$, 1 mM $MgCl_2$, and 1 mM $MnCl_2$)) and a 4 µg/mL biotinylated vitronectin solution (vitronectin (Upstate Biotechnology Inc.) was labeled with EZ-Link Sulfo-NHS-Biotinylation Kit (Pierce/Thermo Fisher Scientific Inc.) and then concentration-adjusted) were each added at 50 µL/well, and the plate was shaken at room temperature for 2 hours. After washing with PBST, a 0.2 µg/mL avidin peroxidase (Pierce/Thermo Fisher Scientific Inc.) solution was added thereto, and the plate was shaken at room temperature for 1 hour. After washing with PBST, color was developed by an o-phenylenediamine (Sigma-Aldrich Inc.) solution (the reaction was terminated by the addition of 4 mol/L sulfuric acid), and the absorbance was measured (490 nm, Reference: 595 nm). The $IC_{50}$ value was calculated using XLfit 3.0 (ID Business Solutions Ltd.). RGDfV (Bachem AG) was measured in duplicate as a QC sample for each plate.

The results of Test Example 1 and Test Example 2 are shown below.

TABLE 2

| $IC_{50}$ value | Evaluation |
|---|---|
| Less than 1 nmol/L | +++ |
| 1~10 nmol/L | ++ |
| 10~100 nmol/L | + |

TABLE 3

| Example No. | Compound No. | $α_vβ_3$ | $α_vβ_5$ |
|---|---|---|---|
| 1 | A8 | +++ | +++ |
| 2 | B2 | +++ | +++ |
| 4 | D3 | +++ | +++ |
| 6 | F3 | +++ | +++ |
| 7 | G3 | +++ | +++ |
| 8 | H9 | +++ | +++ |
| 9 | I21 | +++ | +++ |
| 10 | J9 | +++ | ++ |
| 11 | K8 | +++ | ++ |
| 12 | L10 | +++ | +++ |
| 13 | M2 | +++ | +++ |
| 14 | N3 | +++ | +++ |
| 15 | O10 | +++ | +++ |
| 16 | P2 | +++ | +++ |
| 17 | Q12 | +++ | – |
| 18 | R3 | +++ | +++ |
| 19 | S2 | +++ | +++ |
| 23 | W10 | +++ | ++ |
| 24 | X9 | +++ | ++ |
| 25 | Y13 | +++ | +++ |
| 27 | Aa7 | +++ | +++ |
| 28-1 | Ab9-a | +++ | +++ |
| 28-2 | Ab9-b | +++ | +++ |
| 29-1 | AA | +++ | +++ |
| 29-2 | BB | +++ | +++ |
| 30 | DD | +++ | +++ |
| 31 | EE | +++ | +++ |

The compounds shown in Table 3 exhibited excellent integrin binding affinity.

Test Example 3

Accumulation in Integrin-Expressing Tumor

The integrin-specific accumulation of an $^{111}$In-labeled compound to a tumor of a subcutaneously integrin-expressing cell-transplanted mouse was confirmed by tissue extraction and radioactivity measurement methods.

1. Confirmation of Integrin Expression in Tumor Cell Used in Experiment

The integrin expression levels of tumor masses in which an A375 (human melanoma), A498 (human renal cell cancer), HCT116 (human colorectal cancer), U87MG (human glioblastoma), or T98G (human glioblastoma) cell line was subcutaneously transplanted were confirmed by Western blotting. Cultured cells of each line were subcutaneously transplanted at $1×10^7$ cells/mouse to the right flank of Balb/cAJcl-nu/nu (CLEA Japan, Inc., male, 6 to 8 weeks old). 2 to 12 weeks after transplantation, a tumor was extracted from each mouse. The extracted tumor was minced with scissors and then prepared into a homogenate by using a homogenizer. The protein level of each sample was adjusted to 1 mg/mL (1×Tris/glycine/SDS+100 mM DTT buffer). Integrins $α_vβ_3$ (R&D Systems, Inc., 3050-AV) and $α_vβ_5$ (Chemicon International, Inc., CC1024) were each adjusted to 4 concentrations (1, 2, 5, and 10 ng/well) as standards. These proteins were simultaneously separated by SDS-PAGE (10% gel; manufactured by Bio Craft Co., Ltd.). After the separation, the proteins were transferred to PVDF membranes, which were then blocked with a blocking solution (5% skimmed milk/PBS-T) for 1 hour and then washed twice with PBS-T. After reaction with each of an anti-integrin $β_3$ antibody (Cell Signaling Technology, Inc., #4702), an anti-integrin $β_5$ antibody (Santa Cruz Biotechnology, Inc., SC-5402), and anti-β-actin antibody (Sigma-Aldrich Inc., A5441) as primary antibodies, the membranes were washed three times with PBS-T. ECL Anti-Rabbit IgG horseradish Peroxidase (GE Healthcare Japan Corp., NA934V), ECL Anti-mouse IgG horseradish Peroxidase (GE Healthcare Japan Corp., NA931V), or Donkey Anti-goat antibody HRP conjugate (Bethyl Laboratories, Inc., A50-101P) was used as a secondary antibody in reaction, and the membranes were washed three times with PBS-T. Light was developed using a chemiluminescent reagent (Super Signal West Femto Maximum Sensitivity Substrate; Thermo Fisher Scientific Inc., 34096) and measured using LAS3000 (GE Healthcare Japan Corp.). The integrin expression level per µg of tumor mass was calculated from the standards. The results are shown below.

2. Confirmation of Integrin-Specific Accumulation of [$^{111}$In]-(A8) by Tissue Extraction and Radioactivity Measurement Methods SK-MEL-28 (human melanoma), A375 (human melanoma), A498 (human renal cell cancer), Caki-2 (human renal cell cancer), HCT116, U87MG, and T98G cells were studied as follows: the cells of each line were cultured and subcutaneously transplanted at $1×10^7$ cells/mouse to the right flank of Balb/cAJcl-nu/nu (CLEA Japan, Inc., male, 6 to 8 weeks old). The mice were raised until their tumor volumes reached 85 to 1,075 mm³. Then, the mice were allocated at the time of anatomy to groups each involving 3 individuals so as to prevent the tumor volumes from disproportioning among the groups. Then, the radiolabeled compound [$^{111}$In]-(A8) (740 kBq) was administered to the tail veins of the mice. The animals were sacrificed at the time of anatomy to extract their tumors. The weights of the tumors were measured, and then, the radioactivity was measured using a gamma counter to calculate the concentration of radioactivity in the tumors (% ID/g: % injected dose/g). The results are shown below.

TABLE 4

| Cell line | Integrin expression level (ng/μg) | | Concentration of radioactivity in tumor (% ID/g) | |
| --- | --- | --- | --- | --- |
| | $\beta_3$ | $\beta_5$ | 4 hours later | 24 hours later |
| HCT116 | 1.54 | 1.99 | 3.1 | 2.9 |
| A375 | 3.78 | 3.31 | 3.7 | 3.8 |
| sk-mel-28 | n.t. | n.t. | 2.9 | 4.9 |
| caki-2 | n.t. | n.t. | 6.4 | 8.5 |
| U87MG | 6.68 | 8.79 | 12.0 | 9.3 |
| T98G | 7.92 | 13.51 | 6.5 | 6.7 |
| A498 | 8.28 | 6.72 | 13.1 | 7.9 |

(n.t.: not tested)

The integrin expression level of the tumor masses differed among the cell lines and was 1.54 to 8.28 ng/μg for $\beta_3$ and 1.99 to 13.51 ng/μg for $\beta_5$. The tumor accumulation of [$^{111}$In]-(A8) 4 hours and 24 hours after administration differed among the cell lines and was 3.1 to 13.1% ID/g 4 hours later and 2.9 to 9.3% ID/g 24 hours later. Furthermore, the strong correlation (R=0.827) was confirmed between the expression level of integrin $\beta_3$ in the tumor masses and the accumulation of radioactivity at the tumors 24 hours after administration (FIG. 1).

Test Example 4

Evaluation of $^{111}$In-Labeled Compound, $^{64}$Cu-Labeled Compound, and $^{90}$Y-Labeled Compound on Basis of Concentration of Radioactivity in Tumor U87MG cells were subcutaneously transplanted at 1×10$^7$ cells/mouse to the right flank of Balb/cAJcl-nu/nu (CLEA Japan, Inc. or Japan SLC, Inc., 6 to 9 weeks old). After 2 to 3 weeks, the mice were divided into groups each involving 3 individuals per point in time when their tumors became 200 to 500 mm$^3$. The $^{111}$In-labeled compound (740 kBq) was administered to the tail veins of the mice.

After a given time, the animals were sacrificed to extract their tumors. The weights of the tumors were measured, and the radioactivity was measured using a gamma counter to calculate the concentration of radioactivity in the tumors (% ID/g). In the same way as above, the concentration of radioactivity in the tumors (% ID/g) was calculated for the $^{64}$Cu-labeled compound (500 kBq) and the $^{90}$Y-labeled compound (500 kBq). The results are shown below.

TABLE 5

| Example No. | Radiolabeled compound | Concentration of radioactivity in tumor (% ID/g) | |
| --- | --- | --- | --- |
| | | 4 hours later | 24 hours later |
| 34-(1) | [$^{111}$In] – (P2) | 11.10 | 9.62 |
| 34-(2) | [$^{90}$Y] – (P2) | 12.52 | 15.29 |
| 34-(3) | [$^{64}$Cu] – (P2) | 9.25 | 8.48 |
| 34-(4) | [$^{111}$In] – (D3) | 10.50 | 7.73 |
| 34-(5) | [$^{111}$In] – (A8) | 9.48 | 12.90 |
| 34-(6) | [$^{111}$In] – (H9) | 9.17 | 8.74 |
| 34-(7) | [$^{111}$In] – (I21) | 10.60 | 9.95 |
| 34-(9) | [$^{111}$In] – (N3) | 9.75 | 5.93 |
| 34-(12) | [$^{111}$In] – (B2) | 8.58 | 11.00 |
| 34-(13) | [$^{111}$In] – (E3) | 11.00 | 12.40 |
| 34-(14) | [$^{111}$In] – (F3) | 11.80 | 8.41 |
| 34-(15) | [$^{111}$In] – (G3) | 10.50 | 9.82 |
| 34-(16) | [$^{111}$In] – (O10) | 12.80 | 12.40 |
| 34-(17) | [$^{111}$In] – (Z8) | 6.95 | 3.34 |
| 34-(22) | [$^{111}$In] – (X9) | 8.54 | 8.54 |
| 34-(28) | [$^{64}$Cu] – (Aa7) | 11.19 | 8.53 |
| 34-(29) | [$^{64}$Cu] – (Ab9-a) | 12.33 | 7.42 |
| 34-(30) | [$^{64}$Cu] – (Ab9-b) | 9.83 | 4.53 |

The concentrations of radioactivity in the tumors of the compounds shown in Table 5 were 6.95 to 12.80% ID/g 4 hours after administration and 3.34 to 15.29% ID/g 24 hours after administration.

Test Example 5

Imaging of Integrin-Expressing Tumor by Positron Emission Tomography (PET) Using [$^{64}$Cu]-(P2), [$^{64}$Cu]-(Aa7), [$^{64}$Cu]-(Ab9-a), and [$^{64}$Cu]-(Ab9-b)

U87MG cells were subcutaneously transplanted at 1×10$^7$ cells/mouse to the right flank of Balb/cAJcl-nu/nu (CLEA Japan, Inc. or Japan SLC, Inc., male, 6 to 9 weeks old). After 2 weeks, the radiolabeled compound [$^{64}$Cu]-(P2) was administered at 4.8 MBq/mouse to the tail veins of mice whose tumors became 250 to 650 mm$^3$. After 1, 4, 24, and 48 hours, the images were taken in microPET/CT (Inveon, Siemens AG) under isoflurane anesthesia. After the imaging at 48 hours after administration, the mice were euthanized by the collection of the whole blood from the postcava under deep anesthesia with isoflurane, followed by tumor extraction. The weights of the tumors were measured, and the radioactivity was measured using a gamma counter to calculate the concentration of radioactivity in the tumors (% ID/g). In the same way as above, [$^{64}$Cu]-(Aa7), [$^{64}$Cu]-(Ab9-a), and [$^{64}$Cu]-(Ab9-b) were imaged. However, the concentration of radioactivity in the tumors was not calculated. The PET images of each compound at each time point are shown in FIGS. 2 to 5. The tumor accumulation was confirmed for all of the compounds 1 hour after administration, and the tumors were visualized up to 48 hours later. Because an area with low accumulation in the central portion of the tumor was seen on the images of [$^{64}$Cu]-(P2), the extracted tumors were observed after the completion of the imaging at 48 hours after administration. As a result, hematoma in the central portion was confirmed consistently with the images. The concentration of radioactivity in the tumors was 5.6% ID/g at the time of anatomy (48 hours after administration).

Test Example 6

Imaging of Integrin-Expressing Tumor with Gamma Camera Using [$^{111}$In]-(P2)

U87MG cells were subcutaneously transplanted at 1×10$^7$ cells/mouse to the right flank of Balb/cAJcl-nu/nu (CLEA Japan, Inc., male, 6 weeks old). After 2 weeks, a dosing solution of the radiolabeled compound [$^{111}$In]-(P2) was administered at 1 MBq/mouse to the tail veins of mice whose tumors became 300 to 600 mm$^3$. 24, 48, and 72 hours after administration, the planar images were taken with a gamma camera (Symbia, Siemens AG) under isoflurane anesthesia. The radioactivity in the tumors (% ID) was calculated by image analysis. FIG. 6 shows the images taken at each time point and the radioactivity in the tumor. The radioactivity was higher in the tumor than other organs 24 hours to 72 hours after administration and the tumor was able to be clearly confirmed.

Test Example 7

Imaging of Integrin-Expressing Tumor Using [$^{111}$In]-(P2) (Intracranial Tumor Model)

U87MG cells were intracranially transplanted at 1×10$^7$ cells/mouse to Balb/cAJcl-nu/nu (CLEA Japan, Inc., male, 6 weeks old) using a tapered needle. After 2 to 4 weeks, a dosing solution of the radiolabeled compound [$^{111}$In]-(P2) was administered at 1 MBq/mouse to the tail veins of the mice. 24, 48, and 72 hours after administration, the planar images were taken with a gamma camera (Symbia, Siemens AG) under isoflurane anesthesia (FIG. 7). After the imaging at the final time point, the brain was extracted, and frozen sections were prepared. Several pieces of the tumor sections were contacted with IP plates, and accumulation images were obtained by autoradiography (ARG). The serial sections were stained with hematoxylin-eosin to confirm tumors. The accumulation of [$^{111}$In]-(P2) consistent with the tumor was confirmed in the intracranial tumor models by planar imaging and ARG.

Test Example 8

Treatment Experiment of Subcutaneously U87MG-Transplanted Model Using [90Y]-(P2)

U87MG cells were subcutaneously transplanted at 1×10$^7$ cells/mouse to the right flank of Balb/c Slc-nu/nu (SLC Japan, Inc., male, 6 weeks old). After 2 weeks, mice whose tumors became 100 to 500 mm$^3$ were grouped. Phosphate-buffered saline (PBS) or the radiolabeled compound [90Y]-(P2) was administered to the tail veins of the mice, and their tumor volumes were measured. When the tumor volumes of the mice in the PBS group exceeded 2,000 mm$^3$, which is a humanistic endpoint, the antitumor effect was evaluated. The evaluation values were the rate of inhibition of tumor growth ((1−(Average tumor volume of the compound administration group−Average tumor volume of the compound administration group before administration)/(Average tumor volume of the PBS group−Average tumor volume of the PBS group before administration))×100 (provided that the rate of inhibition exceeding 100% was indicated as 100%)) and the number of individuals having a tumor volume equal to or smaller than that at the start of the experiment (the number of individuals having tumor regression). The results are shown below.

TABLE 6

| Compound | Dose (MBa) | The number of doses | The number of n | Tumor volume (mm$^3$) At start of administration | 16 days after administration | Rate of inhibition (%) | The number of individuals having tumor regression |
|---|---|---|---|---|---|---|---|
| PBS | — | 1 | 8 | 333 ± 117 | 1994 ± 225 | — | 0 |
| [$^{90}$Y]-(P2) | 14.8 | 1 | 8 | 351 ± 72 | 429 ± 188 | 95 | 2 |
| | 22.2 | 1 | 8 | 343 ± 88 | 386 ± 142 | 97 | 2 |

(Mean ± SD)

The compound shown in Table 6 exhibited an excellent antitumor effect.

Test Example 9

Treatment Experiment of Subcutaneously U87MG-Transplanted Model Using [$^{90}$Y]-(A8)

U87MG cells were subcutaneously transplanted at 1×10$^7$ cells/mouse to the right flank of Balb/cAJcl-nu/nu (CLEA Japan, Inc., male, 6 weeks old). After 2 weeks, mice whose tumors became 100 to 500 mm$^3$ were grouped. Phosphate-buffered saline (PBS) or the radiolabeled compound [$^{90}$Y]-(A8) was administered to the tail veins of the mice, and their tumor volumes were measured. The evaluation values were calculated in the same way as in Test Example 8 to evaluate the antitumor effect. The results are shown below.

TABLE 7

| Compound | Dose (MBa) | The number of doses | The number of n | Tumor volume (mm$^3$) At start of administration | 12 days after administration | Rate of inhibition (%) | The number of individuals having tumor regression |
|---|---|---|---|---|---|---|---|
| PBS | — | 1 | 10 | 234 ± 82 | 1930 ± 442 | — | 0 |
| [$^{90}$Y]-(A8) | 5.55 | 1 | 10 | 239 ± 89 | 759 ± 344 | 69 | 0 |
| | 11.1 | 1 | 10 | 243 ± 101 | 199 ± 88 | 100 | 7 |
| | 14.8 | 1 | 10 | 251 ± 110 | 251 ± 112 | 100 | 6 |

(Mean + SD)

The compound shown in Table 7 exhibited an excellent antitumor effect.

Test Example 10

Treatment Experiment of Subcutaneously T98G-Transplanted Model Using [$^{90}$Y]-(P2)

A mixture of a T98G cell suspension (human glioblastoma, 1×10$^7$ cells) and Matrigel (Becton, Dickinson and Company) in equal amounts was subcutaneously transplanted to the right flank of Balb/c Slc-nu/nu (SLC Japan, Inc., male, 6 weeks old). After 77 days, the mice were grouped when their tumors became 300 to 1,200 mm$^3$. Phosphate-buffered saline (PBS) or the radiolabeled compound [$^{90}$Y]-(P2) was administered to the tail veins of the mice, and their tumor volumes were measured. The evaluation values were calculated in the same way as in Test Example 8 to evaluate the antitumor effect. The results are shown below.

TABLE 8

| Compound | Dose (MBa) | The number of doses | The number of n | Tumor volume (mm$^3$) At start of administration | 13 days after administration | Rate of inhibition (%) | The number of individuals having tumor regression |
|---|---|---|---|---|---|---|---|
| PBS | — | 1 | 6 | 754 ± 317 | 1439 ± 638 | — | 0 |
| [$^{90}$Y]-(P2) | 22.2 | 1 | 6 | 755 ± 293 | 882 ± 399 | 82 | 1 |
|  | 29.6 | 1 | 6 | 736 ± 264 | 755 ± 313 | 97 | 3 |

(Mean ± SD)

The compound shown in Table 8 exhibited an excellent antitumor effect.

Test Example 11

Treatment Experiment of Subcutaneously T98G-Transplanted Model Using [$^{90}$Y]-(A8)

A mixture of a T98G cell suspension (human glioblastoma, 1×10$^7$ cells) and Matrigel (Becton, Dickinson and Company) in equal amounts was subcutaneously transplanted to the right flank of Balb/cAJcl-nu/nu (CLEA Japan, Inc., female, 6 weeks old). After 90 days, the mice were grouped when their tumors BECAME 100 to 400 mm$^3$. Phosphate-buffered saline (PBS) or the radiolabeled compound [$^{90}$Y]-(A8) was administered to the tail veins of the mice, and their tumor volumes were measured. The evaluation values were calculated in the same way as in Test Example 8 to evaluate the antitumor effect. The results are shown below.

TABLE 9

| Compound | Dose (MBa) | The number of doses | The number of n | Tumor volume (mm$^3$) At start of administration | 22 days after administration | Rate of inhibition (%) | The number of individuals having tumor regression |
|---|---|---|---|---|---|---|---|
| PBS | — | 1 | 8 | 203 ± 84 | 1339 ± 830 | — | 0 |
| [$^{90}$Y]-(A8) | 11.1 | 1 | 8 | 201 ± 75 | 123 ± 60 | 100 | 6 |

(Mean ± SD)

The compound shown in Table 9 exhibited an excellent antitumor effect.

Test Example 12

Imaging of Monkey Using [$^{111}$In]-(P2)

Blood kinetic parameters were calculated with OLINDA/EXM 1.0 from the blood concentration of radioactivity by blood collection over time from a cynomolgus monkey using [$^{111}$In]-(P2). Also, absorbed doses in each organ in the case of administration to humans were calculated with OLINDA/EXM 1.0 from organ distribution by imaging using [$^{111}$In]-(P2). The radiolabeled compound [$^{111}$In]-(P2) (98 MBq/9.3 g) was administered to a cynomolgus monkey (Hamri Co., Ltd., male, 3 years old, 3.4 kg) under anesthesia. After the administration, blood collection and imaging with a gamma camera were performed over time. The blood collection was carried out 10 minutes, 30 minutes, 60 minutes, 2 hours, 4 hours, 5 hours, 6 hours, 24 hours, 48 hours, 72 hours, and 144 hours after administration. The imaging was carried out 1, 2, 4, 6, 24, 48, 72, and 144 hours after administration with a gamma camera (Symbia, Siemens AG) to take planar images. The anesthesia was carried out using 20 mg/kg ketamine before administration of [$^{111}$In]-(P2) and maintained by inhalation anesthesia (2 to 3% isoflurane, 5 to 8 L/min) until the completion of the imaging at 6 hours after administration. At or after 24 hours after administration, blood collection and imaging were performed by the introduction of 20 mg/kg ketamine and 2 mg/kg xylazine. FIG. 8 shows change in the blood concentration of radioactivity in the monkey using [$^{111}$In]-(P2). The blood kinetic parameters are shown below.

TABLE 10

| Blood kinetic parameter | Evaluation |
| --- | --- |
| AUC (% ID · h/mL) | 0.22 |
| T½ α (h) | 0.46 |
| T½ β (h) | 19.3 |
| Cmax (% ID/mL) | 0.018 |
| CL (mL/h/kg) | 130.2 |
| Vss (L/kg) | 3.52 |

AUC was 0.22 (% ID·h/mL), $T_{1/2\alpha}$ was 0.46 (h), $T_{1/2\beta}$ was 19.3 (h), Cmax was 0.018 (% ID/mL), CL was 130.2 (mL/h/kg), and Vss was 3.52 (L/kg).

FIG. 9 shows the results of time-dependent planar imaging using [$^{111}$In]-(P2). In the imaging, accumulation to the bladder and the gallbladder was increased over time from administration to 6 hours later. The absorbed dose of each labeled compound in humans is shown below.

TABLE 11

| | Absorbed dose (mGy/MBq) | | |
| --- | --- | --- | --- |
| Organ | [$^{90}$Y] – (P2) | [$^{111}$In] – (P2) | [$^{64}$Cu] – (P2) |
| Whole body | 0.27 | 0.05 | 0.02 |
| Red bone marrow | 0.06 | 0.05 | 0.01 |
| Brain | 1.96 | 0.25 | 0.11 |
| Lung | 1.35 | 0.12 | 0.08 |
| Liver | 1.12 | 0.19 | 0.09 |
| Kidney | 14.70 | 1.19 | 0.69 |
| Small intestine | 0.87 | 0.05 | 0.06 |

INDUSTRIAL APPLICABILITY

The complex of the compound or the salt thereof with a metal of the present invention has high accumulation and persistence in integrin-expressing cells such as cancer cells and exhibits fast blood clearance. Therefore, the complex is useful for diagnosis or treatment, etc., of a disease involving integrin expression.

The invention claimed is:

1. A compound represented by the following formula or a salt thereof, or a complex of the compound or the salt with a metal:

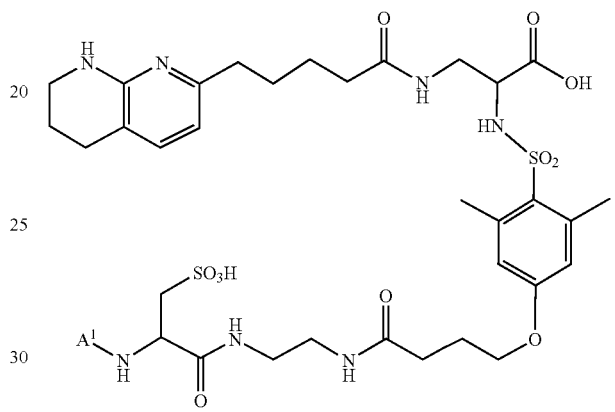

wherein
A$^1$ is a group represented by formula (5a), (6a), (7a), (8a), (8b), (8c), (9a), (10a), (10b), (11a), (11b), (11c), or (12a):

(5a)

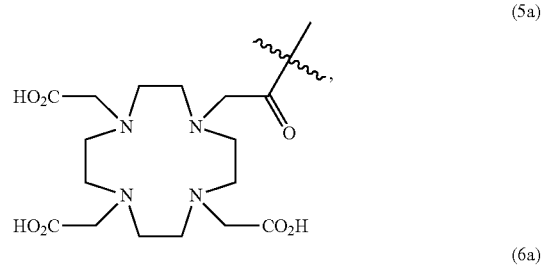

(6a)

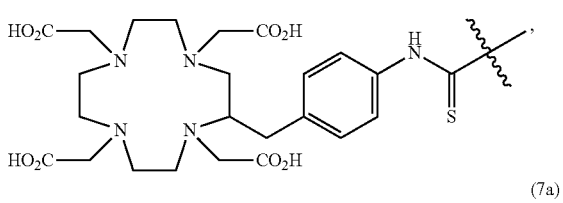

(7a)

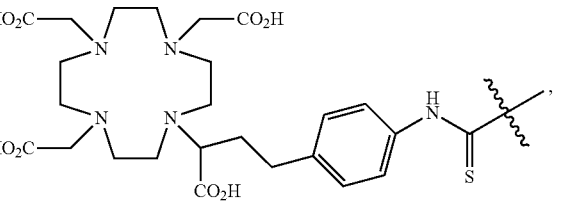

(8a) 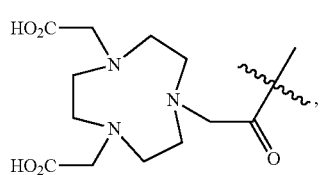
(8b) 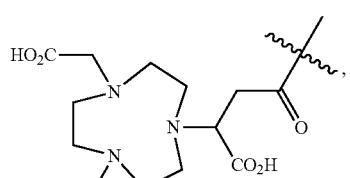
(8c) 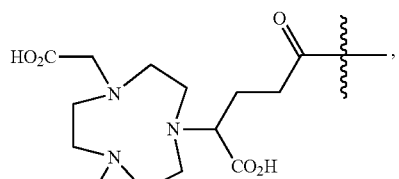
(9a) 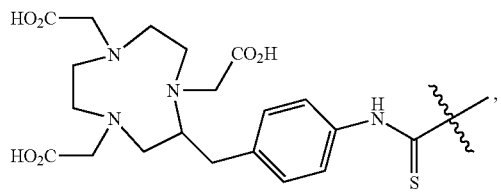
(10a) 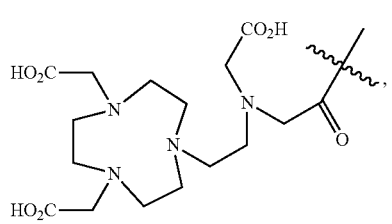
(10b) 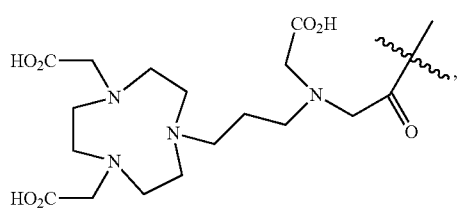
(11a) 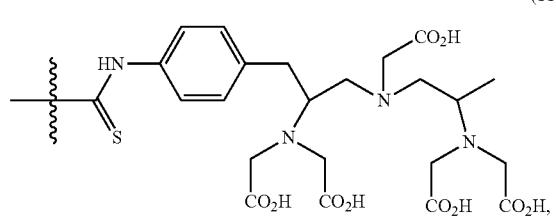
(11b) 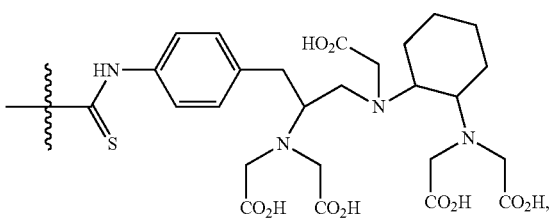
(11c) 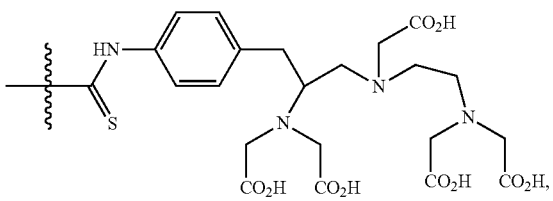
(12a) 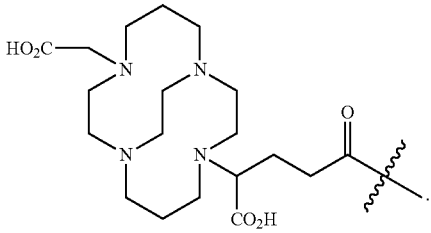
2. The compound or a salt thereof, or a complex of the compound or the salt with a metal according to claim 1, wherein $A^1$ is a group represented by the formula (5a), (6a), (8c), or (12a):
(5a) 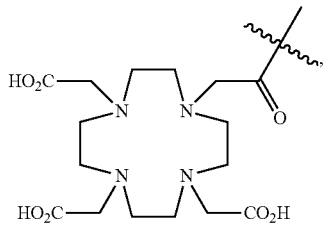
(6a) 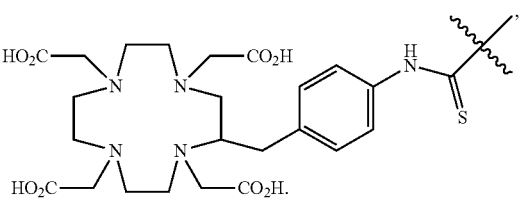
(8c) 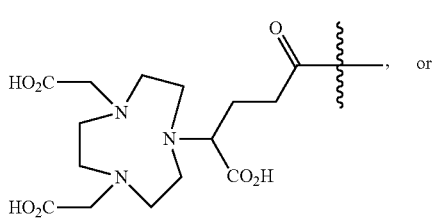
or (12a)

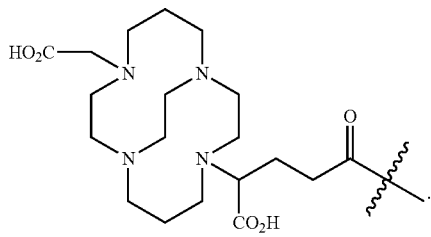

3. The compound or a salt thereof, or a complex of the compound or the salt with a metal according to claim 1, which is selected from 2,2',2"-(10-(2-(((R)-1-((2-(4-(4-(N-((R)-1-carboxy 2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl) triacetic acid, 2,2',2"-(10-(2-(((R)-1-((2-4(4-(N-((S)-1-carboxy-2-(5-(5,6,7,8-tetrahydro-1,8-naphthyridin-2-yl) pentanamido)ethyl)sulfamoyl)-3,5-dimethylphenoxy) butanamido)ethyl amino)-1-oxo-3-sulfopropan-2-yl) amino)-2-oxoethyl)-1,4,7,10-tetraazacyclododecane-1,4,7-triyl)triacetic acid, 2,2'-7-((R)-1-carboxy-4-(((R)-1-((2-(4-(4-(N-((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-4-oxobutyl)-1,4,7-triazonane-1,4-diyl)diacetic acid, and 5-(((R)-1-((2-(4-(4-(N-((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl) amino)-1-oxo-3-sulfopropan-2-yl)amino)-2-(11-(carboxymethyl)-1,4,8,11-tetraazabicyclo[6.6.2] hexadecan-4-yl)-5-oxopentanoic acid.

4. The complex according to claim 1, wherein the metal is a cytotoxic radioactive metal.

5. The complex according to claim 4, wherein the cytotoxic radioactive metal is $^{64}$Cu, $^{67}$Cu, $^{90}$Y, $^{166}$Ho, $^{153}$Sm, $^{177}$Lu, $^{212}$Pb, or $^{225}$Ac.

6. A pharmaceutical composition comprising the complex according to claim 4 and a pharmacologically acceptable additive.

7. The complex according to claim 1, wherein the metal is a noncytotoxic radioactive metal.

8. The complex according to claim 7, wherein the noncytotoxic radioactive metal is an $^{18}$F aluminum complex, $^{111}$In, $^{64}$Cu, $^{67}$Ga, $^{68}$Ga, or $^{89}$Zr.

9. A pharmaceutical composition comprising the complex according to claim 7 and a pharmacologically acceptable additive.

10. A kit for preparing an agent for diagnosis or treatment by adding a metal, the kit comprising the compound or a salt thereof according to claim 1.

11. A method for treating a disease involving an integrin, comprising administering the complex according to claim 4.

12. A method for diagnosing a disease involving an integrin, comprising administering the complex according to claim 7 and performing a diagnostic imaging step.

13. A compound or a salt thereof, or a complex of the compound or the salt with a metal, wherein the compound or the salt thereof is 2,2',2"-(10-(2-(((R)-1-((2-(4-(4-(N-((S)-1-carboxy-2-(5-(5,6,7,8-tetrahydro-1,8-naphthyridin-2-yl) pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl) triacetic acid or a salt thereof.

14. The method for treating a disease involving an integrin according to claim 11, wherein the disease is cancer.

15. The method for treating a disease involving an integrin according to claim 14, wherein the cancer is solid cancer.

16. The method for treating a disease involving an integrin according to claim 14, wherein the cancer is head and neck cancer, colorectal cancer, breast cancer, small-cell lung cancer, non-small cell lung cancer, glioma, brain tumor, glioblastoma, astrocytoma, malignant melanoma, pancreatic cancer, or prostate cancer.

17. The method for diagnosing a disease involving an integrin according to claim 12, wherein the disease is cancer.

18. The method for diagnosing a disease involving an integrin according to claim 17, wherein the cancer is solid cancer.

19. The method for diagnosing a disease involving an integrin according to claim 17, wherein the cancer is head and neck cancer, colorectal cancer, breast cancer, small-cell lung cancer, non-small cell lung cancer, glioma, brain tumor, glioblastoma, astrocytoma, malignant melanoma, pancreatic cancer, or prostate cancer.

20. The complex according to claim 4, wherein the cytotoxic radioactive metal is α-ray-emitting nuclide or β-ray-emitting nuclide.

21. The complex according to claim 4, wherein the cytotoxic radioactive metal is $^{90}$Y, $^{114}$In, $^{117}$Sn, $^{186}$Re, $^{188}$Re, $^{64}$Cu, $^{67}$Cu, $^{59}$Fe, $^{89}$Sr, $^{198}$Au, $^{203}$Hg, $^{212}$Pb, $^{165}$Dy, $^{103}$Ru, $^{149}$Tb, $^{161}$Tb, $^{212}$Bi, $^{166}$Ho, $^{165}$Er, $^{153}$Sm, $^{177}$Lu, $^{213}$Bi, $^{223}$Ra, $^{225}$Ac, $^{227}$Th, $^{211}$At, $^{175}$Yb, $^{105}$Rh, $^{166}$Dy, $^{149}$Pm, $^{44}$Sc or $^{47}$Sc.

22. The complex according to claim 4, wherein the cytotoxic radioactive metal is $^{177}$Lu.

23. The complex according to claim 7, wherein the noncytotoxic radioactive metal is a gamma ray-emitting nuclide or a positron-emitting nuclide.

24. The complex according to claim 7, wherein the noncytotoxic radioactive metal is an $^{18}$F aluminum complex, $^{18}$F gallium complex, $^{18}$F indium complex, $^{181}$F lutetium complex, $^{18}$F thallium complex, $^{99}$Tc, $^{111}$In, $^{113m}$In, $^{114m}$In, $^{67}$Ga, $^{68}$Ga, $^{82}$Rb, $^{86}$Y, $^{87}$Rb, $^{152}$Tb, $^{155}$Tb, $^{201}$Tl, $^{51}$Cr, $^{52}$Fe, $^{57}$Co, $^{58}$Co, $^{60}$Co, $^{82}$Sr, $^{85}$Sr, $^{197}$Hg, $^{44}$Sc, $^{62}$Cu, $^{64}$Cu, $^{89}$Zr, $^{72}$As, or $^{52}$Mn.

25. The complex according to claim 7, wherein the noncytotoxic radioactive metal is $^{68}$Ga.

26. The complex according to claim 4, wherein the cytotoxic radioactive metal is $^{255}$Ac.

27. The complex according to claim 7, wherein the noncytotoxic radioactive metal is $^{67}$Ga, $^{68}$Ga or $^{64}$Cu.

28. A complex of a cytotoxic radioactive metal selected from $^{177}$Lu and $^{225}$Ac, and a compound which is 2,2',2"-(10-(2-(((R)-1-((2-(4-(4-(N-((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid or a salt thereof.

29. The complex according to claim 28, wherein the cytotoxic radioactive metal is $^{177}$Lu.

30. A pharmaceutical composition comprising the complex according to claim 28 and a pharmacologically acceptable additive.

31. A pharmaceutical composition comprising the complex according to claim 29 and a pharmacologically acceptable additive.

32. A complex of a noncytotoxic radioactive metal selected from $^{67}$Ga, $^{68}$Ga and $^{64}$Cu and a compound which is 2,2',2"-(10-(2-(((R)-1((2-(4-(4-(N-((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-2-oxoethyl)-1,4,7,10-tetraazacyclododecane-1,4,7-triyl)triacetic acid or a salt thereof.

33. The complex according to claim 32, wherein the noncytotoxic radioactive metal is $^{68}$Ga.

34. A pharmaceutical composition co p sing the complex according to claim 32 and a pharmacologically acceptable additive.

35. A pharmaceutical composition comprising the complex according to claim 33 and a pharmacologically acceptable additive.

36. A complex of a noncytotoxic radioactive metal selected from $^{67}$Ga, $^{68}$Ga and $^{64}$Cu, and a compound which is 2,2'-(7-((R)-1-carboxy-4(((R)-1-((2-(4-(4-(N-((S)-1-carboxy-2-(5-(5,6,7,8-tetrahydro-1,8-naphthyridin-2-yl)pentanamido)ethyl)sulfamoyl)-3,5-dimethylphenoxy)butanamido)ethyl)amino)-1-oxo-3-sulfopropan-2-yl)amino)-4-oxobutyl)-1,4,7-triazonane-1,4-diyl)diacetic acid or a salt thereof.

* * * * *